(12) United States Patent
Jung et al.

(10) Patent No.: US 10,026,906 B2
(45) Date of Patent: *Jul. 17, 2018

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Hyejin Jung, Yongin (KR); Sooyon Kim, Jinju (KR); Youngkook Kim, Yongin (KR); Sanghyun Han, Yongin (KR); Seokhwan Hwang, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 184 days.

This patent is subject to a terminal disclaimer.

(21) Appl. No.: 14/789,672

(22) Filed: Jul. 1, 2015

(65) Prior Publication Data

US 2016/0204353 A1 Jul. 14, 2016

(30) Foreign Application Priority Data

Jan. 12, 2015 (KR) ........................ 10-2015-0004460

(51) Int. Cl.
*H01L 51/00* (2006.01)
*C07D 311/78* (2006.01)
(Continued)

(52) U.S. Cl.
CPC ........ *H01L 51/0061* (2013.01); *C07D 311/78* (2013.01); *C07D 407/14* (2013.01);
(Continued)

(58) Field of Classification Search
CPC combination set(s) only.
See application file for complete search history.

(56) References Cited

U.S. PATENT DOCUMENTS 3,968,051 A 7/1976 Stamm et al.
5,635,308 A 6/1997 Inoue et al.
(Continued)

FOREIGN PATENT DOCUMENTS

CN 102925139 A 2/2013
JP 8-12600 A 1/1996
(Continued)

OTHER PUBLICATIONS

Machine English translation of Shin et al. (KR 10-2009-0010763), 27 pages.
(Continued)

*Primary Examiner* — Jennifer A Chriss
*Assistant Examiner* — Sean M DeGuire
(74) *Attorney, Agent, or Firm* — Lewis Roca Rothgerber Christie LLP

(57) ABSTRACT

An organic light-emitting device includes a first electrode; a second electrode; and an organic layer between the first
(Continued)

electrode and the second electrode, the organic layer including an emission layer and a condensed cyclic compound of Formula 1. The emission layer includes a host and a dopant, and the condensed cyclic compound acts as the dopant.

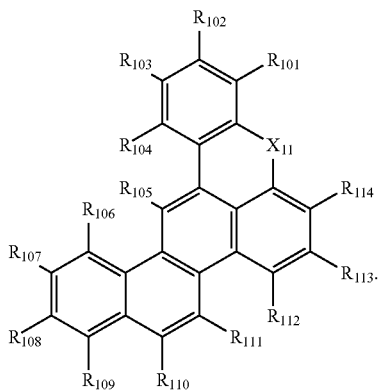

Formula 1

20 Claims, 1 Drawing Sheet

(51) Int. Cl.
C09K 11/02 (2006.01)
C09K 11/06 (2006.01)
C07D 407/14 (2006.01)
C07F 7/08 (2006.01)
H01L 51/50 (2006.01)

(52) U.S. Cl.
CPC .......... C07F 7/0812 (2013.01); C07F 7/0814 (2013.01); C09K 11/025 (2013.01); C09K 11/06 (2013.01); H01L 51/0058 (2013.01); H01L 51/0094 (2013.01); C09K 2211/1007 (2013.01); C09K 2211/1011 (2013.01); C09K 2211/1014 (2013.01); C09K 2211/1029 (2013.01); C09K 2211/1088 (2013.01); C09K 2211/1092 (2013.01); H01L 51/0073 (2013.01); H01L 51/5012 (2013.01)

(56) References Cited

U.S. PATENT DOCUMENTS

| | | |
|---|---|---|
| 5,972,247 A | 10/1999 | Shi et al. |
| 6,465,115 B2 | 10/2002 | Shi et al. |
| 6,582,837 B1 | 6/2003 | Toguchi et al. |
| 6,596,415 B2 | 7/2003 | Shi et al. |
| 7,053,255 B2 | 5/2006 | Ikeda et al. |
| 7,233,019 B2 | 6/2007 | Ionkin et al. |
| 7,732,063 B2 | 6/2010 | Matsuura et al. |
| 7,839,074 B2 | 11/2010 | Ikeda et al. |
| 8,221,905 B2 | 7/2012 | Lin et al. |
| 8,324,802 B2 | 12/2012 | Matsuura et al. |
| 8,334,648 B2 | 12/2012 | Matsuura et al. |
| 9,711,736 B2 | 7/2017 | Han et al. |
| 2004/0076853 A1 | 4/2004 | Jarikov |
| 2004/0137270 A1 | 7/2004 | Seo et al. |
| 2004/0214036 A1 | 10/2004 | Bentsen et al. |
| 2005/0064233 A1 | 3/2005 | Matsuura et al. |
| 2005/0089717 A1 | 4/2005 | Cosimbescu et al. |
| 2005/0156164 A1 | 7/2005 | Sotoyama |
| 2005/0214565 A1 | 9/2005 | Ikeda et al. |
| 2005/0245752 A1 | 11/2005 | Conley et al. |
| 2005/0249972 A1 | 11/2005 | Hatwar et al. |
| 2006/0052641 A1 | 3/2006 | Funahashi |
| 2006/0083945 A1 | 4/2006 | Morishita et al. |
| 2006/0113905 A1 | 6/2006 | Nakamura |
| 2006/0152146 A1 | 7/2006 | Funahashi |
| 2006/0159952 A1 | 7/2006 | Ricks et al. |
| 2007/0114917 A1 | 5/2007 | Funahashi et al. |
| 2007/0152565 A1 | 7/2007 | Kubota et al. |
| 2007/0155991 A1 | 7/2007 | Funahashi |
| 2007/0170419 A1 | 7/2007 | Gerhard et al. |
| 2007/0237984 A1 | 10/2007 | Matsuura et al. |
| 2008/0160342 A1 | 7/2008 | Meng et al. |
| 2008/0193796 A1 | 8/2008 | Arakane et al. |
| 2009/0004458 A1 | 1/2009 | Falster et al. |
| 2009/0004485 A1 | 1/2009 | Zheng et al. |
| 2009/0026930 A1 | 1/2009 | Shin et al. |
| 2010/0013381 A1 | 1/2010 | Stoessel et al. |
| 2010/0032658 A1 | 2/2010 | Lee et al. |
| 2010/0052526 A1 | 3/2010 | Je et al. |
| 2010/0127618 A1 | 5/2010 | Ohrui et al. |
| 2010/0187521 A1 | 7/2010 | Park et al. |
| 2010/0244012 A1 | 9/2010 | Mazur et al. |
| 2010/0270913 A1 | 10/2010 | Matsuura et al. |
| 2010/0277061 A1 | 11/2010 | Matsuura et al. |
| 2010/0279156 A1 | 11/2010 | Kim et al. |
| 2010/0295445 A1 | 11/2010 | Kuma et al. |
| 2010/0314615 A1 | 12/2010 | Mizuki et al. |
| 2011/0001130 A1 | 1/2011 | Nishimura et al. |
| 2011/0006289 A1 | 1/2011 | Mizuki et al. |
| 2011/0057116 A1 | 3/2011 | Trogler et al. |
| 2011/0156016 A1 | 6/2011 | Kawamura et al. |
| 2011/0210320 A1 | 9/2011 | Shin et al. |
| 2011/0284832 A1 | 11/2011 | In et al. |
| 2012/0001158 A1 | 1/2012 | Asari et al. |
| 2012/0032152 A1 | 2/2012 | Kim et al. |
| 2012/0056165 A1 | 3/2012 | Kawamura et al. |
| 2012/0091885 A1 | 4/2012 | Kim et al. |
| 2012/0138915 A1 | 6/2012 | Nishimura et al. |
| 2012/0181518 A1 | 7/2012 | Ogiwara et al. |
| 2012/0181922 A1 | 7/2012 | Kawamura et al. |
| 2012/0235561 A1 | 9/2012 | Ikeda et al. |
| 2012/0305904 A1 | 12/2012 | Kai et al. |
| 2012/0313511 A1 | 12/2012 | Tsurutani et al. |
| 2013/0001526 A1 | 1/2013 | Kwak et al. |
| 2013/0049581 A1 | 2/2013 | Nishide et al. |
| 2013/0090446 A1 | 4/2013 | Zhou et al. |
| 2013/0105786 A1 | 5/2013 | Watanabe et al. |
| 2013/0112949 A1 | 5/2013 | Sim et al. |
| 2013/0119355 A1 | 5/2013 | Han et al. |
| 2013/0221332 A1 | 8/2013 | Xia et al. |
| 2013/0228752 A1 | 9/2013 | Shin et al. |
| 2013/0295706 A1 | 11/2013 | Goto et al. |
| 2013/0306958 A1 | 11/2013 | Ito et al. |
| 2014/0008641 A1 | 1/2014 | Kubota et al. |
| 2014/0048792 A1 | 2/2014 | Chun et al. |
| 2014/0124763 A1 | 5/2014 | Funahashi |
| 2014/0175395 A1 | 6/2014 | Kim et al. |
| 2014/0264301 A1* | 9/2014 | Takaku ............... C09K 11/06 257/40 |
| 2014/0332772 A1 | 11/2014 | Han et al. |
| 2014/0346406 A1 | 11/2014 | Lee et al. |
| 2014/0346464 A1 | 11/2014 | Kim et al. |
| 2014/0346482 A1 | 11/2014 | Mizuki et al. |
| 2015/0001479 A1 | 1/2015 | Lee et al. |
| 2015/0053946 A1 | 2/2015 | Kim et al. |
| 2015/0069344 A1 | 3/2015 | Kim et al. |
| 2015/0090964 A1 | 4/2015 | Hwang et al. |
| 2015/0090965 A1 | 4/2015 | Park et al. |
| 2015/0108448 A1 | 4/2015 | Dai et al. |
| 2015/0171337 A1* | 6/2015 | Jung ................... H01L 51/0058 257/40 |
| 2015/0236273 A1 | 8/2015 | Jang et al. |
| 2015/0255736 A1 | 9/2015 | Kim et al. |
| 2015/0318508 A1 | 11/2015 | Kim et al. |
| 2015/0333266 A1 | 11/2015 | Ito et al. |
| 2015/0333268 A1* | 11/2015 | Han ................... H01L 51/0073 257/40 |
| 2015/0349265 A1 | 12/2015 | Hwang et al. |
| 2015/0357574 A1 | 12/2015 | Ito et al. |
| 2015/0364693 A1 | 12/2015 | Ito et al. |

(56) References Cited

U.S. PATENT DOCUMENTS

| | | | |
|---|---|---|---|
| 2016/0005980 A1 | 1/2016 | Ito et al. | |
| 2016/0020404 A1 | 1/2016 | Ito et al. | |
| 2016/0133845 A1* | 5/2016 | Jung | H01L 51/0058 257/40 |

FOREIGN PATENT DOCUMENTS

| | | |
|---|---|---|
| JP | 11-003782 A | 1/1999 |
| JP | 2002-63989 | 2/2002 |
| JP | 2003-306454 | 10/2003 |
| JP | 2005-041843 A | 2/2005 |
| JP | 2006-273737 A | 10/2006 |
| JP | 2008-291263 | 12/2008 |
| JP | 2009-212238 | 9/2009 |
| JP | 2011-176267 A | 9/2011 |
| JP | 2012-82209 | 4/2012 |
| JP | 2012-119592 A | 6/2012 |
| JP | 2012-156499 A | 8/2012 |
| JP | 2013-063930 | 4/2013 |
| JP | 2013-063931 | 4/2013 |
| JP | 2013-63931 A | 4/2013 |
| JP | 52-08271 B2 | 6/2013 |
| JP | 5281304 | 9/2013 |
| KR | 10-2005-0058465 | 6/2005 |
| KR | 10-2005-0086518 A | 8/2005 |
| KR | 10-2005-0107809 | 11/2005 |
| KR | 10-2006-0006760 | 1/2006 |
| KR | 10-2006-0109524 | 10/2006 |
| KR | 10-2006-0113954 | 11/2006 |
| KR | 10-2006-0127138 | 12/2006 |
| KR | 10-2007-0009074 | 1/2007 |
| KR | 10-2007-0015195 | 2/2007 |
| KR | 10-2007-0050393 A | 5/2007 |
| KR | 10-2008-0068720 A | 7/2008 |
| KR | 10-2009-0010763 A | 1/2009 |
| KR | 10-2009-0033493 | 4/2009 |
| KR | 10-2009-0122922 A | 12/2009 |
| KR | 10-2010-0007552 | 1/2010 |
| KR | 10-2010-0007780 A | 1/2010 |
| KR | 10-2010-0024894 | 3/2010 |
| KR | 10-2010-0048203 | 5/2010 |
| KR | 10-2010-0057465 | 5/2010 |
| KR | 10-2010-0070979 | 6/2010 |
| KR | 10-2010-0070992 | 6/2010 |
| KR | 10-2010-0093085 | 8/2010 |
| KR | 10-2010-0097182 | 9/2010 |
| KR | 10-2010-0099327 | 9/2010 |
| KR | 10-2010-0105099 | 9/2010 |
| KR | 10-2011-0015213 | 2/2011 |
| KR | 10-2011-0041728 | 4/2011 |
| KR | 10-2011-0043625 A | 4/2011 |
| KR | 10-2011-0047278 A | 5/2011 |
| KR | 10-2011-0094271 A | 8/2011 |
| KR | 10-2011-0107679 | 10/2011 |
| KR | 10-2011-0134885 | 12/2011 |
| KR | 10-2012-0002865 | 1/2012 |
| KR | 10-2012-0026513 | 3/2012 |
| KR | 10-2012-0039470 | 4/2012 |
| KR | 10-2012-0041110 | 4/2012 |
| KR | 10-1132635 B1 | 4/2012 |
| KR | 10-2012-0057611 | 6/2012 |
| KR | 10-2012-0066390 | 6/2012 |
| KR | 10-2012-0093354 | 8/2012 |
| KR | 10-2012-0117622 | 10/2012 |
| KR | 10-2012-0117675 | 10/2012 |
| KR | 10-2013-0007495 | 1/2013 |
| KR | 10-2013-0009765 | 1/2013 |
| KR | 10-1233377 | 2/2013 |
| KR | 10-1262420 | 5/2013 |
| KR | 10-2013-0100948 | 9/2013 |
| WO | WO 2010/050781 A1 | 5/2010 |
| WO | WO 2010/058995 A1 | 5/2010 |
| WO | WO 2010/107244 A2 | 9/2010 |
| WO | WO 2010/137678 A1 | 12/2010 |
| WO | WO 2012/070226 A1 | 5/2012 |
| WO | WO 2012/070234 A1 | 5/2012 |
| WO | WO 2013/051875 A2 | 4/2013 |

OTHER PUBLICATIONS

U.S. Notice of Allowance dated Mar. 15, 2017, issued in U.S. Appl. No. 14/513,144 (9 pages).
U.S. Office Action dated Aug. 23, 2017, issued in U.S. Appl. No. 14/702,970 (9 pages).
U.S. Notice of Allowance dated Jan. 25, 2018, issued in U.S. Appl. No. 14/075,573 (8 pages).
Ding et al., "A Succinct Synthesis of the Vaulted Biaryl Ligand Vanol via a Dienone-Phenol Rearrangement," Full Papers, 2011, Chemistry an Asian Journal 2011, vol. 6, pp. 2130-2146.
Kaminaga, et al., Machine Translation of JP 2011-176267A, Published Sep. 2011, Retrieved from Google Patents on Feb. 3, 2017, pp. 1-44.
Katritzky, A., et al., "Polycyclic Fused Phenanthridines: An Alternative Approach from Benzotriazoles", Center for Heterocyclic Compounds., Department of Chemistry, Univ. of Florida, pp. 1-27.
Leem et al., "Highly efficient tandem p-i-n organic light-emitting diodes adopting a low temperature evaporated rhenium oxide interconnecting later," Applied Physics Letters, 93, 103304-1-3, 2008.
Yumiko et al., Machine English translation of KR 10-2010-0097182. Mar. 10, 2017.
Machine translation for JP 2012-119592 A, publication date Jun. 21, 2012, 27 pages.
Machine Translation for KR 10-2011-0041728, publication date Apr. 22, 2011, 19 pages.
U.S. Office action dated Feb. 19, 2016, for cross referenced U.S. Appl. No. 14/072,478, (12 pages).
U.S. Office Action dated Apr. 20, 2016, issued in cross-reference U.S. Appl. No. 14/075,573 (10 pages).
Notice of Allowance dated Jul. 15, 2016, for cross reference U.S. Appl. No. 14/533,004.
STIC Search Report for cross reference U.S. Appl. No. 14/533,004, dated Dec. 1, 2015 (15 pages).
U.S. Office action dated Dec. 8, 2015, for cross reference U.S. Appl. No. 14/533,004, (12 pages).
U.S. Office action dated May 5, 2016, for cross reference U.S. Appl. No. 14/195,836, (18 pages).
U.S. Office action dated Oct. 6, 2016, for cross referenced U.S. Appl. No. 14/550,801, (9 pages).
U.S. Notice of Allowance dated Feb. 10, 2017, issued in cross-reference U.S. Appl. No. 14/533,004 (12 pages).
U.S. Office Action dated Feb. 16, 2017, issued in cross-reference U.S. Appl. No. 14/075,573 (14 pages).
U.S. Notice of Allowance dated Mar. 27, 2017, issued in cross-reference U.S. Appl. No. 14/550,801 (9 pages).
U.S. Office Action dated Jul. 13, 2017, issued in cross-reference U.S. Appl. No. 14/508,677 (10 pages).
Machine translation for JP 2012-119592 A (publication date: Jun. 2012), 52 pages.
U.S. Office Action dated Dec. 18, 2017, issued in U.S. Appl. No. 14/550,801 (9 pages).
U.S. Office Action dated Dec. 20, 2017, issued in U.S. Appl. No. 14/195,836 (9 pages).

* cited by examiner

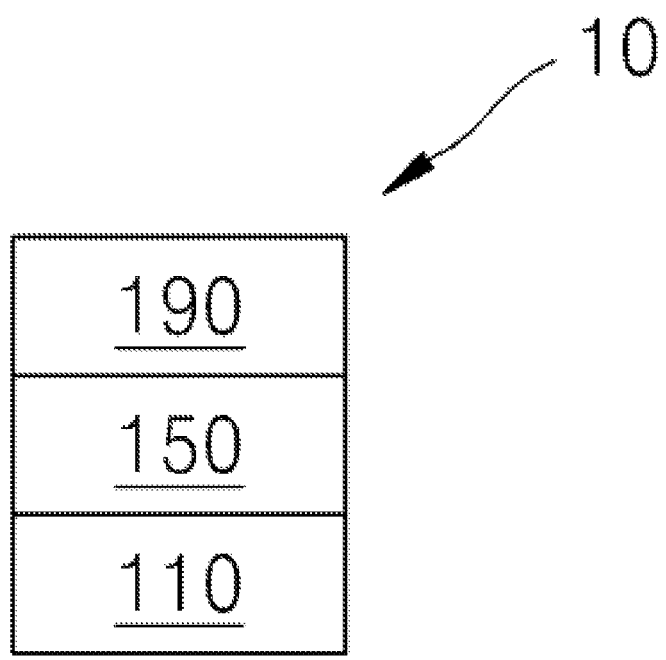

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0004460, filed on Jan. 12, 2015, in the Korean Intellectual Property Office, the entire content of which is incorporated herein by reference.

BACKGROUND

1. Field

One or more aspects of embodiments of the present invention are directed to a condensed cyclic compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and can produce full-color images.

An organic light-emitting device may include a first electrode positioned on a substrate, and a hole transport region, an emission layer, an electron transport region, and a second electrode, sequentially positioned on the first electrode. Holes provided from the first electrode may move toward the emission layer through the hole transport region, and electrons provided from the second electrode may move toward the emission layer through the electron transport region. Carriers (e.g., holes and electrons), are then recombined in the emission layer to produce excitons. These excitons change from an excited state to a ground state, thereby generating light.

SUMMARY

One or more aspects of embodiments of the present invention are directed to a condensed cyclic compound and an organic light-emitting device including the same.

In one or more embodiments, a condensed cyclic compound is represented by Formula 1 below:

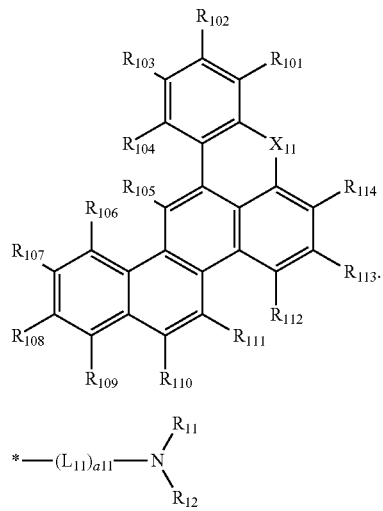

Formula 1

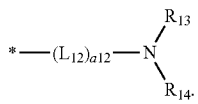

Formula 10-2

In Formula 1, $X_{11}$ is selected from an oxygen atom (O) and a sulfur atom (S);

$R_{101}$ to $R_{114}$ are each independently selected from a group represented by Formula 10-1, a group represented by Formula 10-2, hydrogen, deuterium, —F, —Cl, —Br, —I, a hydroxyl group, a cyano group, a nitro group, an amino group, an amidino group, a hydrazine group, a hydrazone group, a carboxylic acid (herein also referring to a carboxylic acid group) or a salt thereof, a sulfonic acid (herein also referring to a sulfonic acid group) or a salt thereof, a phosphoric acid (herein also referring to a phosphoric acid group) or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

at least one selected from $R_{101}$ to $R_{114}$ is a group represented by Formula 10-1;

at least one selected from $R_{101}$ to $R_{114}$ is a group represented by Formula 10-2;

at least one selected from $R_{101}$ to $R_{114}$ is selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

$L_{11}$ and $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ Formula 10-1 heteroarylene group, a substituted or unsubstituted divalent non-aromatic condensed polycyclic group, and a substituted or unsubstituted divalent non-aromatic condensed heteropolycyclic group;

a11 and a12 are each independently selected from 0, 1, 2, 3, 4, and 5;

$R_{11}$ to $R_{14}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and at least one substituent selected from the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$)

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$) and —B($Q_{36}$)($Q_{37}$);

where $Q_1$ to $Q_3$, $Q_{11}$ to $Q_{17}$, $Q_{21}$ to $Q_{27}$ and $Q_{31}$ to $Q_{37}$ are each independently selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In one or more embodiments of the present invention, an organic light-emitting device includes a first electrode; a second electrode facing the first electrode; and an organic layer between the first electrode and the second electrode, the organic layer including an emission layer, wherein the organic layer includes the condensed cyclic compound of Formula 1.

BRIEF DESCRIPTION OF THE DRAWING

Features will become apparent to those of ordinary skill in the art by describing in more detail the present embodiments with reference to the attached drawing which illustrates a schematic view of an organic light-emitting device according to one or more embodiments of the present invention.

DETAILED DESCRIPTION

Reference will now be made in more detail to embodiments, examples of which are illustrated in the accompanying drawing, wherein like reference numerals refer to like elements throughout. In this regard, the present embodiments may have different forms and should not be construed as being limited to the descriptions set forth herein. Accordingly, the embodiments are merely described below, by referring to the drawing, to explain aspects of the present description. Sizes of components in the drawing may be exaggerated for convenience of explanation, and the following embodiments are not limited thereto.

A condensed cyclic compound according to one or more embodiments of the present invention is represented by Formula 1:

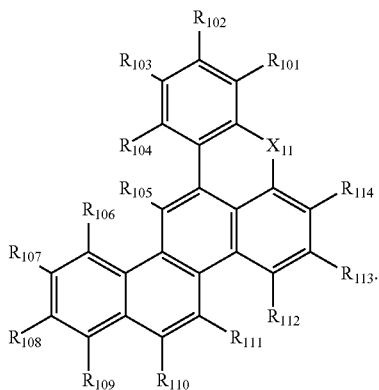

Formula 1

In Formula 1, $X_{11}$ may be an oxygen atom (O) or a sulfur atom (S).

For example, $X_{11}$ in Formula 1 may be an oxygen atom, but is not limited thereto.

$R_{101}$ to $R_{114}$ in Formula 1 may be each independently selected from a group represented by Formula 10-1, a group represented by Formula 10-2, hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

where at least one selected from $R_{101}$ to $R_{114}$ may be a group represented by Formula 10-1:

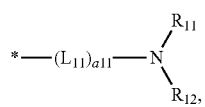

Formula 10-1 at least one selected from $R_{101}$ to $R_{114}$ may be a group represented by Formula 10-2:

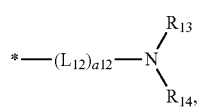

Formula 10-2 and at least one selected from $R_{101}$ to $R_{114}$ may be selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, where $Q_1$ to $Q_3$, $Q_{11}$ to $Q_{17}$, $Q_{21}$ to $Q_{27}$, and $Q_{31}$ to $Q_{37}$ may be each independently selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one selected from $R_{101}$ to $R_{104}$ in Formula 1 may be a group represented by Formula 10-1; and at least one selected from $R_{105}$ to $R_{114}$ may be a group represented by Formula 10-2, but embodiments of the present invention are not limited thereto.

In some embodiments, at least one selected from $R_{101}$ to $R_{104}$ in Formula 1 may be a group represented by Formula 10-1; and at least one selected from $R_{106}$ to $R_{111}$ may be a group represented by Formula 10-2, but embodiments of the present invention are not limited thereto.

In some embodiments, $R_{102}$ in Formula 1 may be a group represented by Formula 10-1; and $R_{110}$ may be a group represented by Formula 10-2, but embodiments of the present invention are not limited thereto.

For example, $R_{101}$ to $R_{114}$ in Formula 1 may be selected from deuterium, a substituted or unsubstituted $C_1$-$C_{60}$ alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —$Si(Q_1)(Q_2)(Q_3)$, where $Q_1$ to $Q_3$ may be each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, but embodiments of the present invention are not limited thereto.

In some embodiments, at least one selected from $R_{101}$ to $R_{114}$ in Formula 1 may be selected from a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —$Si(Q_1)(Q_2)(Q_3)$, where $Q_1$ to $Q_3$ may be each independently selected from a $C_1$-$C_{60}$ alkyl group and a $C_6$-$C_{60}$ aryl group, but embodiments of the present invention are not limited thereto.

In some embodiments, at least one selected from $R_{101}$ to $R_{114}$ in Formula 1 may be selected from:

a $C_1$-$C_{60}$ alkyl group;

a $C_6$-$C_{60}$ aryl group, a $C_1$-$C_{60}$ heteroaryl group, a monovalent non-aromatic condensed polycyclic group, and a monovalent non-aromatic condensed heteropolycyclic group;

a $C_6$-$C_{60}$ aryl group, a $C_1$-$C_{60}$ heteroaryl group, a monovalent non-aromatic condensed polycyclic group, and a monovalent non-aromatic condensed heteropolycyclic group, each substituted with at least one selected from a $C_1$-$C_{60}$ alkyl group and a $C_1$-$C_{60}$ alkoxy group; and —$Si(Q_1)(Q_2)(Q_3)$, where $Q_1$ to $Q_3$ may be each independently selected from a $C_1$-$C_{60}$ alkyl group and a $C_6$-$C_{60}$ aryl group, but embodiments of the present invention are not limited thereto.

In some embodiments, at least one selected from $R_{101}$ to $R_{114}$ in Formula 1 may be selected from:

a methyl group, an ethyl group, an n-propyl group, an iso-propyl group, an n-butyl group, a sec-butyl group, an iso-butyl group, a tert-butyl group, an n-pentyl group, a sec-pentyl group, an iso-pentyl group, neo-pentyl group, a tert-pentyl group, a 3-pentyl group, an n-hexyl group, an n-heptyl group, an n-octyl group, an n-nonyl group, and an n-decanyl group;

a phenyl group, a naphthyl group, a fluorenyl group, a spiro-fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyridinyl group, a pyrazinyl group, a pyrimidinyl group, a pyridazinyl group, an indolyl group, a quinolinyl group, an isoquinolinyl group, a benzoquinolinyl group, a benzoisoquinolinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a triazolyl group, a triazinyl group, a dibenzofuranyl group, a dibenzothiophenyl group, a carbazolyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyridinyl group, a pyrazinyl group, a pyrimidinyl group, a pyridazinyl group, an indolyl group, a quinolinyl group, an isoquinolinyl group, a benzoquinolinyl group, a benzoisoquinolinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a triazolyl group, a triazinyl group, a dibenzofuranyl group, a dibenzothiophenyl group, a carbazolyl group, a benzocarbazolyl group, and a dibenzocarbazolyl group, each substituted with at least one selected from a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an n-butoxy group, and a tert-butoxy group; and —$Si(Q_1)(Q_2)(Q_3)$;

where $Q_1$ to $Q_3$ are each independently selected from a methyl group, an ethyl group, an n-propyl group, an isopropyl group, an n-butyl group, a sec-butyl group, an iso-butyl group, a tert-butyl group, a phenyl group, and a naphthyl group, but embodiments of the present invention are not limited thereto.

In some embodiments, $R_{101}$ to $R_{114}$ in Formula 1 may be selected from:

a methyl group, an ethyl group, an n-propyl group, an iso-propyl group, an n-butyl group, a sec-butyl group, an iso-butyl group, and a tert-butyl group;

a phenyl group, a naphthyl group, a fluorenyl group, a phenalenyl group, a phenanthrenyl group, and an anthracenyl group;

a phenyl group, a naphthyl group, a fluorenyl group, a phenalenyl group, a phenanthrenyl group, and an anthracenyl group, each substituted with at least one selected from a methyl group, an ethyl group, an n-propyl group, an iso-propyl group, an n-butyl group, a sec-butyl group, an iso-butyl group, and a tert-butyl group; and —Si($Q_1$)($Q_2$)($Q_3$), where $Q_1$ to $Q_3$ may be each independently selected from a methyl group, an ethyl group, an n-propyl group, an iso-propyl group, an n-butyl group, a sec-butyl group, an iso-butyl group, and a tert-butyl group, but embodiments of the present invention are not limited thereto.

In some embodiments, at least one selected from $R_{101}$ to $R_{114}$ in Formula 1 may be selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$, but embodiments of the present invention are not limited thereto.

In some embodiments, at least one selected from $R_{107}$, $R_{108}$, $R_{113}$, and $R_{114}$ in Formula 1 may be selected from:

a methyl group, an ethyl group, an n-propyl group, an iso-propyl group, an n-butyl group, a sec-butyl group, an iso-butyl group, and a tert-butyl group;

a phenyl group, a naphthyl group, a fluorenyl group, a phenalenyl group, a phenanthrenyl group, and an anthracenyl group;

a phenyl group, a naphthyl group, a fluorenyl group, a phenalenyl group, a phenanthrenyl group, and an anthracenyl group, each substituted with at least one selected from a methyl group, an ethyl group, an n-propyl group, an iso-propyl group, an n-butyl group, a sec-butyl group, an iso-butyl group, and a tert-butyl group; and —Si($Q_1$)($Q_2$)($Q_3$);

where $Q_1$ to $Q_3$ may be each independently selected from a methyl group, an ethyl group, an n-propyl group, an iso-propyl group, an n-butyl group, a sec-butyl group, an iso-butyl group, and a tert-butyl group, but embodiments of the present invention are not limited thereto.

In some embodiments, at least one selected from $R_{107}$, $R_{108}$, $R_{113}$ and $R_{114}$ in Formula 1 may be selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$, but embodiments of the present invention are not limited thereto.

In some embodiments, $R_{107}$, $R_{108}$, $R_{113}$ and $R_{114}$ in Formula 1 may be each independently selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$, but embodiments of the present invention are not limited thereto.

In some embodiments, $R_{107}$ and $R_{113}$ in Formula 1 may be each independently selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$, but embodiments of the present invention are not limited thereto.

In some embodiments, $R_{108}$ and $R_{114}$ in Formula 1 may be each independently selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl; and —Si($CH_3$)$_3$, but embodiments of the present invention are not limited thereto.

In some embodiments, $R_{107}$, $R_{108}$, $R_{113}$ or $R_{114}$ in Formula 1 may be selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$, but embodiments of the present invention are not limited thereto.

In some embodiments, $R_{107}$ and $R_{113}$ in Formula 1 may be the same, but embodiments of the present invention are not limited thereto.

In some embodiments, $R_{108}$ and $R_{114}$ in Formula 1 may be the same, but embodiments of the present invention are not limited thereto.

$L_{11}$ and $L_{12}$ in Formulae 10-1 and 10-2 may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group; and at least one substitutent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group and, substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), where $Q_{11}$ to $Q_{17}$, $Q_{21}$ to $Q_{27}$ and $Q_{31}$ to $Q_{37}$ may be each independently selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, $L_{11}$ and $L_{12}$ in Formulae 10-1 and 10-2 may be each independently selected from a phenylene group, a pentalenylene group, an indenylene group, a naphthylene group, an azulenylene group, a heptalenylene group, an indacenylene group, an acenaphthylene group, a fluorenylene group, an spiro-fluorenylene group, an benzofluorenylene group, an dibenzofluorenylene group, a phenalenylene group, a phenanthrenylene group, an anthracenylene group, a fluoranthenylene group, an triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, a oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group, but embodiments of the present invention are not limited thereto.

In some embodiments, $L_{11}$ and $L_{12}$ in Formulae 10-1 and 10-2 may be each independently selected from a phenylene group, a naphthylene group, a fluorenylene group, a phenanthrenylene group, an anthracenylene group, a triphenylenylene group, a pyrrolylene group, a thiophenylene group, a furanylene group, a pyridinylene group, a pyrazinylene group, a pyrimidinylene group, an indolylene group, a quinolinylene group, an isoquinolinylene group, a benzoquinolinylene group, a naphthyridinylene group, a quinoxalinylene group, a quinazolinylene group, a cinnolinylene group, a carbazolylene group, a phenanthridinylene group, a benzimidazolylene group, a benzofuranylene group, a benzothiophenylene group, a triazolylene group, a dibenzofuranylene group, and a dibenzothiophenylene group; and a phenylene group, a naphthylene group, a fluorenylene group, a phenanthrenylene group, an anthracenylene group, a triphenylenylene group, a pyrrolylene group, a thiophenylene group, a furanylene group, a pyridinylene group, a pyrazinylene group, a pyrimidinylene group, an indolylene group, a quinolinylene group, an isoquinolinylene group, a benzoquinolinylene group, a naphthyridinylene group, a quinoxalinylene group, a quinazolinylene group, a cinnolinylene group, a carbazolylene group, a phenanthridinylene group, a benzimidazolylene group, a benzofuranylene group, a benzothiophenylene group, a triazolylene group, a dibenzofuranylene group, and a dibenzothiophenylene group, each substituted with at least one selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present invention are not limited thereto.

In some embodiments, $L_{11}$ and $L_{12}$ in Formulae 10-1 and 10-2 may be each independently selected from groups represented by Formulae 3-1 to 3-31, but embodiments of the present invention are not limited thereto:

3-1

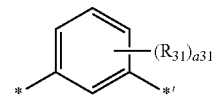

3-2

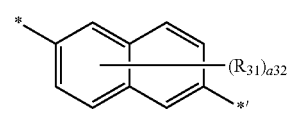

3-3

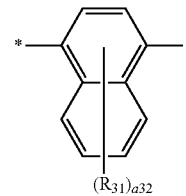

3-4

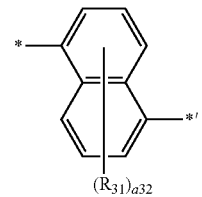

3-5

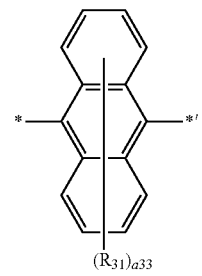

3-6

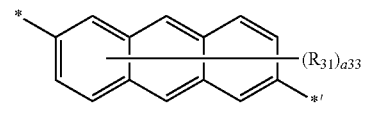

3-7

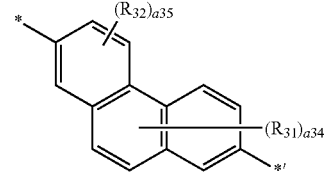

3-8

-continued
3-9
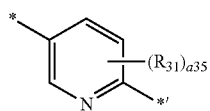
3-10
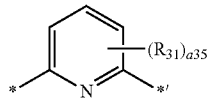
3-11
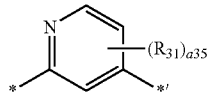
3-12
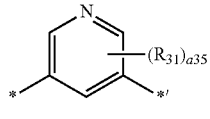
3-13
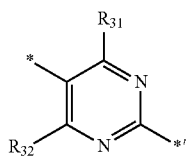
3-14
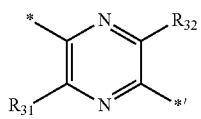
3-15
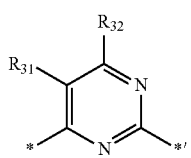
3-16
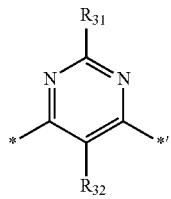
3-17
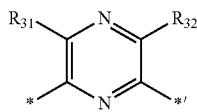
3-18
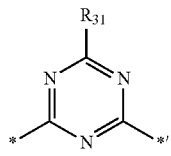
3-19
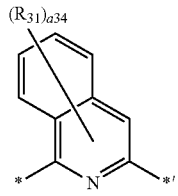
-continued
3-20
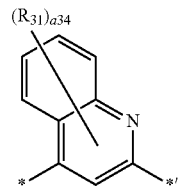
3-21
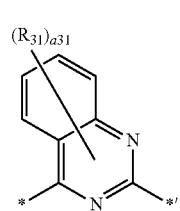
3-22
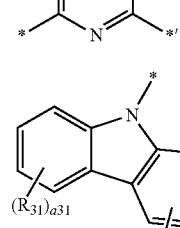
3-23
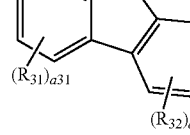
3-24
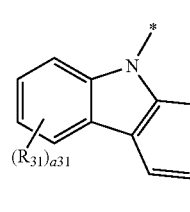
3-25
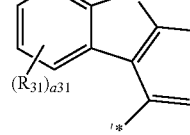
3-26
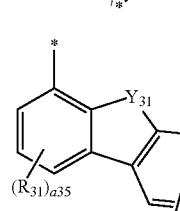
3-27
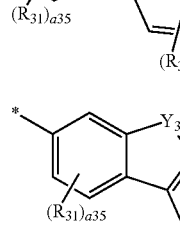

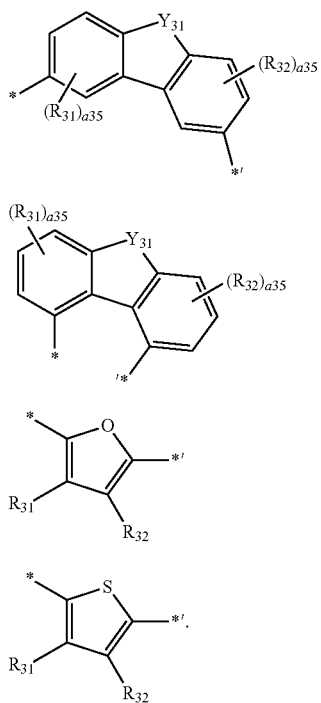

3-28

3-29

3-30

3-31

In Formulae 3-1 to 3-31, $Y_{31}$ may be selected from $C(R_{33})(R_{34})$, $N(R_{33})$, O, and S;

$R_{31}$ to $R_{34}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a31 is selected from 1, 2, 3, and 4;

a32 is selected from 1, 2, 3, 4, 5, and 6;

a33 is selected from 1, 2, 3, 4, 5, 6, 7, and 8;

a34 is selected from 1, 2, 3, 4, and 5;

a35 is selected from 1, 2, and 3; and

* and *' are each independently a binding site to a neighboring atom.

In some embodiments, $L_{11}$ and $L_{12}$ in Formulae 10-1 and 10-2 may be each independently selected from groups represented by Formulae 4-1 to 4-56, but embodiments of the present invention are not limited thereto:

4-1

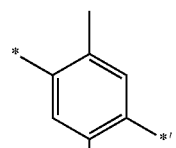

4-2

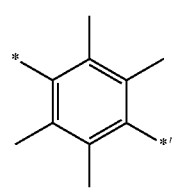

4-3

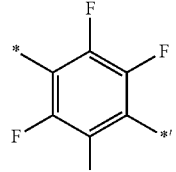

4-4

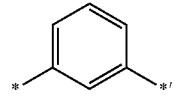

4-5

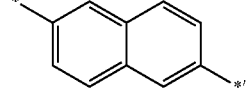

4-6

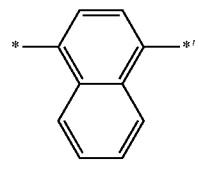

4-7

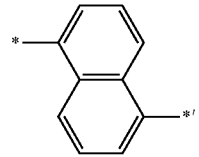

4-8

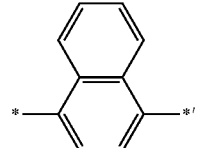

4-9

4-10

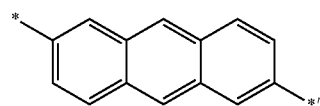

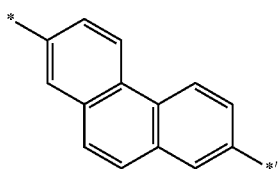
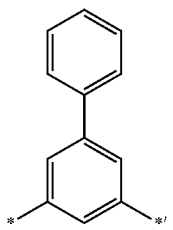
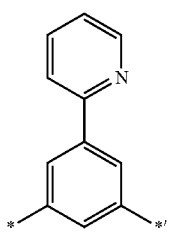
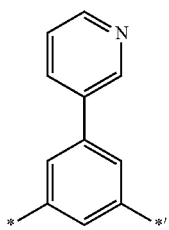
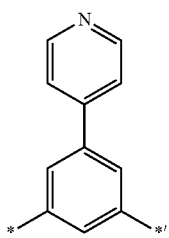
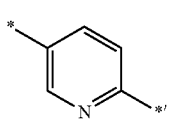
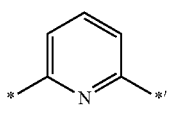

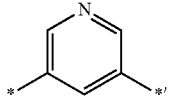
4-11

4-12

4-13

4-14

4-15
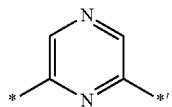
4-16
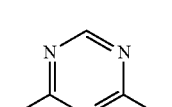
4-17
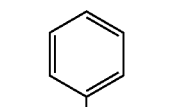
4-18
4-19
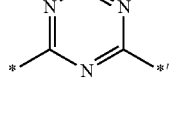
4-20
4-21
4-22
4-23
4-24
4-25
4-26
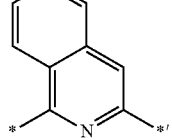
4-27
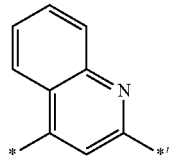
4-28
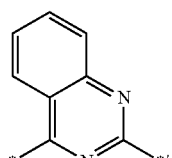
4-29
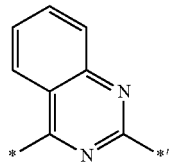

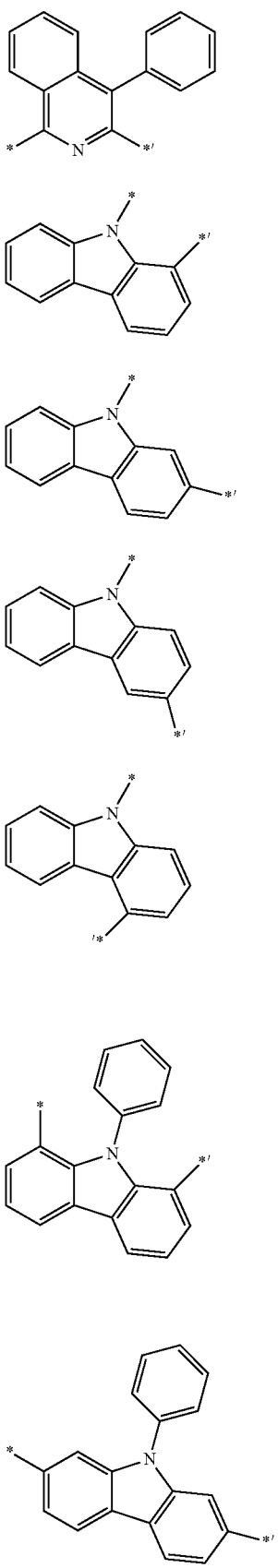
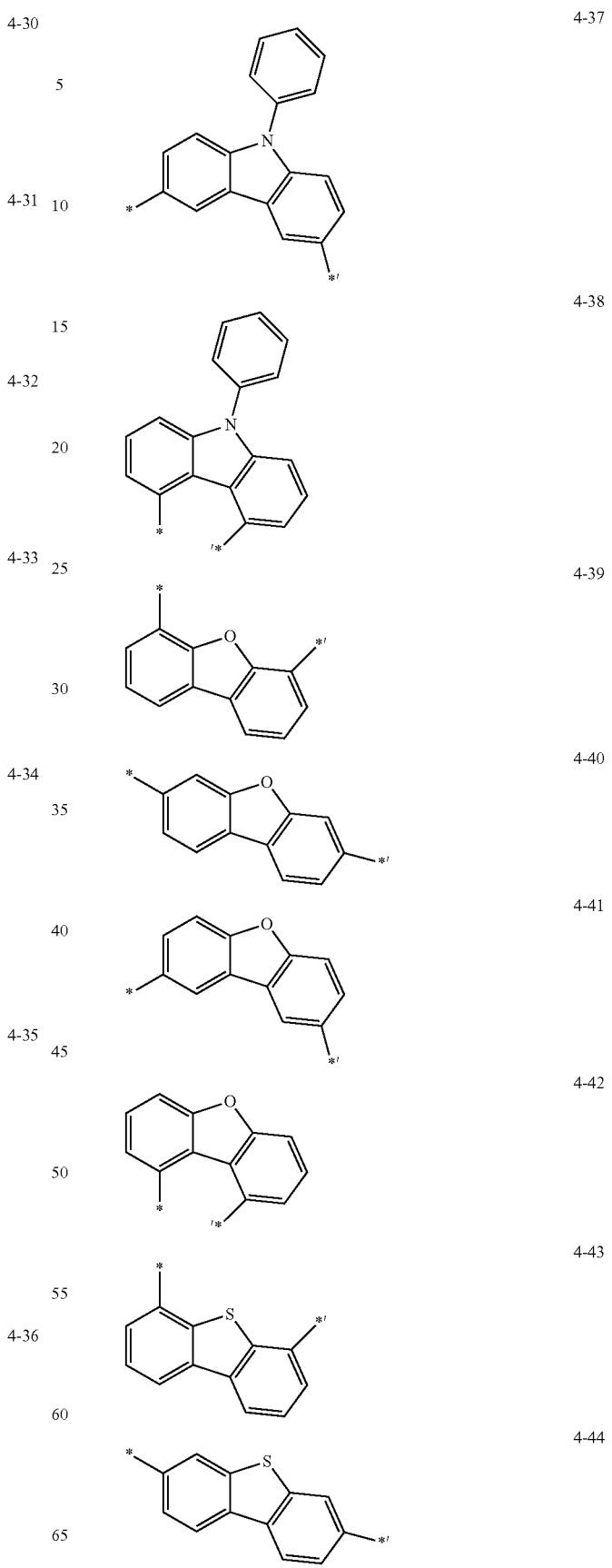

-continued 4-45

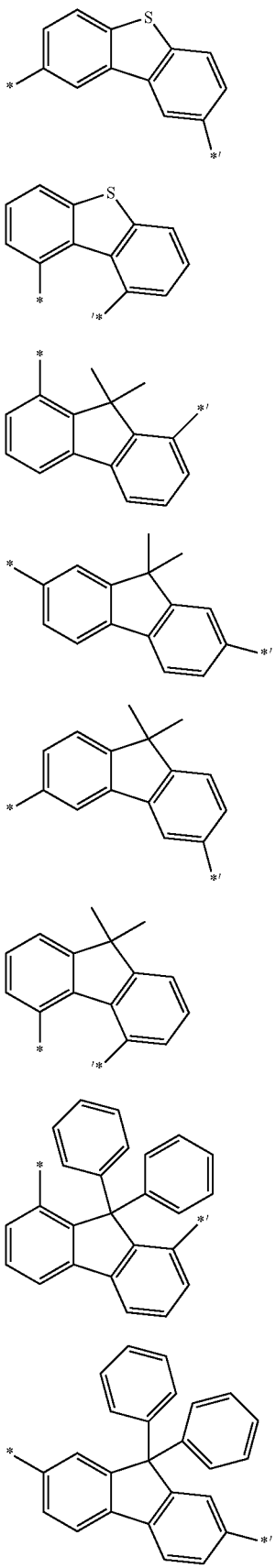

4-46

4-47

4-48

4-49

4-50

4-51

4-52

-continued

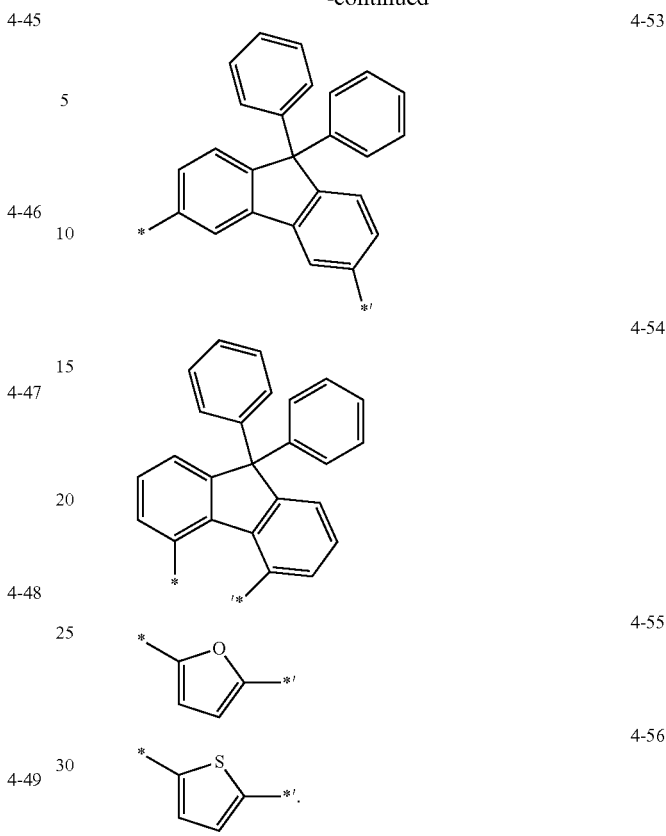

4-53

4-54

4-55

4-56

In Formulae 4-1 to 4-56,

* and *' may be each independently a binding site to a neighboring atom.

a11 in Formula 10-1 indicates the number of $L_{11}$, and may be selected from 0, 1, 2, 3, 4, and 5. For example, a11 in Formula 10-1 may be selected from 0 and 1, but embodiments of the present invention are not limited thereto. When a11 is 0, $(1\text{-}11)_{a11}$ indicates a single bond. When a11 is 2 or more, a plurality of $L_{11}$ may be identical to or different from each other.

a12 in Formula 10-2 indicates the number of $L_{12}$, and may be selected from 0, 1, 2, 3, 4, and 5. For example, a12 in Formula 10-2 may be selected from 0 and 1, but embodiments of the present invention are not limited thereto. When a12 is 0, $(L_{12})_{a12}$ indicates a single bond. When a12 is 2 or more, a plurality of $L_{12}$ may be identical to or different from each other.

For example, the sum of a11 and a12 in Formula 1 may be selected from 0, 1, and 2, but embodiments of the present invention are not limited thereto.

In some embodiments, a11 and a12 in Formula 1 may each be 0, but embodiments of the present invention are not limited thereto.

In some embodiments, in Formula 1, a11 may be 0 and a12 may be 1, but embodiments of the present invention are not limited thereto.

In some embodiments, in Formula 1, a11 may be 1 and a12 may be 0, but embodiments of the present invention are not limited thereto.

In some embodiments, a11 and a12 in Formula 1 may be 1, but embodiments of the present invention are not limited thereto.

$R_{11}$ to $R_{14}$ in Formulae 10-1 and 10-2 may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and at least one substituent of the substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$) and —B($Q_{36}$)($Q_{37}$), where $Q_{11}$ to $Q_{17}$, $Q_{21}$ to $Q_{27}$ and $Q_{31}$ to $Q_{37}$ may be each independently selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, $R_{11}$ to $R_{14}$ in Formulae 10-1 and 10-2 may be each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a biphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), where $Q_{33}$ to $Q_{35}$ may be each independently selected from a $C_1$-$C_{60}$ alkyl group and a $C_6$-$C_{60}$ aryl group, but embodiments of the present invention are not limited thereto.

In some embodiments, $R_{11}$ to $R_{14}$ in Formulae 10-1 and 10-2 may be each independently selected from a phenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group;

a phenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{33}$)($Q_{34}$)($Q_{35}$); and a phenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group, each substituted with at least one selected from a $C_1$-$C_{20}$ alkyl group that is substituted with at least one selected from deuterium, —F, —Cl, —Br, —I, a cyano group, and a nitro group, where $Q_{33}$ to $Q_{35}$ are each independently selected from a $C_1$-$C_{20}$ alkyl group and a $C_6$-$C_{60}$ aryl group, but embodiments of the present invention are not limited thereto.

In some embodiments, $R_{11}$ to $R_{14}$ in Formulae 10-1 and 10-2 may be each independently selected from a phenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, and a dibenzothiophenyl group; and a phenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, —CD$_3$, —CF$_3$, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{33}$)($Q_{34}$)($Q_{35}$), where $Q_{33}$ to $Q_{35}$ may be each independently selected from a methyl group, an ethyl group, ter-butyl group, a phenyl group, and a naphthyl group, but embodiments of the present invention are not limited thereto.

In some embodiments, $R_{11}$ to $R_{14}$ in Formulae 10-1 and 10-2 may be each independently selected from Formulae 5-1 to 5-33, but embodiments of the present invention are not limited thereto:

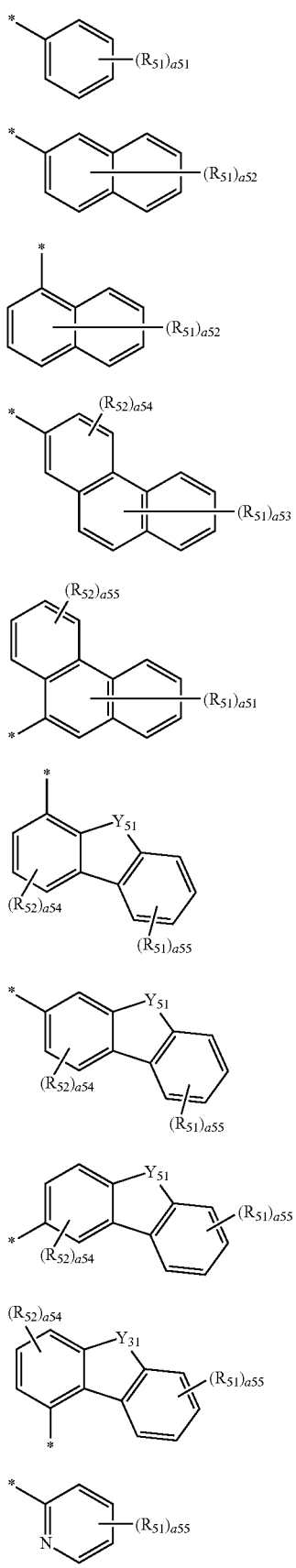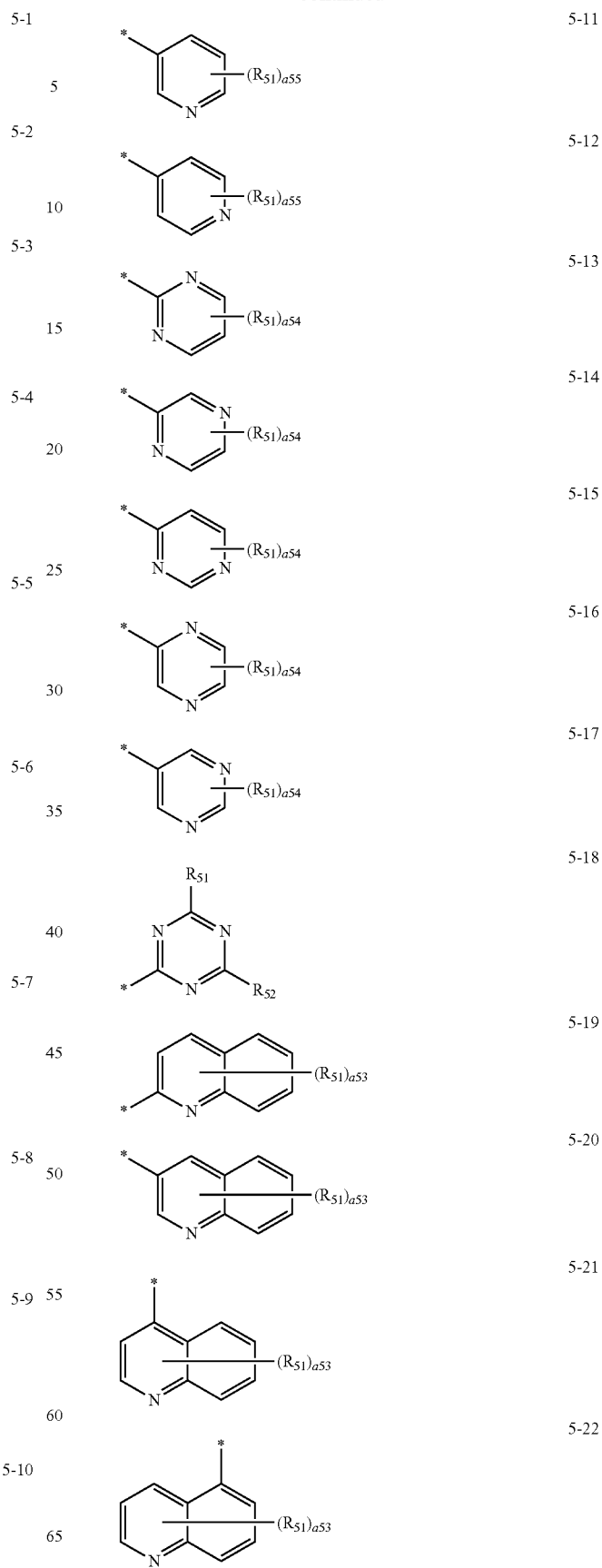

-continued

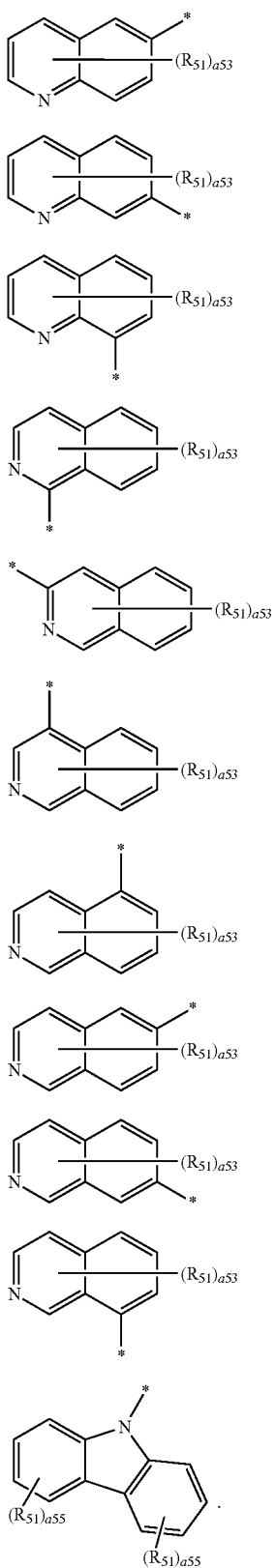

5-23
5-24
5-25
5-26
5-27
5-28
5-29
5-30
5-31
5-32
5-33

In Formulae 5-1 to 5-33,
Y$_{51}$ may be selected from C(R$_{53}$)(R$_{54}$), N(R$_{53}$), O, and S; and R$_{51}$ to R$_{54}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a C$_1$-C$_{20}$ alkyl group, —CD$_3$, —CF$_3$, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, —Si(Q$_{33}$)(Q$_{34}$)(Q$_{35}$), where Q$_{33}$ to Q$_{35}$ may be each independently selected from a methyl group, an ethyl group, ter-butyl group, a phenyl group, and a naphthyl group;

a51 may be selected from 1, 2, 3, 4, and 5;

a52 may be selected from 1, 2, 3, 4, 5, 6, and 7;

a53 may be selected from 1, 2, 3, 4, 5, and 6;

a54 may be selected from 1, 2, and 3;

a55 may be selected from 1, 2, 3, and 4; and

* indicates a binding site to a neighboring atom.

In some embodiments, R$_{11}$ to R$_{14}$ in Formulae 10-1 and 10-2 may be each independently selected from groups represented by Formulae 6-1 to 6-155, but embodiments of the present invention are not limited thereto:

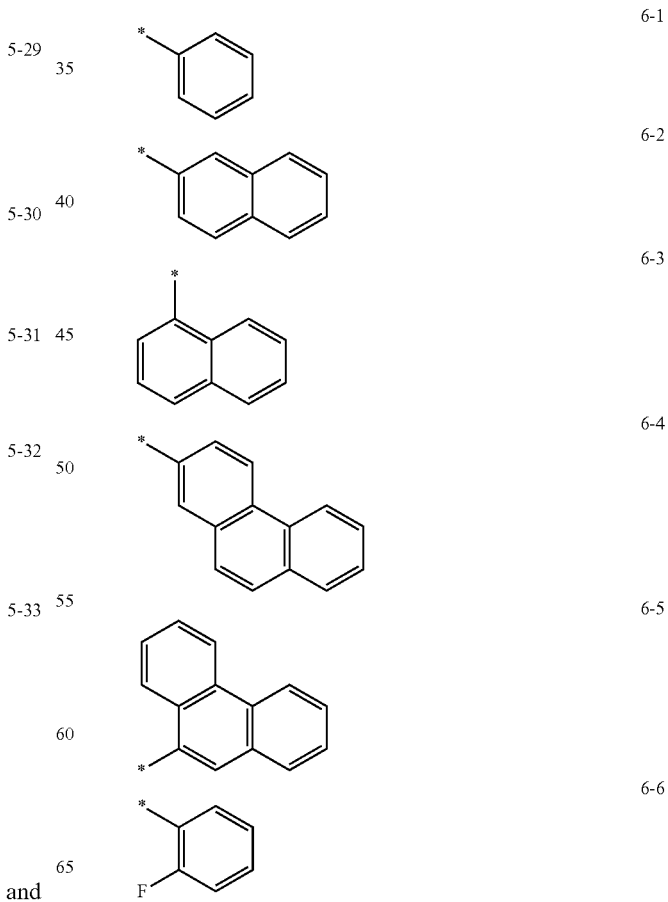

6-1
6-2
6-3
6-4
6-5
6-6

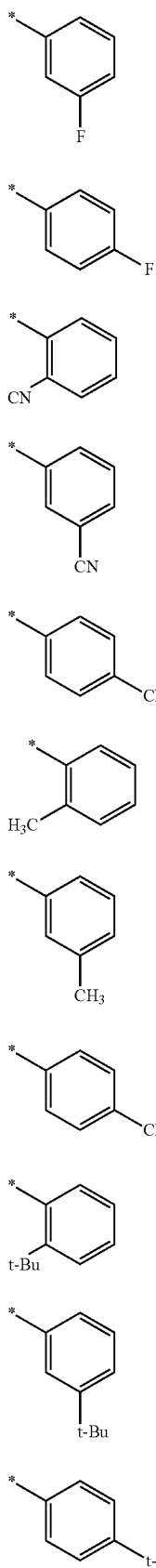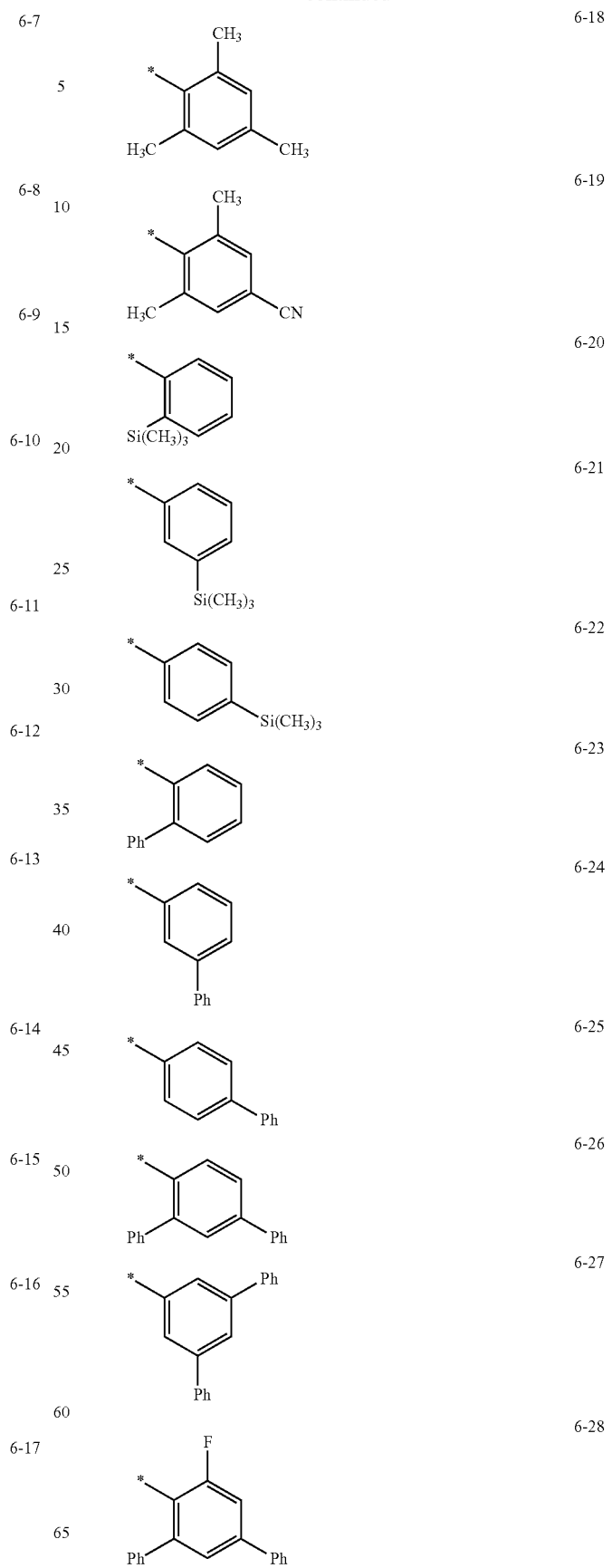

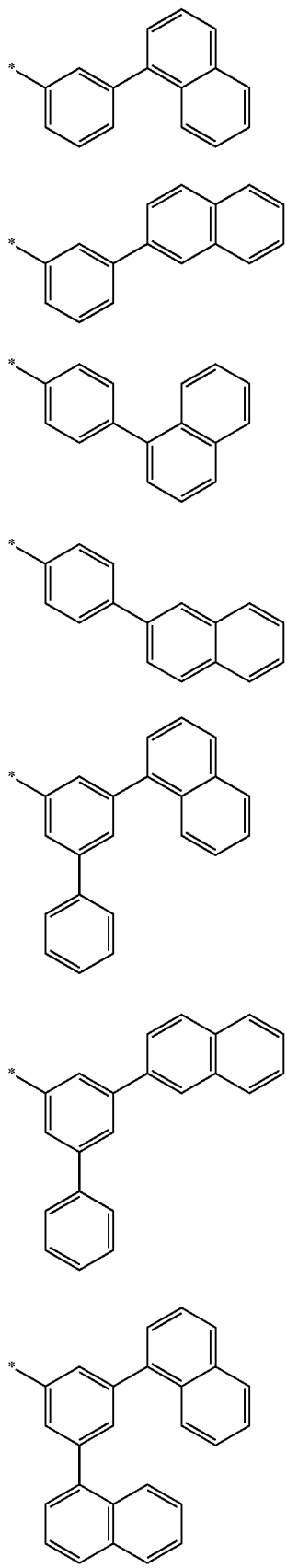
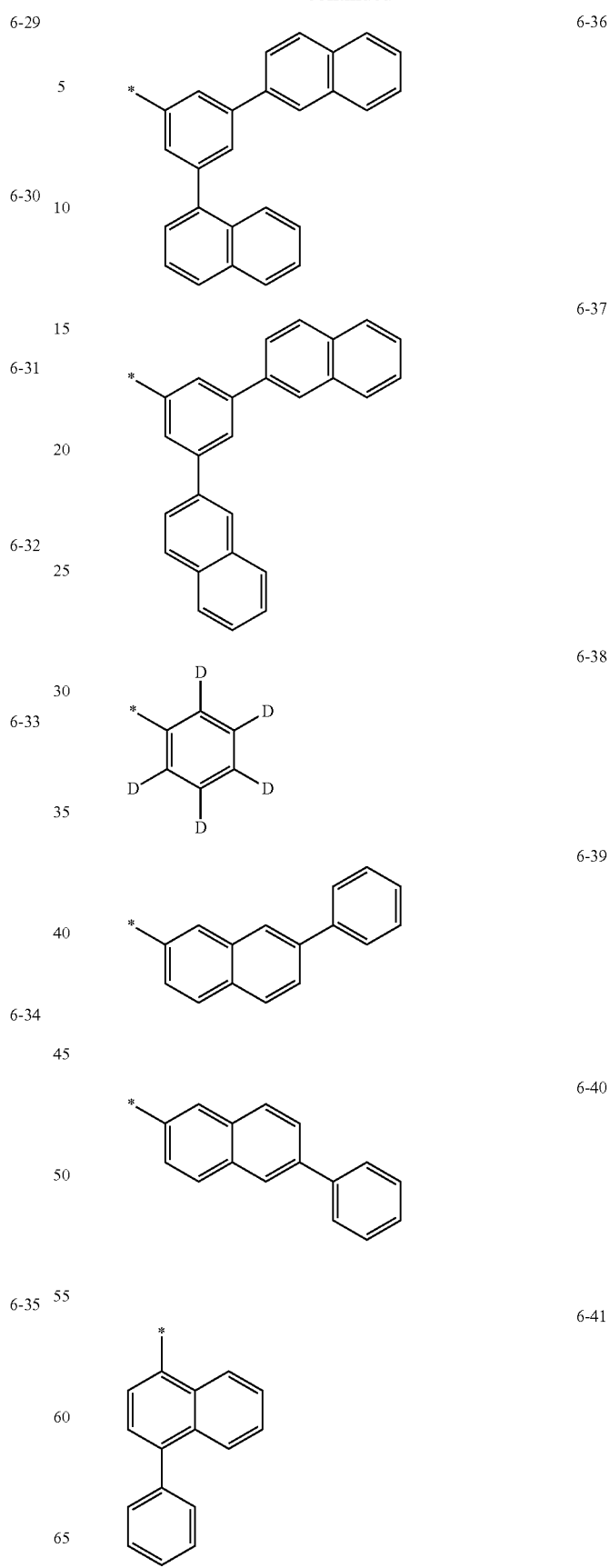

6-42 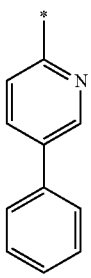
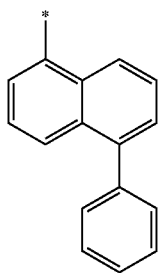
6-43 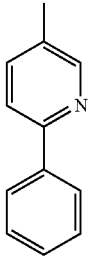
6-44
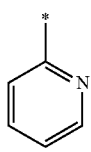
6-45 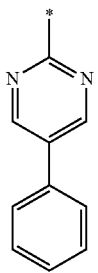
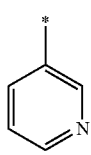
6-46
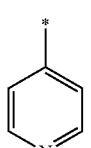
6-47 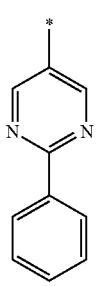
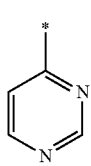
6-48 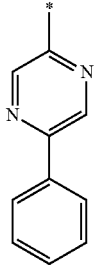

6-49
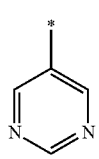
6-50 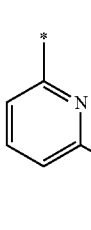
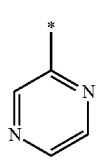
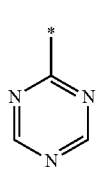
6-51
6-52
6-53
6-54
6-55
6-56

6-57 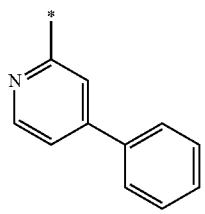
6-58 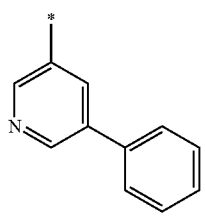
6-59 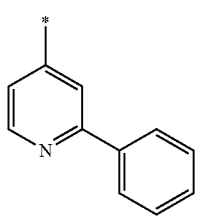
6-60 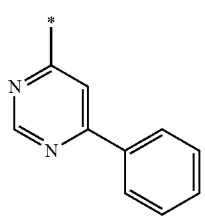
6-61 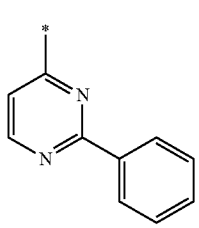
6-62 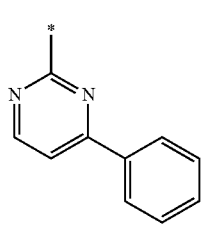
6-63 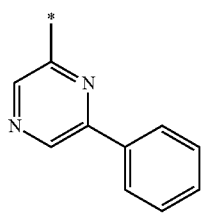
6-64 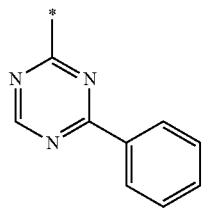
6-65 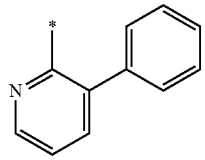
6-66 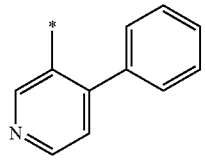
6-67 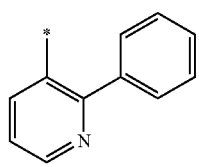
6-68 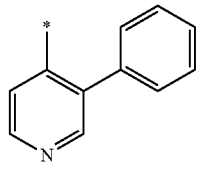
6-69 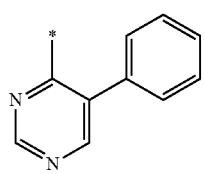
6-70 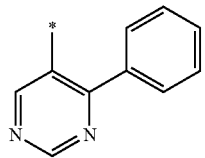
6-71 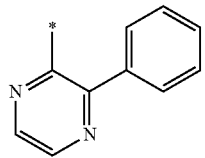

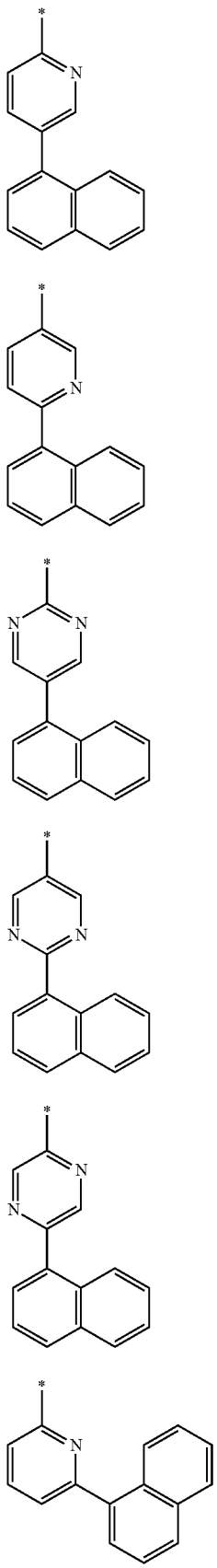
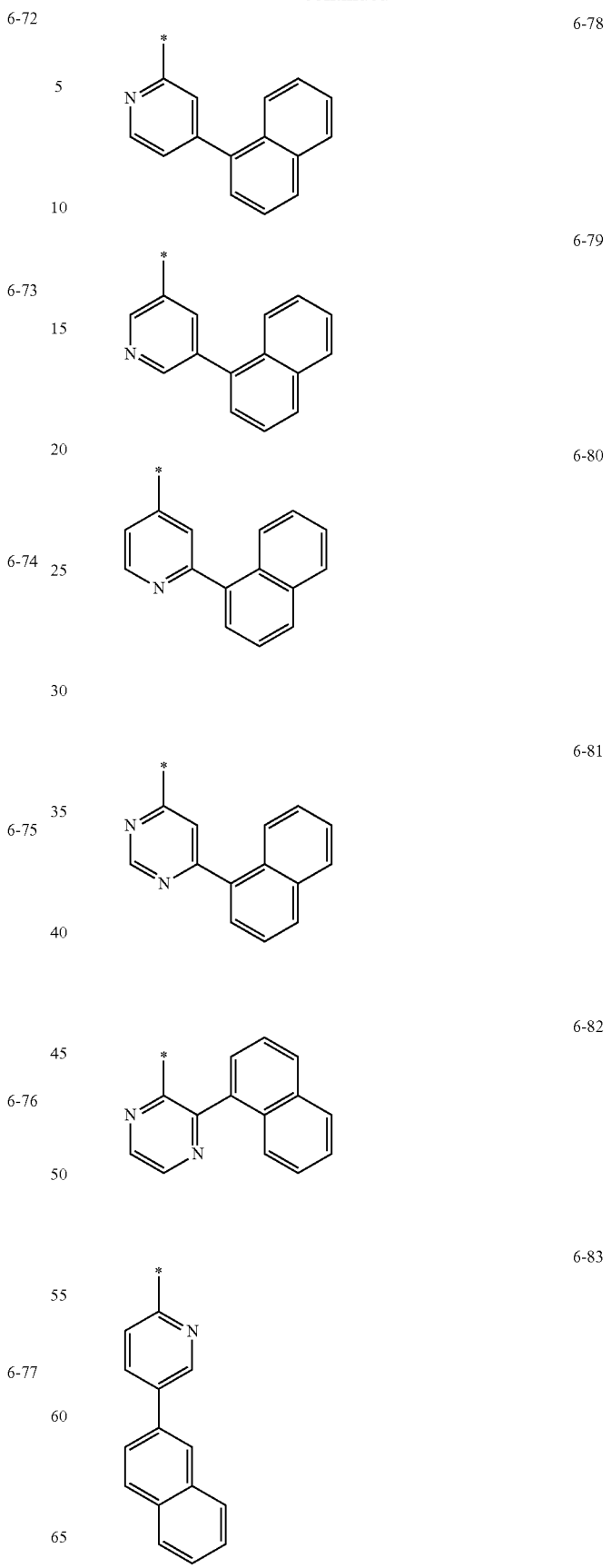

6-84
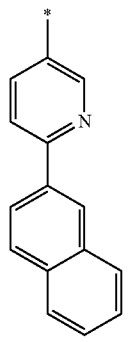
6-85
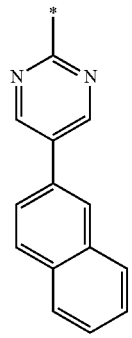
6-86
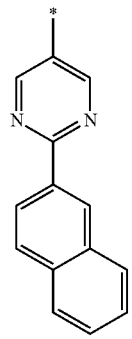
6-87
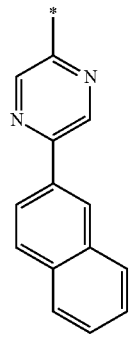
6-88
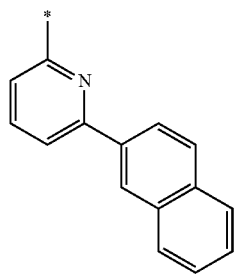
6-89
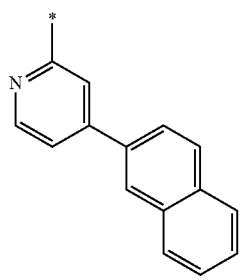
6-90
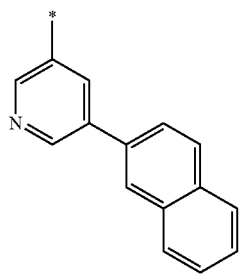
6-91
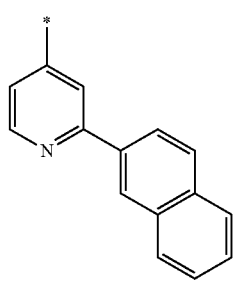
6-92
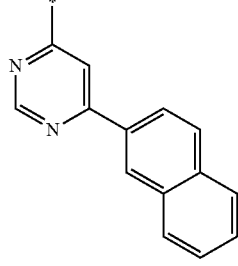
6-93
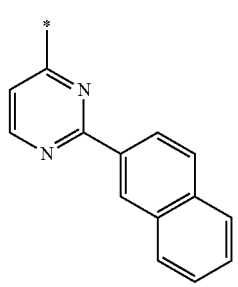

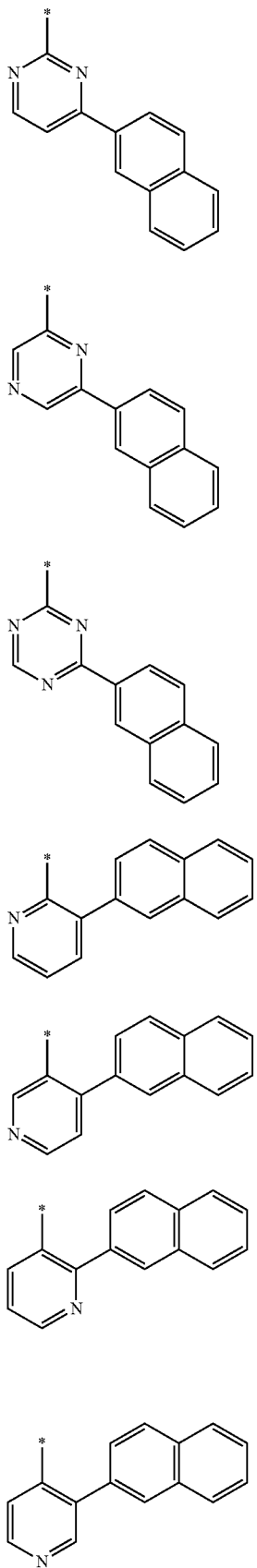
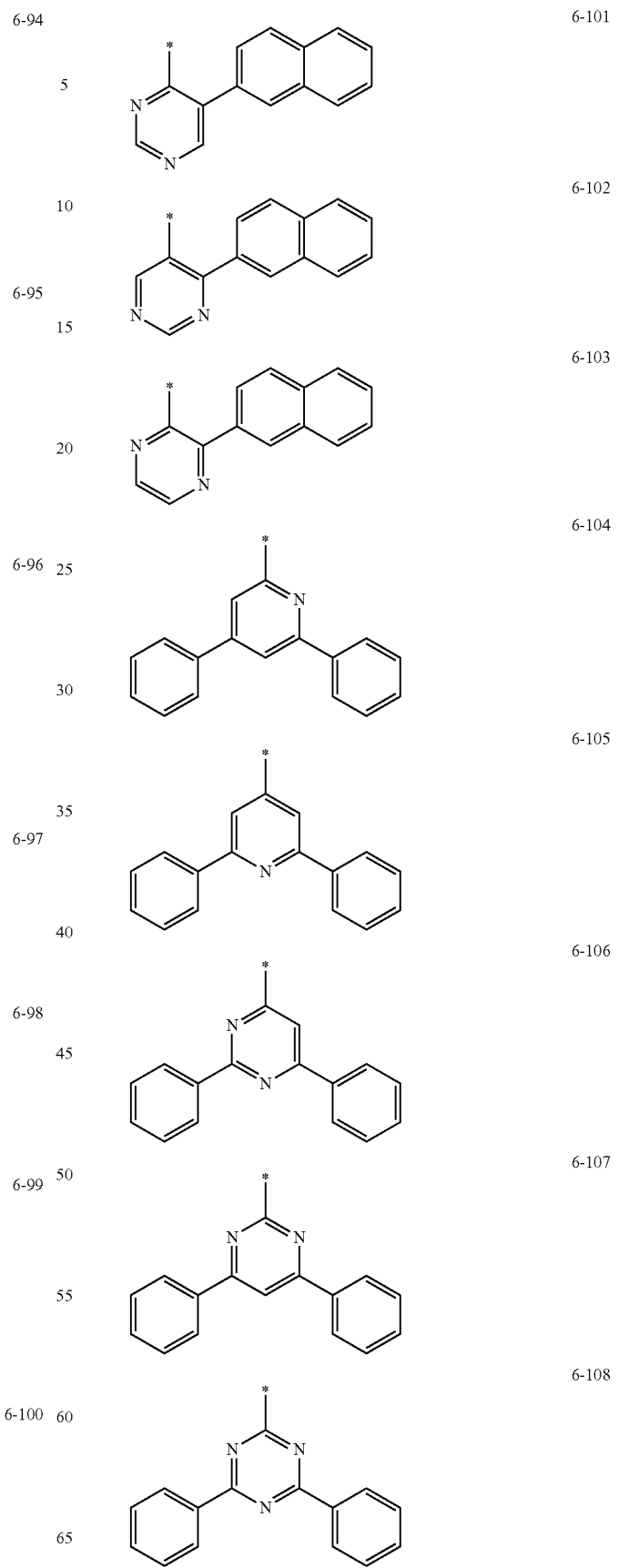

6-109
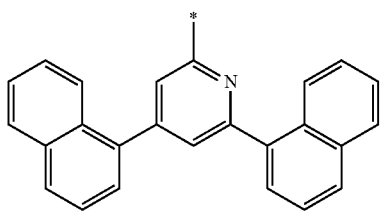
6-110
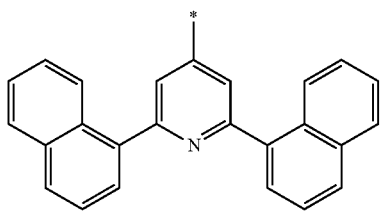
6-111
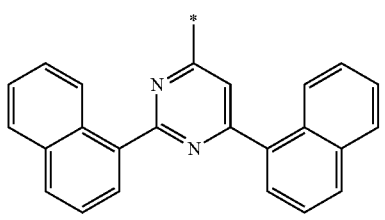
6-112
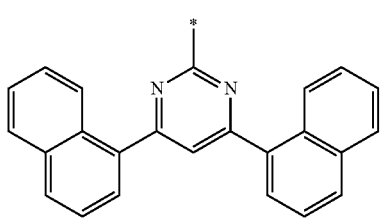
6-113
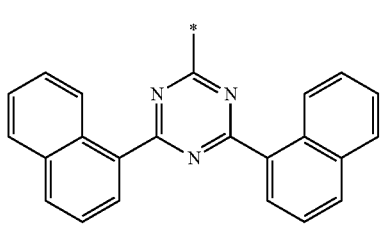
6-114
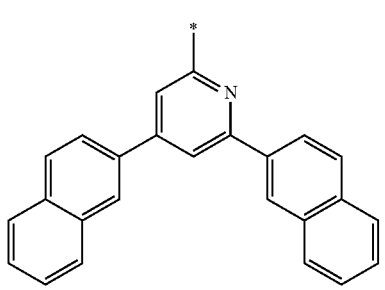
6-115
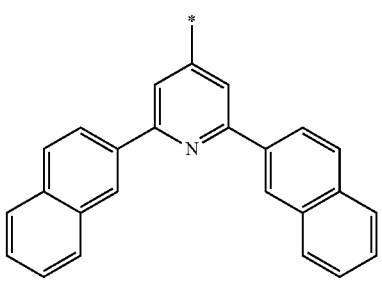
6-116

6-117
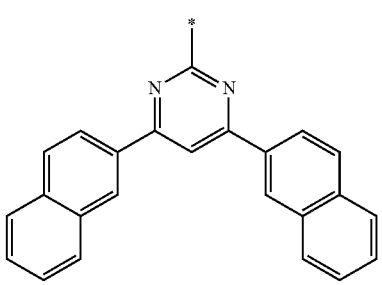
6-118
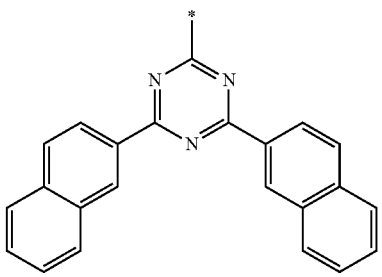
6-119
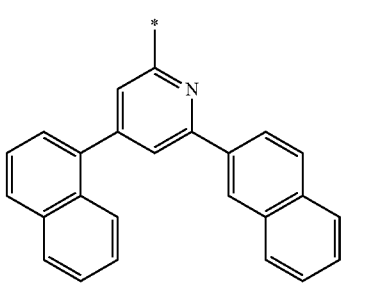

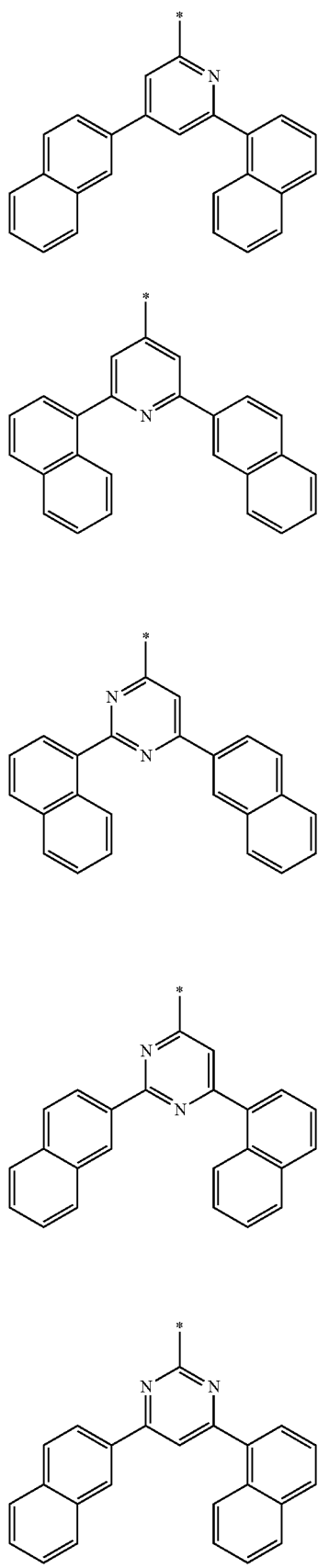
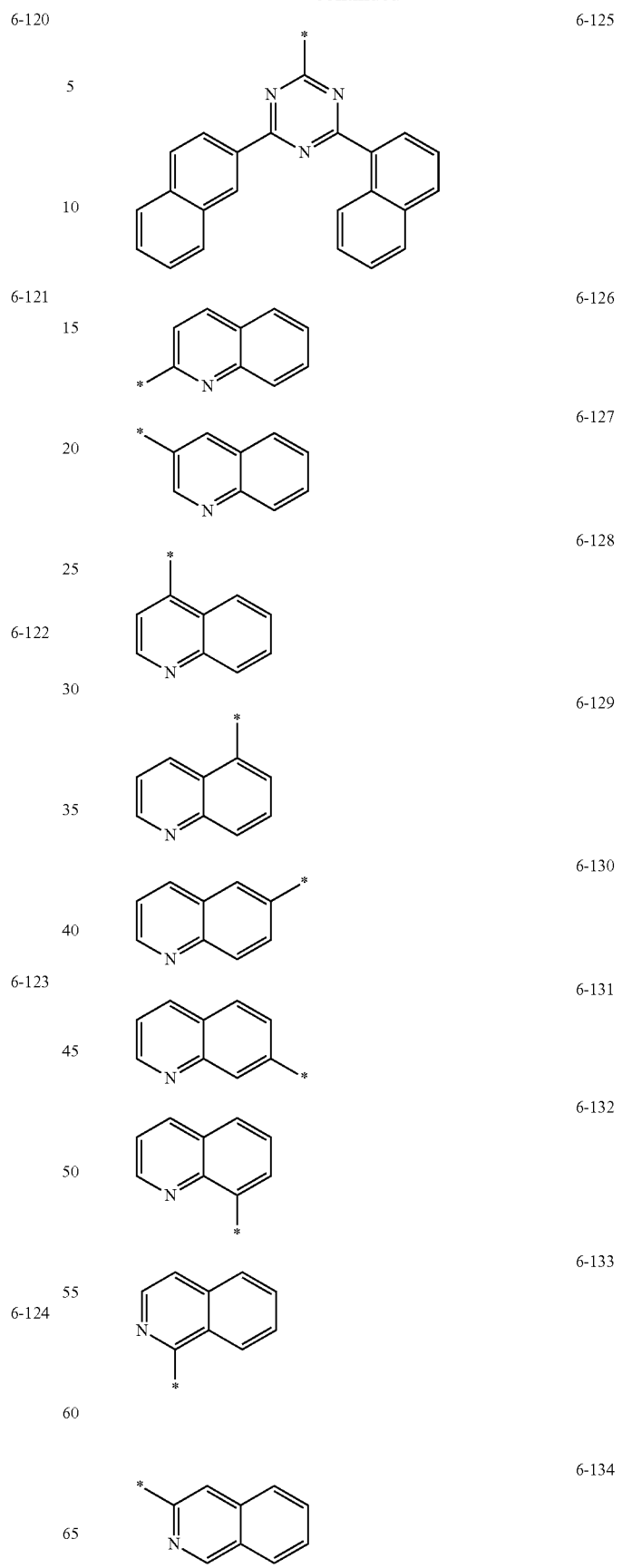

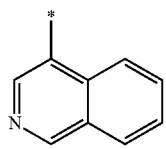
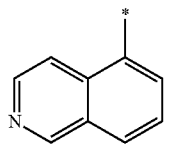
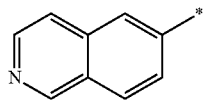
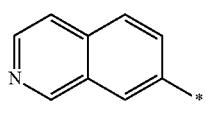
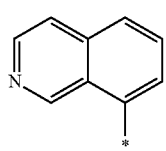
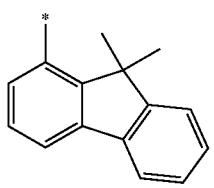
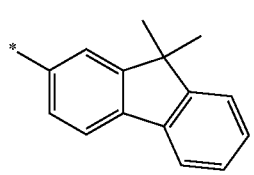
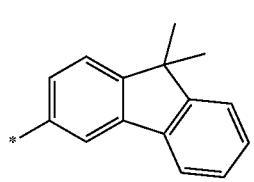
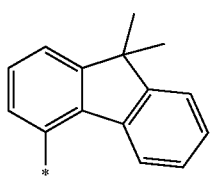
6-135
6-136
6-137
6-138
6-139
6-140
6-141
6-142
6-143
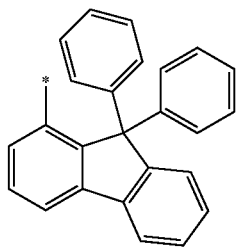
6-144
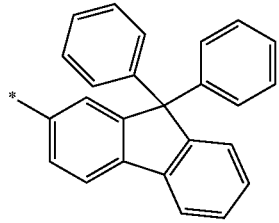
6-145
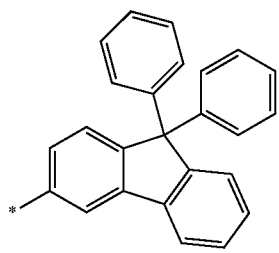
6-146
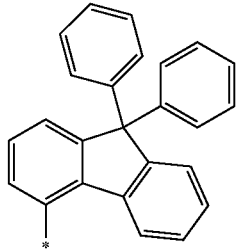
6-147
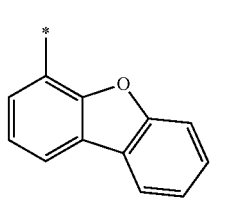
6-148
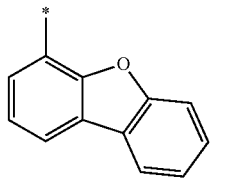
6-149
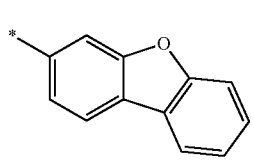
6-150
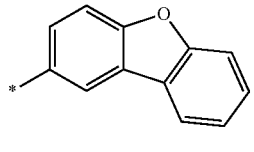
6-151

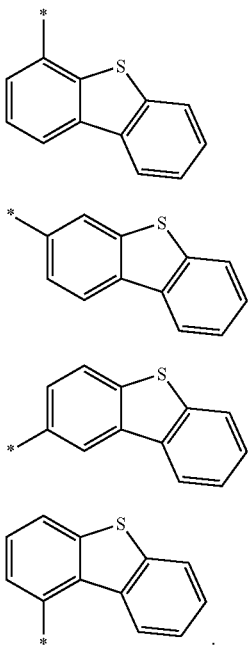

6-152

6-153

6-154

6-155

In Formulae 6-1 to 6-155,
t-Bu is a tert-butyl group;
Ph is a phenyl group; and
* indicates a binding site to a neighboring atom.

For example, in Formula 1, a group represented by Formula 10-1 and a group represented by Formula 10-2 may be identical to each other, but embodiments of the present invention are not limited thereto.

In some embodiments, in Formula 1, a group represented by Formula 10-1 and a group represented by Formula 10-2 may be different from each other, but embodiments of the present invention are not limited thereto.

In some embodiments, the condensed cyclic compound represented by Formula 1 may be represented by Formula 1-1, but embodiments of the present invention are not limited thereto:

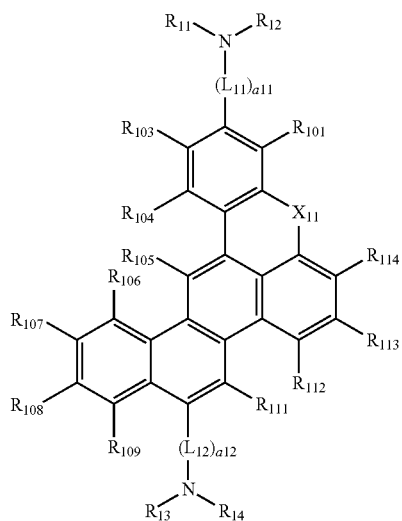

Formula 1-1

In Formula 1-1,
descriptions of $X_{11}$, $L_{11}$, $L_{12}$, a11, a12, $R_{11}$ to $R_{14}$, $R_{101}$, $R_{103}$ to $R_{109}$ and $R_{111}$ to $R_{114}$ are the same as defined above in connection with Formulae 1, 10-1 and 10-2.

For example, $L_{11}$ and $L_{12}$ in Formula 1-1 may be each independently selected from groups represented by Formulae 4-1 to 4-56, but embodiments of the present invention are not limited thereto.

For example, $R_{11}$ to $R_{14}$ in Formula 1-1 may be each independently selected from groups represented by Formulae 6-1 to 6-155, but embodiments of the present invention are not limited thereto.

For example, $R_{101}$, $R_{103}$ to $R_{109}$ and $R_{111}$ to $R_{114}$ in Formula 1-1 may be each independently selected from:
hydrogen, a methyl group, an iso-propyl group, and an n-butyl group;
a phenyl group and a naphthyl group;
a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and
—Si(CH$_3$)$_3$, but embodiments of the present invention are not limited thereto.

In some embodiments, the condensed cyclic compound represented by Formula 1 may be represented by Formula 1-11, but embodiments of the present invention are not limited thereto:

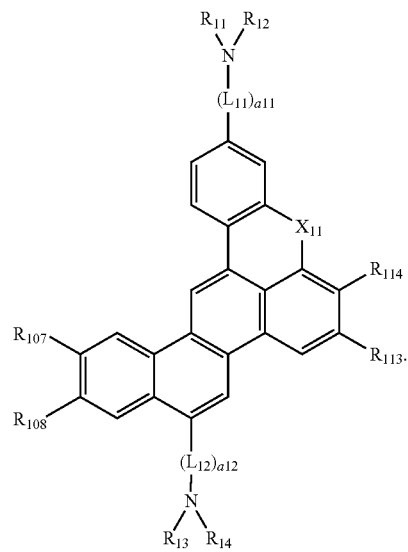

Formula 1-11

In Formula 1-11, descriptions of $X_{11}$, $L_{11}$, $L_{12}$, a11, a12, $R_{11}$ to $R_{14}$, $R_{107}$, $R_{108}$, $R_{113}$ and $R_{114}$ in Formula 1-11 are the same as defined above in connection with Formulae 1, 10-1 and 10-2.

For example, $L_{11}$ and $L_{12}$ in Formula 1-11 may be each independently selected from groups represented by Formulae 4-1 to 4-56, but embodiments of the present invention are not limited thereto.

For example, $R_{11}$, $R_{12}$, $R_{13}$ and $R_{14}$ in Formula 1-11 may be each independently selected from groups represented by Formulae 6-1 to 6-155, but embodiments of the present invention are not limited thereto.

For example, $R_{107}$, $R_{108}$, $R_{113}$ and $R_{114}$ in Formula 1-11 may be each independently selected from:

hydrogen, a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si(CH$_3$)$_3$, but embodiments of the present invention are not limited thereto.

In some embodiments, the condensed cyclic compound represented by Formula 1 may be represented by any one of Formulae 1-21 to 1-26, but embodiments of the present invention are not limited thereto:

1-21
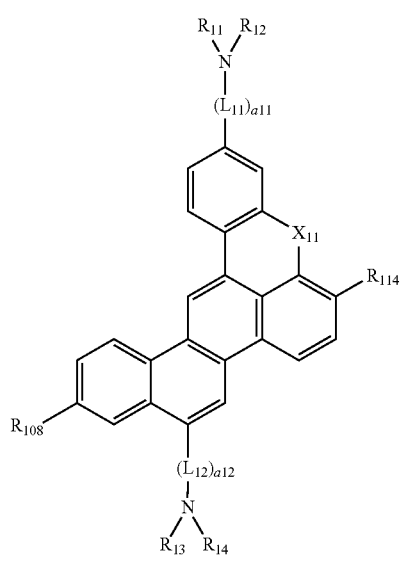

1-22
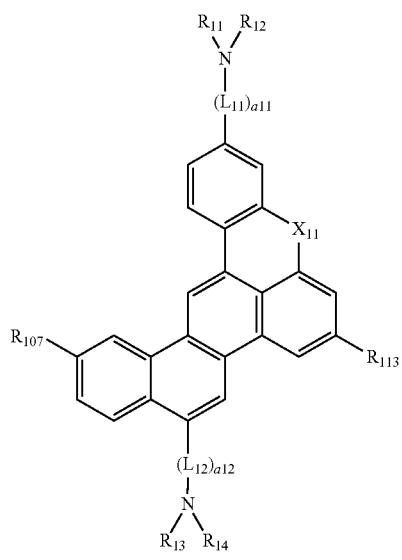

1-23
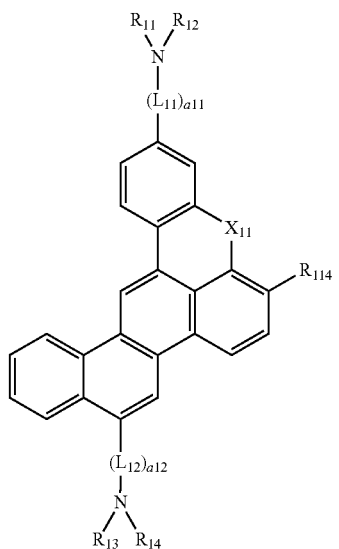

1-24
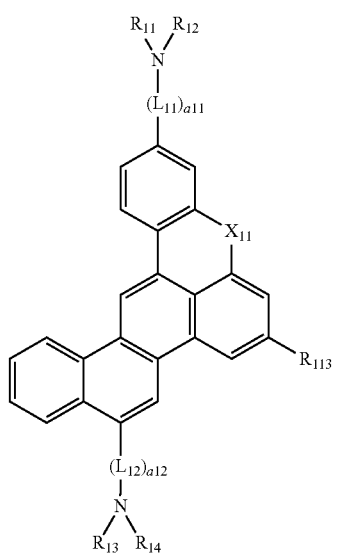

1-25
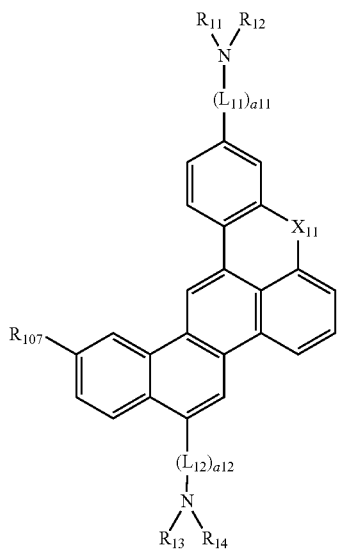

1-26

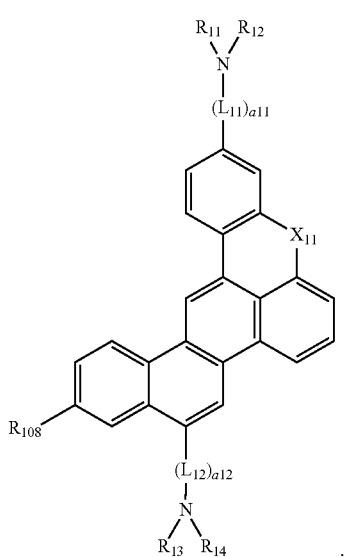

1-32

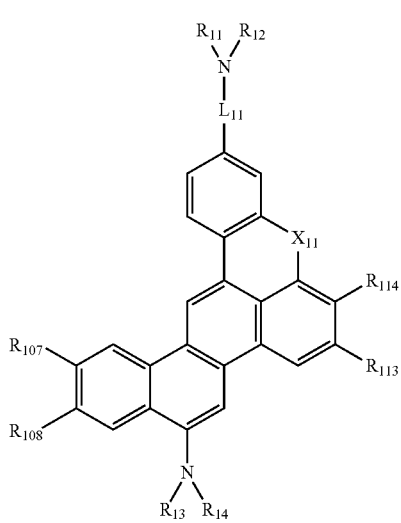

1-33

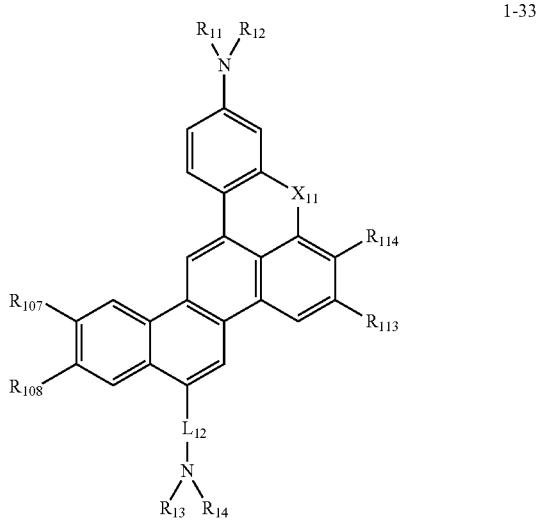

In Formulae 1-21 to 1-26, descriptions of $X_{11}$, $L_{11}$, $L_{12}$, a11, a12, $R_{11}$ to $R_{14}$, $R_{107}$, $R_{108}$, $R_{113}$ and $R_{114}$ are the same as defined above in connection with Formulae 1, 10-1 and 10-2.

In some embodiments, the condensed cyclic compound represented by Formula 1 may be selected from any one of Formulae 1-31 to 1-34, but embodiments of the present invention are not limited thereto:

1-31

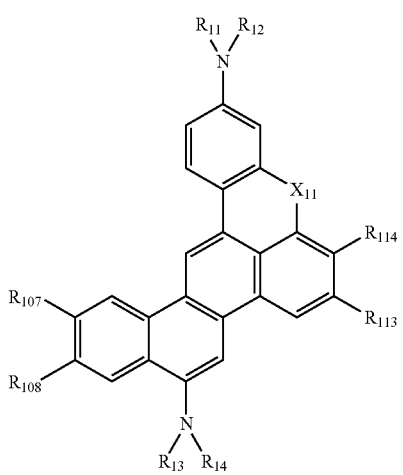

1-34

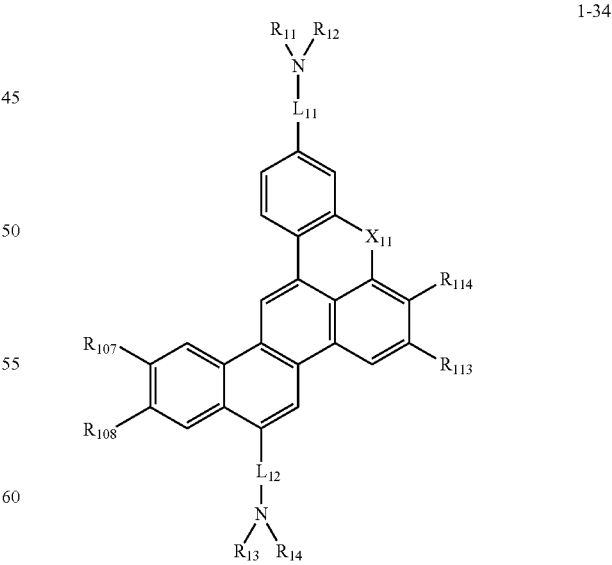

In Formulae 1-31 to 1-34, descriptions $X_{11}$, $L_{11}$, $L_{12}$, $R_{11}$ to $R_{14}$, $R_{107}$, $R_{108}$, $R_{113}$ and $R_{114}$ are the same as defined above in connection with Formulae 1, 10-1 and 10-2.

In some embodiments, the condensed cyclic compound represented by Formula 1 may be selected from Compounds 1 to 111, but embodiments of the present invention are not limited thereto:
1
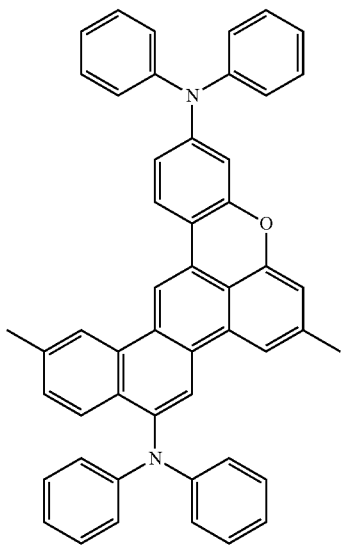
2
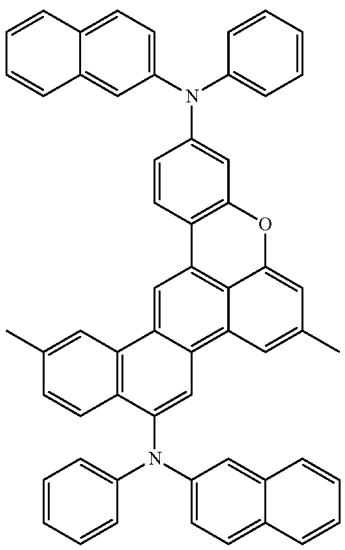
3
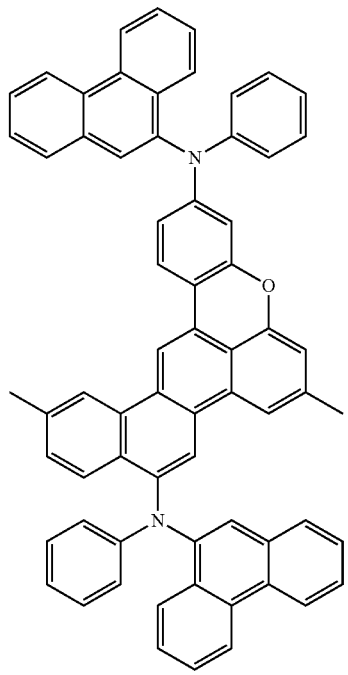
4
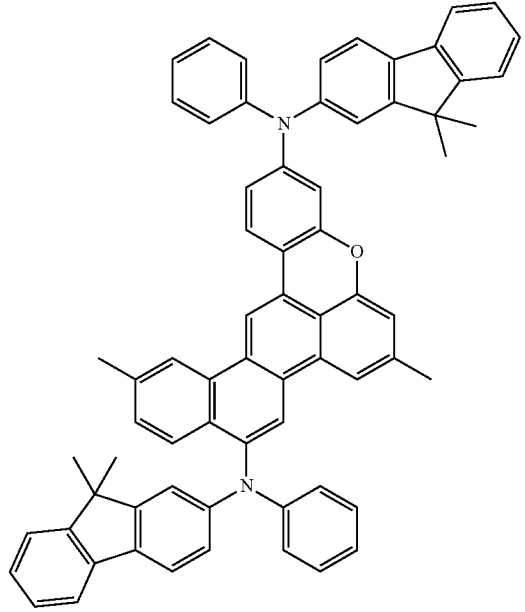

61
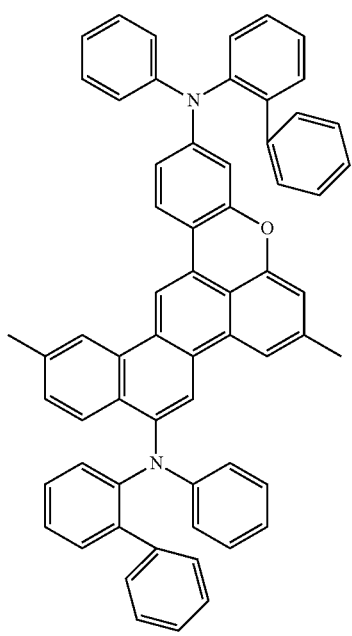
62
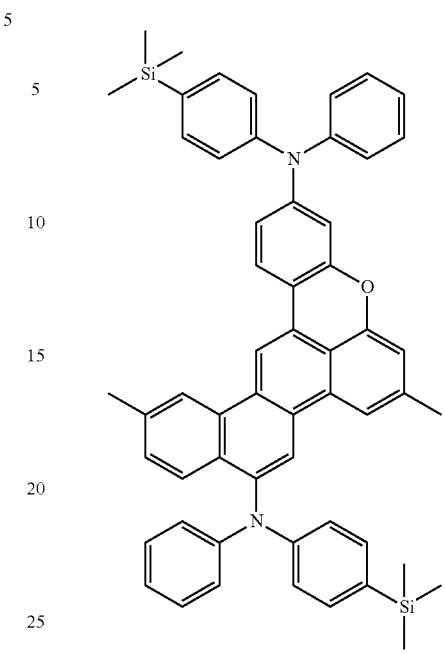
6
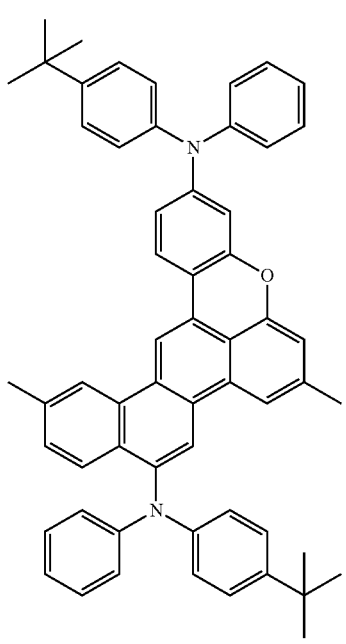
8
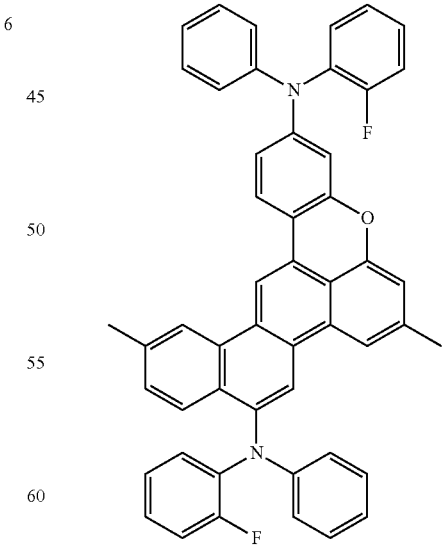

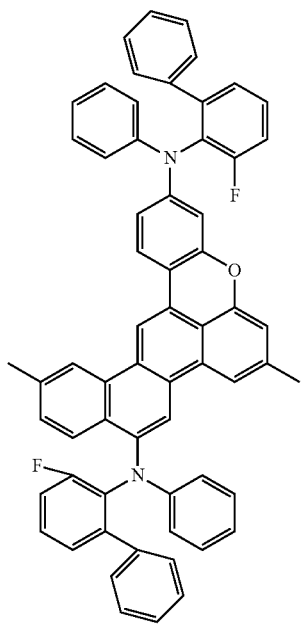
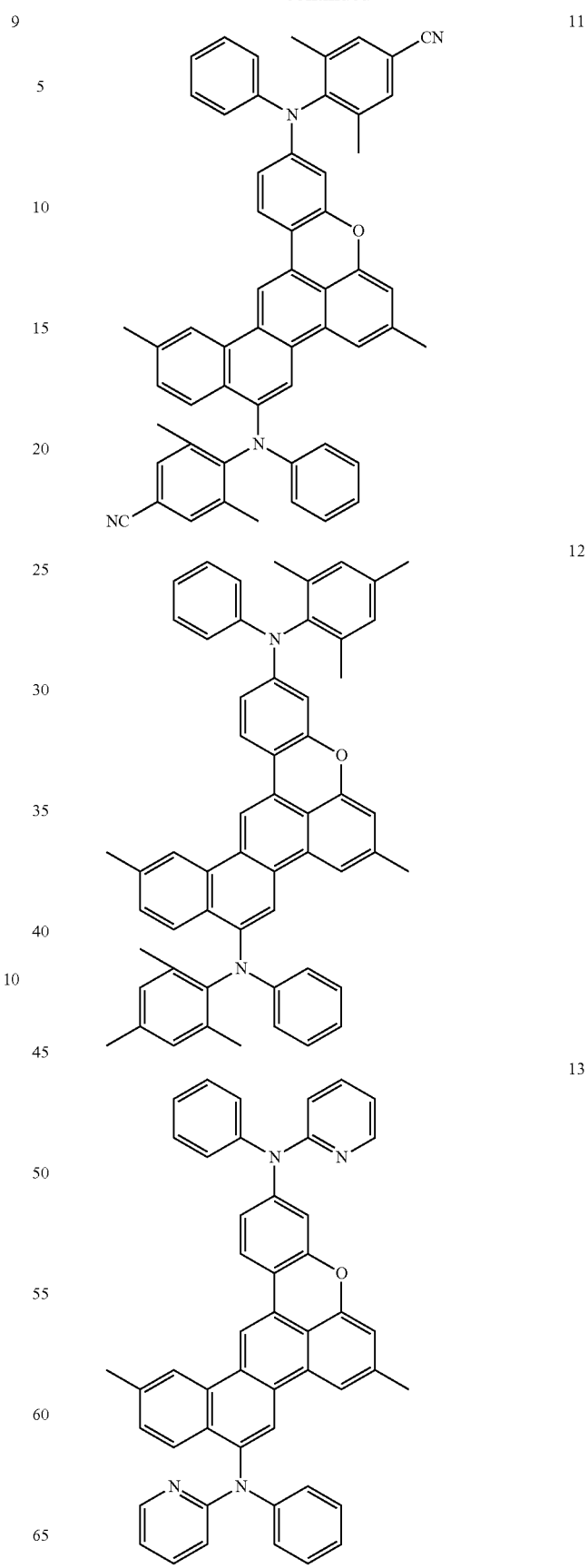

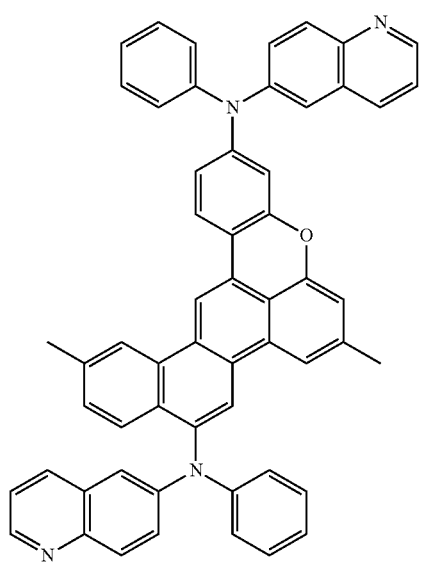
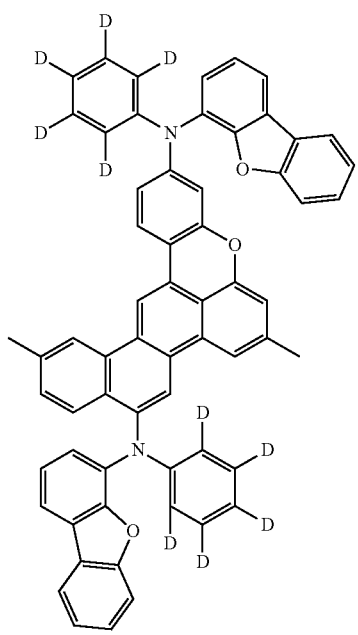
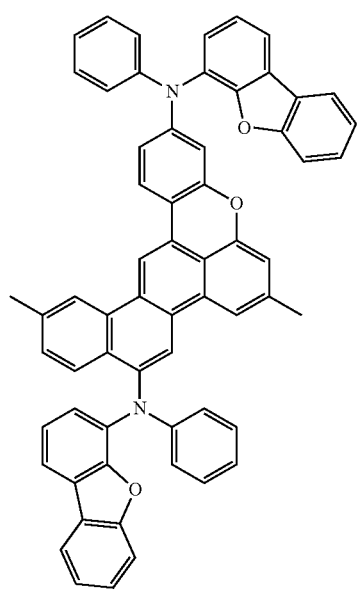
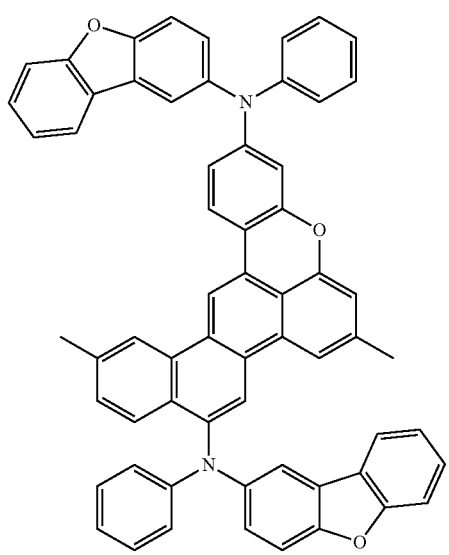

18
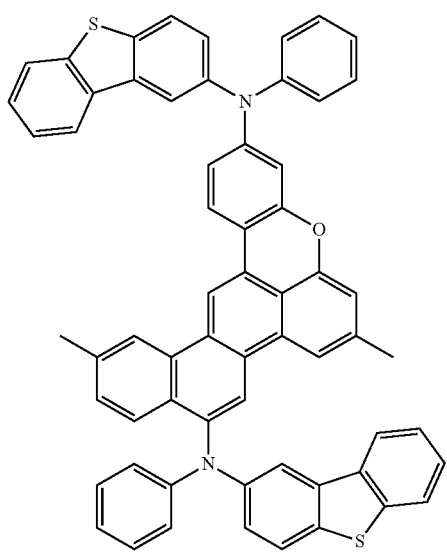
20
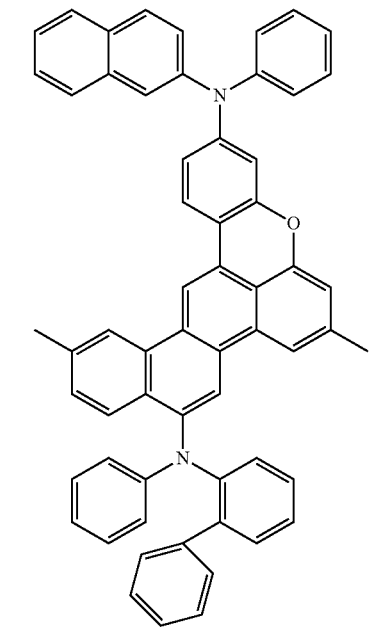
19
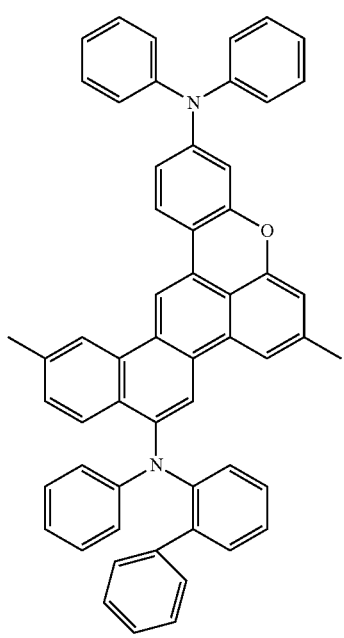
21
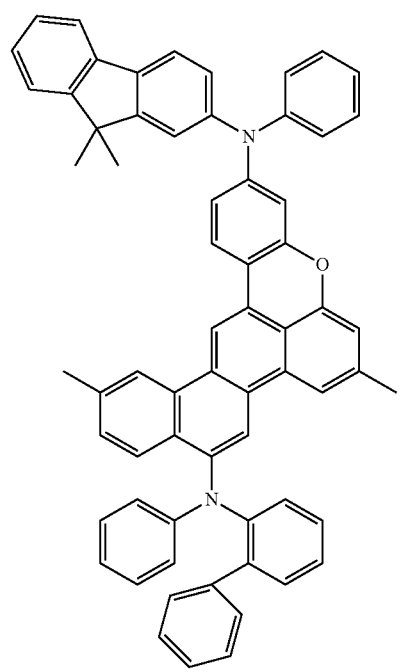

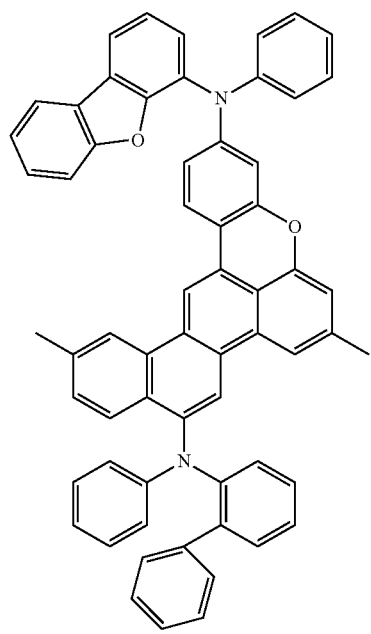
22
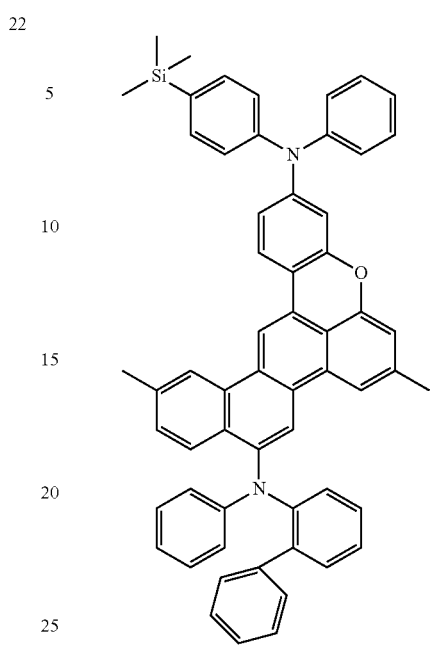
24
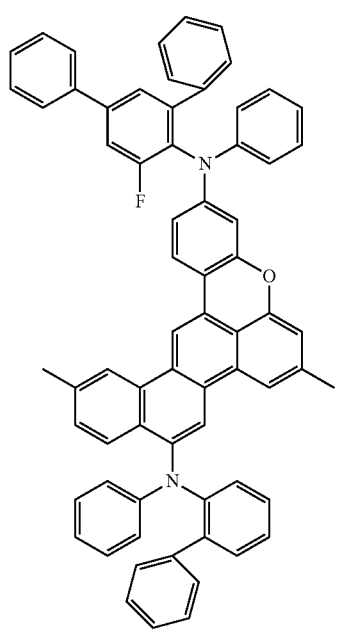
23
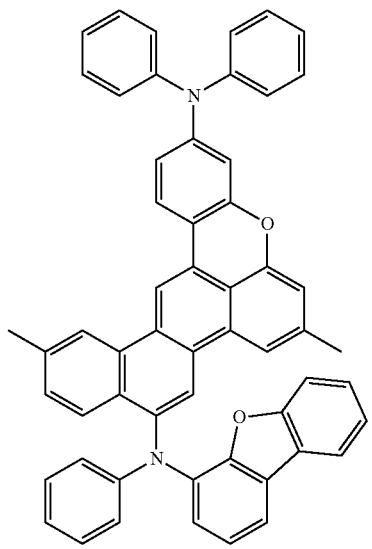
25

71
-continued
26
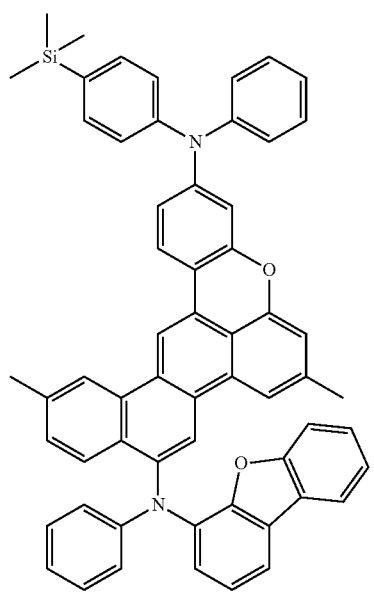
27
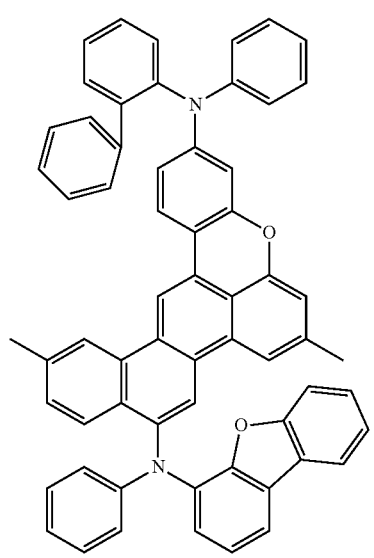
72
-continued
28
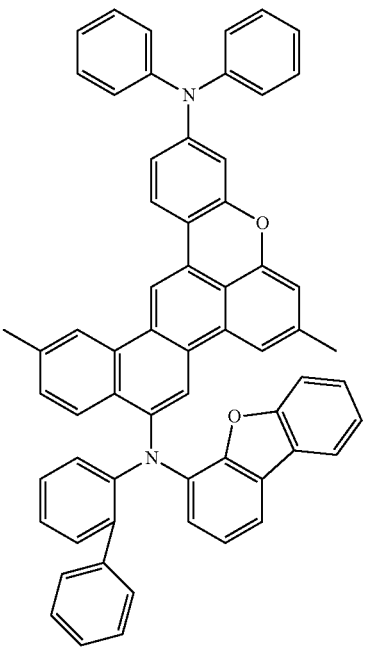
29
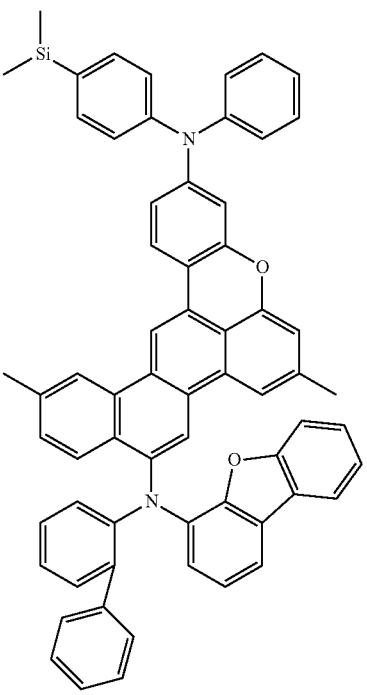

30
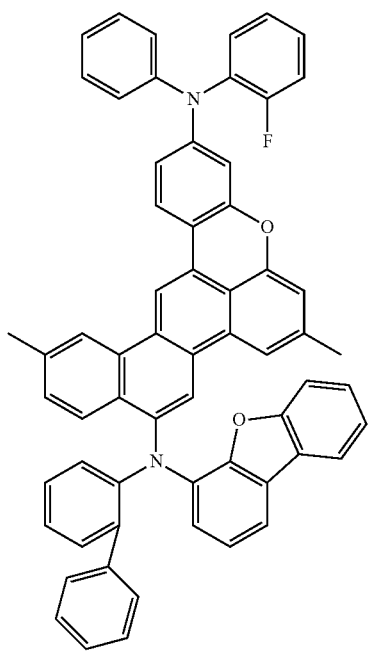
32
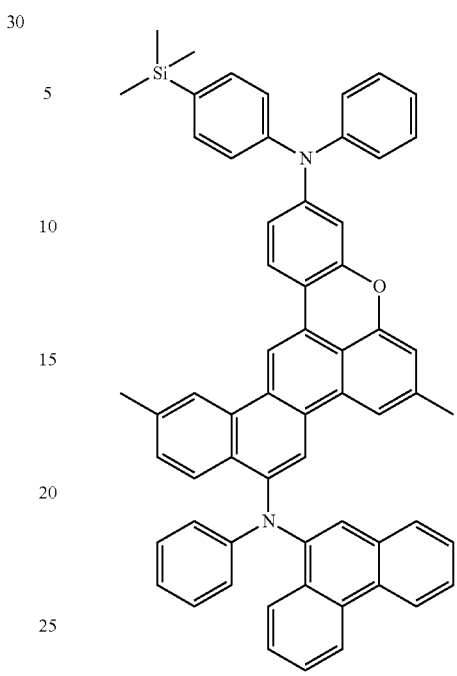
31
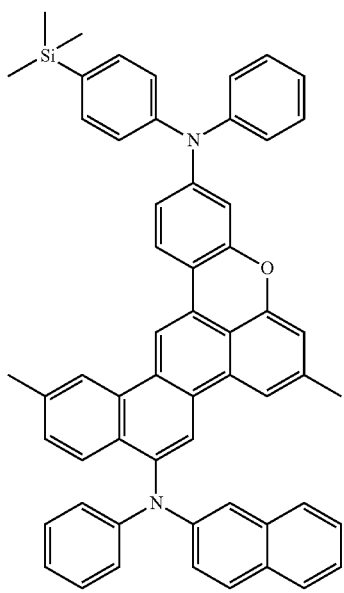
33
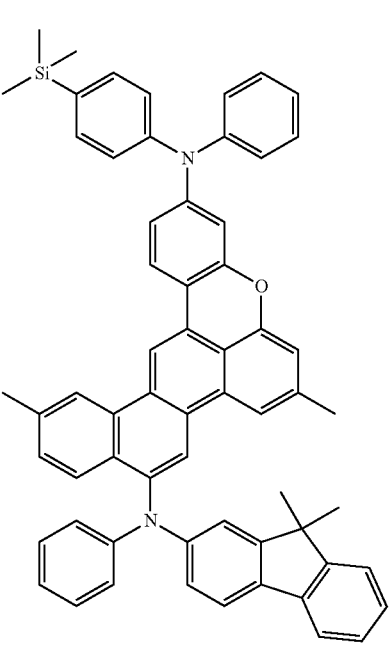

34
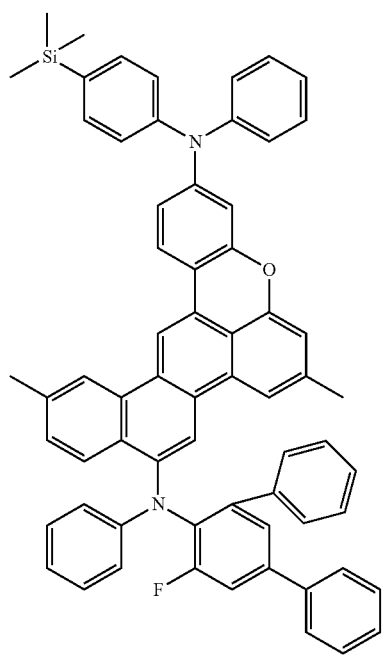
36
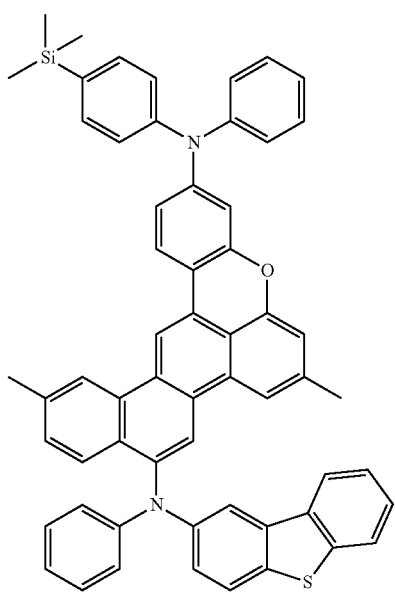
35
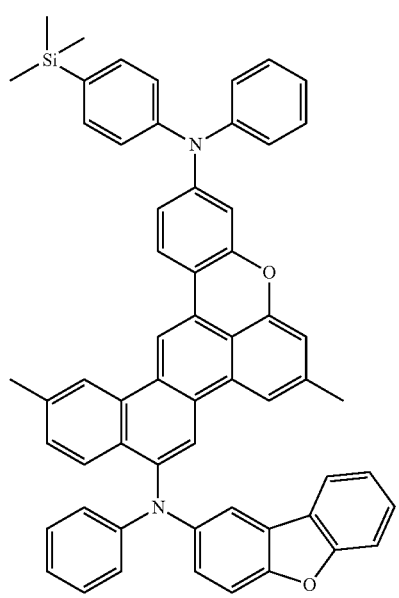
37
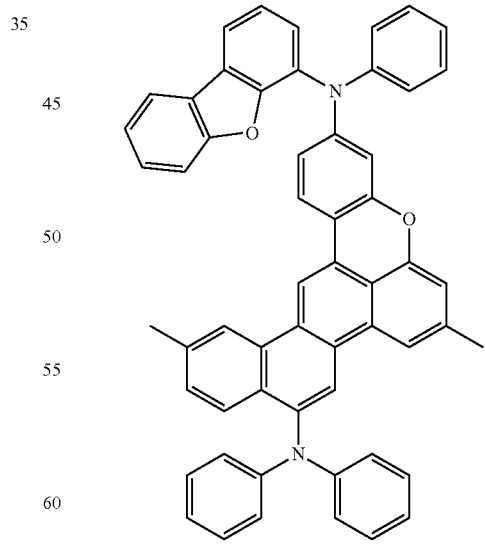

38
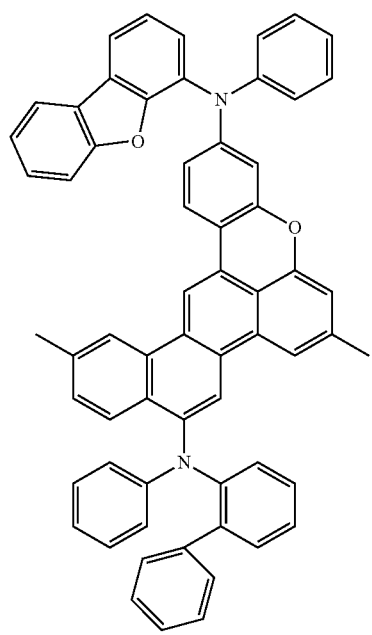
39
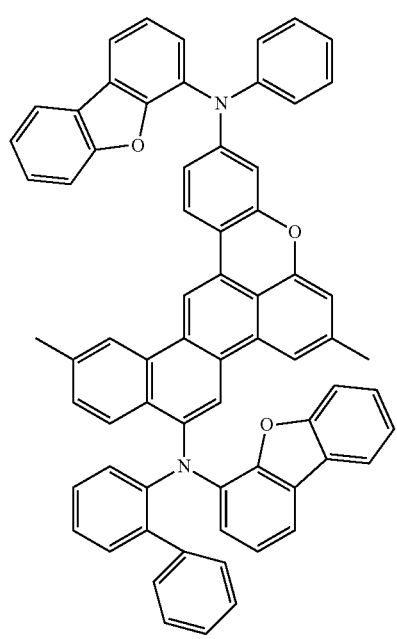
40
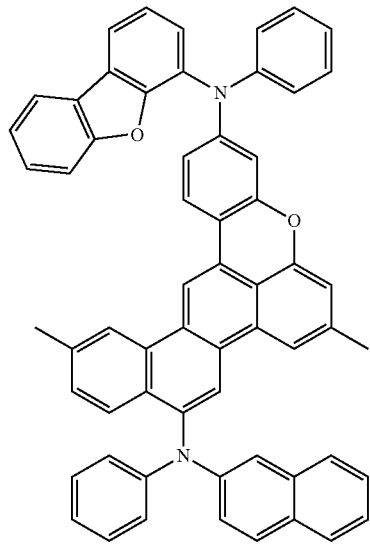
41
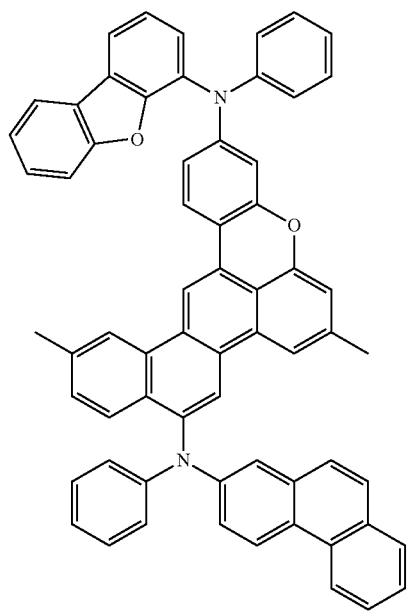

42
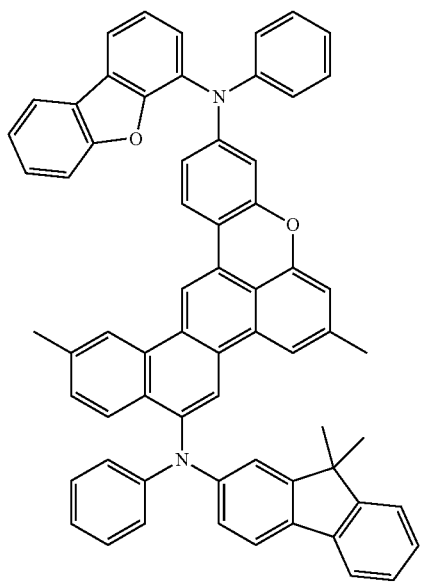
44
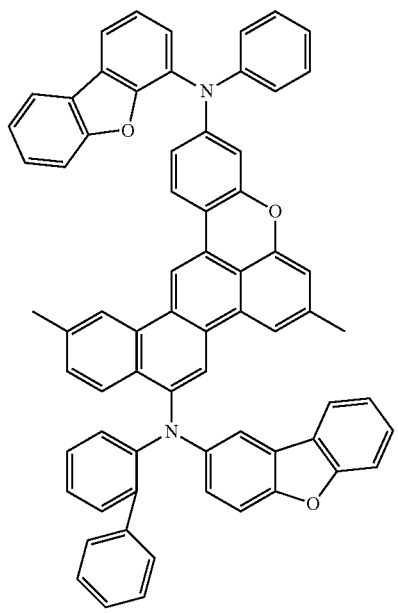
43
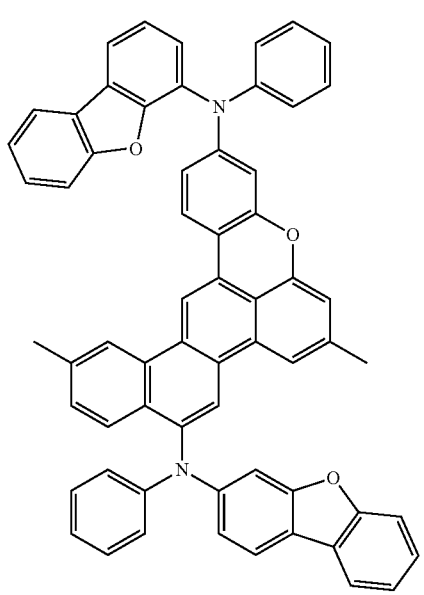
45
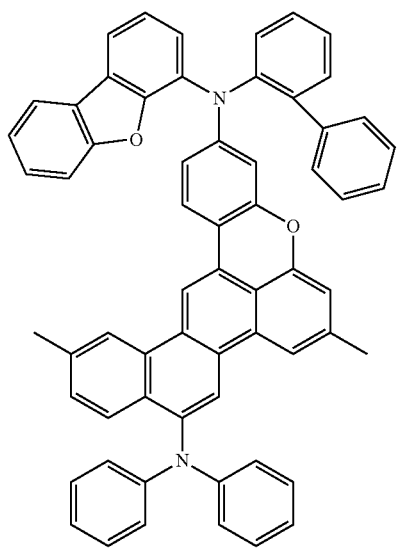

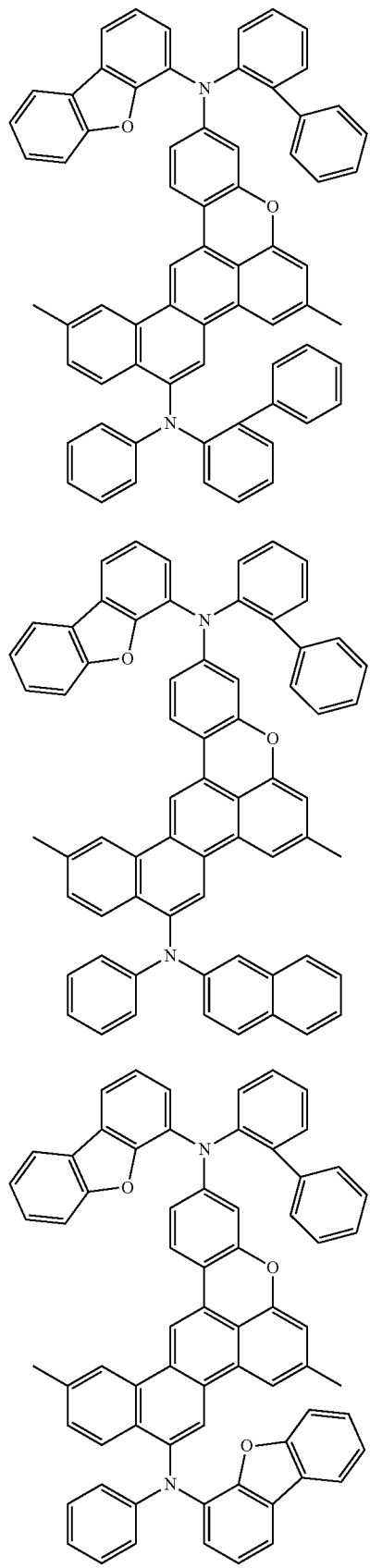
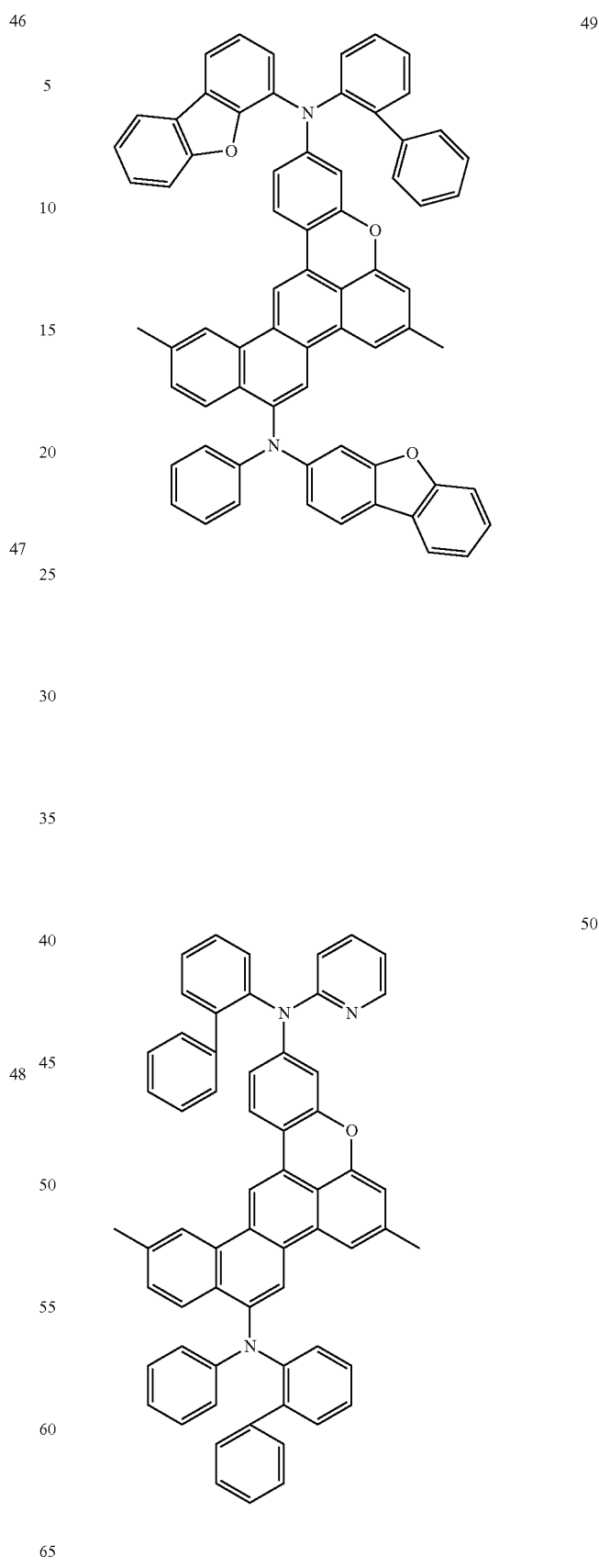

51
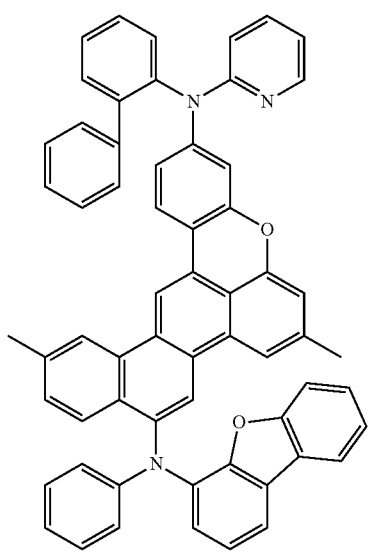
53
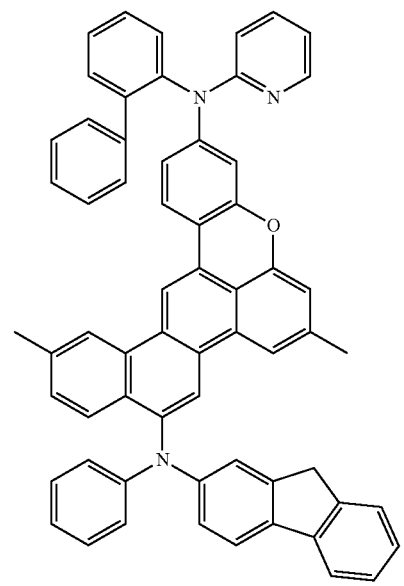
52
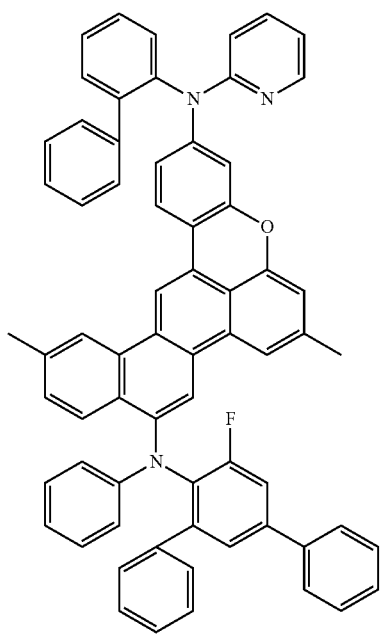
54
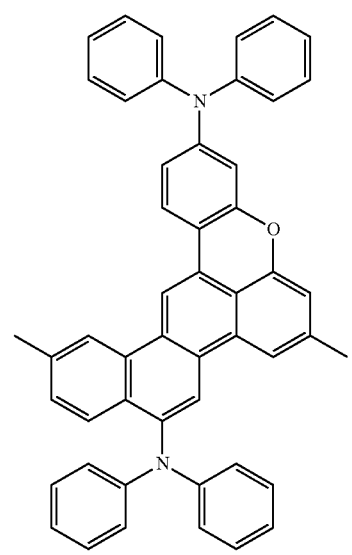

85
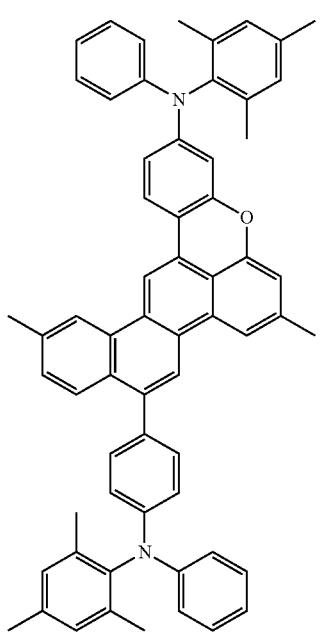
86
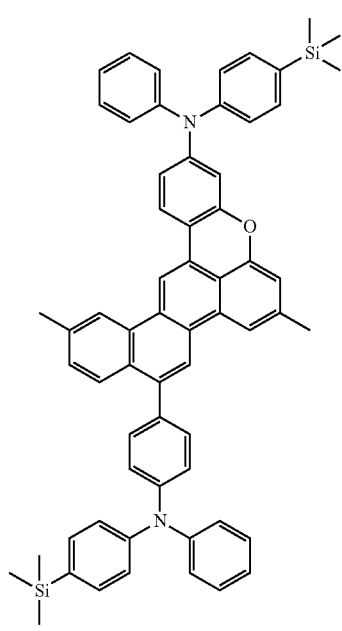
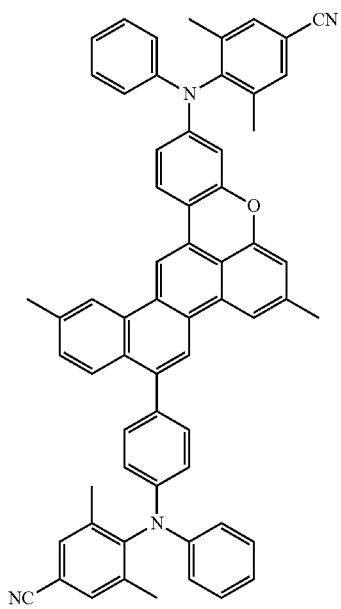
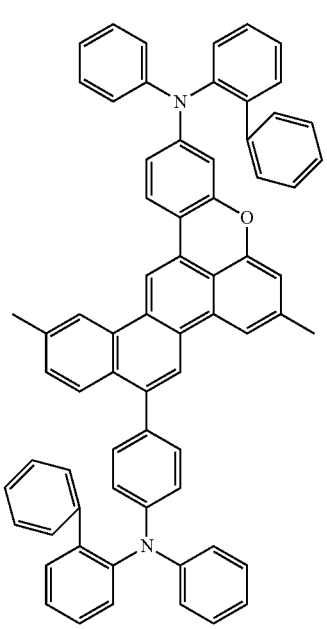

59
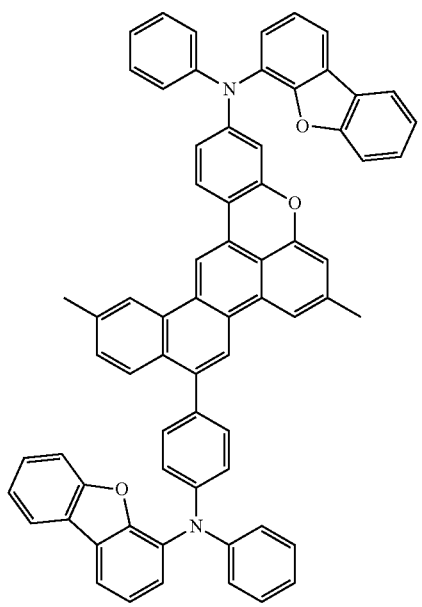
60
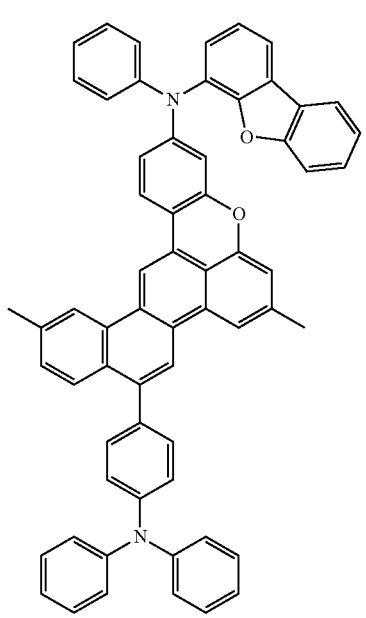
61
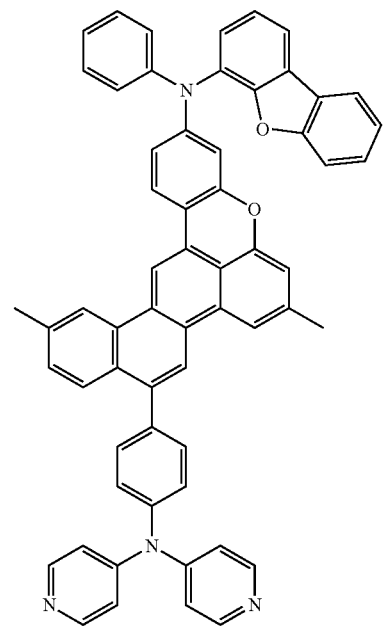
62
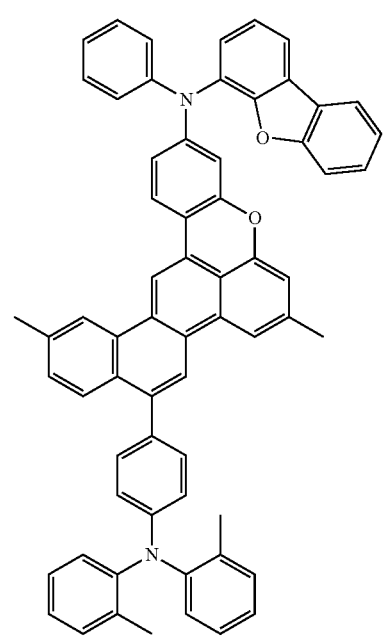

63
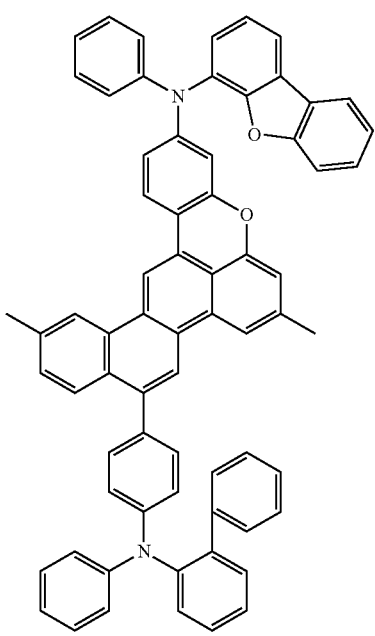
64
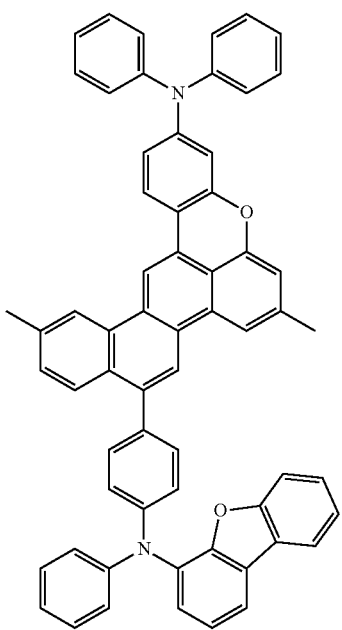
65
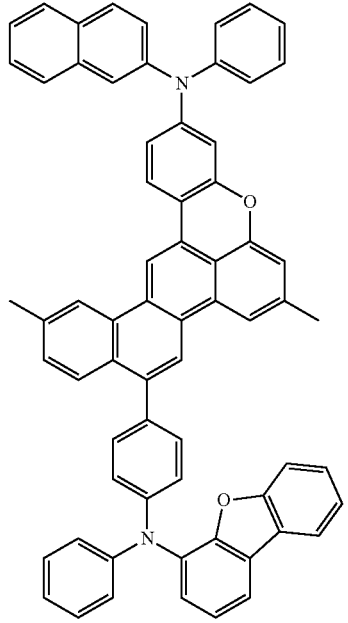
66
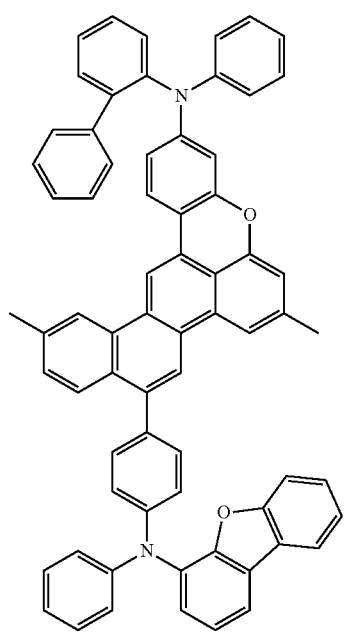

91
-continued
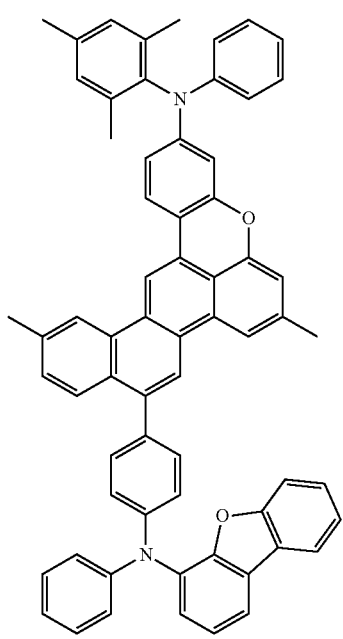
67
68
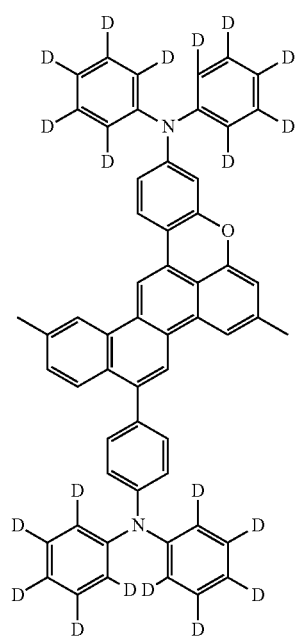
92
-continued
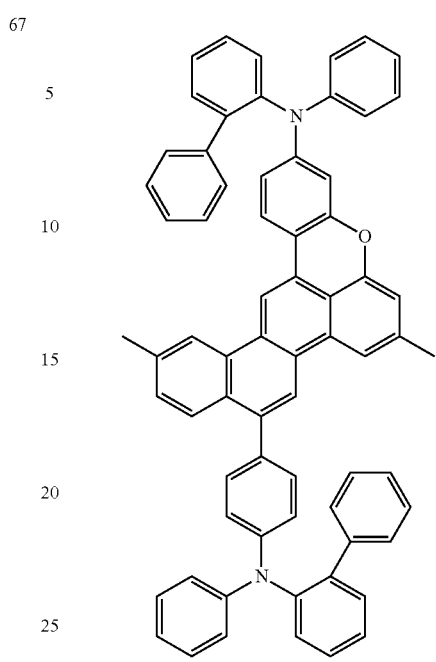
69
70
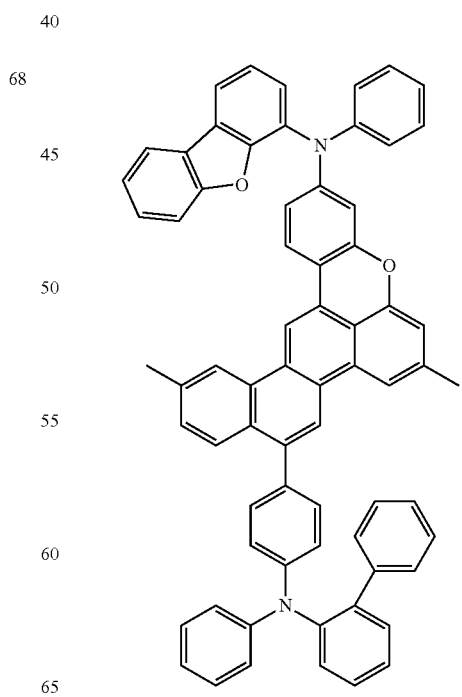

71
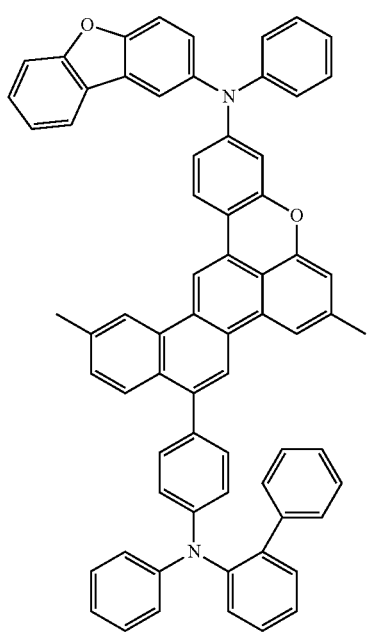
72
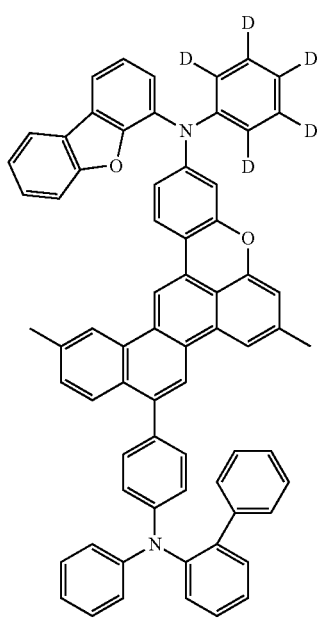
73
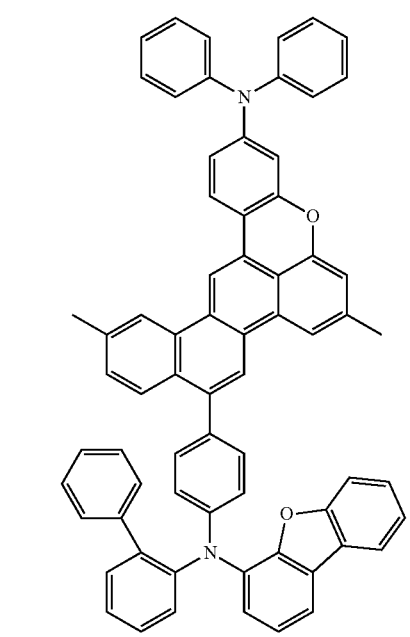
74
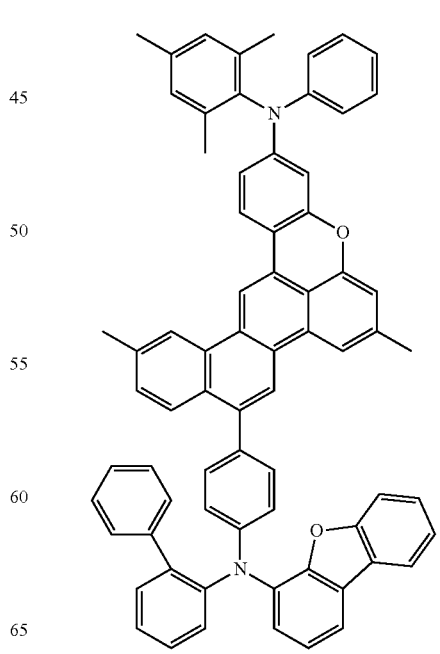

95
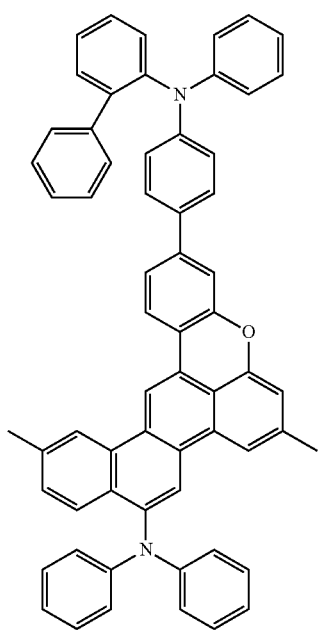
76
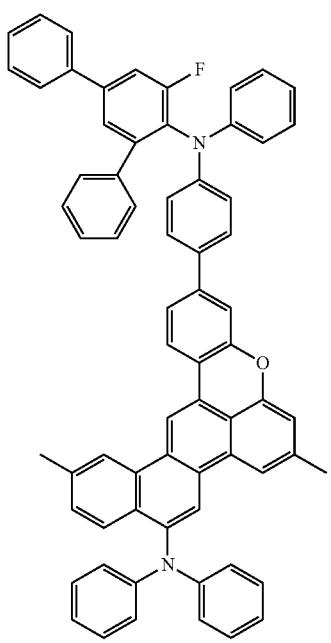
96
75
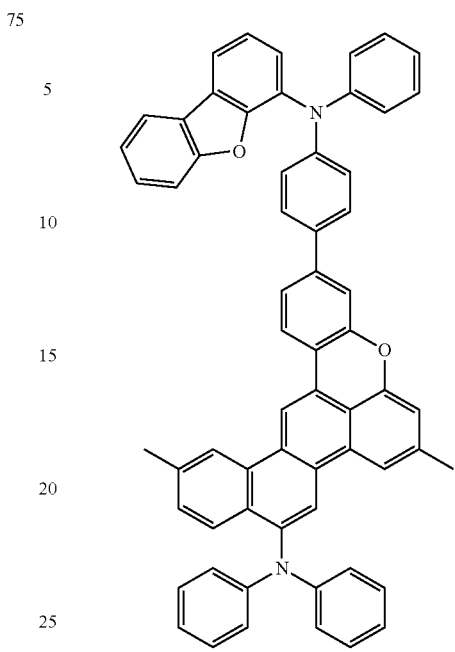
77
78
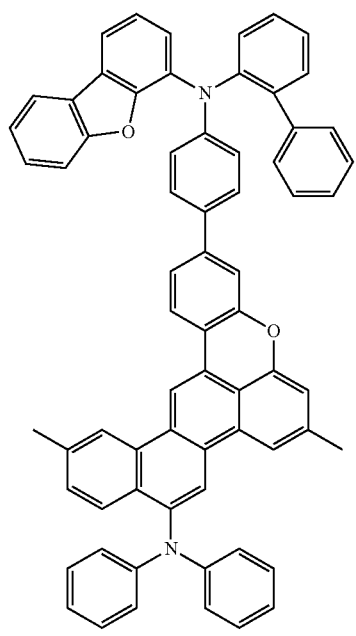

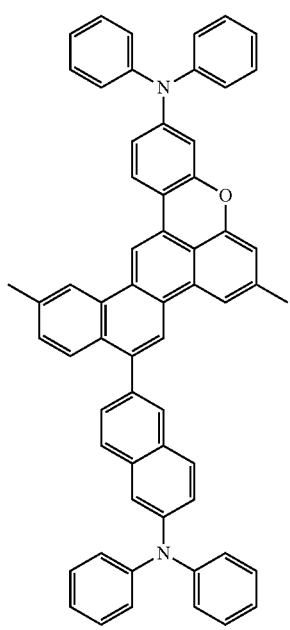
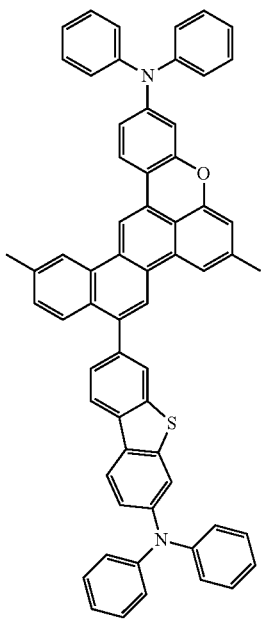
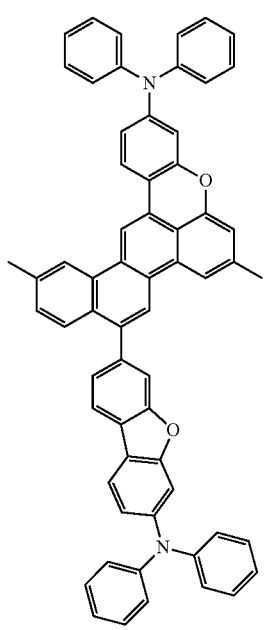
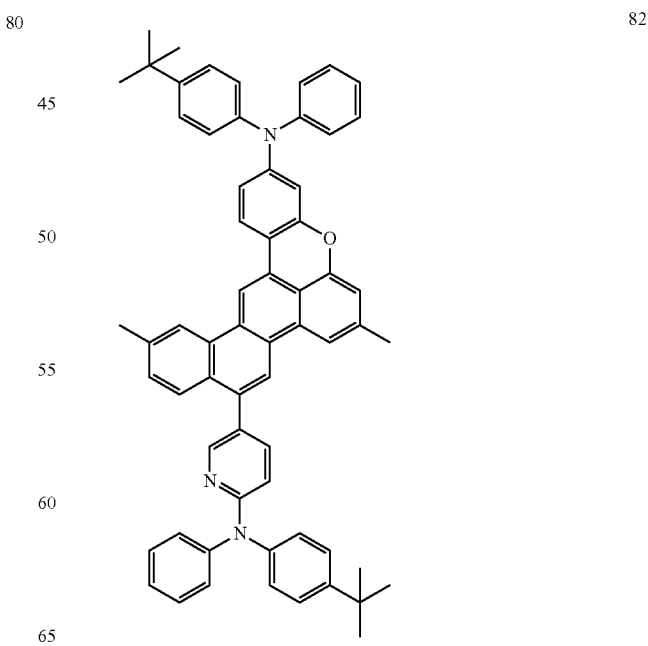

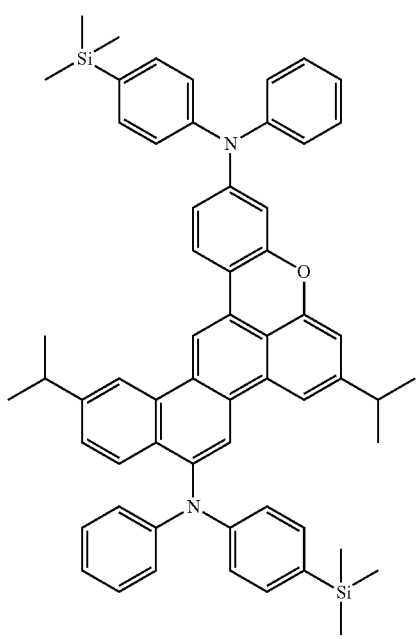
83
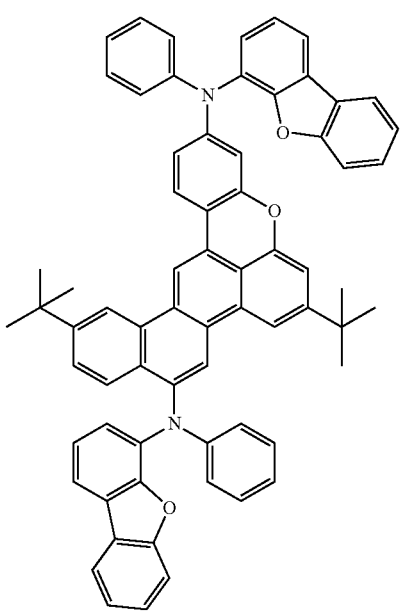
85
84
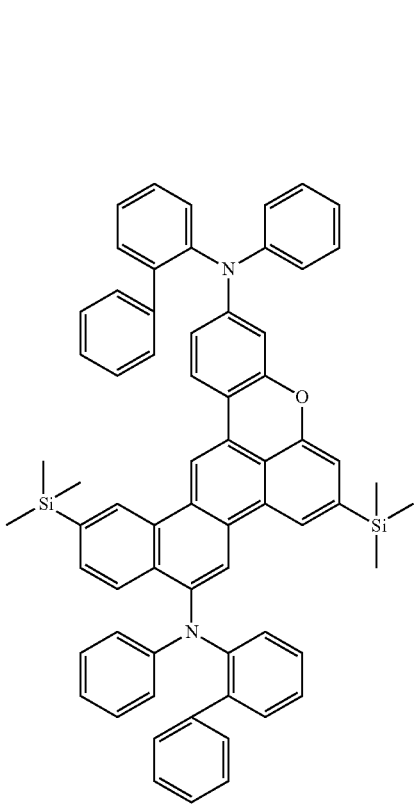
86

101
-continued
87
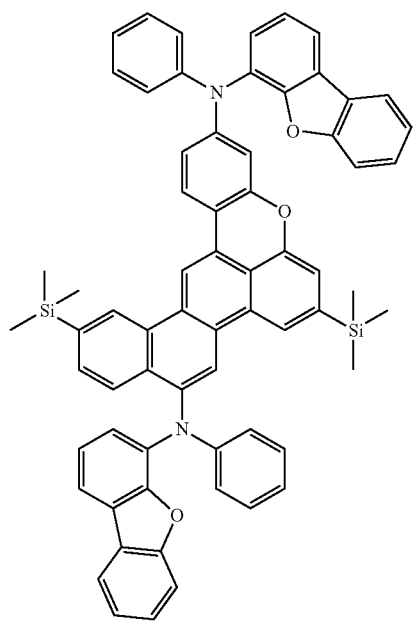
88
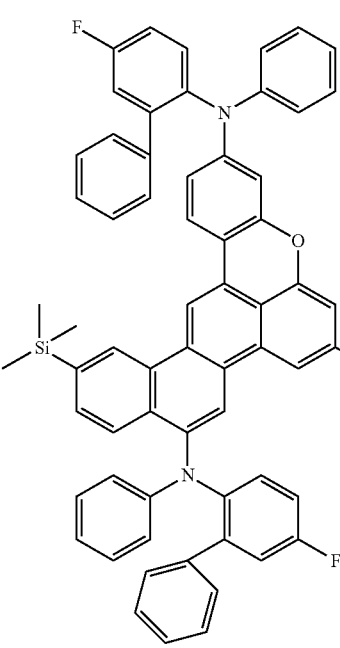
102
-continued
89
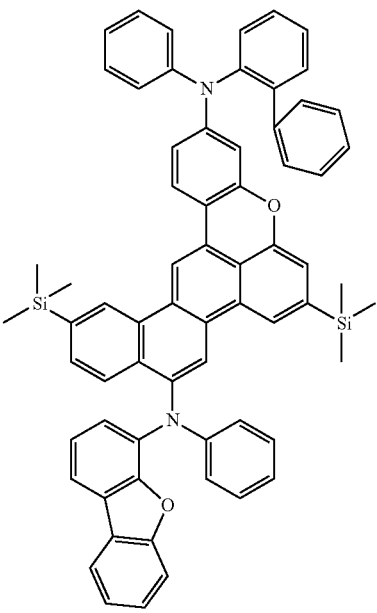
90

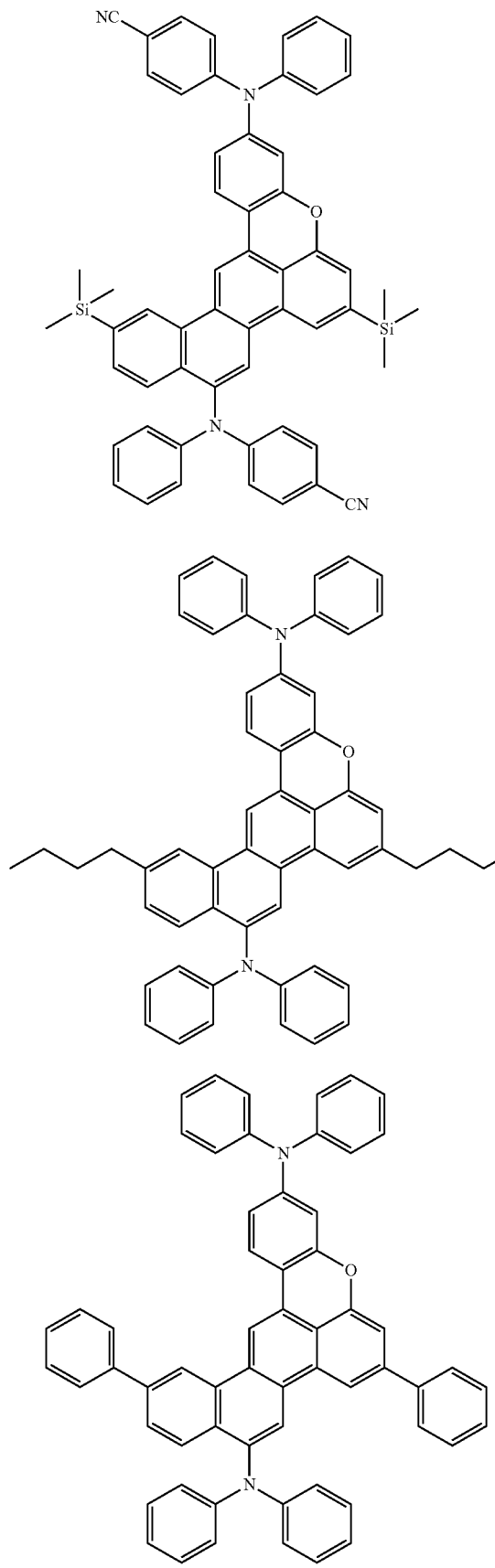
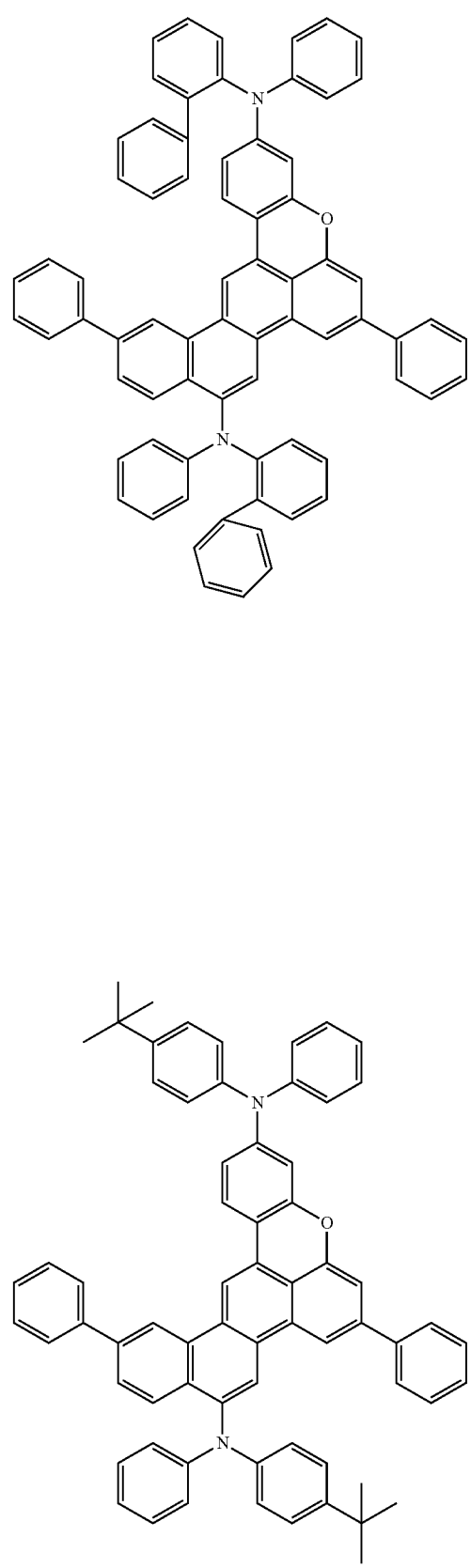

96
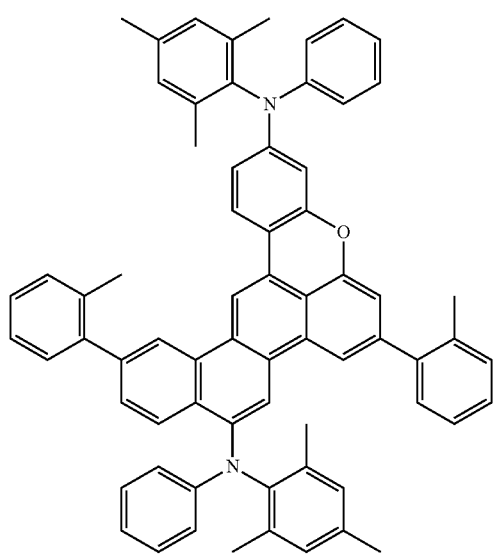
97
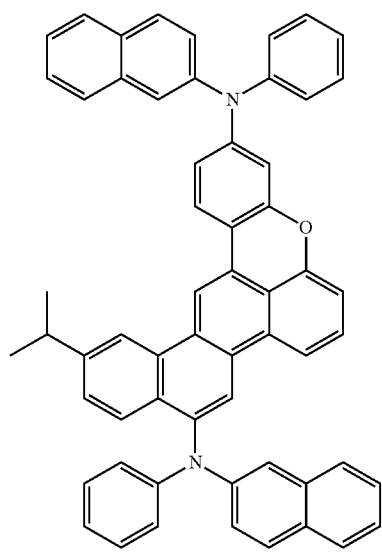
98
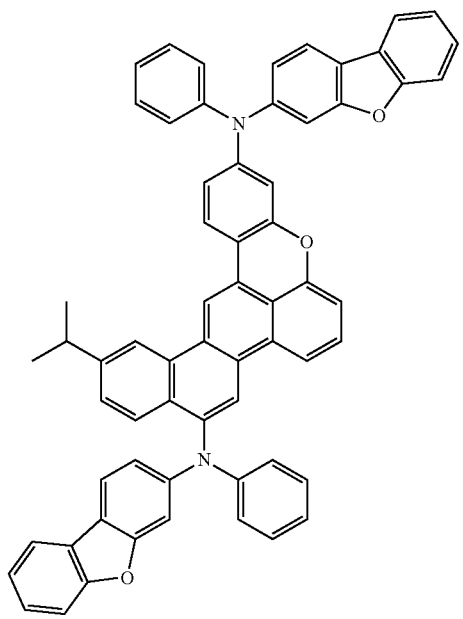
99
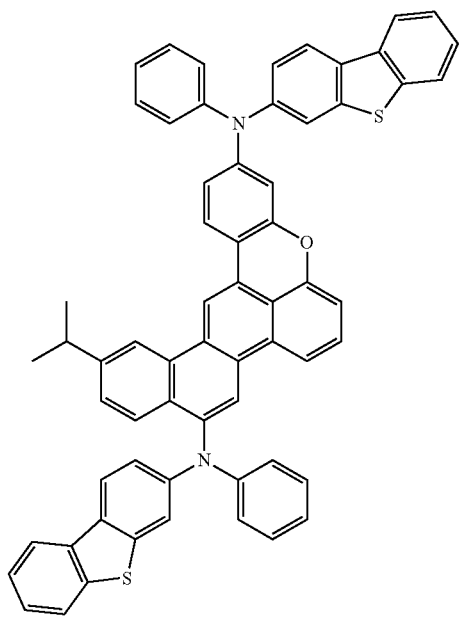

107
-continued
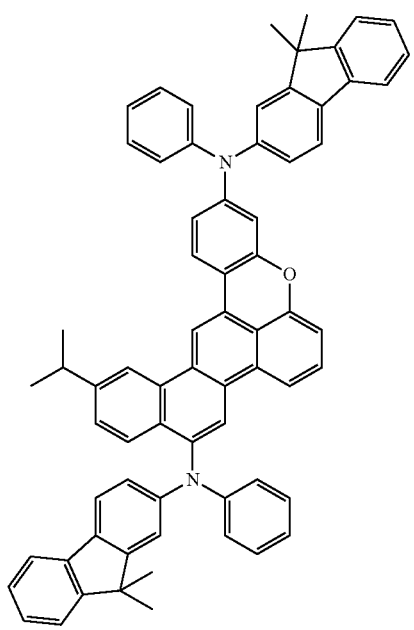
100
108
-continued
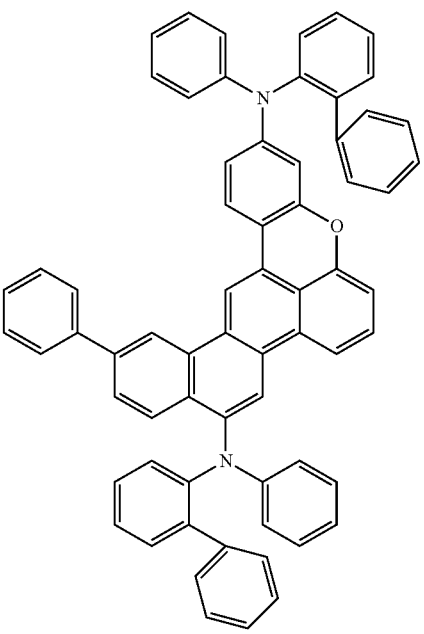
102
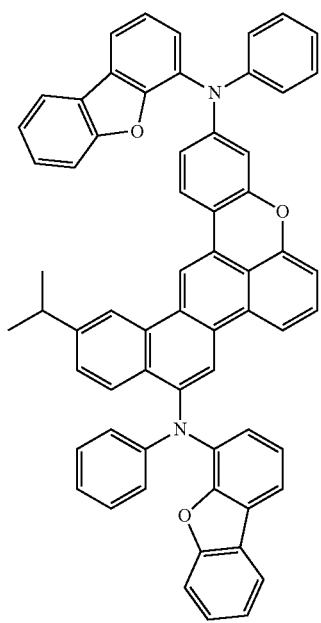
101
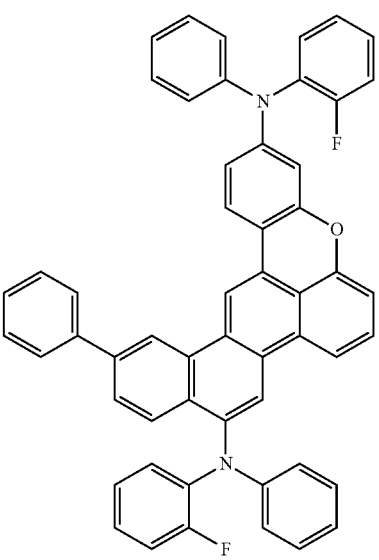
103

109
-continued
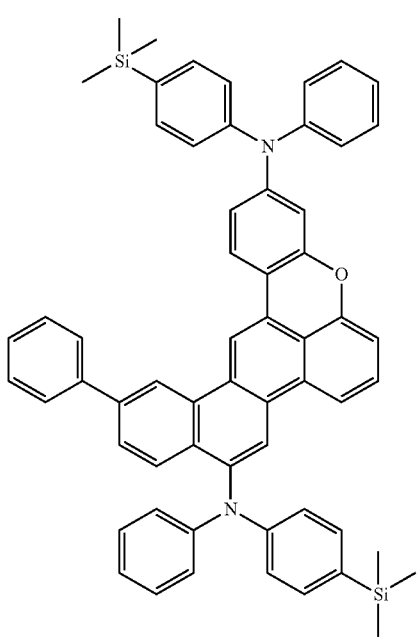
104
105
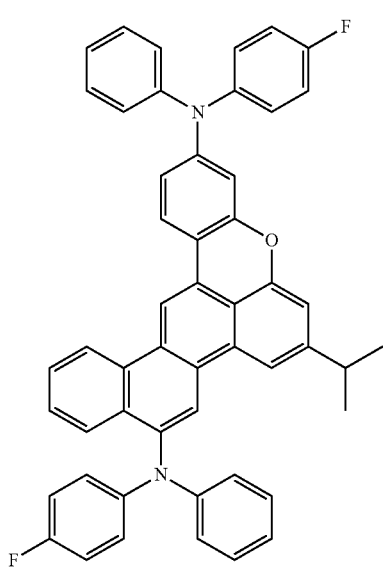
110
-continued
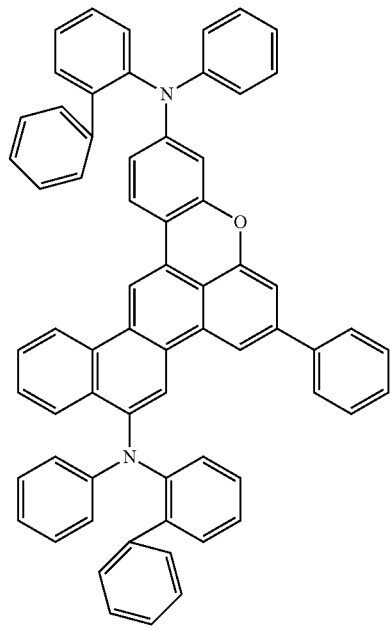
106
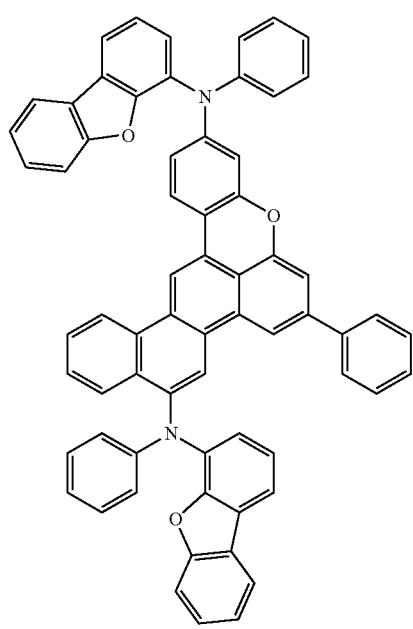
107

111
-continued
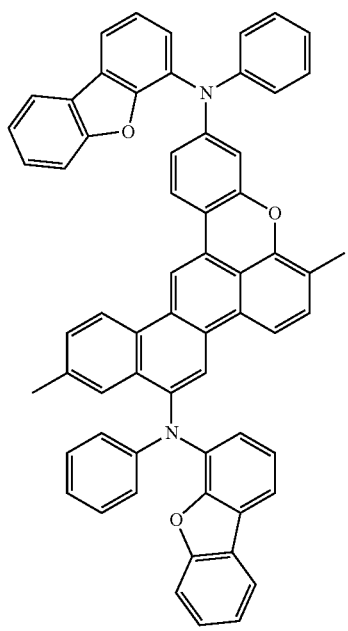
108
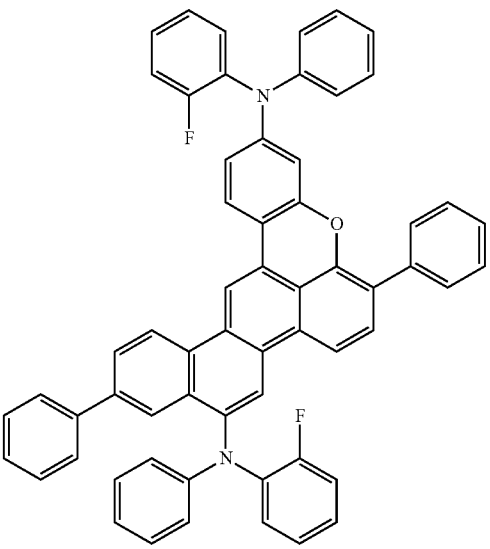
110
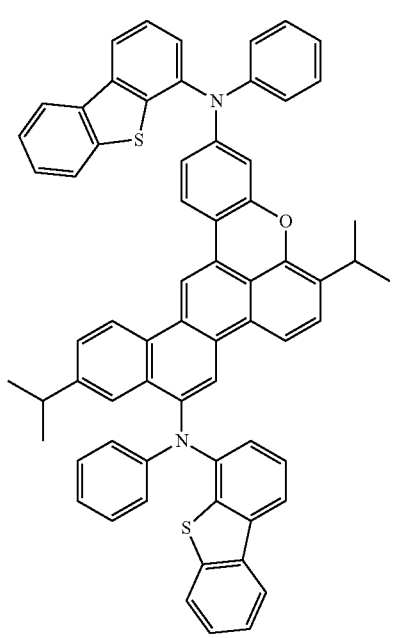
109
112
-continued
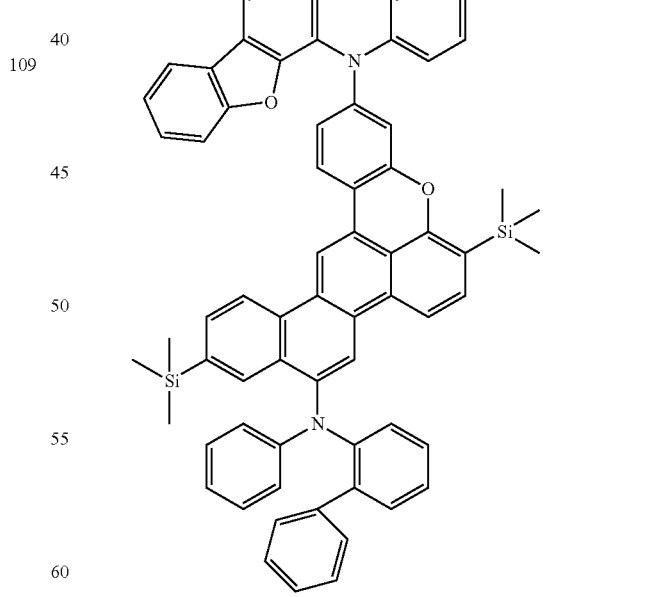
111
The condensed cyclic compound represented by Formula 1 has a core in which a benzene ring is linked to a chrysene moiety via an oxygen atom or a sulfur atom (see Formula 1' illustrated below).

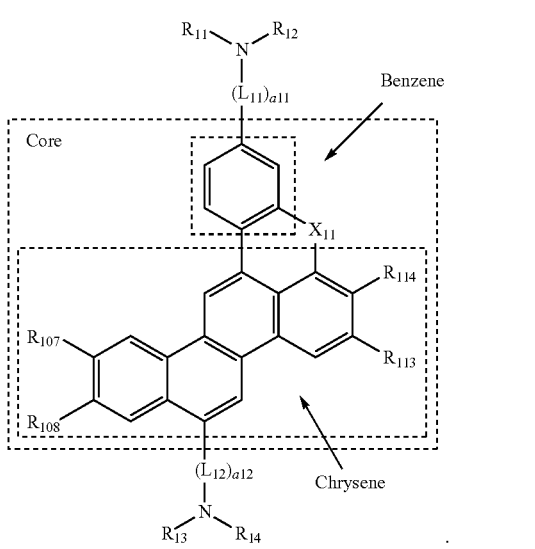

Formula 1'

Since in the condensed cyclic compound represented by Formula 1 a benzene is linked to a chrysene via $X_{11}$ (where $X_{11}$ is an oxygen atom or a sulfur atom), π-electron is non-polarized. Also, since in the condensed cyclic compound represented by Formula 1, $X_{11}$ has two lone pairs of non-covalent electrons, excess electrons may be provided to the core through delocalization.

Accordingly, when the core of the condensed cyclic compound represented by Formula 1 is enriched with π-electrons, π→π* transition and n→π* transition are highly likely to occur.

The core of the condensed cyclic compound represented by Formula 1 may have at least one substituent (see Formula 1″ illustrated below):

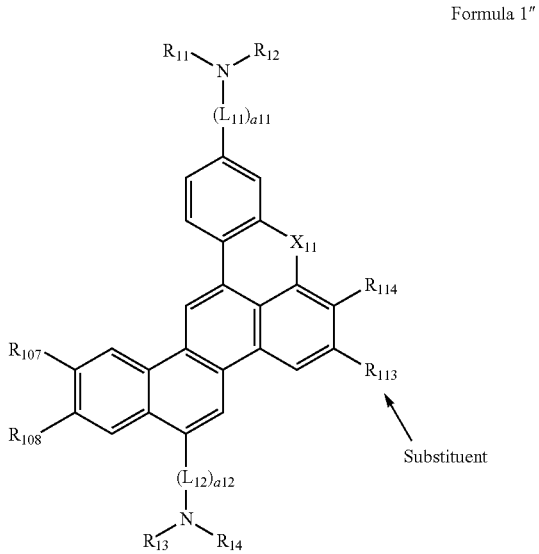

Formula 1″

Since the core of the condensed cyclic compound represented by Formula 1 has at least one substituent, the compound may have a high glass transition temperature (Tg) or a high melting point. Accordingly, the condensed cyclic compound represented by Formula 1 may have high durability.

Accordingly, an organic light-emitting device including the condensed cyclic compound represented by Formula 1 may have high efficiency and a long lifespan.

The condensed cyclic compound represented by Formula 1 may be synthesized by using (utilizing) any known and/or suitable organic synthetic method. A synthesis method of the condensed cyclic compound according to embodiments of the present invention should become apparent to those of ordinary skill in the art in view of the following embodiments.

In some embodiments, the condensed cyclic compound represented by Formula 1 is included in an organic layer of an organic light-emitting device, for example, as a dopant in an emission layer of the organic layer. In some embodiments, an organic light-emitting device includes: a first electrode; a second electrode; and an organic layer between the first electrode and the second electrode, the organic layer including an emission layer and at least one of the condensed cyclic compounds represented by Formula 1.

The condensed cyclic compound of Formula 1 may be included between a pair of electrodes of an organic light-emitting device. For example, the condensed cyclic compound may be included in at least one selected from an emission layer, a hole transport region positioned between the first electrode and the emission layer and including, for example, at least one selected from a hole injection layer, a hole transport layer, a buffer layer, and an electron blocking layer, and an electron transport region positioned between the emission layer and the second electrode and including, for example, at least one selected from a hole blocking layer, an electron transport layer, and an electron injection layer. For example, the condensed cyclic compound represented by Formula 1 may be included in the emission layer. In this regard, the emission layer may further include a host, and the condensed cyclic compound included in the emission layer may act as a dopant. The emission layer may be a green emission layer emitting green light or a blue emission layer emitting blue light, and the dopant may be a fluorescent dopant.

The expression that "an organic layer includes a condensed cyclic compound of Formula 1" used herein may refer to a case in which an organic layer includes one or more identical condensed cyclic compounds represented by Formula 1, and a case in which an organic layer includes two or more different condensed cyclic compounds represented by Formula 1.

For example, the organic layer may include, as the condensed cyclic compound, only Compound 1. In this regard, Compound 1 may be included in the emission layer of the organic light-emitting device. In some embodiments, the organic layer may include, as the condensed cyclic compound, Compound 1 and Compound 2. In this regard, Compound 1 and Compound 2 may both be included in the same layer (for example, Compound 1 and Compound 2 may both be included in an emission layer), or different layers (for example, Compound 1 may be included in an emission layer and Compound 2 may be included in an electron transport region).

In some embodiments, the first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, and the second electrode may be a cathode, and the organic layer may include: i) a hole transport region between the first electrode and the emission layer, the hole transport region including at least one selected from a hole injection layer, a hole transport layer, and an electron blocking layer, and ii) an electron transport region between the emission layer and the second electrode, the electron transport region including at least one selected from a hole blocking layer, an electron transport layer, and an electron injection layer.

The term "organic layer" used herein refers to a single layer and/or a plurality of layers between the first electrode and the second electrode of an organic light-emitting device. The materials included in the "organic layer" are not limited to organic materials. For example, the "organic layer" may include, in addition to an organic compound, an organometallic complex including metal.

The drawing is a schematic view of an organic light-emitting device 10 according to one or more embodiments of the present invention. The organic light-emitting device 10 includes a first electrode 110, an organic layer 150, and a second electrode 190.

Hereinafter, the structure of an organic light-emitting device according to one or more embodiments of the present invention and a method of manufacturing the organic light-emitting device will be described in connection with the drawing.

In the drawing, a substrate may be additionally disposed under the first electrode 110 or above the second electrode 190. The substrate may be a glass substrate or transparent plastic substrate, each with excellent mechanical strength, thermal stability, transparency, surface smoothness, ease of handling, and/or water-resistance.

The first electrode 110 may be formed by depositing or sputtering a material for forming the first electrode on the substrate. When the first electrode 110 is an anode, the material for the first electrode 110 may be selected from materials with a high work function so as to facilitate hole injection. The first electrode 110 may be a reflective electrode or a transmissive electrode. The material for the first electrode 110 may be a transparent and highly conductive material, and non-limiting examples of such material include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), and magnesium-silver (Mg—Ag) may be used (utilized).

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

An organic layer 150 is positioned on the first electrode 110. The organic layer 150 may include an emission layer.

The organic layer 150 may further include a hole transport region between the first electrode 110 and the emission layer. The organic layer 150 may further include an electron transport region between the emission layer and the second electrode 190.

The hole transport region may include at least one selected from a hole injection layer (HIL), a hole transport layer (HTL), a buffer layer, and an electron blocking layer (EBL); and the electron transport region may include at least one selected from a hole blocking layer (HBL), an electron transport layer (ETL), and an electron injection layer (EIL), but they are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, where the layers of each structure are sequentially stacked from the first electrode 110 in the stated order, but the structure of the hole transport region is not limited thereto.

When the hole transport region includes a hole injection layer, the hole injection layer may be formed on the first electrode 110 by using (utilizing) one or more suitable methods, such as vacuum deposition, spin coating casting, a Langmuir-Blodgett (LB) method, ink-jet printing, laser-printing, and/or laser-induced thermal imaging.

When the hole injection layer is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec, depending on the compound for forming the hole injection layer, and the structure of the hole injection layer to be formed.

When the hole injection layer is formed by spin coating, the spin coating may be performed at a coating rate of about 2000 rpm to about 5000 rpm, and at a temperature of about 80° C. to 200° C., depending on the compound for forming the hole injection layer, and the structure of the hole injection layer to be formed.

When the hole transport region includes a hole transport layer, the hole transport layer may be formed on the first electrode 110 or the hole injection layer by using one or more suitable methods, such as vacuum deposition, spin coating, casting, a LB method, ink-jet printing, laser-printing, and/or laser-induced thermal imaging.

When the hole transport layer is formed by vacuum deposition and/or spin coating, deposition and coating conditions for the hole transport layer may be the same as (or similar to) the deposition and coating conditions for the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below:

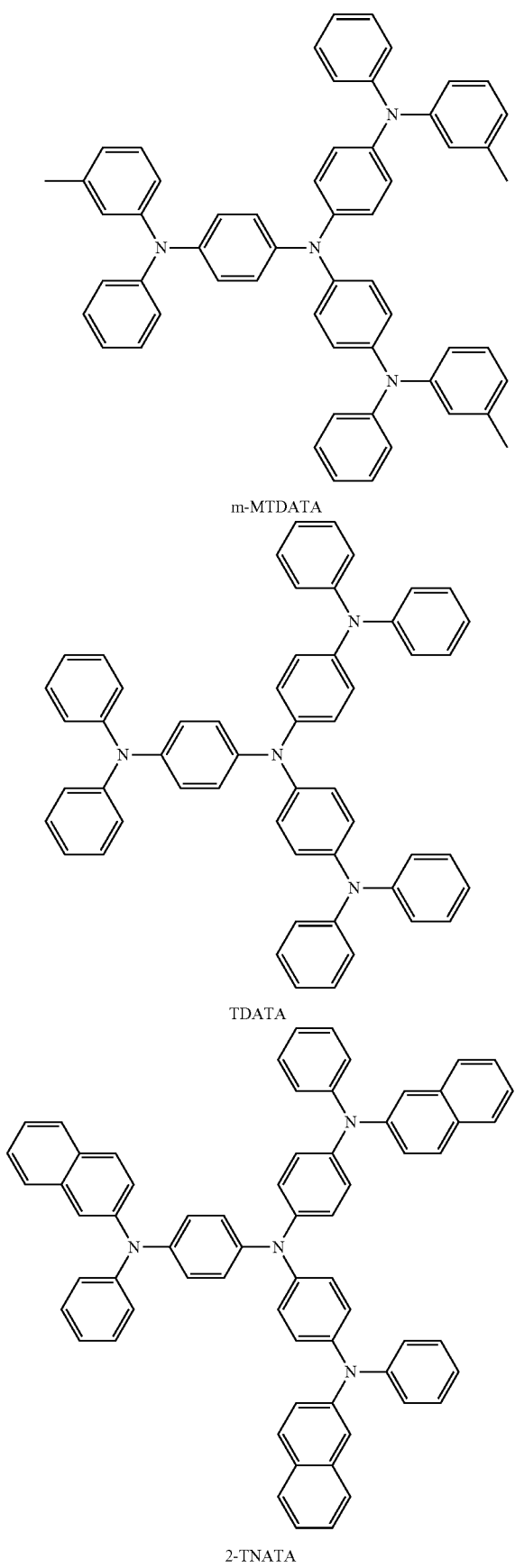
m-MTDATA
TDATA
2-TNATA
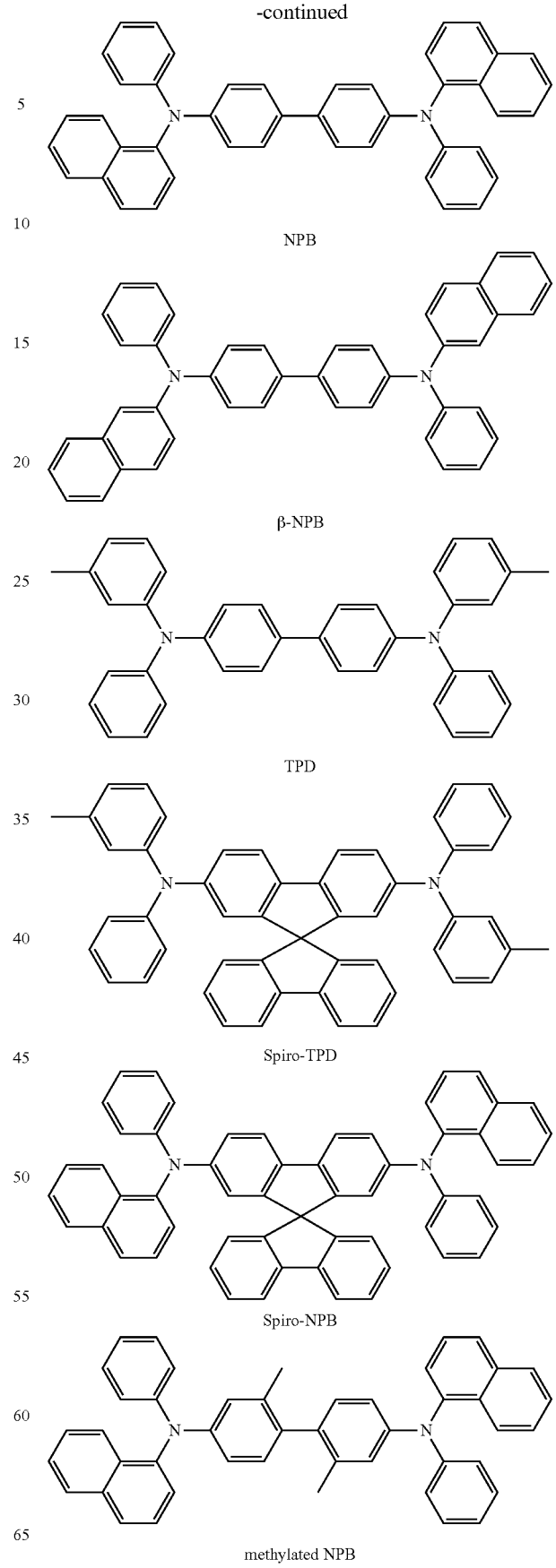
NPB
β-NPB
TPD
Spiro-TPD
Spiro-NPB
methylated NPB -continued

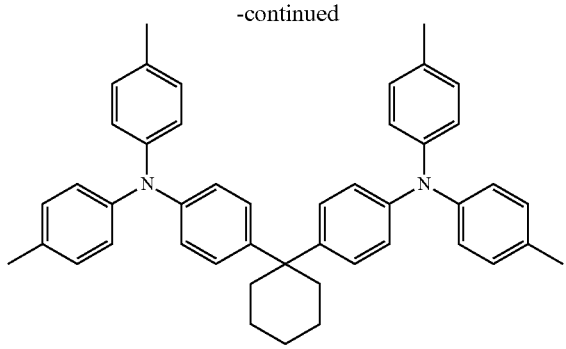

TAPC

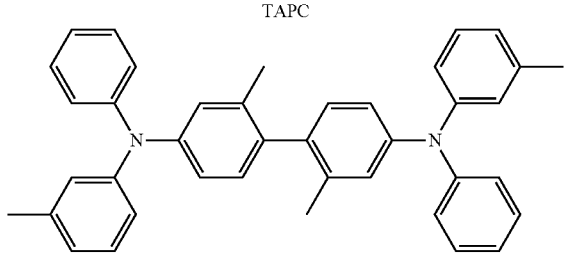

HMTPD

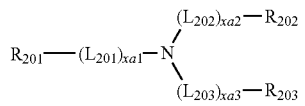
Formula 201

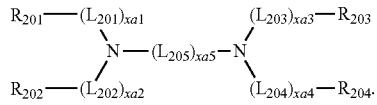
Formula 202

In Formulae 201 and 202, $L_{201}$ to $L_{205}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{201}$)($Q_{202}$), —Si($Q_{203}$)($Q_{204}$)($Q_{205}$), and —B($Q_{206}$)($Q_{207}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{211}$)($Q_{212}$), —Si($Q_{213}$)($Q_{214}$)($Q_{215}$), and —B($Q_{216}$)($Q_{217}$); and —N($Q_{221}$)($Q_{222}$), —Si($Q_{223}$)($Q_{224}$)($Q_{225}$), and —B($Q_{226}$)($Q_{227}$);

xa1 to xa4 may be each independently selected from 0, 1, 2, and 3;

xa5 may be selected from 1, 2, 3, 4, and 5; and $R_{201}$ to $R_{204}$ may be each independently selected from a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{231}$)($Q_{232}$), —Si($Q_{233}$)($Q_{234}$)($Q_{235}$), and —B($Q_{236}$)($Q_{237}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{241}$)($Q_{242}$), —Si($Q_{243}$)($Q_{244}$)($Q_{245}$), and —B($Q_{246}$)($Q_{247}$), where $Q_{201}$ to $Q_{207}$, $Q_{211}$ to $Q_{217}$, $Q_{221}$ to $Q_{227}$, $Q_{231}$ to $Q_{237}$ and $Q_{241}$ to $Q_{247}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201 and 202, $L_{201}$ to $L_{205}$ may be each independently selected from a phenylene group, a naphthylenylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylenylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, $C_1$-$C_{20}$ alkyl group, $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present invention are not limited thereto.

The compound represented by Formula 201 may be represented by Formula 201A:

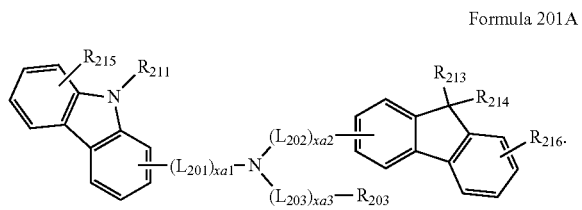

Formula 201A

For example, the compound represented by Formula 201 may be represented by Formula 201A-1, but embodiments of the present invention are not limited thereto:

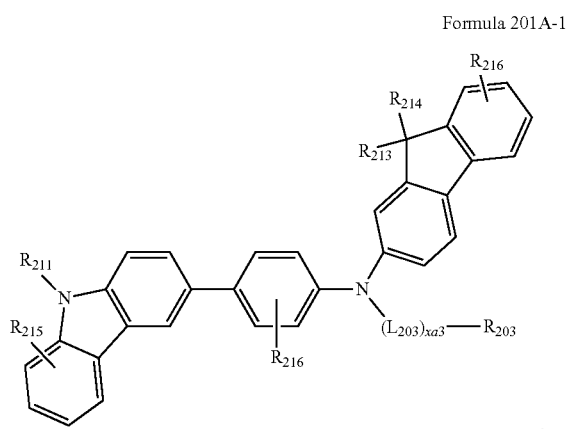

Formula 201A-1

The compound represented by Formula 202 may be represented by Formula 202A, but embodiments of the present invention are not limited thereto:

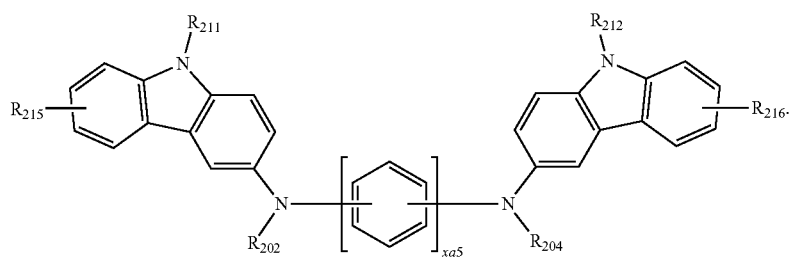

Formula 202A

In Formulae 201A, 201A-1 and 202A, descriptions of $L_{201}$ to $L_{203}$, xa1 to xa3, xa5, and $R_{202}$ to $R_{204}$ are the same as described above, descriptions of $R_{211}$ and $R_{212}$ are the same as described in connection with $R_{203}$, and $R_{213}$ to $R_{216}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, $L_{201}$ to $L_{203}$ in Formulae 201A, 201A-1 and 202A may be each independently selected from a phenylene group, a naphthylenylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylenylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at 10 least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, $C_1$-$C_{20}$ alkyl group, $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

$R_{213}$ and $R_{214}$ in Formulae 201A and 201A-1 may bind to each other to form a saturated or unsaturated ring.

The compound represented by Formula 201 and the compound represented by Formula 202 may each independently include at least one selected from Compound HT1 to HT20, but embodiments of the present invention are not limited thereto:

HT1
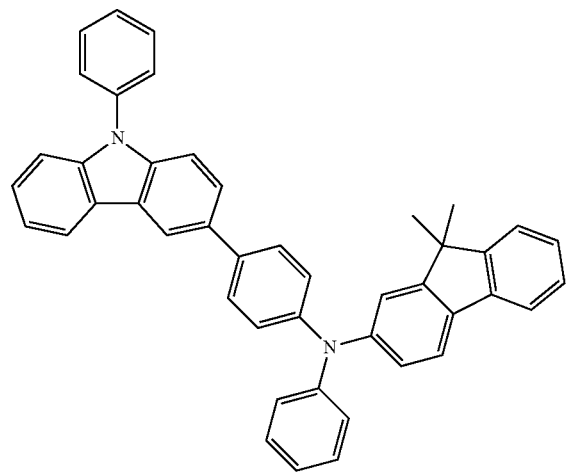
HT2
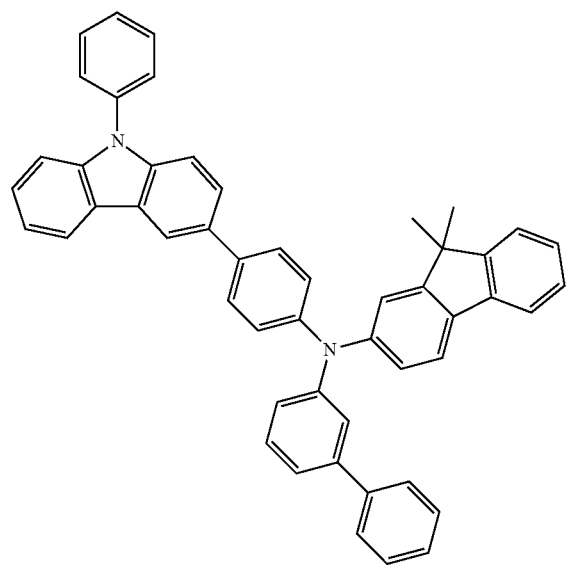
HT3
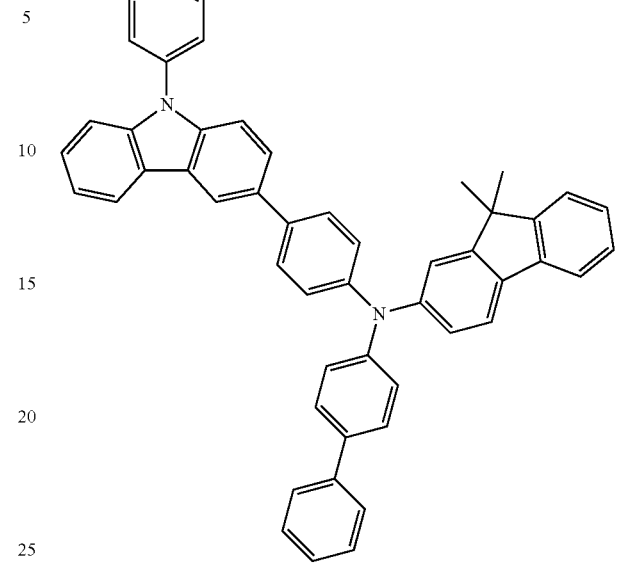
HT4
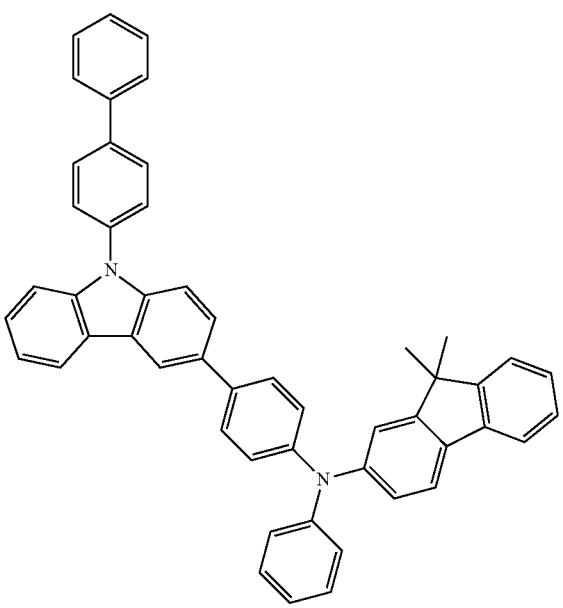

HT5
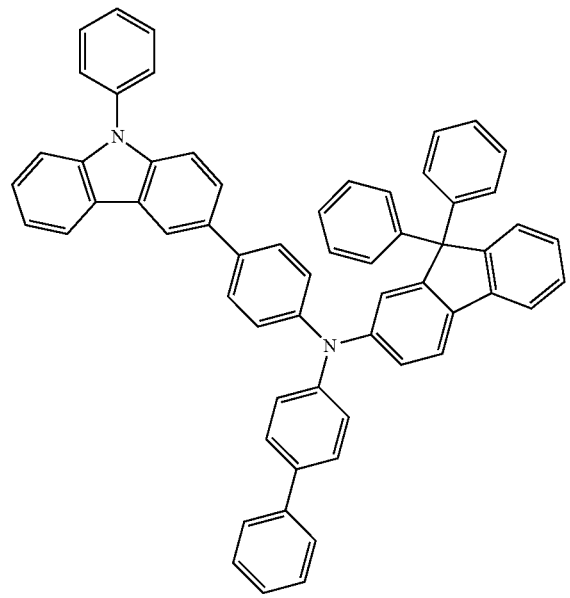
HT6
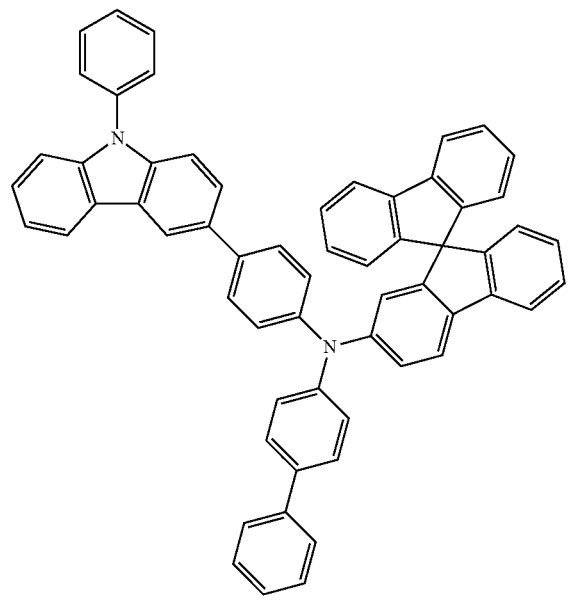
HT7
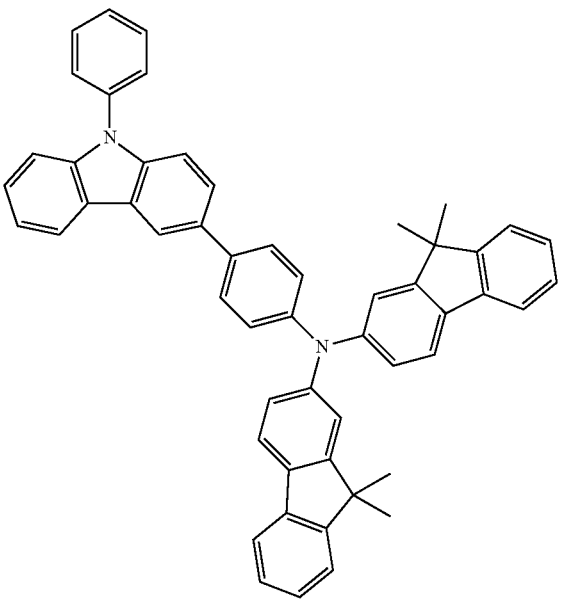
HT8
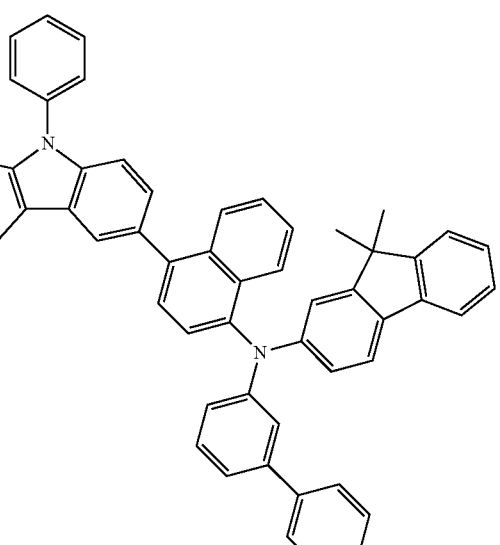

-continued
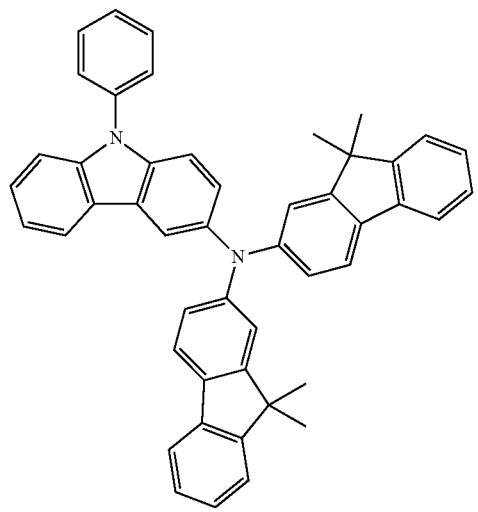
HT9
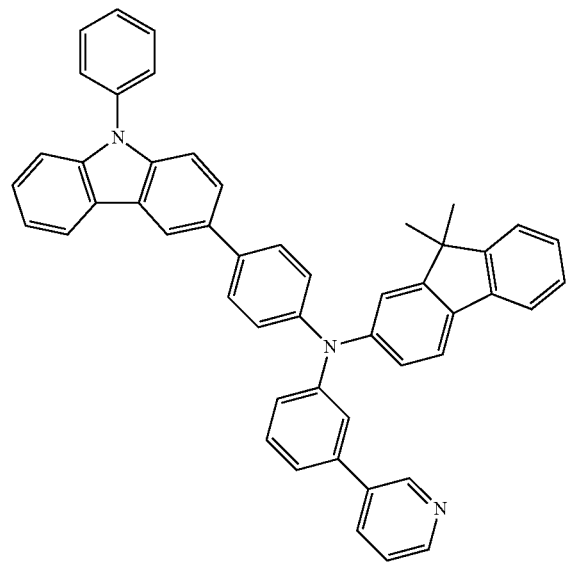
HT11
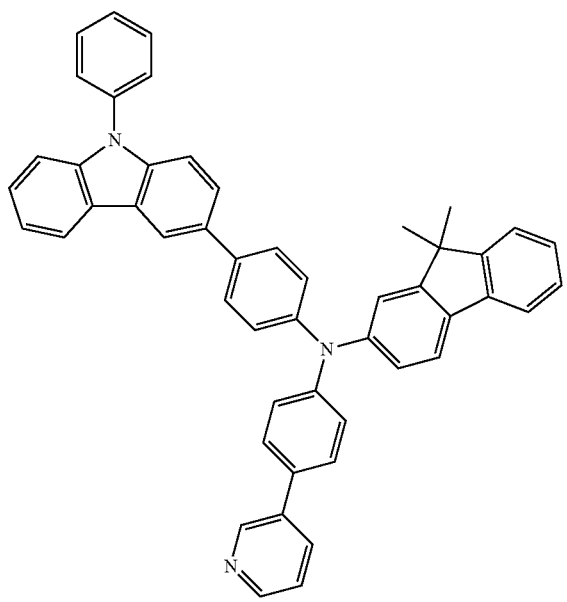
HT10
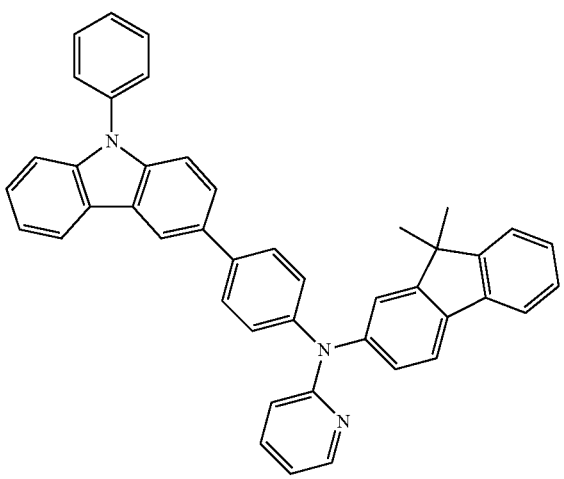
HT12
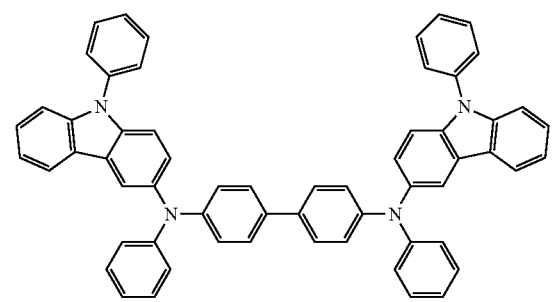
HT13

-continued

HT14
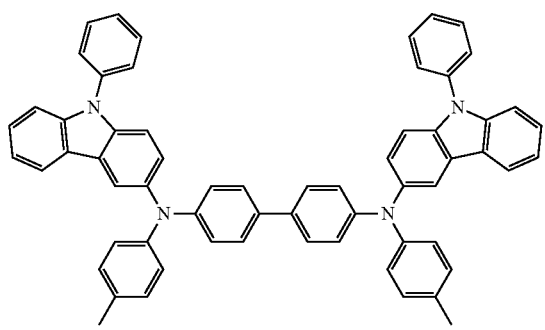

HT15
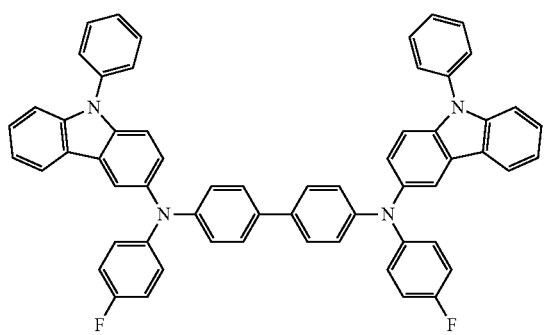

HT16
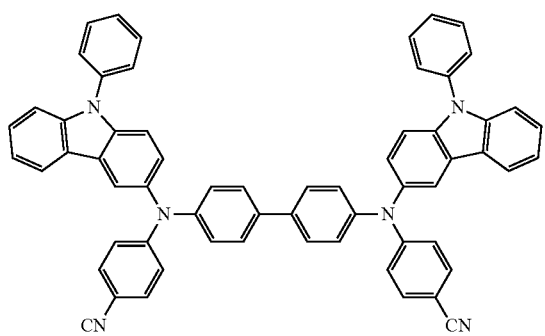

HT17
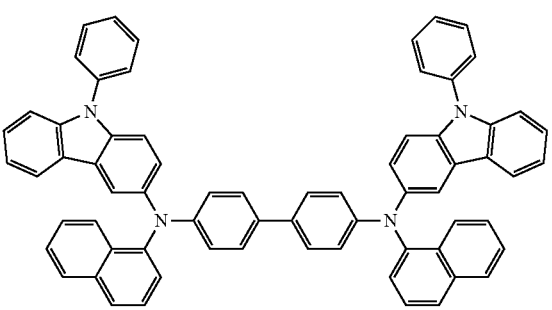

-continued

HT18
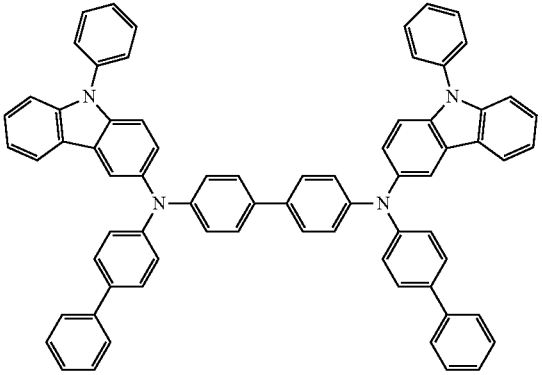

HT19
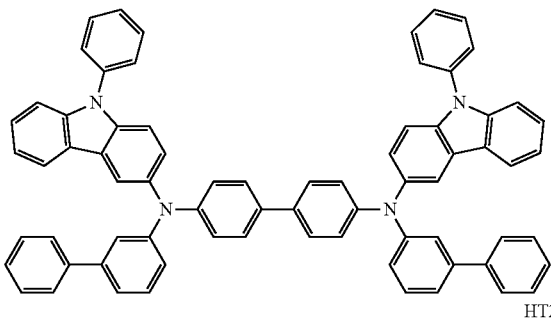

HT20
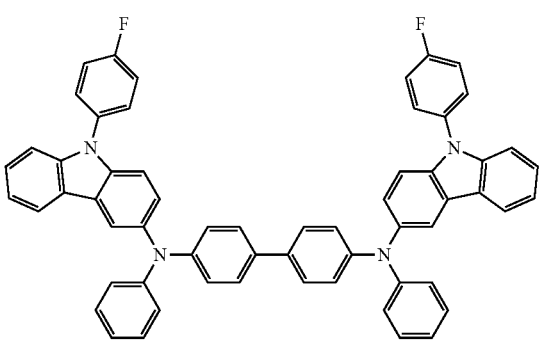

A thickness of the hole transport region may be in a range of about 100 Å to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within any of these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or unhomogeneously dispersed in the hole transport region.

The charge-generation material may be, for example, a p-dopant. The p-dopant may be selected from a quinone derivative, a metal oxide, and a cyano group-containing compound, but embodiments of the present invention are not limited thereto. Non-limiting examples of the p-dopant include quinone derivatives, such as tetracyanoquinonedimethane (TCNQ) and/or 2,3,5,6-tetrafluoro-tetracyano-1,4-benzoquinonedimethane (F4-TCNQ); metal oxides, such as tungsten oxide and/or molybdenum oxide, and Compound HT-D1 illustrated below.

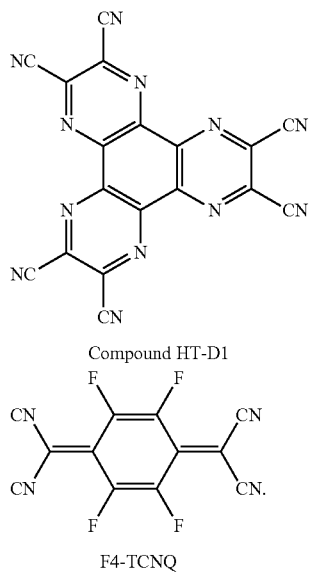

Compound HT-D1

F4-TCNQ

The hole transport region may further include, in addition to the hole injection layer and the hole transport layer, at least one of a buffer layer and an electron blocking layer. Since the buffer layer may compensate for an optical resonance distance according to a wavelength of light emitted from the emission layer, light-emission efficiency of the resulting organic light-emitting device may be improved. For use as a material included in the buffer layer, materials that are included in the hole transport region may be used. The electron blocking layer prevents or substantially blocks the injection of electrons from the electron transport region.

An emission layer is formed on the first electrode 110 or the hole transport region by using one or more suitable methods, such as vacuum deposition, spin coating, casting, a LB method, ink-jet printing, laser-printing, and/or laser-induced thermal imaging. When the emission layer is formed by vacuum deposition and/or spin coating, deposition and coating conditions for the emission layer may be the same as (or similar to) those for the hole injection layer.

When the organic light-emitting device 10 is a full color organic light-emitting device, the emission layer may be patterned into a red emission layer, a green emission layer, or a blue emission layer, according to a sub pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light. In some embodiments, the emission layer may be a white emission layer, and may further include a color converting layer or a color filter to turn white light into light of a desired color.

The emission layer may include a host and a dopant.

The host may include at least one selected from TPBi, TBADN, ADN (also referred to herein as "DNA"), CBP, CDBP, and TCP:

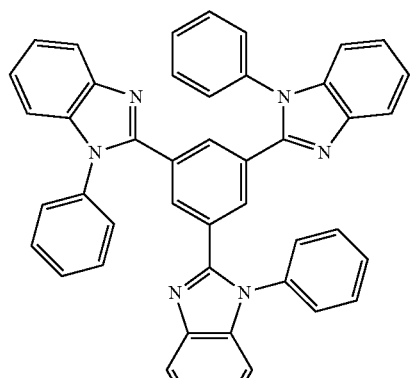

TPBi

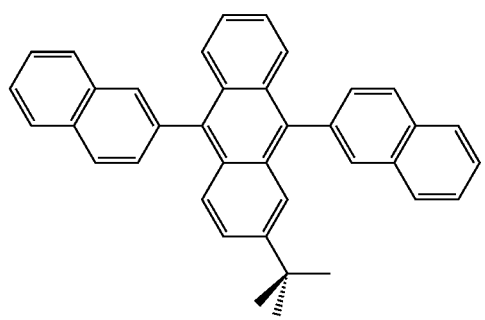

TBADN

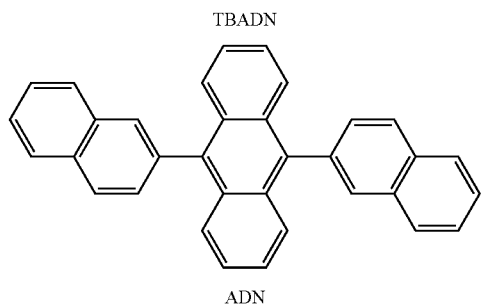

ADN

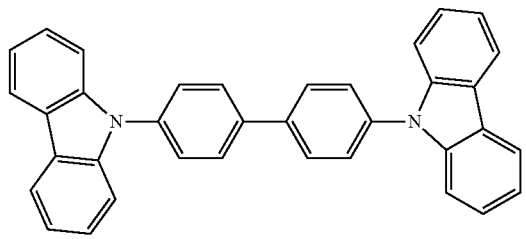

CBP

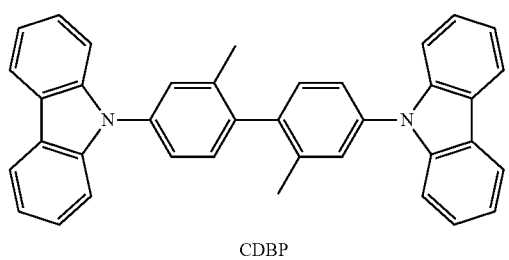

CDBP

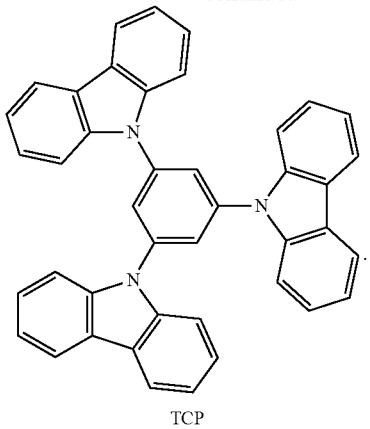

TCP

In some embodiments, the host may include a compound represented by Formula 301 below.

$$Ar_{301}-[(L_{301})_{xb1}-R_{301}]_{xb2}.$$ Formula 301

$Ar_{301}$ in Formula 301 may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{301}$)($Q_{302}$)($Q_{303}$) (where $Q_{301}$ to $Q_{303}$ may be each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

a description of $L_{301}$ may be understood by referring to the description provided in connection with $L_{201}$;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xb1 may be selected from 0, 1, 2, and 3;

xb2 may be selected from 1, 2, 3, and 4.

In some embodiments, $L_{301}$ in Formula 301 may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments of the present invention are not limited thereto.

The compound represented by Formula 301 may be represented by one of Compounds H1 to H25, but is not limited thereto:

H1
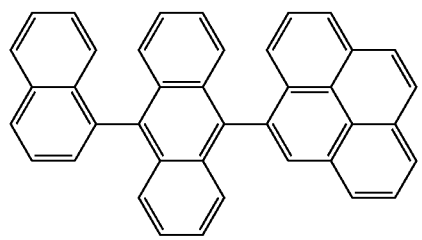

H2
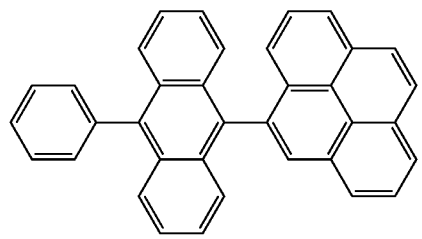

H3
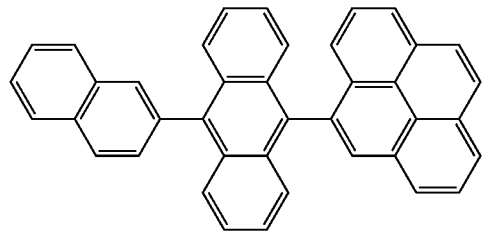

H4
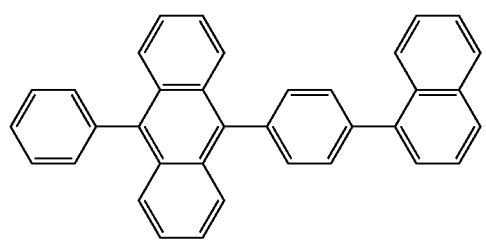

H5
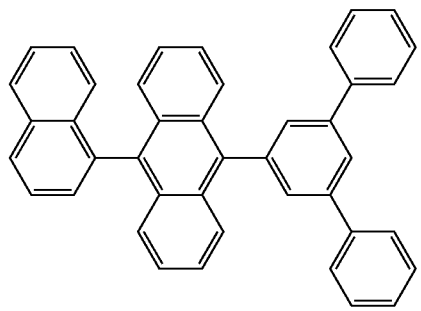

H6
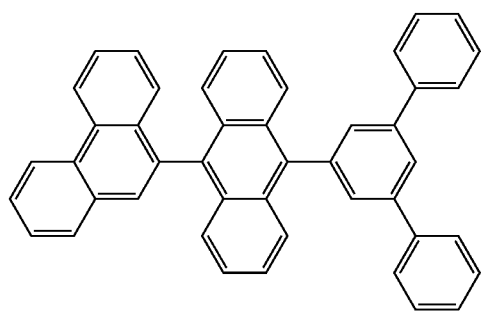

H7
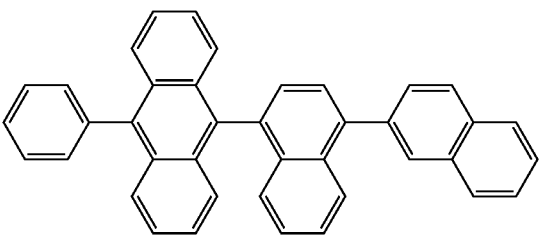

H8
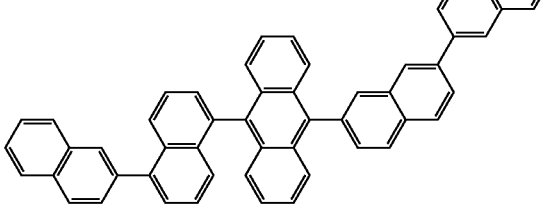

H9
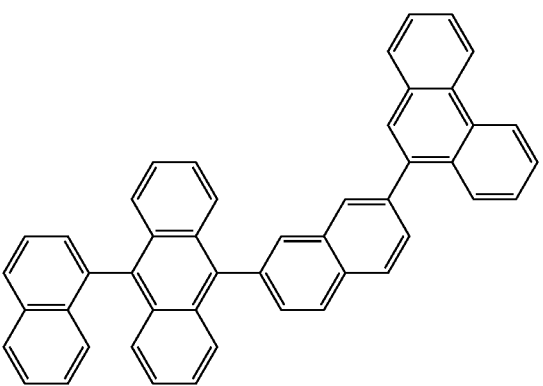

H10
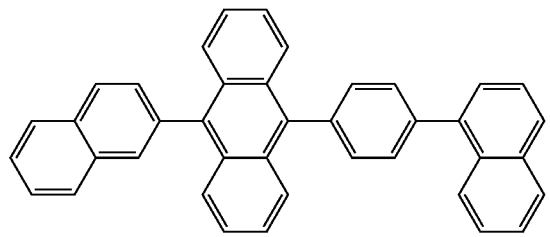
H11
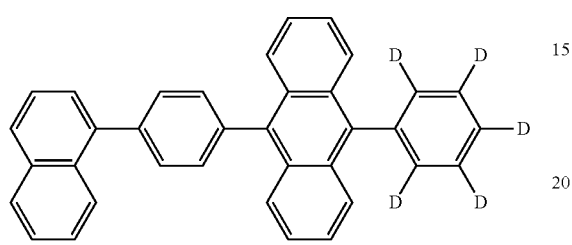
H12
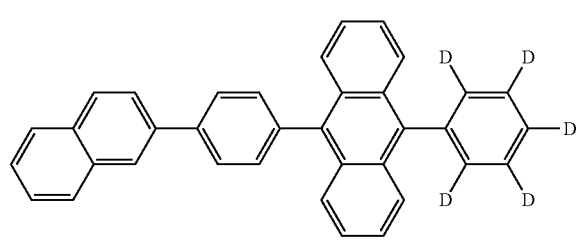
H13
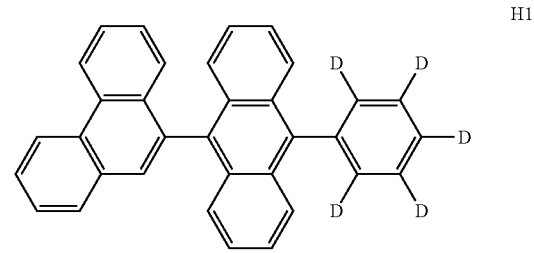
H14
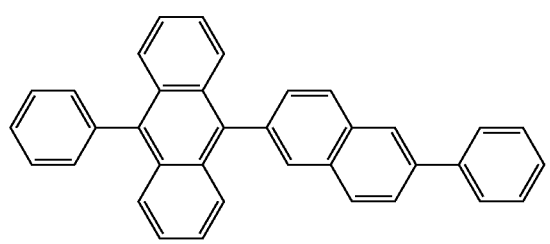
H15
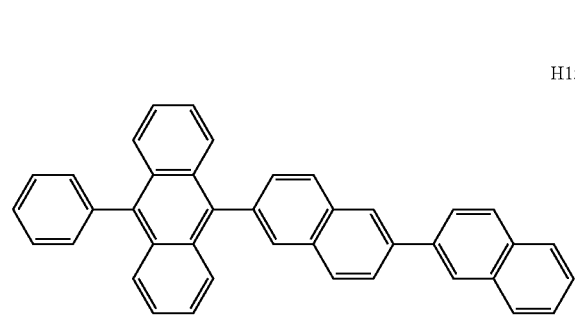
H16
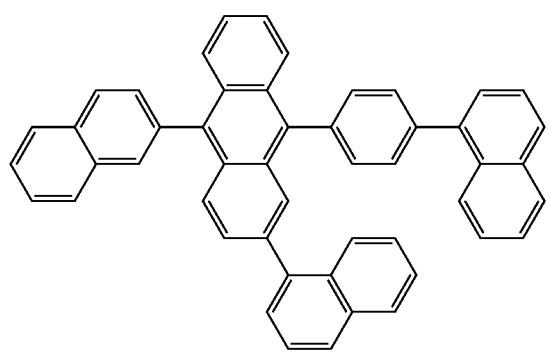
H17
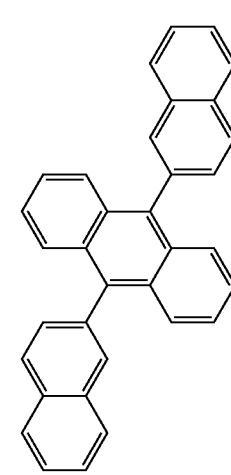
H18
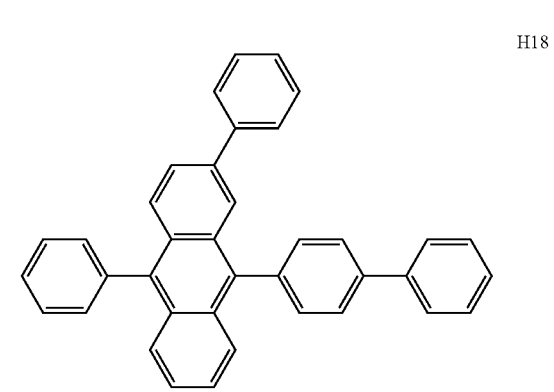

H19
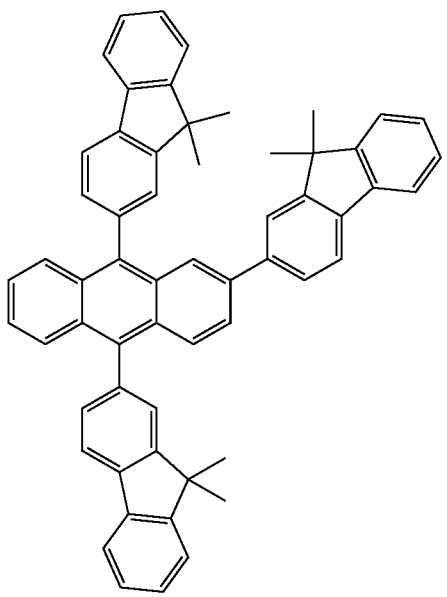
H20
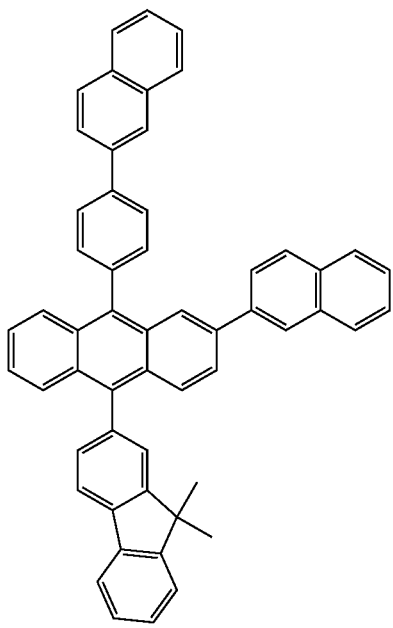
H21
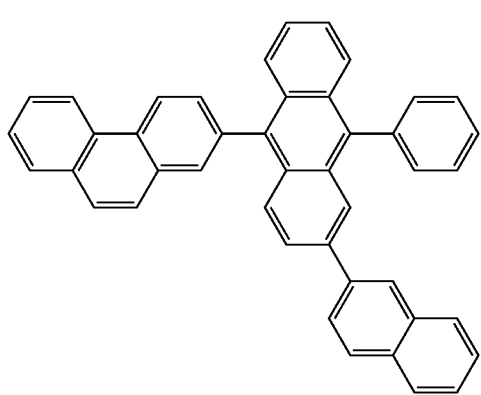
H22
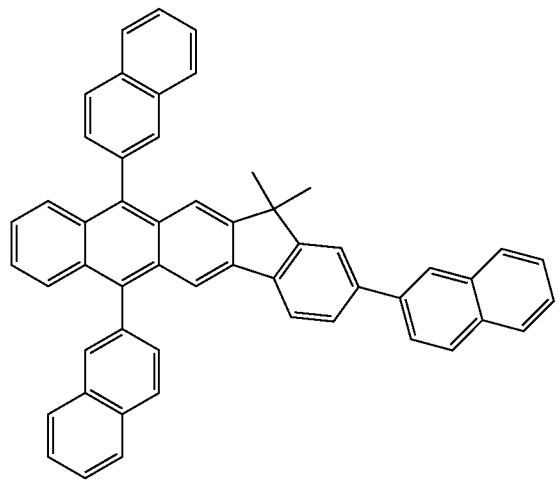
H23
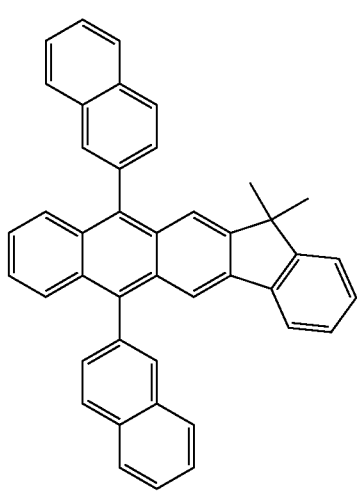
H24
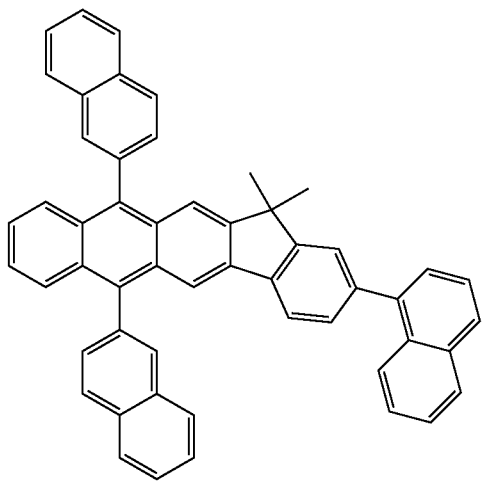

H25
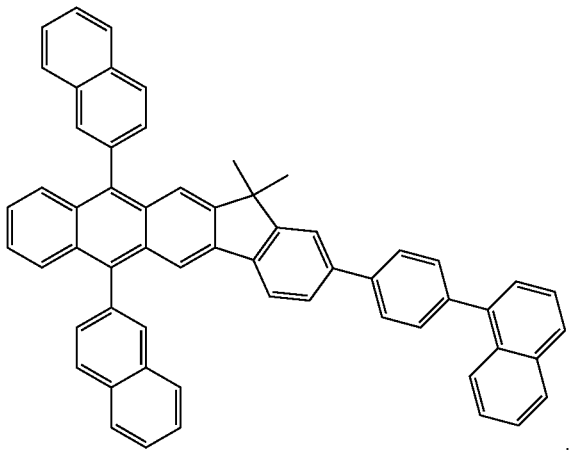
In some embodiments, the host may include at least one of Compounds H26 to H32 below, but is not limited thereto:
H26
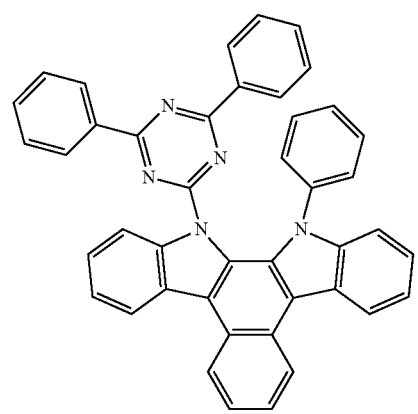
H27
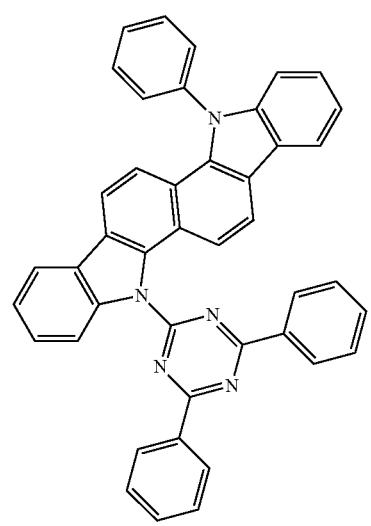
H28
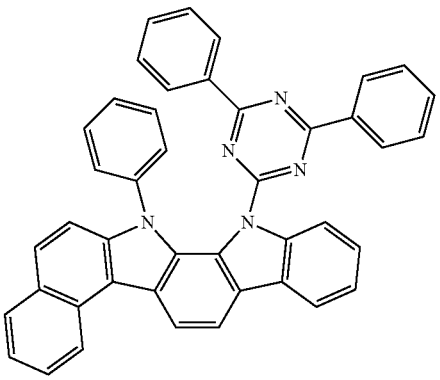
H29
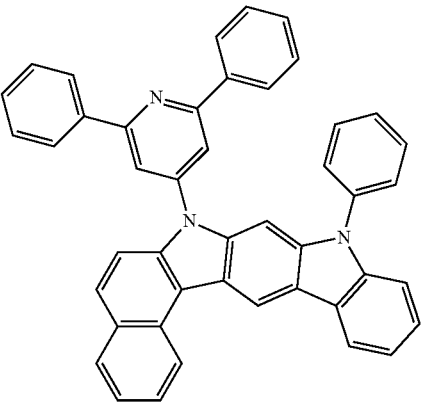
H30
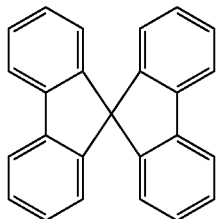
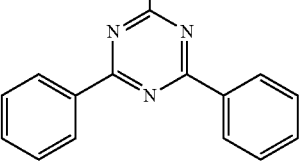
H31
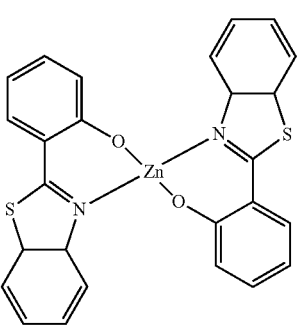

H32

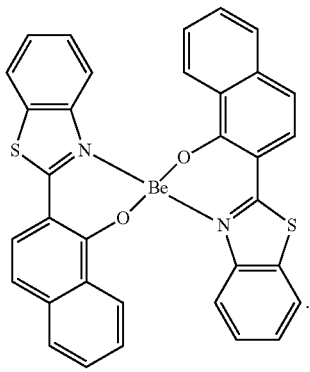

In some embodiments, the host may include a second material represented by Formula 2 below:

Formula 2

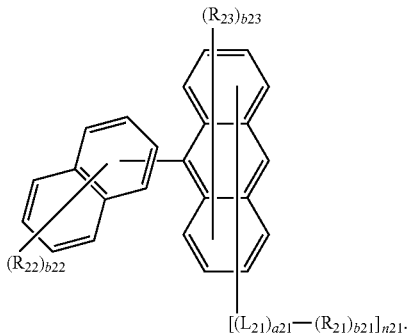

In Formula 2, $L_{21}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a21 is selected from 0, 1, 2, and 3; and when a21 is 2 or more, a plurality of $L_{21}$ may be identical to or different from each other;

$R_{21}$ to $R_{23}$ may be each independently selected from hydrogen, deuterium, F, —Cl, —Br, —I, a hydroxyl group, a cyano group, a nitro group, a substituted or unsubstituted $C_1$-$C_{60}$ alkyl group, a substituted or unsubstituted $C_2$-$C_{60}$ alkenyl group, a substituted or unsubstituted $C_1$-$C_{60}$ alkoxy group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b21 to b23 may be each independently selected from 1, 2, 3, 4, 5, and 6;

n21 may be selected from 1, 2, and 3; and at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_1$-$C_{60}$ alkoxy group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, $C_1$-$C_{60}$ alkyl group, $C_2$-$C_{60}$ alkenyl group, $C_2$-$C_{60}$ alkynyl group, $C_1$-$C_{60}$ alkoxy group, $C_3$-$C_{10}$ cycloalkyl group, $C_1$-$C_{10}$ heterocycloalkyl group, $C_3$-$C_{10}$ cycloalkenyl group, $C_1$-$C_{10}$ heterocycloalkenyl group, $C_6$-$C_{60}$ aryl group, $C_6$-$C_{60}$ aryloxy group, $C_6$-$C_{60}$ arylthio group, $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

where $Q_1$ to $Q_7$, $Q_{11}$ to $Q_{17}$, $Q_{21}$ to $Q_{27}$ and $Q_{31}$ to $Q_{37}$ may be each independently selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, $L_{21}$ in Formula 2 may be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group, but this is not limited thereto.

In some embodiments, $L_{21}$ in Formula 2 may be selected from a phenylene group, a naphthylene group, a fluorenylene group, a phenanthrenylene group, an anthracenylene group, a triphenylenylene group, a carbazolylene group, a dibenzofunanylene group, and a dibenzothiophenylene group; and a phenylene group, a naphthylene group, a fluorenylene group, a phenanthrenylene group, an anthracenylene group, a triphenylenylene group, a carbazolylene group, a dibenzofunanylene group, and a dibenzothiophenylene group, each substituted with at least one selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present invention are not limited thereto.

In some embodiments, $L_{21}$ in Formula 2 may be selected from Formulae 3-1 to 3-8 and 3-22 to 3-29, but embodiments of the present invention are not limited thereto:

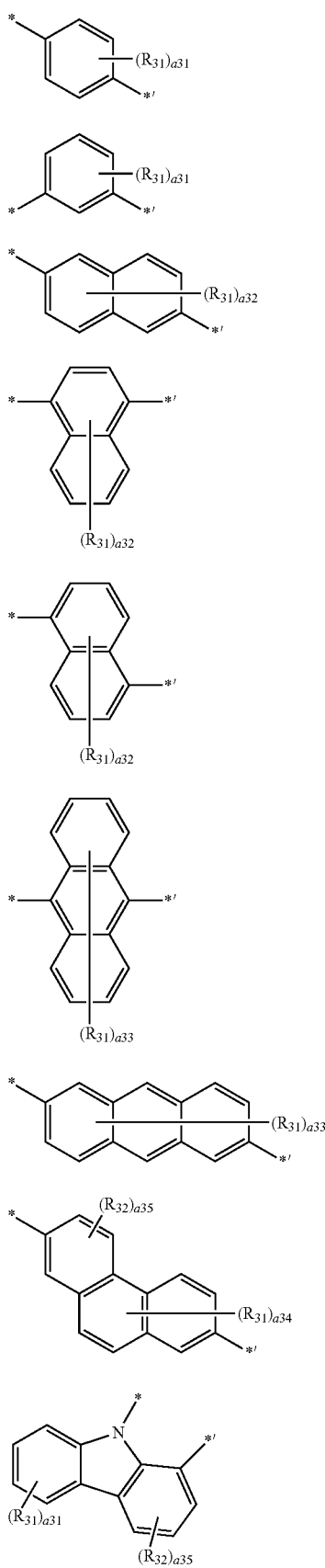
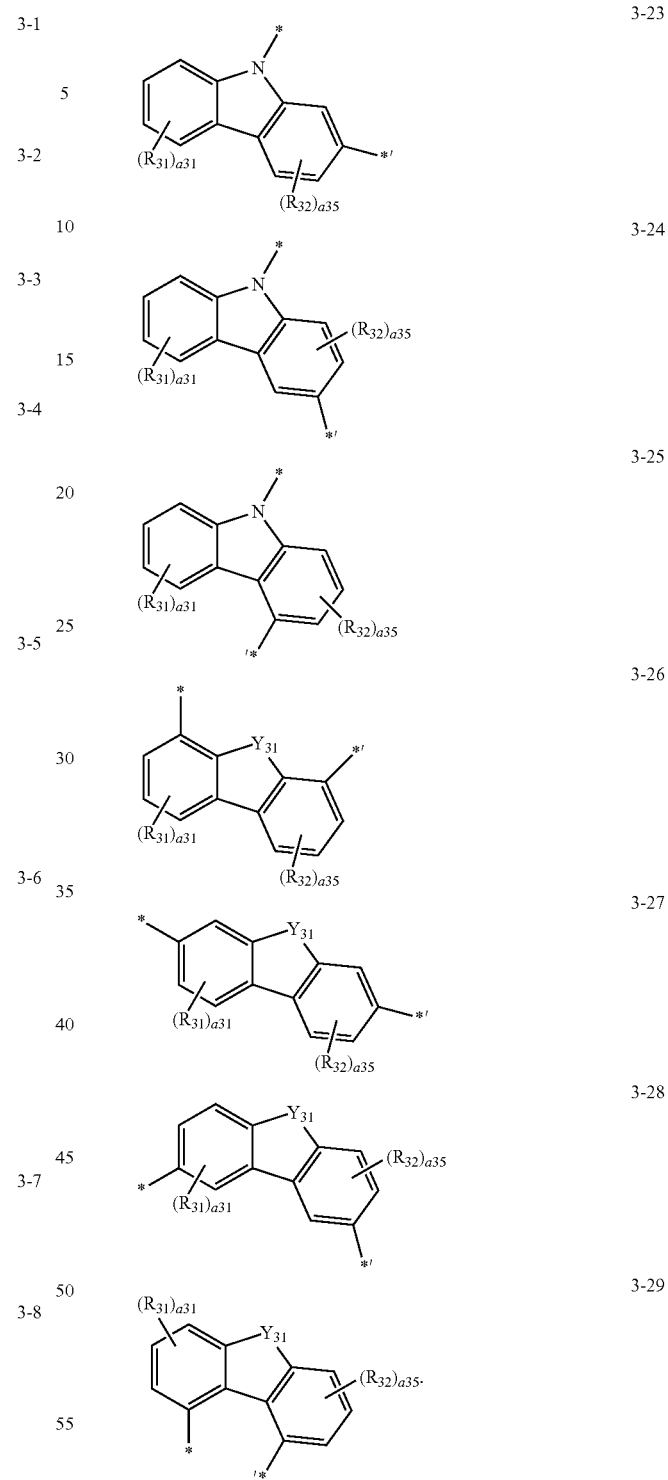

In Formulae 3-1 to 3-8 and 3-22 to 3-29, $Y_{31}$ is selected from $C(R_{33})(R_{34})$, $N(R_{33})$, O, S, and $Si(R_{33})(R_{34})$;

$R_{31}$ to $R_{34}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a31 is selected from 1, 2, 3, and 4;
a32 is selected from 1, 2, 3, 4, 5, and 6;
a33 is selected from 1, 2, 3, 4, 5, 6, 7, and 8;
a34 is selected from 1, 2, 3, 4, and 5;
a35 is selected from 1, 2, and 3; and
* and *' may be each independently a binding site to a neighboring atom.

In some embodiments, $L_{21}$ in Formula 2 may be represented by one of Formulae 3-1 to 3-8 and 3-22 to 3-29, and $R_{31}$ to $R_{34}$ in Formulae 3-1 to 3-8 and 3-22 to 3-29 may be each independently selected from hydrogen, deuterium, —F, —Cl, —Br, —I, a methyl group, an ethyl group, a tert-butyl group, a methoxy group, an ethoxy group, tert-butoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present invention are not limited thereto.

In some embodiments, $L_{21}$ in Formula 2 may be selected from Formulae 4-1 to 4-11 and 4-31 to 4-54, but embodiments of the present invention are not limited thereto:

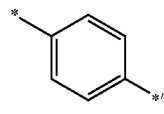

4-1

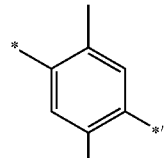

4-2

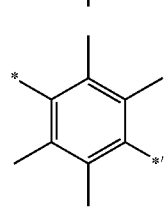

4-3

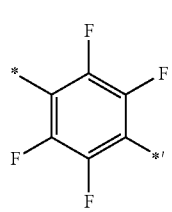

4-4

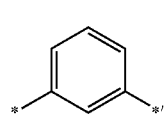

4-5

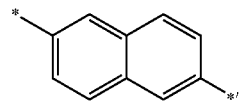

4-6

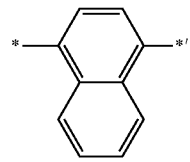

4-7

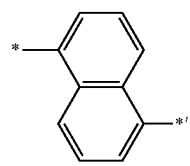

4-8

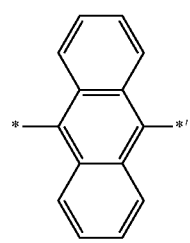

4-9

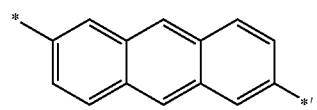

4-10

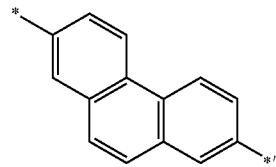

4-11

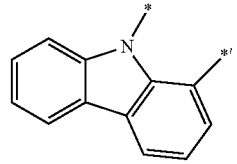

4-31

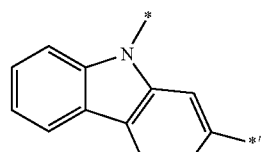

4-32

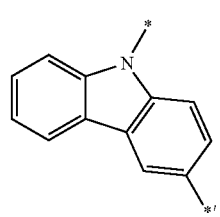

4-33

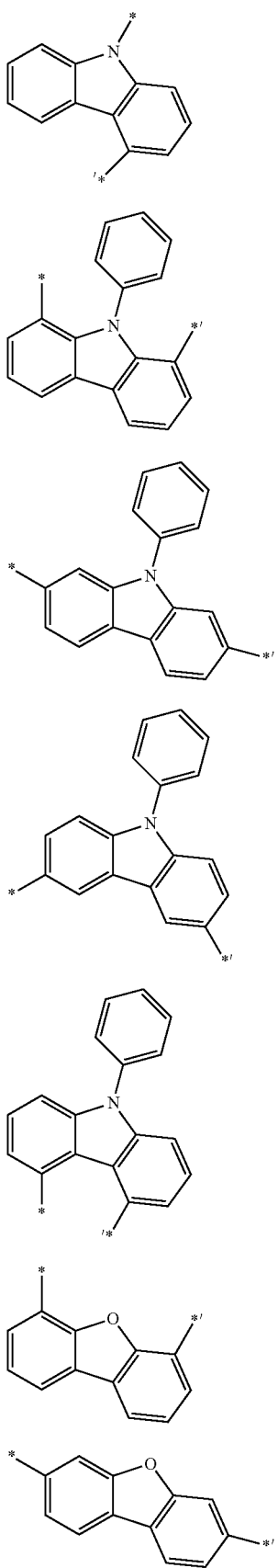
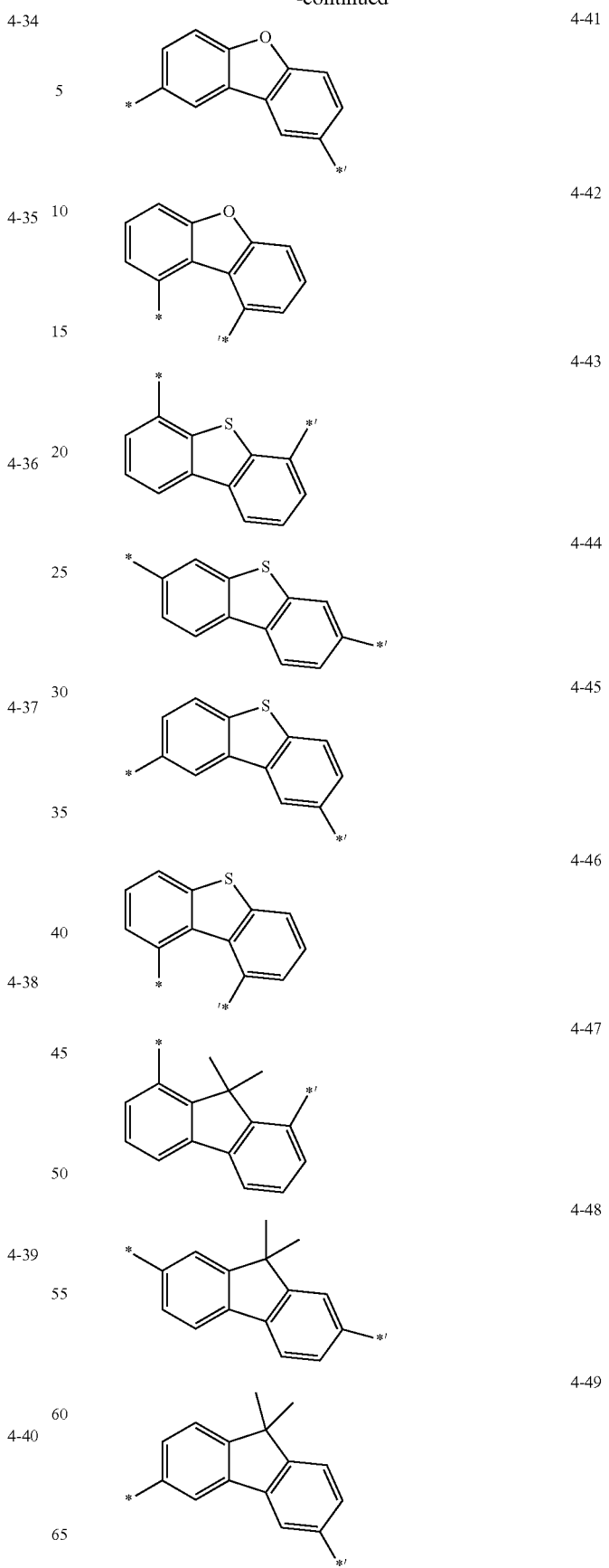

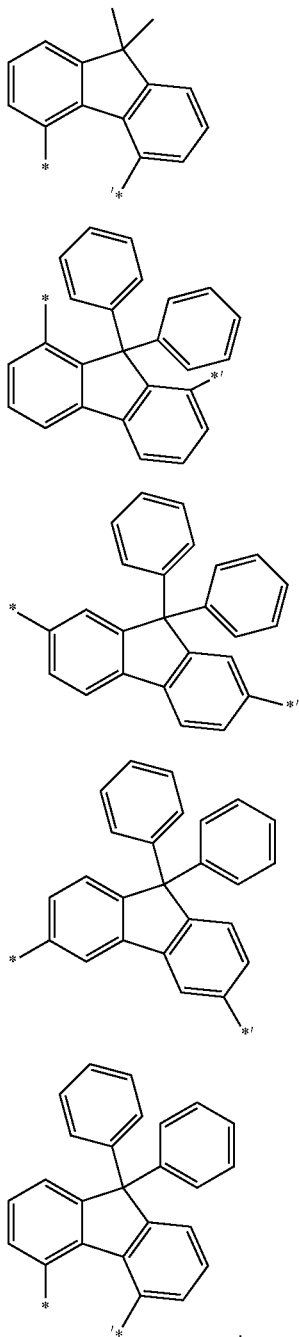

In Formulae 4-1 to 4-11 and 4-31 to 4-54,

* and *' may be each independently a binding site to a neighboring atom.

For example, a21 in Formula 2 may be selected from 0 and 1, but is not limited thereto.

For example, $R_{21}$ and $R_{22}$ in Formula 2 may be each independently selected from hydrogen, deuterium, —F, —Cl, —Br, —I, a cyano group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, —$N(Q_1)(Q_2)$, and —$Si(Q_3)(Q_4)(Q_5)$; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a biphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si$(Q_{33})(Q_{34})(Q_{35})$;

where $Q_1$ to $Q_5$ and $Q_{33}$ to $Q_{35}$ may be each independently selected from a $C_1$-$C_{60}$ alkyl group and a $C_6$-$C_{60}$ aryl group, but embodiments of the present invention are not limited thereto.

In some embodiments, $R_{21}$ and $R_{22}$ in Formula 2 may be each independently selected from hydrogen, deuterium, —F, —Cl, —Br, —I, a cyano group, a phenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, a dibenzosilolyl group, —N$(Q_1)(Q_2)$, and —Si$(Q_3)(Q_4)(Q_5)$; and a phenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si$(Q_{33})(Q_{34})(Q_{35})$; and a phenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group, each substituted with at least one selected from a $C_1$-$C_{20}$ alkyl group substituted with at least one selected from deuterium, —F, —Cl, —Br, —I, a cyano group, and a nitro group, where $Q_1$ to $Q_5$ and $Q_{33}$ to $Q_{35}$ may be each independently selected from a $C_1$-$C_{20}$ alkyl group and a $C_6$-$C_{60}$ aryl group, but embodiments of the present invention are not limited thereto.

In some embodiments, $R_{21}$ and $R_{22}$ in Formula 2 may be each independently selected from hydrogen, deuterium, —F, —Cl, —Br, —I, a cyano group, a phenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, —N$(Q_1)(Q_2)$, and —Si$(Q_3)(Q_4)(Q_5)$; and a phenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, —$CD_3$, —$CF_3$, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si$(Q_{33})(Q_{34})(Q_{35})$, where $Q_1$ to $Q_5$ and $Q_{33}$ to $Q_{35}$ may be each independently selected from a methyl group, an ethyl group, a tert-butyl group, a phenyl group, and a naphthyl group, but embodiments of the present invention are not limited thereto.

In some embodiments, $R_{21}$ and $R_{22}$ in Formula 2 may be each independently selected from hydrogen, deuterium, —F, —Cl, —Br, —I, a cyano group, —N(Ph)$_2$, —Si(CH$_3$)$_3$, —Si(Ph)$_3$, and groups represented by Formulae 5-1 to 5-9 and 5-33, but embodiments of the present invention are not limited thereto:

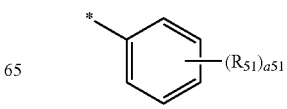

5-1

-continued

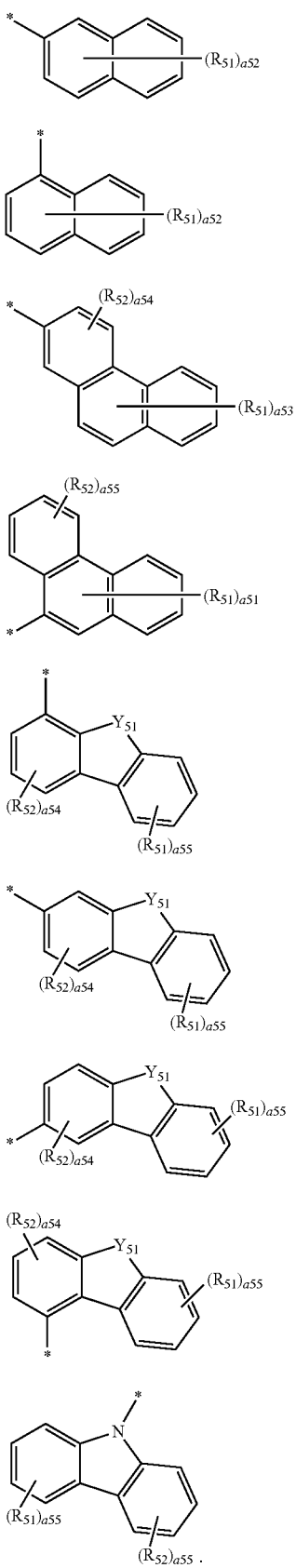

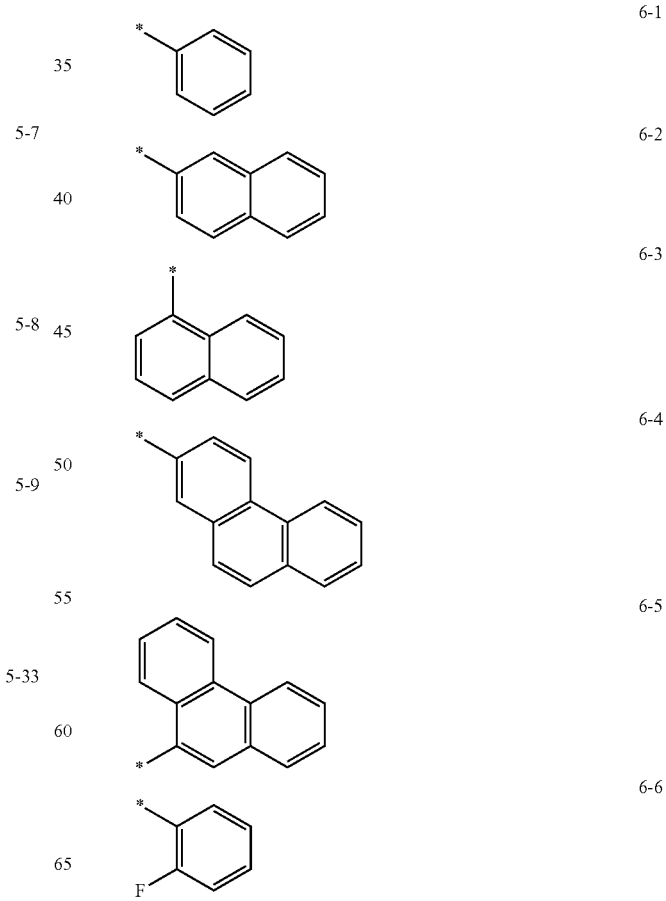

In Formulae 5-1 to 5-9 and 5-33, $Y_{51}$ is selected from $C(R_{53})(R_{54})$, $N(R_{53})$, O, and S; and $R_{51}$ to $R_{54}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, —$CD_3$, —$CF_3$, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{33})(Q_{34})(Q_{35})$, where $Q_{33}$ to $Q_{35}$ may be each independently selected from a methyl group, an ethyl group, ter-butyl group, a phenyl group, and a naphthyl group;

a51 may be selected from 1, 2, 3, 4, and 5;
a52 may be selected from 1, 2, 3, 4, 5, 6, and 7;
a53 may be selected from 1, 2, 3, 4, 5, and 6;
a54 may be selected from 1, 2, and 3;
a55 may be selected from 1, 2, 3, and 4; and
* indicates a binding site to a neighboring atom.

In some embodiments, $R_{21}$ and $R_{22}$ in Formula 2 may be each independently selected from groups represented by Formulae 6-1 to 6-42 and 6-140 to 6-155, but embodiments of the present invention are not limited thereto:

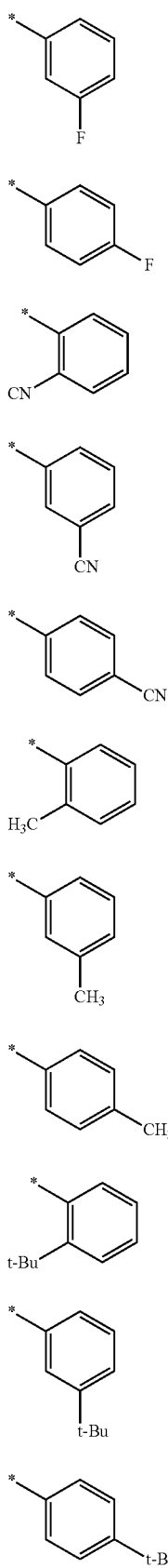
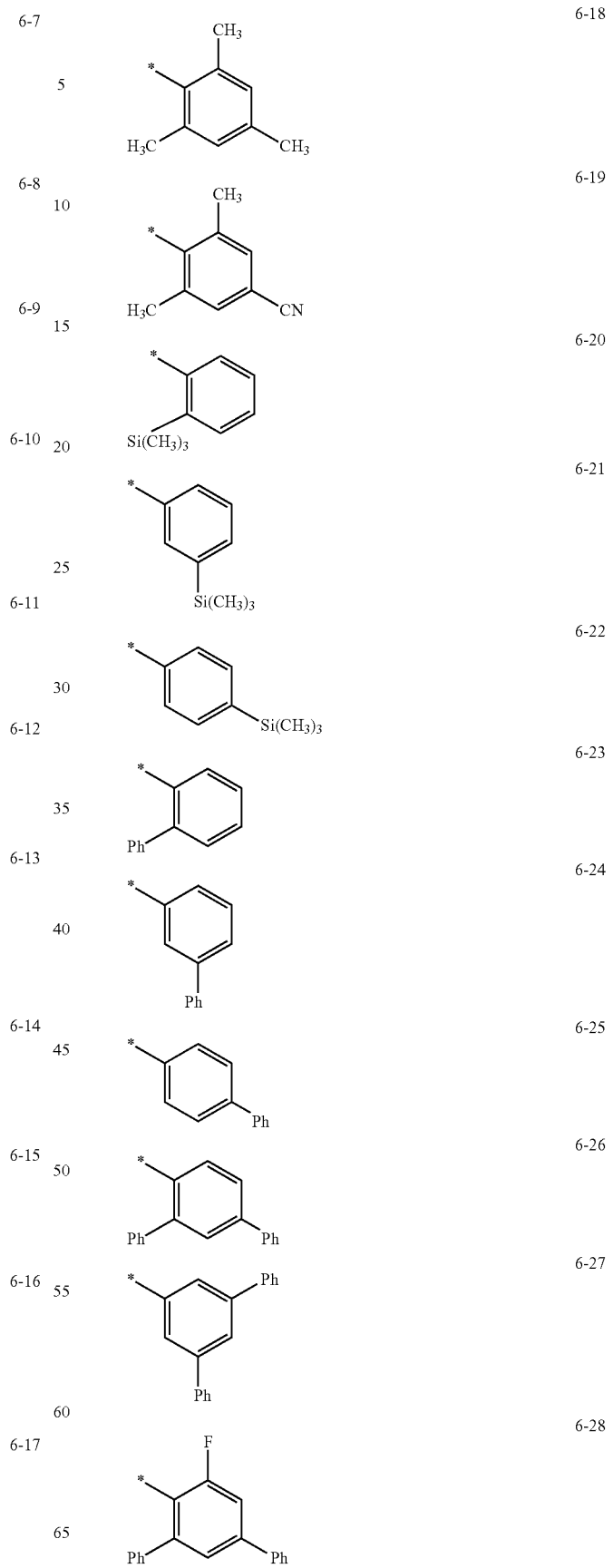

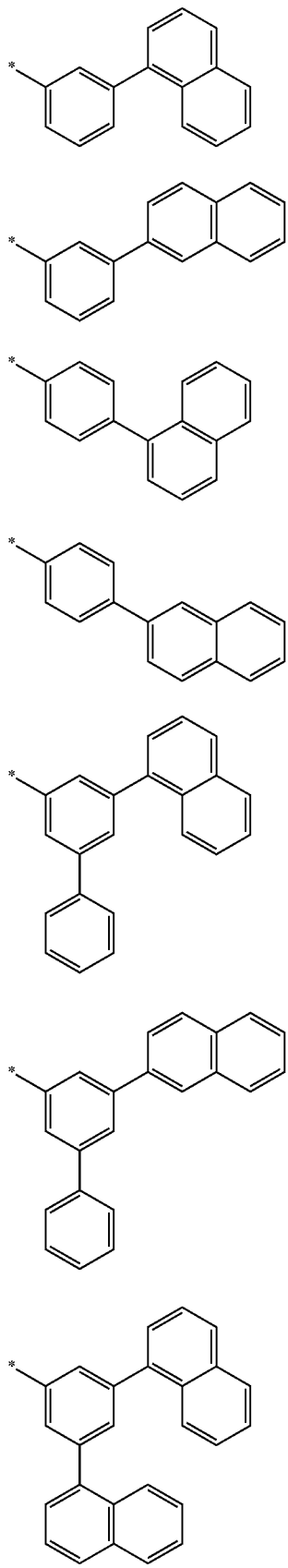
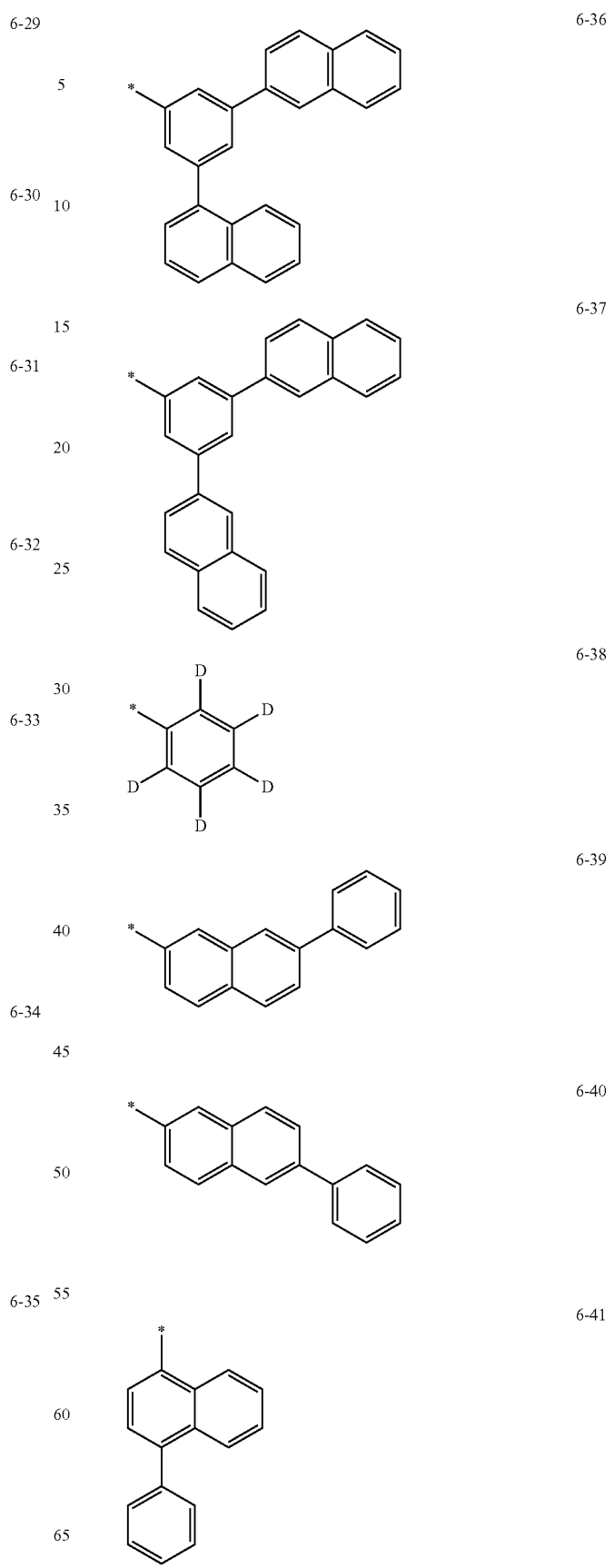

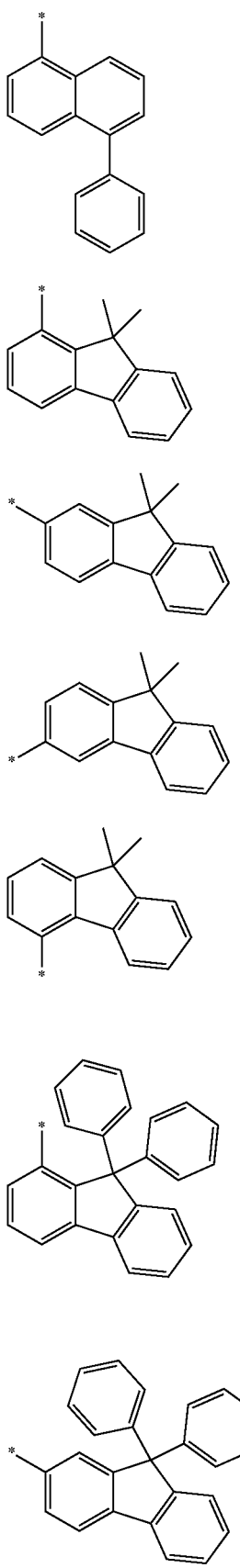
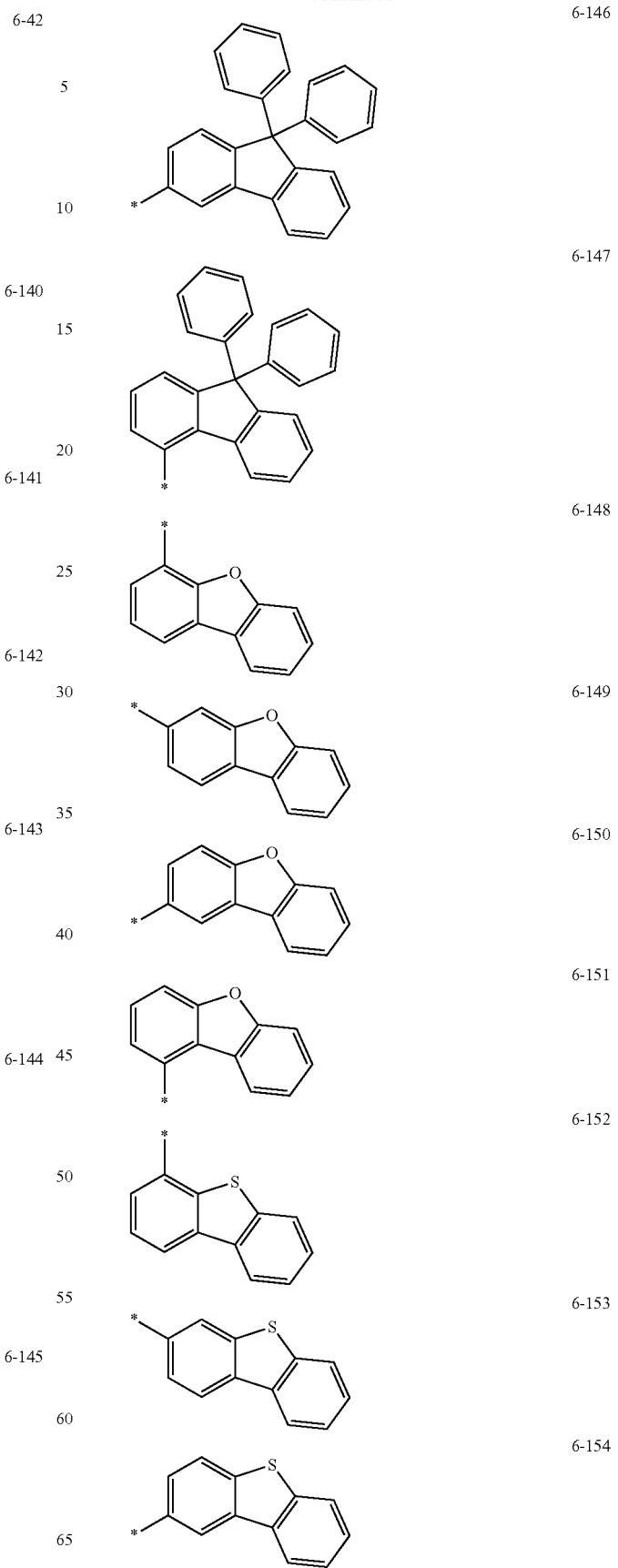

-continued 6-155

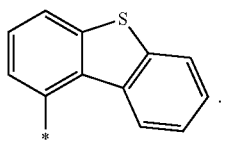

In Formulae 6-1 to 6-42 and 6-140 to 6-155,
t-Bu indicates a tert-butyl group;
Ph indicates a phenyl group; and
* indicates a binding site to a neighboring atom.

For example, $R_{23}$ in Formula 2 may be selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, and —Si($Q_3$)($Q_4$)($Q_5$), where $Q_3$ to $Q_5$ may be each independently selected from a $C_1$-$C_{60}$ alkyl group and a $C_6$-$C_{60}$ aryl group, but embodiments of the present invention are not limited thereto.

In some embodiments, $R_{23}$ in Formula 2 may be selected from hydrogen, deuterium, —F, —Cl, —Br, —I, a cyano group, a nitro group, a $C_1$-$C_{60}$ alkyl group, a $C_1$-$C_{60}$ alkoxy group, a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, a triazinyl group, —Si($CH_3$)$_3$, and —Si(Ph)$_3$, but embodiments of the present invention are not limited thereto.

In some embodiments, $R_{23}$ in Formula 2 may be selected from hydrogen, a methyl group, an ethyl group, a tert-butyl group, a methoxy group, an ethoxy group, ter-butoxy group, —Si($CH_3$)$_3$, a phenyl group, and a naphthyl group, but embodiments of the present invention are not limited thereto.

For example, b21 to b23 in Formula 2 may be each independently selected from 1 and 2, but embodiments of the present invention are not limited thereto.

For example, n21 in Formula 2 may be 1, but embodiments of the present invention are not limited thereto.

In some embodiments, the second material represented by Formula 2 may be represented by one of Formulae 2A and 2B, but embodiments of the present invention are not limited thereto:

Formula 2A

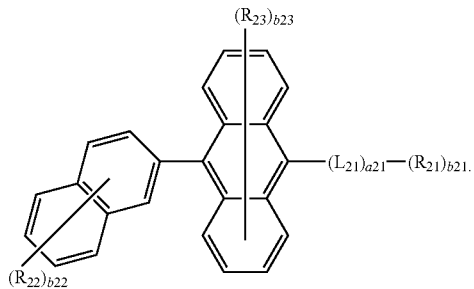

Formula 2B

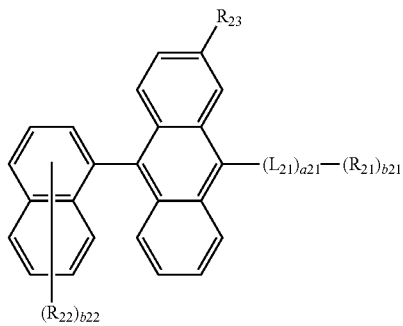

In Formulae 2A and 2B,
descriptions of $L_{21}$, a21, $R_{21}$ to $R_{23}$, and b21 to b23 are the same as described in connection with Formula 2.

In some embodiments, the second material represented by Formula 2 may be represented by one of Formulae 2A-1 and 2B-1, but embodiments of the present invention are not limited thereto:

Formula 2A-1

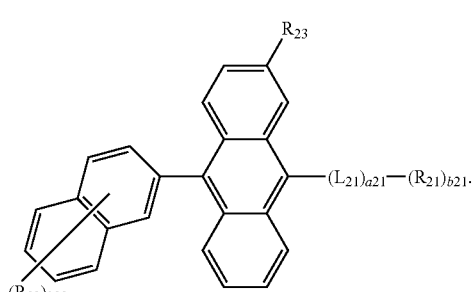

Formula 2B-1

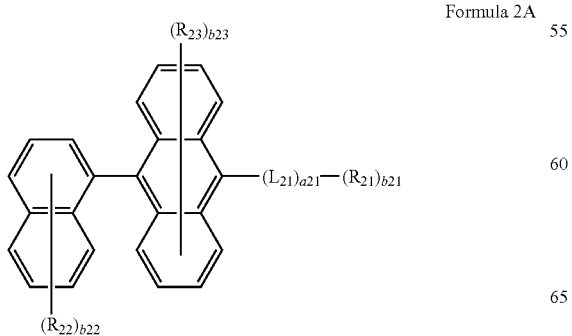

In Formulae 2A-1 and 2B-1,
descriptions of $L_{21}$, a21, $R_{21}$ to $R_{23}$, b21, and b22 may be the same as described in connection with Formula 2.

For example, the second material represented by Formula 2 may be represented by one selected from Compounds H101 to H188 and H201 to H218, but embodiments of the present invention are not limited thereto:

171  172
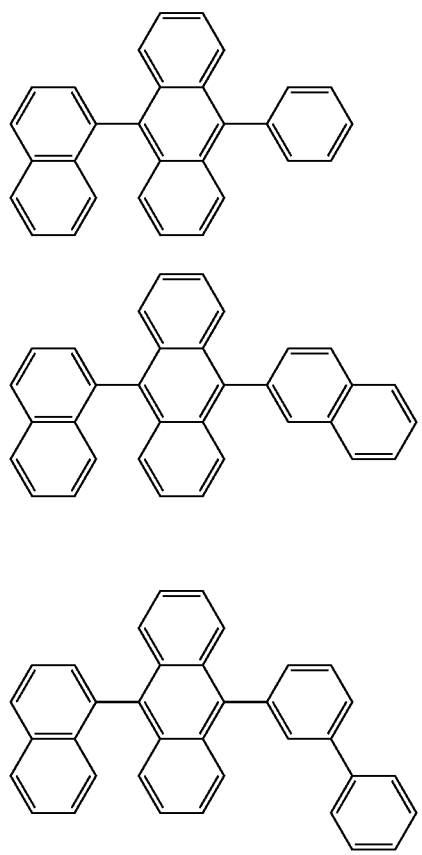
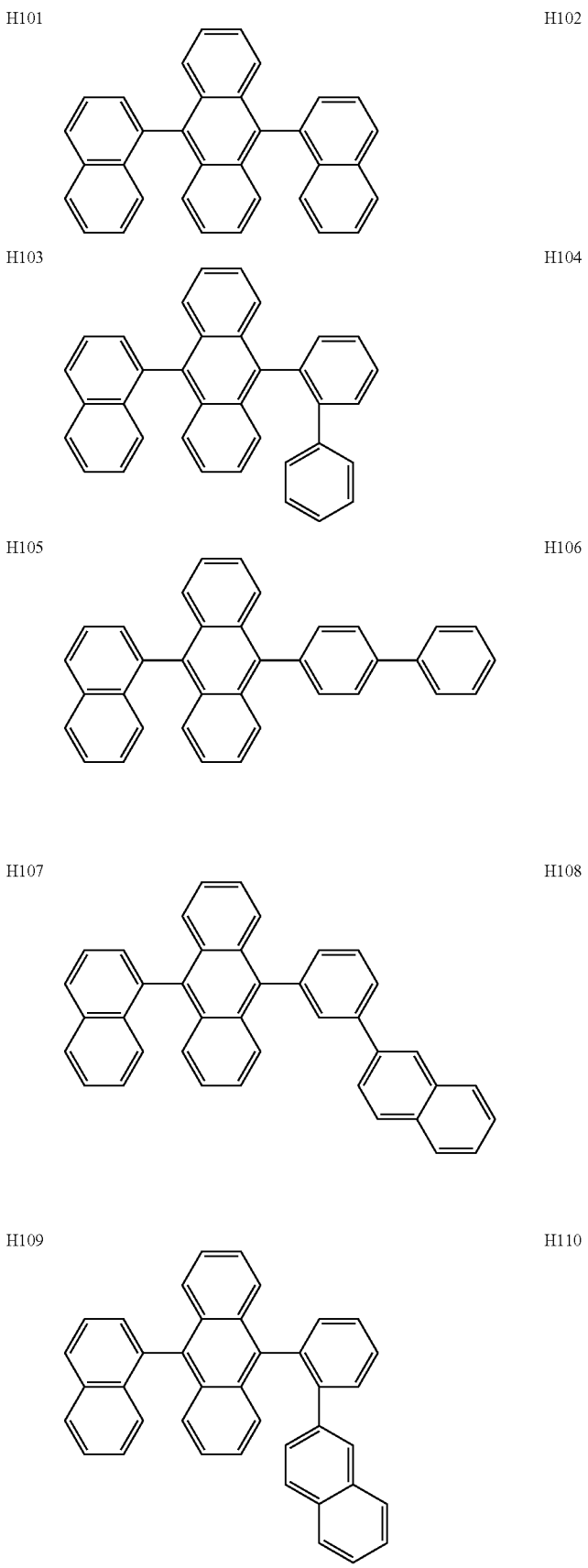

-continued
H111
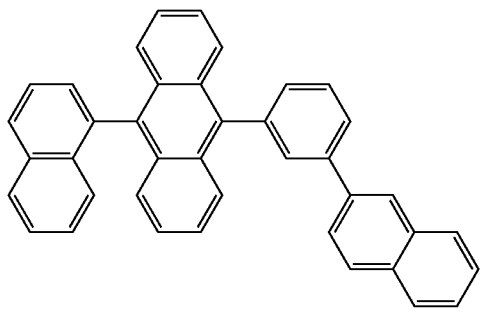
H112
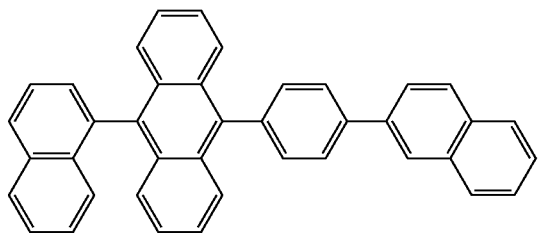
H113
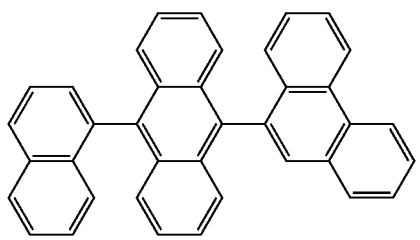
H114
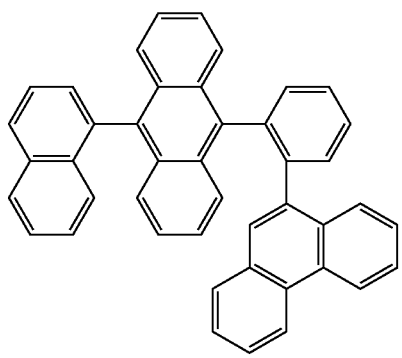
H115
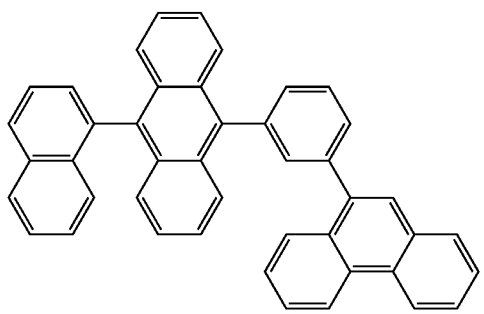
H116
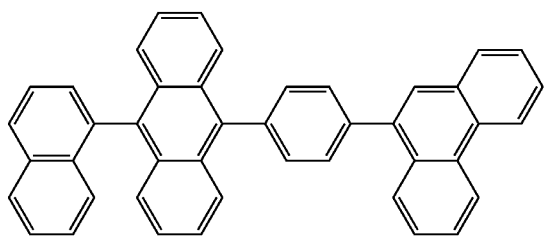
H117
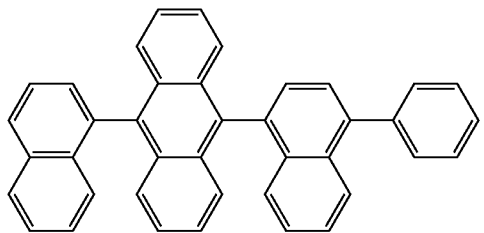
H118
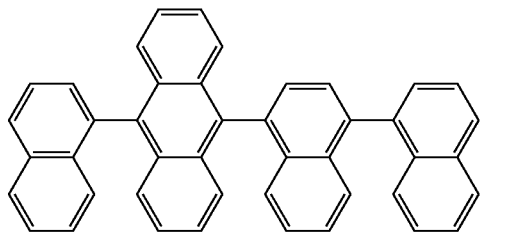
H119
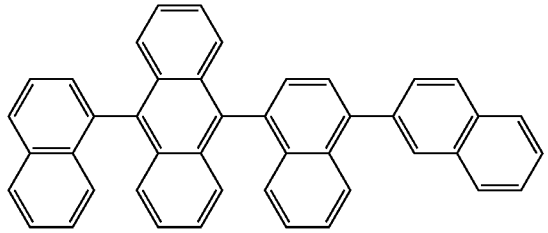
H120
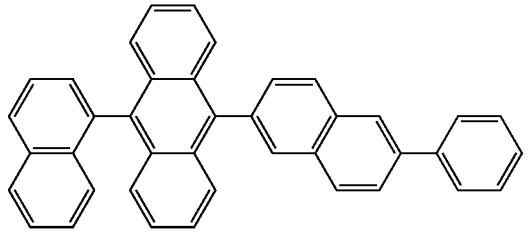

-continued
H121
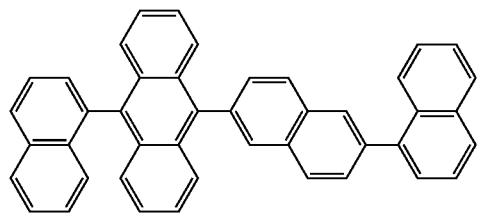
H122
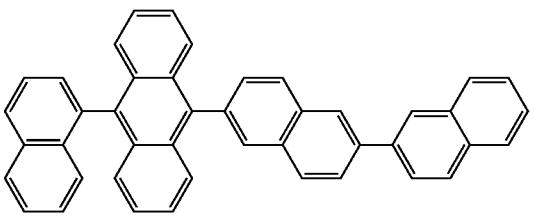
H123
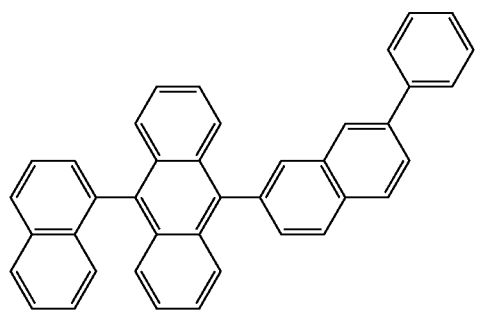
H124
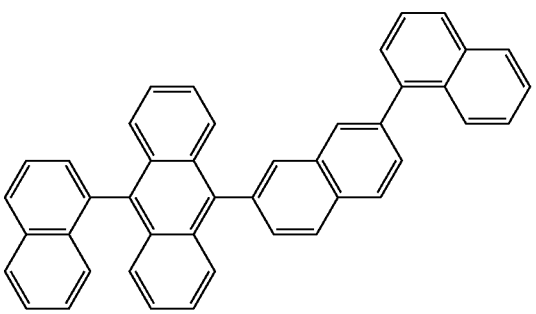
H125
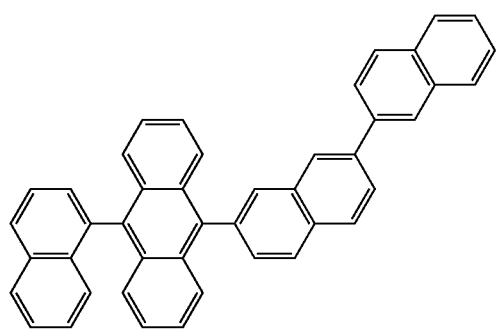
H126
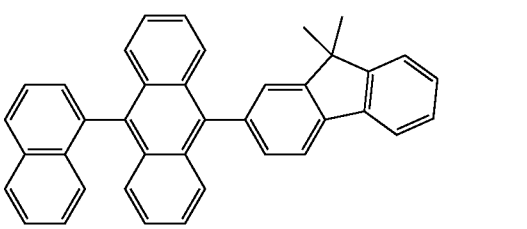
H127
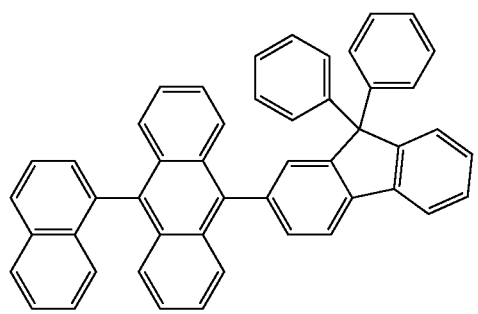
H128
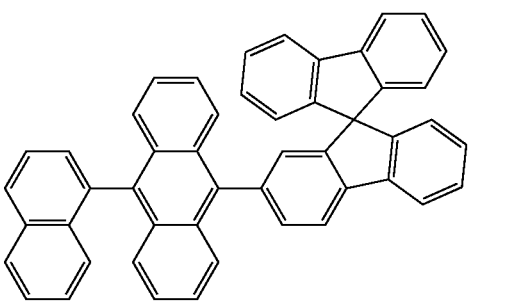
H129
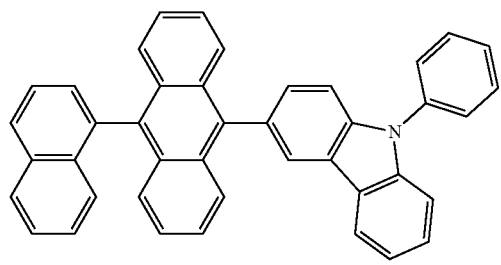
H130
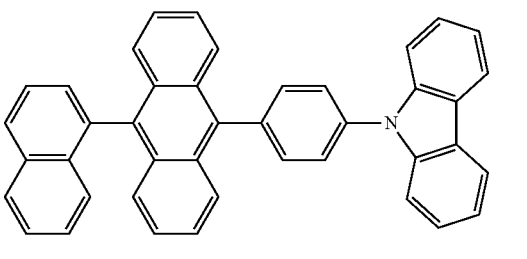

-continued
H131
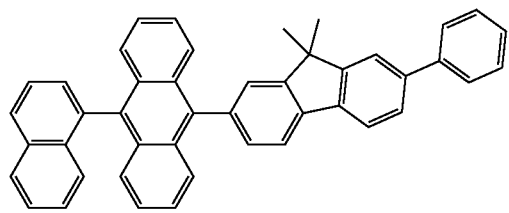
H132
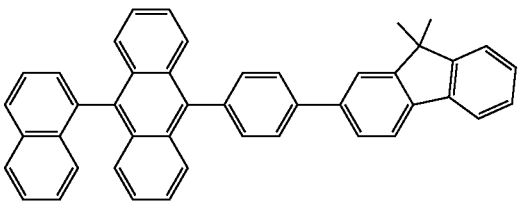
H133
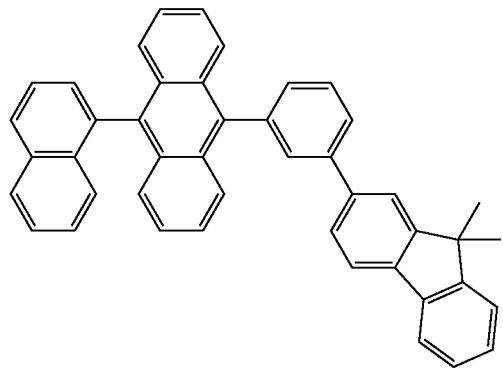
H134
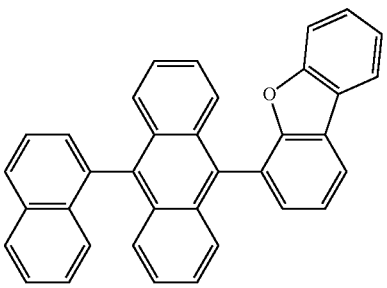
H135
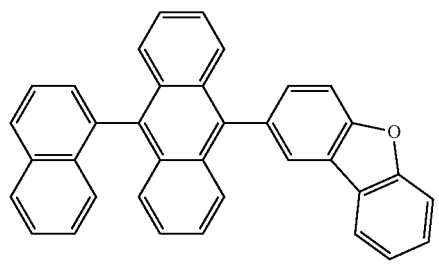
H136
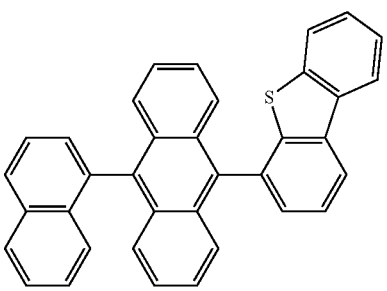
H137
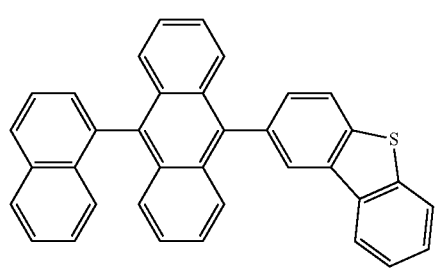
H138
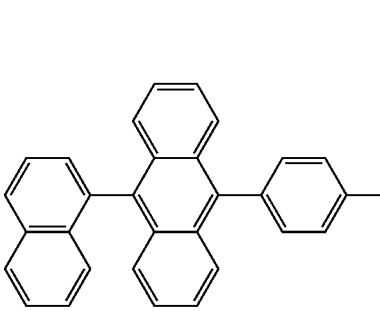
H139
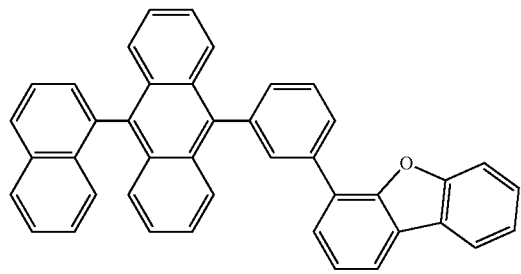
H140
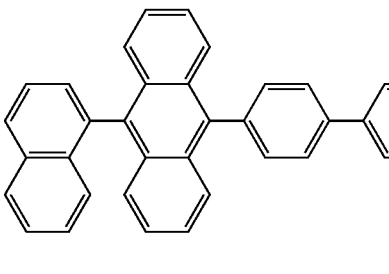

-continued
H141
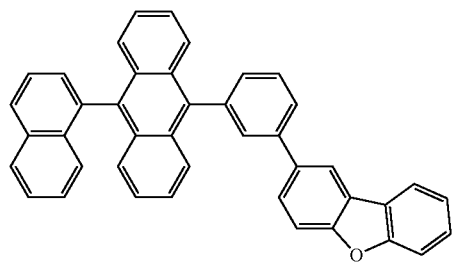
H142
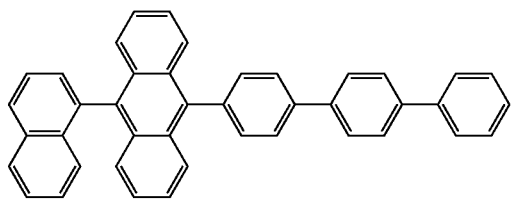
H143
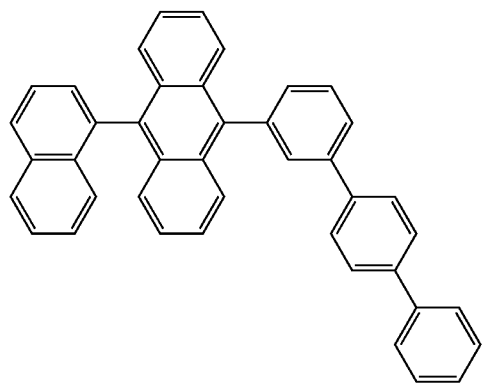
H144
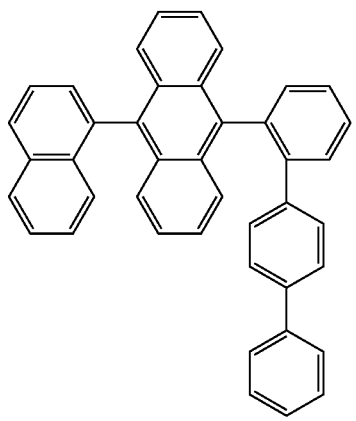
H145
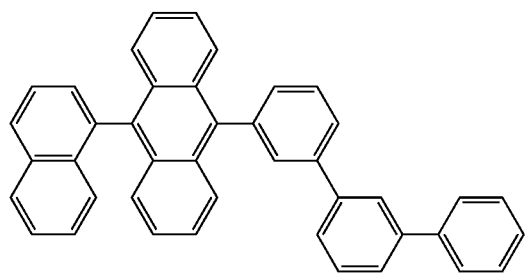
H146
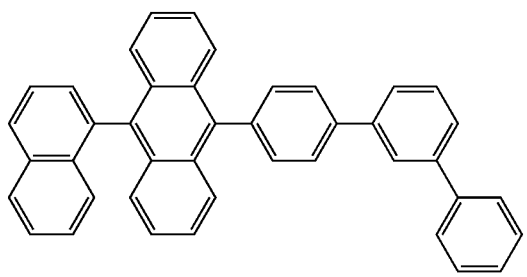
H147
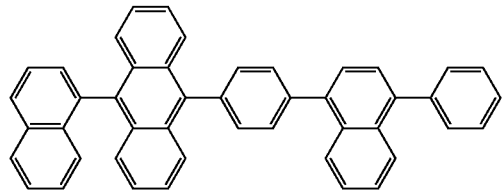
H148
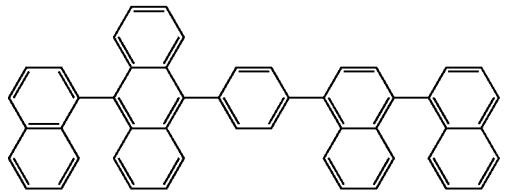
H149
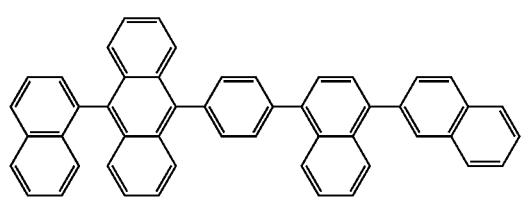
H150
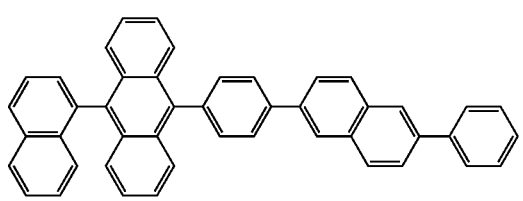
H151
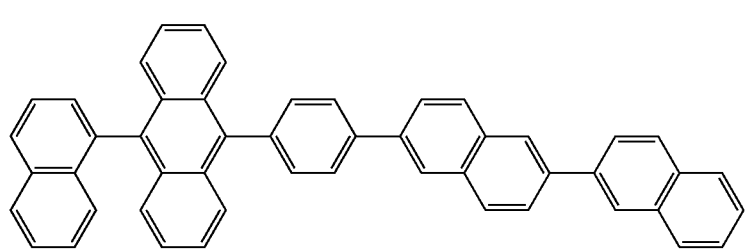

-continued
H152
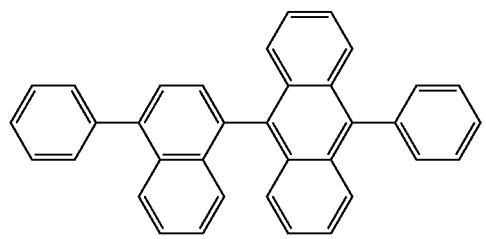
H153
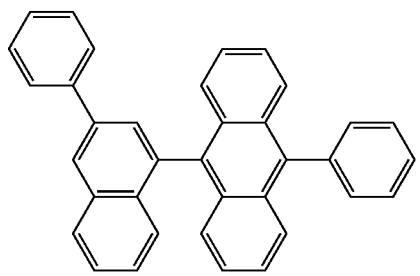
H154
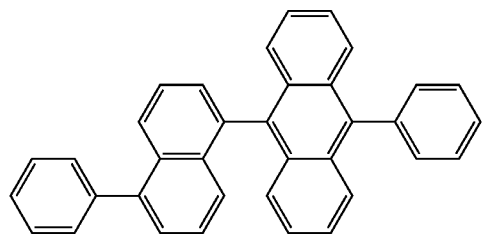
H155
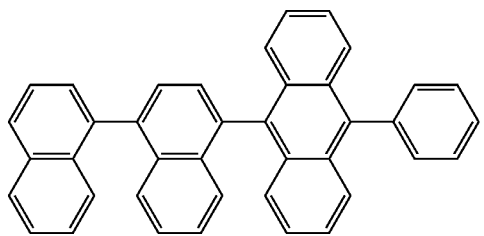
H156
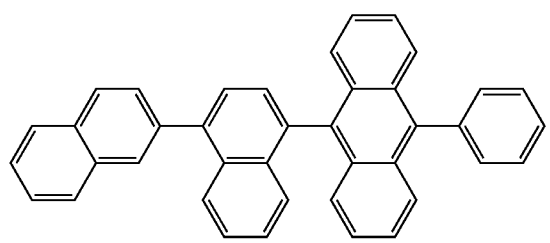
H157
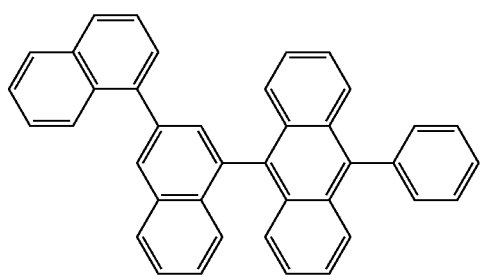
H158
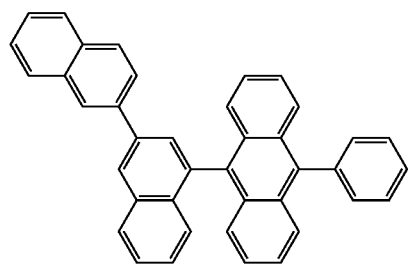
H159
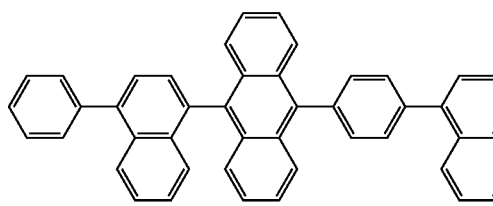
H160
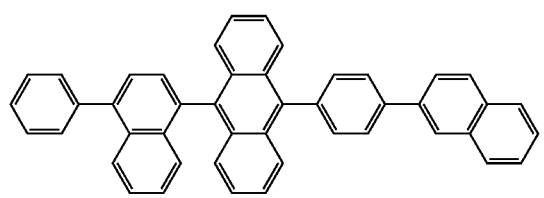
H161
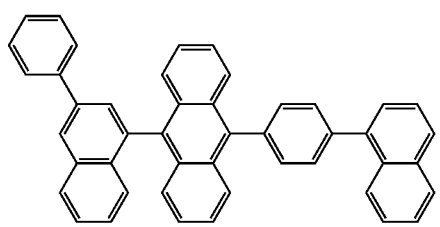
H162
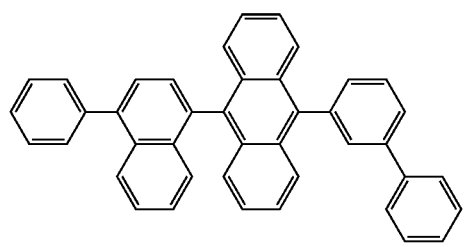
H163
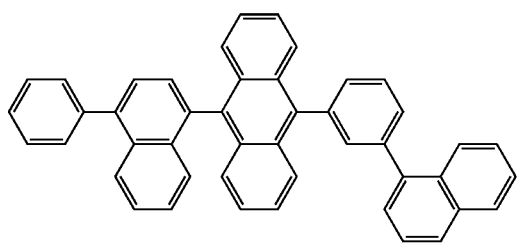

-continued
H164
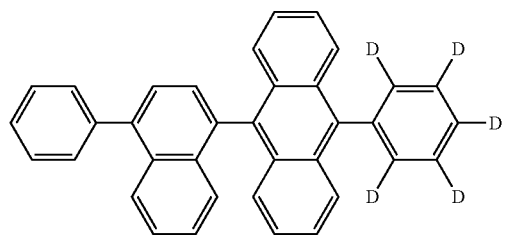
H165
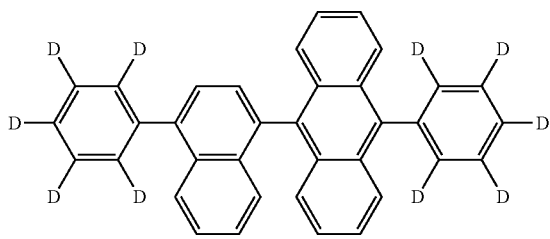
H166
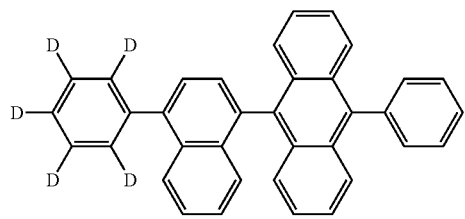
H167
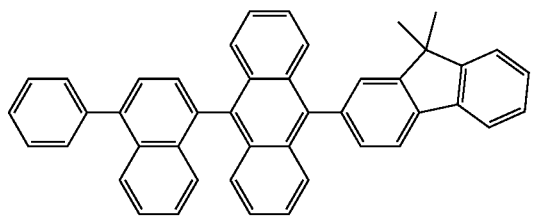
H168
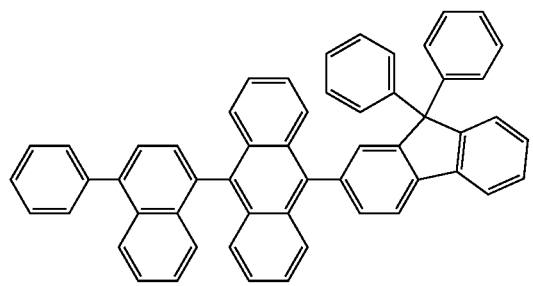
H169
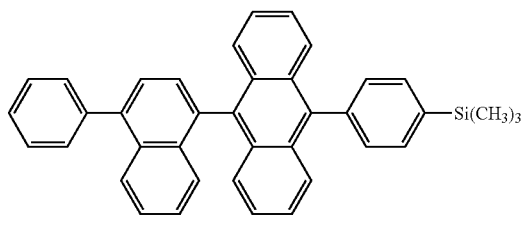
H170
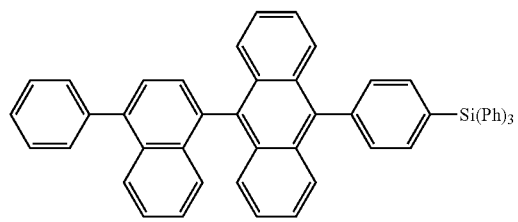
H171
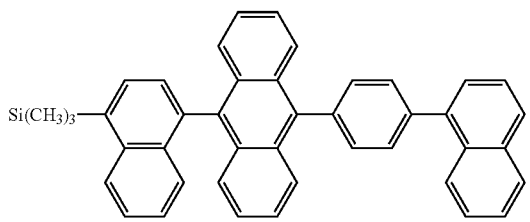
H172
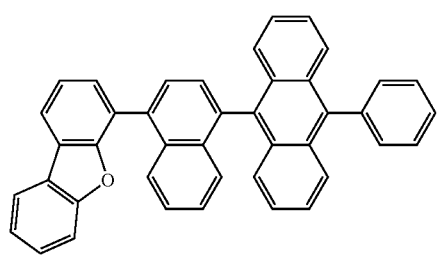
H173
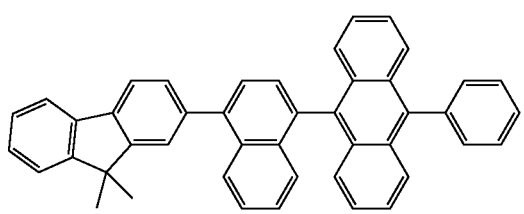
H174
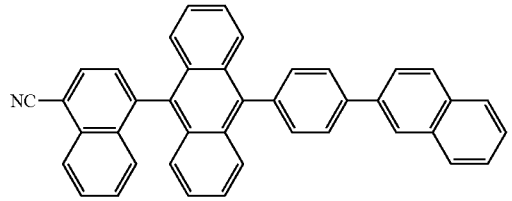
H175
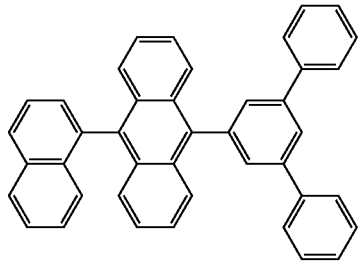

-continued
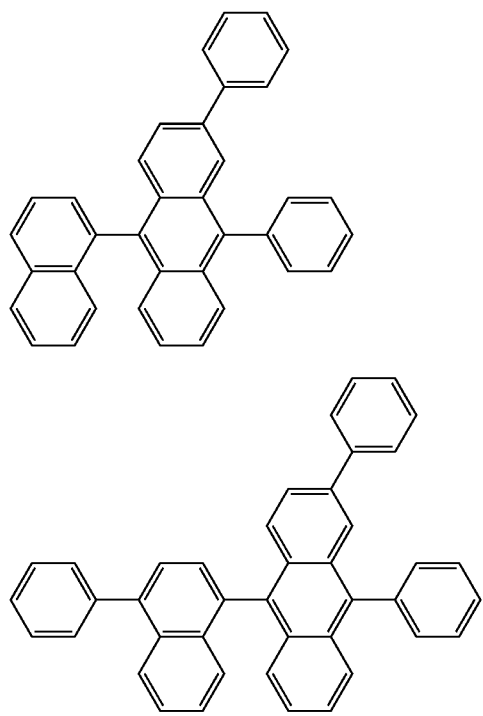
H176
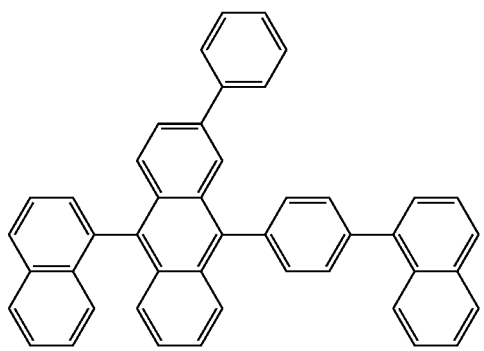
H177
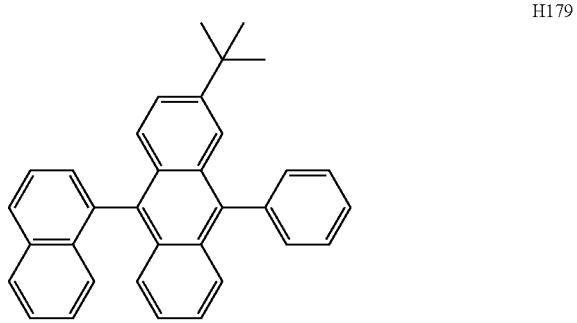
H178 H179
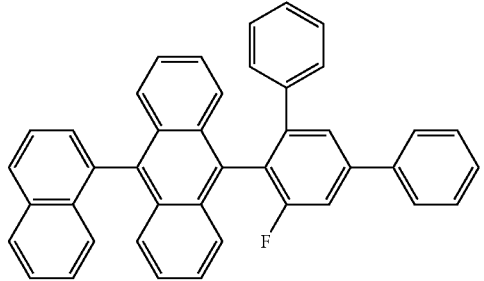
H180 H181
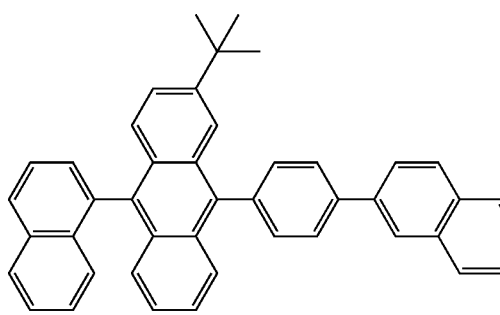
H182 H183
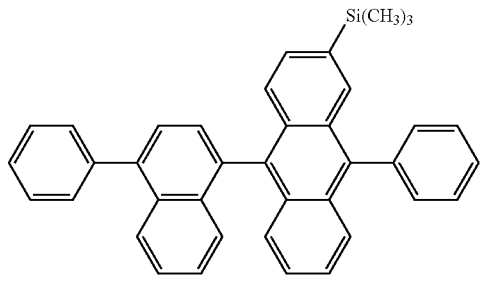
H184 H185

-continued
H186
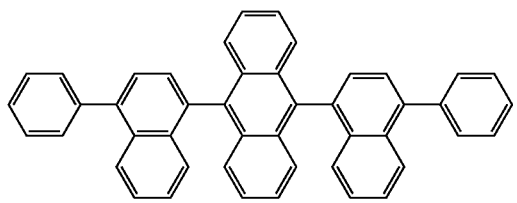
H187
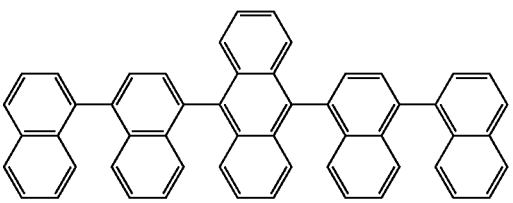
H188
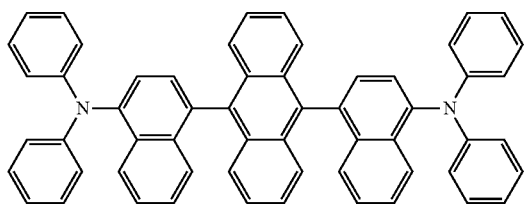
H201
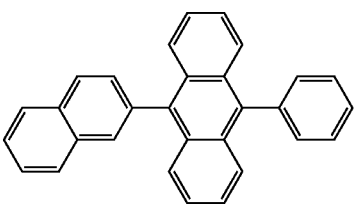
H202
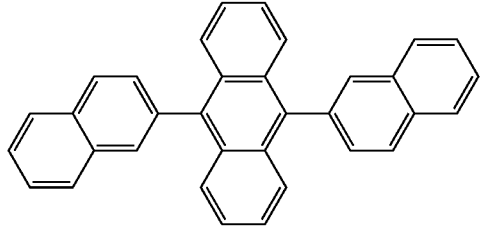
H203
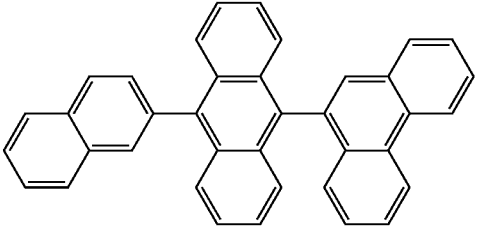
H204
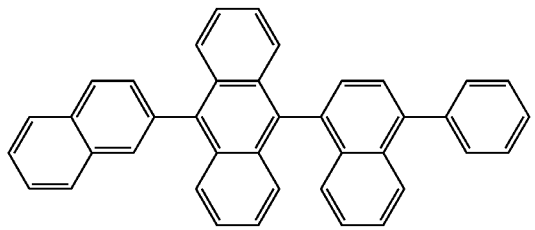
H205
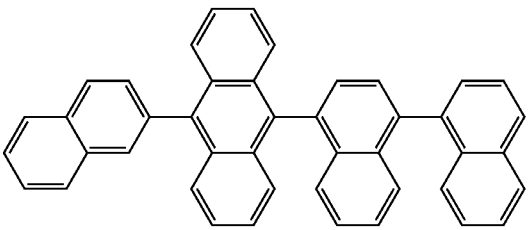
H206
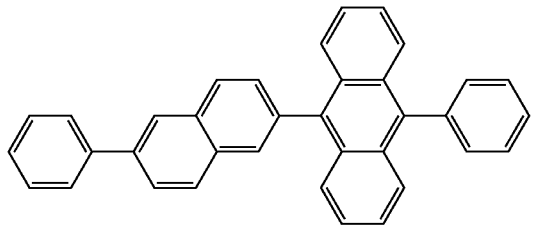
H207
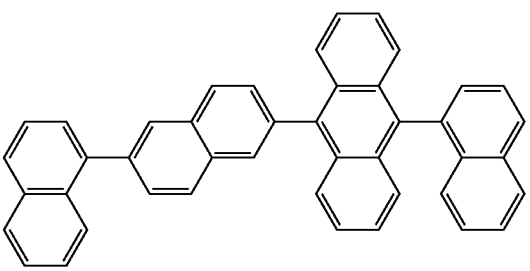
H208
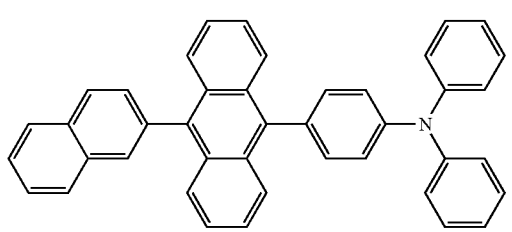
H209
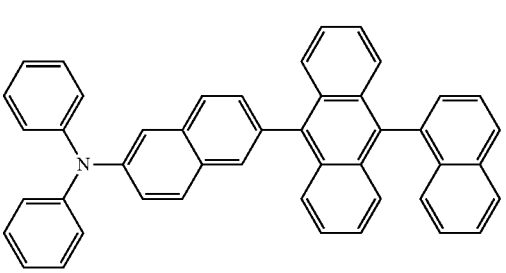

-continued
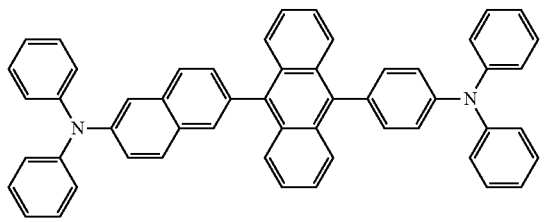
H210
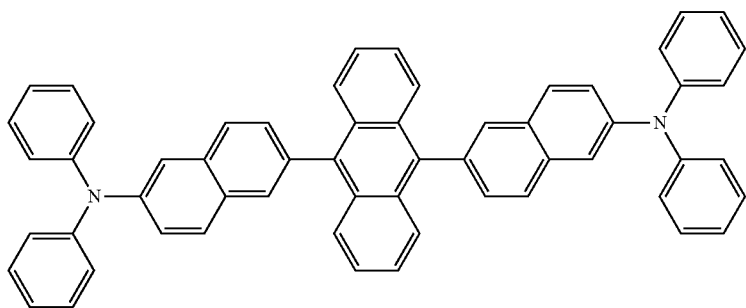
H211
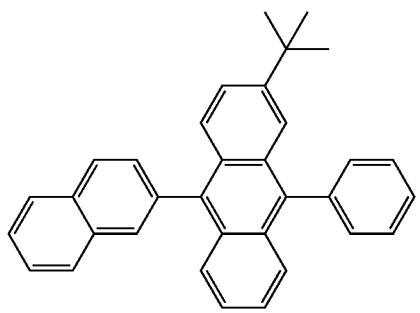
H212
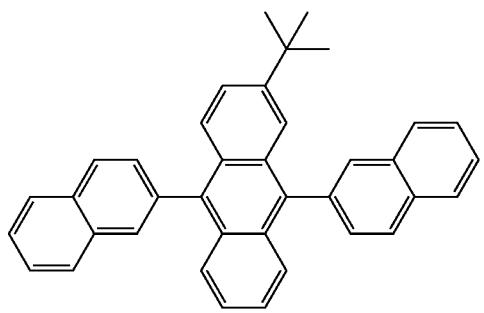
H213
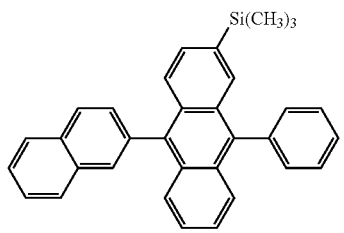
H214
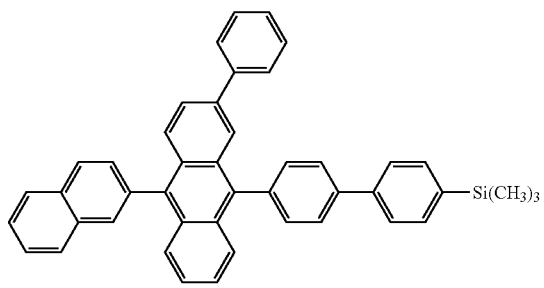
H215
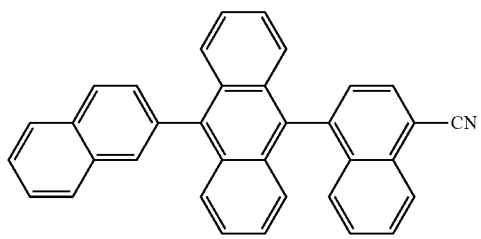
H216
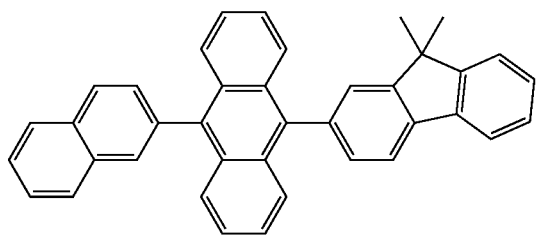
H217

H218

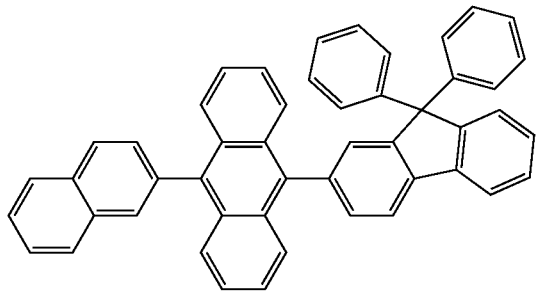

In some embodiments, the host may include a second material represented by one of Formulae 2-1 to 2-4:

Formula 2-1

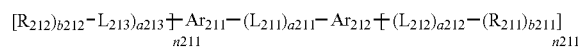

Formula 2-2

Formula 2-3

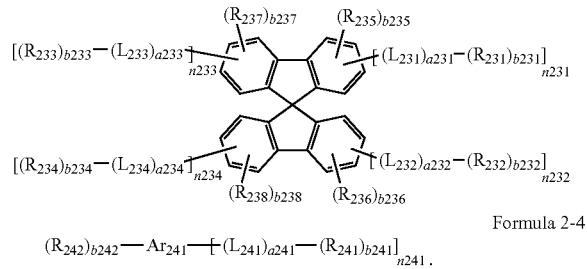

Formula 2-4

$(R_{242})_{b242}-Ar_{241}+(L_{241})_{a241}-(R_{241})_{b241}]_{n241}$.

In Formulae 2-1 to 2-4, $Ar_{211}$ may be selected from a naphthalene, an anthracene, a triphenylene, a pyrene, a chrysene, and a perylene;

$Ar_{212}$ may be selected from an anthracene, a triphenylene, a pyrene, a chrysene, and a perylene;

$Ar_{241}$ may be selected from a benzene, a biphenyl, and a triphenylene;

$L_{211}$ to $L_{213}$, $L_{221}$, $L_{231}$ to $L_{234}$, and $L_{241}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a211 to a213, a221, a231 to a234, and a241 may be each independently selected from 0, 1, and 2;

$R_{231}$ to $R_{234}$ and $R_{241}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b231 to b234 and b241 may be each independently selected from 1, 2, and 3;

$R_{211}$, $R_{212}$, $R_{221}$, $R_{222}$, $R_{235}$ to $R_{238}$, and $R_{242}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{211}$)($Q_{212}$)($Q_{213}$), —N($Q_{214}$)($Q_{215}$), and —B($Q_{216}$)($Q_{217}$);

b211, b212, b221, b222, b235 to b238 and b242 may be each independently selected from 1, 2, and 3;

n211, n212 and n221 may be each independently selected from 1, 2, and 3;

n231 to n234 may be each independently selected from 0, 1, and 2, provided that the sum of n231 to n234 may be selected from 1, 2, 3, 4, 5, and 6;

n241 may be selected from 3, 4, 5, 6, 7 and 8; and at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$) and —B($Q_{36}$)($Q_{37}$), where $Q_{211}$ to $Q_{217}$, $Q_{11}$ to $Q_{17}$, $Q_{21}$ to $Q_{27}$ and $Q_{31}$ to $Q_{37}$ may be each independently selected from hydrogen, $C_1$-$C_{60}$ alkyl group, $C_1$-$C_{60}$ alkoxy group, $C_6$-$C_{60}$ aryl group, $C_1$-$C_{60}$ heteroaryl group, a monovalent non-aromatic condensed polycyclic group, and a monovalent non-aromatic condensed heteropolycyclic group.

For example, $Ar_{211}$ and $Ar_{212}$ in Formula 2-1 may be each independently selected from an anthracene, a triphenylene, a pyrene, a chrysene, and a perylene, but embodiments of the present invention are not limited thereto.

In some embodiments, $Ar_{211}$ and $Ar_{212}$ in Formula 2-1 may be identical to each other, but embodiments of the present invention are not limited thereto.

In some embodiments, $Ar_{211}$ and $Ar_{212}$ in Formula 2-1 may be an anthracene, but embodiments of the present invention are not limited thereto.

For example, $L_{211}$ to $L_{213}$, $L_{221}$, $L_{231}$ to $L_{234}$ and $L_{241}$ in Formulae 2-1 to 2-4 may be each independently selected from a phenylene group, a pentalenylene group, an indenylene group, a naphthylene group, an azulenylene group, a heptalenylene group, an indacenylene group, an acenaphthylene group, a fluorenylene group, an spiro-fluorenylene group, an benzofluorenylene group, an dibenzofluorenylene group, a phenalenylene group, a phenanthrenylene group, an anthracenylene group, a fluoranthenylene group, an triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, a imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, a oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group, but embodiments of the present invention are not limited thereto.

In some embodiments, $L_{211}$ to $L_{213}$, $L_{221}$, $L_{231}$ to $L_{234}$ and $L_{241}$ in Formulae 2-1 to 2-4 may be each independently selected from a phenylene group, a naphthylene group, a fluorenylene group, a phenanthrenylene group, an anthracenylene group, a triphenylenylene group, a pyrrolylene group, a thiophenylene group, a furanylene group, a pyridinylene group, a pyrazinylene group, a pyrimidinylene group, an indolylene group, a quinolinylene group, an isoquinolinylene group, a benzoquinolinylene group, a naphthyridinylene group, a quinoxalinylene group, a quinazolinylene group, a cinnolinylene group, a carbazolylene group, a phenanthridinylene group, a benzimidazolylene group, a benzofuranylene group, a benzothiophenylene group, a triazolylene group, a dibenzofuranylene group, and a dibenzothiophenylene group; and a phenylene group, a naphthylene group, a fluorenylene group, a phenanthrenylene group, an anthracenylene group, a triphenylenylene group, a pyrrolylene group, a thiophenylene group, a furanylene group, a pyridinylene group, a pyrazinylene group, a pyrimidinylene group, an indolylene group, a quinolinylene group, an isoquinolinylene group, a benzoquinolinylene group, a naphthyridinylene group, a quinoxalinylene group, a quinazolinylene group, a cinnolinylene group, a carbazolylene group, a phenanthridinylene group, a benzimidazolylene group, a benzofuranylene group, a benzothiophenylene group, a triazolylene group, a dibenzofuranylene group, and a dibenzothiophenylene group, each substituted with at least one selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present invention are not limited thereto.

In some embodiments, $L_{211}$ to $L_{213}$, $L_{221}$, $L_{231}$ to $L_{234}$ and $L_{241}$ in Formulae 2-1 to 2-4 may be each independently selected from groups represented by Formulae 3-1 to 3-31, but embodiments of the present invention are not limited thereto:

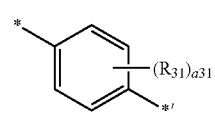

3-1

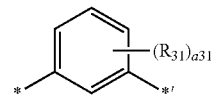

3-2

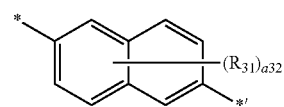

3-3

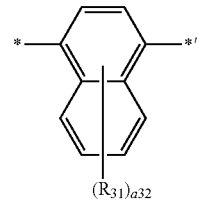

3-4

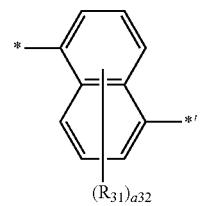

3-5

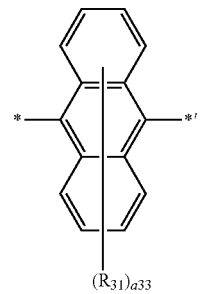

3-6

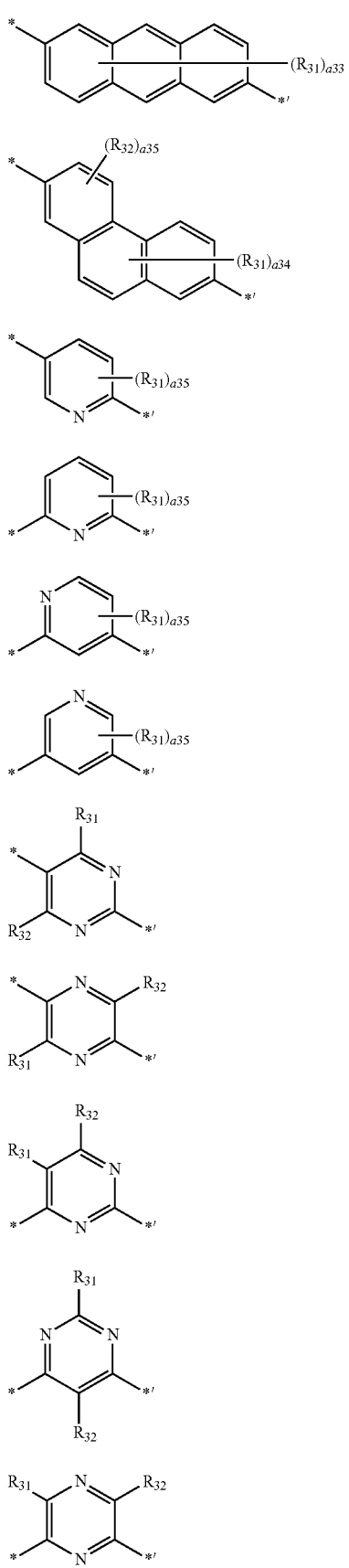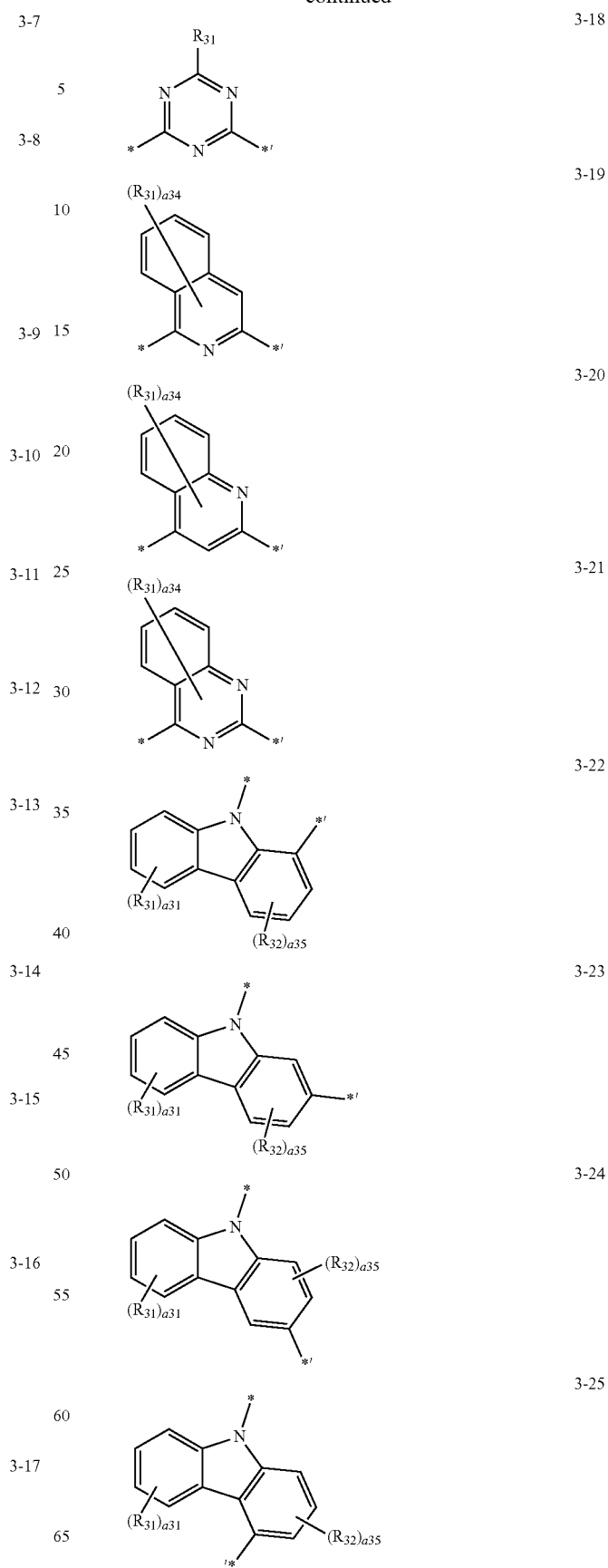

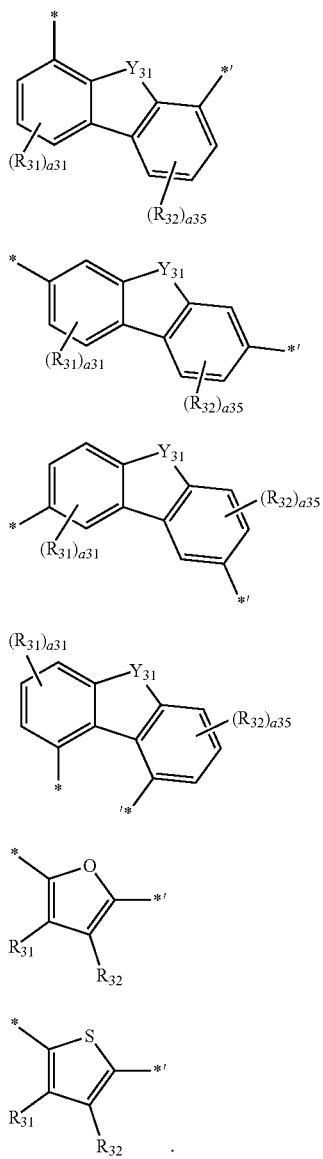

a34 is selected from 1, 2, 3, 4, and 5;

a35 is selected from 1, 2, and 3; and

* and *' each independently indicate a binding site to a neighboring atom.

In some embodiments, $L_{211}$ to $L_{213}$, $L_{221}$, $L_{231}$ to $L_{234}$ and $L_{241}$ in Formulae 2-1 to 2-4 may be each independently selected from groups represented by Formulae 3-1 to 3-31; $Y_{31}$ in Formulae 3-2 to 3-31 may be selected from $C(R_{33})(R_{34})$, $N(R_{33})$, O, and S; $R_{31}$ to $R_{34}$ may be each independently selected from hydrogen, deuterium, —F, —Cl, —Br, —I, a methyl group, an ethyl group, a tert-butyl group, a methoxy group, an ethoxy group, tert-butoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present invention are not limited thereto.

In some embodiments, $L_{211}$ to $L_{213}$, $L_{221}$, $L_{231}$ to $L_{234}$, and $L_{241}$ in Formulae 2-1 to 2-4 may be each independently selected from groups represented by Formulae 4-1 to 4-56, but embodiments of the present invention are not limited thereto:

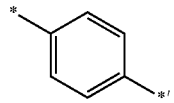

4-1

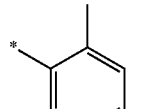

4-2

4-3

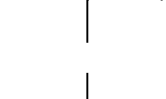

4-4

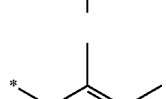

4-5

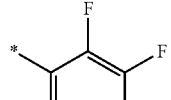

4-6

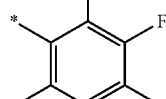

In Formulae 3-1 to 3-31, $Y_{31}$ is selected from $C(R_{33})(R_{34})$, $N(R_{33})$, O, S, and $Si(R_{33})(R_{34})$;

$R_{31}$ to $R_{34}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, $C_1$-$C_{20}$ alkyl group, $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a31 is selected from 1, 2, 3, and 4;

a32 is selected from 1, 2, 3, 4, 5, and 6;

a33 is selected from 1, 2, 3, 4, 5, 6, 7, and 8;

201
-continued
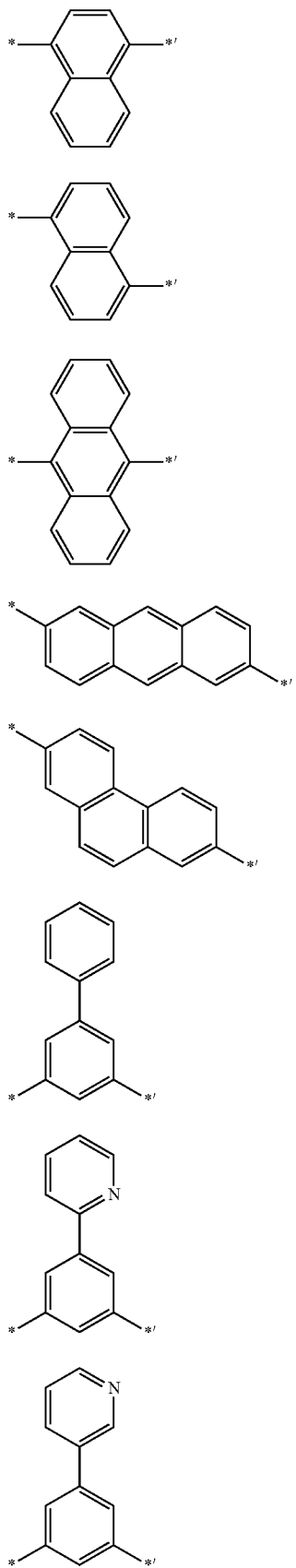
202
-continued
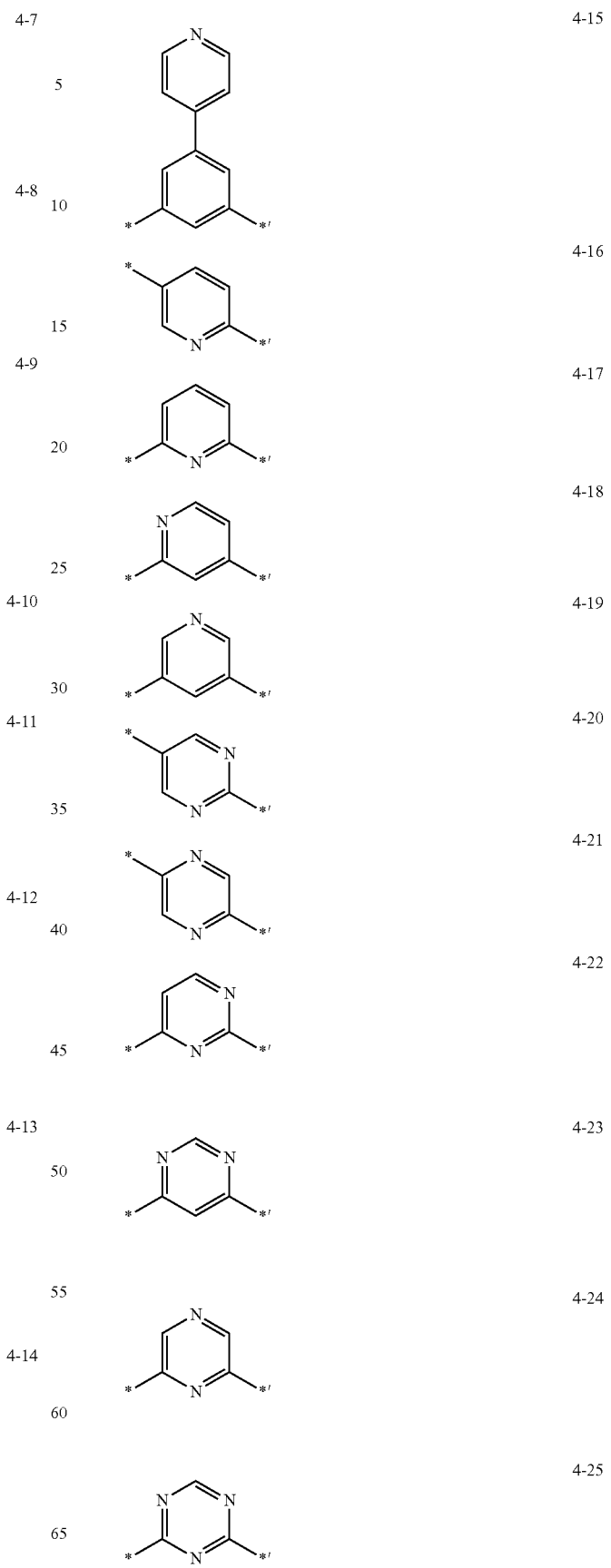

203
-continued
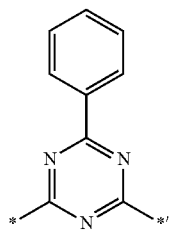
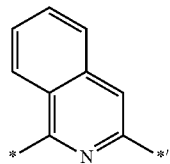
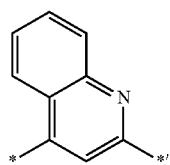
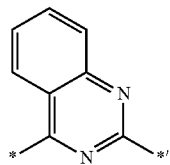
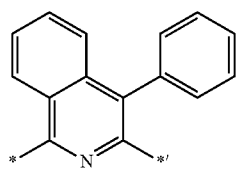
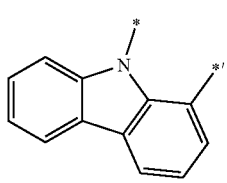
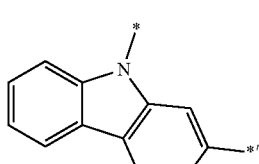
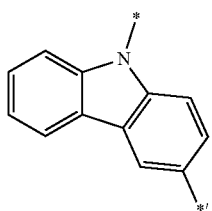
204
-continued
4-26
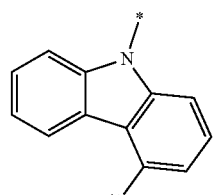
4-27
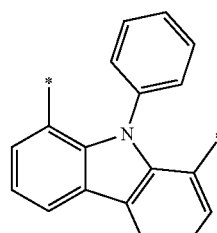
4-28
4-29
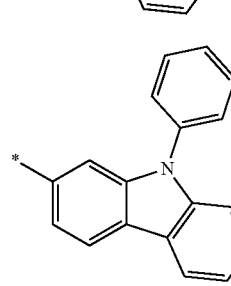
4-30
4-31
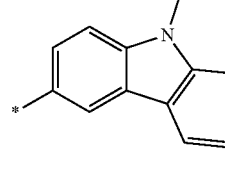
4-32
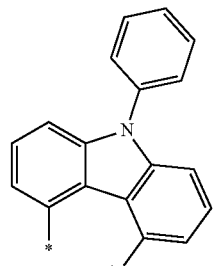
4-33
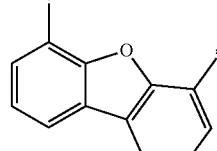
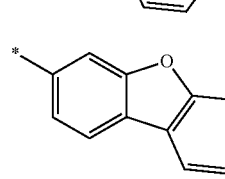
4-34
4-35
4-36
4-37
4-38
4-39
4-40

205
-continued
4-41
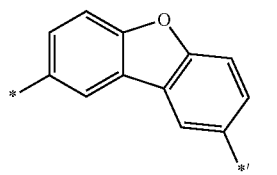
4-42
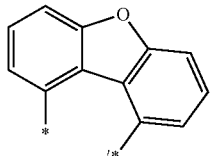
4-43
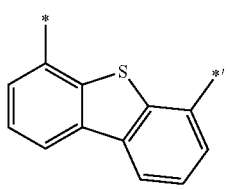
4-44
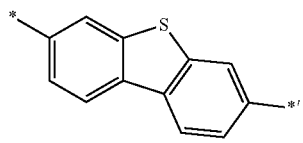
4-45
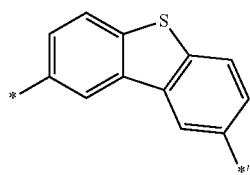
4-46
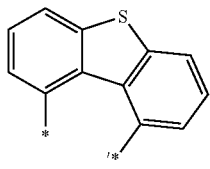
4-47
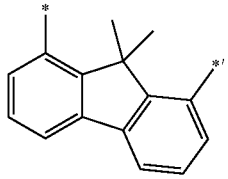
4-48
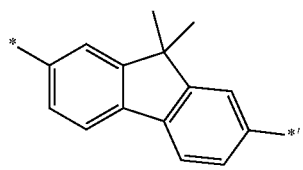
4-49
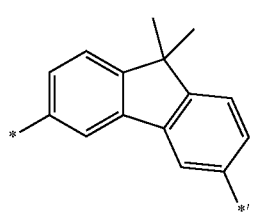
206
-continued
4-50
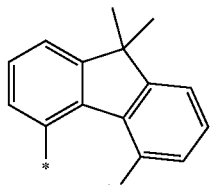
4-51
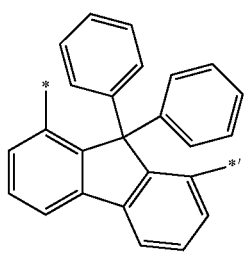
4-52
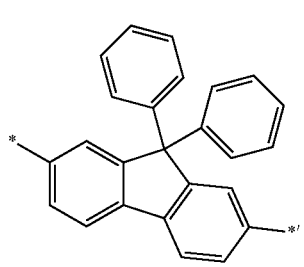
4-53
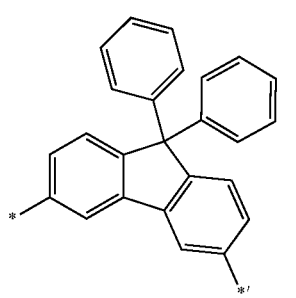
4-54
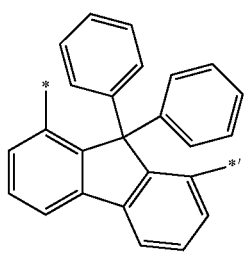
4-55
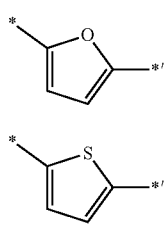
4-56
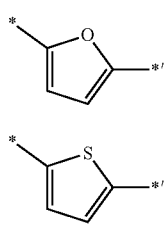
In Formulae 4-1 to 4-56,
* and *' each independently indicate a binding site to a neighboring atom.
In some embodiments, $L_{211}$ to $L_{213}$, $L_{221}$, $L_{231}$ to $L_{234}$ and $L_{241}$ in Formulae 2-1 to 2-4 may be each independently selected from groups represented by Formulae 4-1 to 4-12 and 4-31 to 4-54, but embodiments of the present invention are not limited thereto.

For example, a211, a212, a213, a221, a231 to a234 and a241 in Formulae 2-1 to 2-4 may be each independently 0 or 1, but embodiments of the present invention are not limited thereto.

For example, $R_{231}$ to $R_{234}$ and $R_{241}$ in Formulae 2-3 and 2-4 may be each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a biphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si$(Q_{33})(Q_{34})(Q_{35})$, where $Q_{33}$ to $Q_{35}$ may be each independently selected from a $C_1$-$C_{60}$ alkyl group and a $C_6$-$C_{60}$ aryl group, but embodiments of the present invention are not limited thereto.

In some embodiments, $R_{231}$ to $R_{234}$ and $R_{241}$ in Formulae 2-3 and 2-4 may be each independently selected from a phenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group; and a phenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, $C_1$-$C_{20}$ alkyl group, $C_1$-$C_{20}$ alkoxy group, a phenyl group, and a naphthyl group, but embodiments of the present invention are not limited thereto.

In some embodiments, $R_{231}$ to $R_{234}$ and $R_{241}$ in Formulae 2-3 and 2-4 may be each independently selected from groups represented by Formulae 7-1 to 7-16, but embodiments of the present invention are not limited thereto:

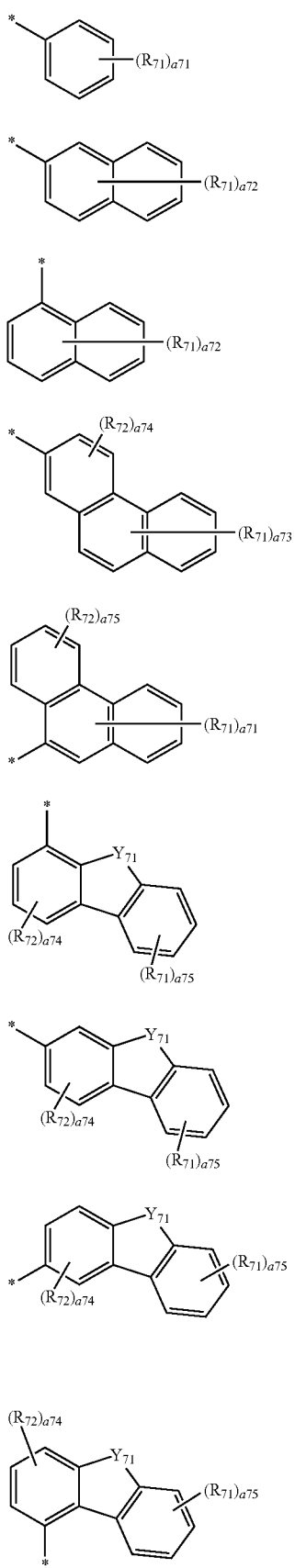
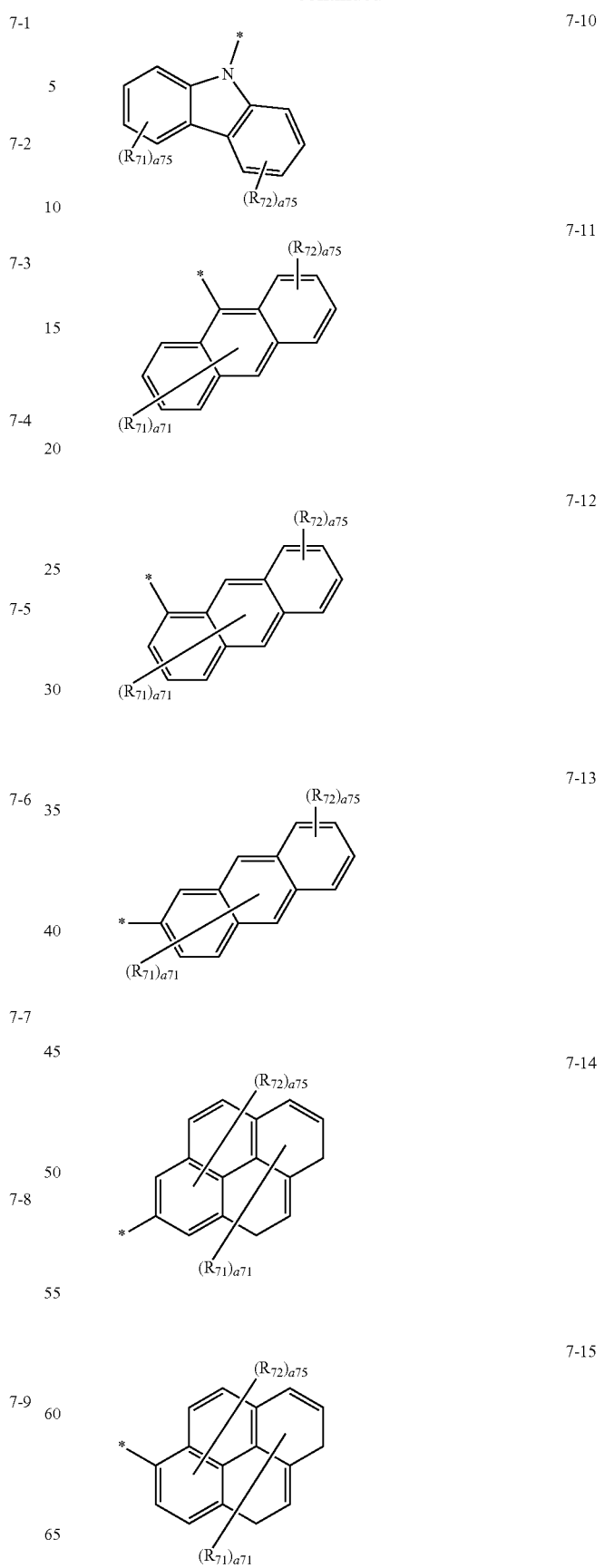

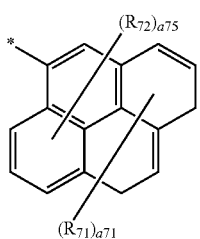
7-16

In Formulae 7-1 to 7-16, $Y_{71}$ may be selected from $C(R_{73})(R_{74})$, $N(R_{73})$, O, and S;

$R_{71}$ to $R_{74}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, $C_1$-$C_{20}$ alkyl group, $C_1$-$C_{20}$ alkoxy group, a phenyl group, and a naphthyl group;

a71 is selected from 1, 2, 3, 4, and 5;

a72 is selected from 1, 2, 3, 4, 5, 6, and 7;

a73 is selected from 1, 2, 3, 4, 5, and 6;

a74 is selected from 1, 2, and 3;

a75 is selected from 1, 2, 3, and 4; and

* indicates a binding site to a neighboring atom.

In some embodiments, $R_{231}$ to $R_{234}$ and $R_{241}$ in Formulae 2-3 and 2-4 may be each independently selected from Formulae 8-1 to 8-29, but embodiments of the present invention are not limited thereto:

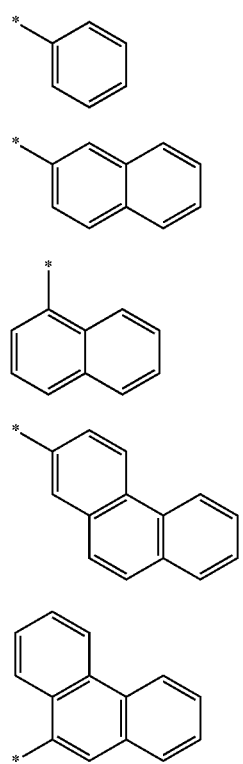

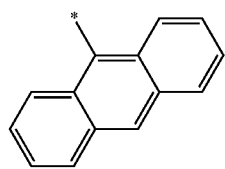

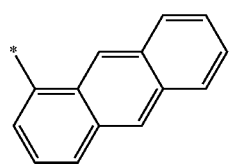

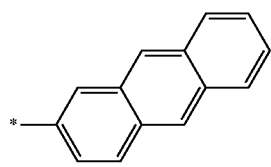

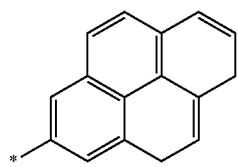

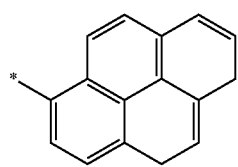

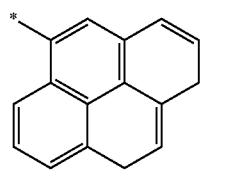

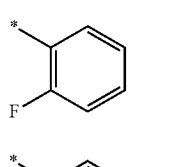

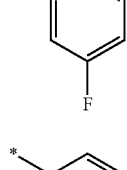

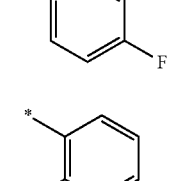

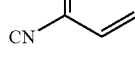

-continued

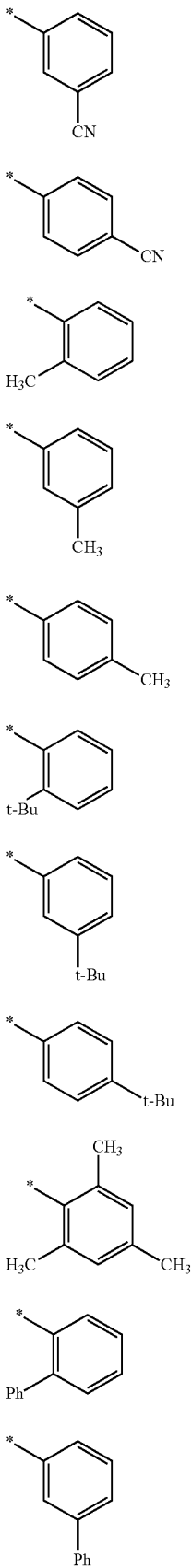

8-16
8-17
8-18
8-19
8-20
8-21
8-22
8-23
8-24
8-25
8-26

-continued

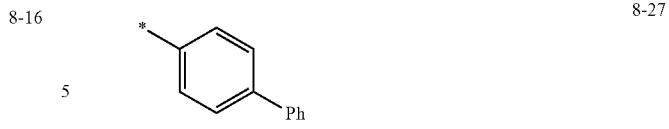

8-27

8-28

8-29

In Formulae 8-1 to 8-29,

* indicates a binding site to a neighboring atom.

For example, b231 to b234, and b241 in Formulae 2-3 and 2-4 may be each independently selected from 1 and 2, but embodiments of the present invention are not limited thereto.

For example, $R_{211}$, $R_{212}$, $R_{221}$, $R_{222}$, $R_{235}$ to $R_{238}$ and $R_{242}$ in Formulae 2-1 to 2-4 may be each independently selected from hydrogen, deuterium, —F, —Cl, —Br, —I, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and $C_1$-$C_{60}$ alkoxy group, each substituted with at least one selected from deuterium, —F, —Cl, —Br, —I, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{31}$)($Q_{32}$), —Si($Q_{33}$)($Q_{34}$)($Q_{35}$), and —B($Q_{36}$)($Q_{37}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, $C_1$-$C_{60}$ alkyl group, $C_2$-$C_{60}$ alkenyl group, $C_2$-$C_{60}$ alkynyl group, $C_1$-$C_{60}$ alkoxy group, $C_6$-$C_{60}$ aryl group, $C_6$-$C_{60}$ aryloxy group, $C_6$-$C_{60}$ arylthio group, $C_1$-$C_{60}$ heteroaryl group, a monovalent non-aromatic condensed polycyclic group, a monovalent non-aromatic condensed heteropolycyclic group, —N($Q_{31}$)($Q_{32}$), —Si($Q_{33}$)($Q_{34}$)($Q_{35}$), and —B($Q_{36}$)($Q_{37}$); and —Si($Q_{211}$)($Q_{212}$)($Q_{213}$), —N($Q_{214}$)($Q_{215}$), and —B($Q_{216}$)($Q_{217}$);

where $Q_{31}$ to $Q_{37}$ and $Q_{211}$ to $Q_{217}$ may be each independently selected from a $C_1$-$C_{60}$ alkyl group and a $C_6$-$C_{60}$ aryl group, but embodiments of the present invention are not limited thereto.

In some embodiments, $R_{211}$, $R_{212}$, $R_{221}$, $R_{222}$, $R_{235}$ to $R_{238}$ and $R_{242}$ in Formulae 2-1 to 2-4 may be each independently selected from hydrogen, deuterium, —F, —Cl, —Br, —I, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a phenyl group, a naphthyl group, a phenoxy group, a phenylthio group, —N($Q_{31}$)($Q_{32}$), —Si($Q_{33}$)($Q_{34}$)($Q_{35}$), and —B($Q_{36}$)($Q_{37}$);

a phenoxy group, a phenylthio group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group;

a phenoxy group, a phenylthio group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenoxy group, a phenylthio group, a phenyl group, a biphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{31}$)($Q_{32}$), —Si($Q_{33}$)($Q_{34}$)($Q_{35}$) and —B($Q_{36}$)($Q_{37}$); and —Si($Q_{211}$)($Q_{212}$)($Q_{213}$), —N($Q_{214}$)($Q_{215}$), and —B($Q_{216}$)($Q_{217}$), where $Q_{31}$ to $Q_{37}$ and $Q_{211}$ to $Q_{217}$ may be each independently selected from a $C_1$-$C_{60}$ alkyl group and a $C_6$-$C_{60}$ aryl group, but embodiments of the present invention are not limited thereto.

In some embodiments, $R_{211}$, $R_{212}$, $R_{221}$, $R_{222}$, $R_{235}$ to $R_{238}$ and $R_{242}$ in Formulae 2-1 to 2-4 may be each independently selected from hydrogen, deuterium, —F, —Cl, —Br, —I, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a phenyl group, a naphthyl group, a phenoxy group, a phenylthio group, —N($Q_{31}$)($Q_{32}$), —Si($Q_{33}$)($Q_{34}$)($Q_{35}$), and —B($Q_{36}$)($Q_{37}$);

a phenoxy group, a phenylthio group, a phenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group;

a phenoxy group, a phenylthio group, a phenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, $C_1$-$C_{20}$ alkyl group, $C_1$-$C_{20}$ alkoxy group, a phenoxy group, a phenylthio group, a phenyl group, a naphthyl group, —N($Q_{31}$)($Q_{32}$), —Si($Q_{33}$)($Q_{34}$)($Q_{35}$), and —B($Q_{36}$)($Q_{37}$); and —Si($Q_{211}$)($Q_{212}$)($Q_{213}$), —N($Q_{214}$)($Q_{215}$), and —B($Q_{216}$)($Q_{217}$), where $Q_{31}$ to $Q_{37}$ and $Q_{211}$ to $Q_{217}$ may be each independently selected from a $C_1$-$C_{69}$ alkyl group and a $C_6$-$C_{60}$ aryl group, but embodiments of the present invention are not limited thereto.

In some embodiments, $R_{211}$, $R_{212}$, $R_{221}$, $R_{222}$, $R_{235}$ to $R_{238}$ and $R_{242}$ in Formulae 2-1 to 2-4 may be each independently selected from hydrogen, deuterium, —F, —Cl, —Br, —I, a methyl group, an ethyl group, an n-propyl group, an iso-propyl group, an n-butyl group, an iso-butyl group, a sec-butyl group, a tert-butyl group, a methoxy group, an ethoxy group, an iso-propoxy group, an n-butoxy group, an iso-butoxy group, sec-butoxy group, tert-butoxy group, —Si($CH_3$)$_3$, —Si(Ph)$_3$, —N(Ph$_2$)$_2$, —B(Ph)$_2$, and groups represented by Formula 9-1 to 9-13, but embodiments of the present invention are not limited thereto:

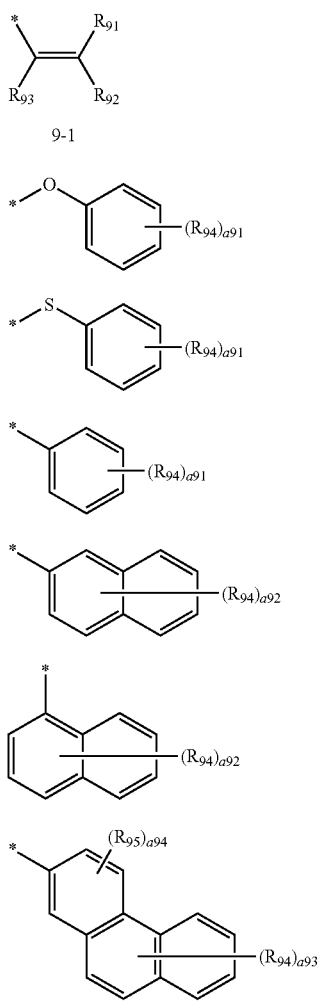
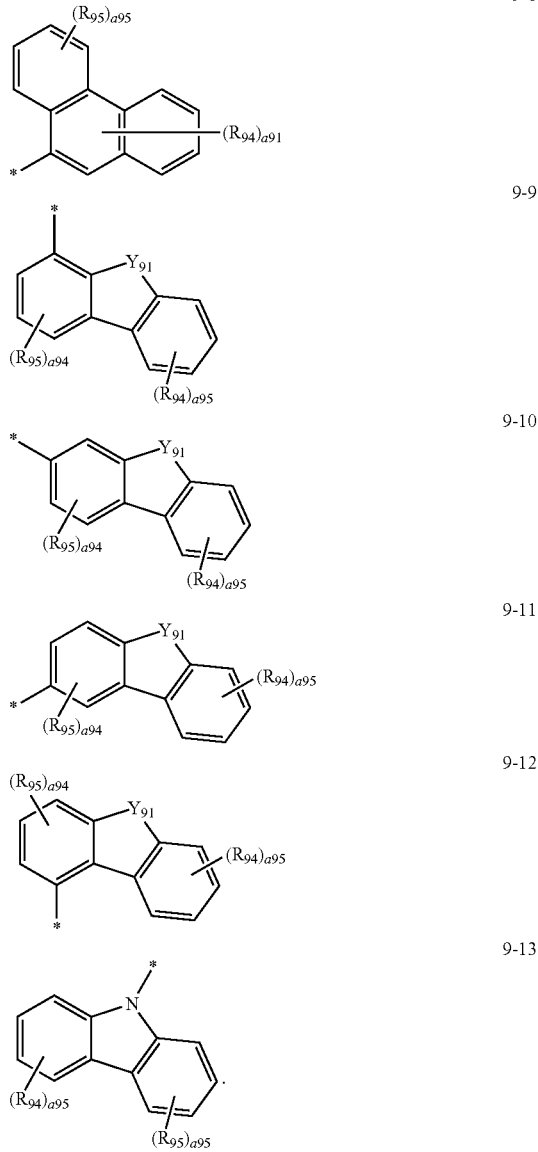

In Formulae 9-1 to 9-13, $Y_{91}$ may be selected from C($R_{96}$)($R_{97}$), N($R_{96}$), O, and S;

$R_{91}$ to $R_{93}$ may be each independently selected from hydrogen, deuterium, —F, —Cl, —Br, —I, a phenyl group, and a naphthyl group;

$R_{94}$ to $R_{97}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenoxy group, a phenylthio group, a phenyl group, and a naphthyl group;

a91 may be selected from 1, 2, 3, 4, and 5;
a92 may be selected from 1, 2, 3, 4, 5, 6, and 7;
a93 may be selected from 1, 2, 3, 4, 5, and 6;
a94 may be selected from 1, 2, and 3;
a95 may be selected from 1, 2, 3, and 4; and
* indicates a binding site to a neighboring atom.

In some embodiments, $R_{211}$, $R_{212}$, $R_{221}$, $R_{222}$, $R_{235}$ to $R_{238}$, and $R_{242}$ in Formulae 2-1 to 2-4 may be each independently selected from hydrogen, deuterium, —F, —Cl, —Br, —I, a methyl group, an ethyl group, an n-propyl group, an iso-propyl group, an n-butyl group, an iso-butyl group, a sec-butyl group, a tert-butyl group, a methoxy group, an ethoxy group, an iso-propoxy group, an n-butoxy group, an iso-butoxy group, sec-butoxy group, tert-butoxy group, —Si(CH$_3$)$_3$, —Si(Ph)$_3$, —N(Ph$_2$)$_2$, —B(Ph)$_2$, and groups represented by Formulae 10-1 to 10-24, but embodiments of the present invention are not limited thereto:

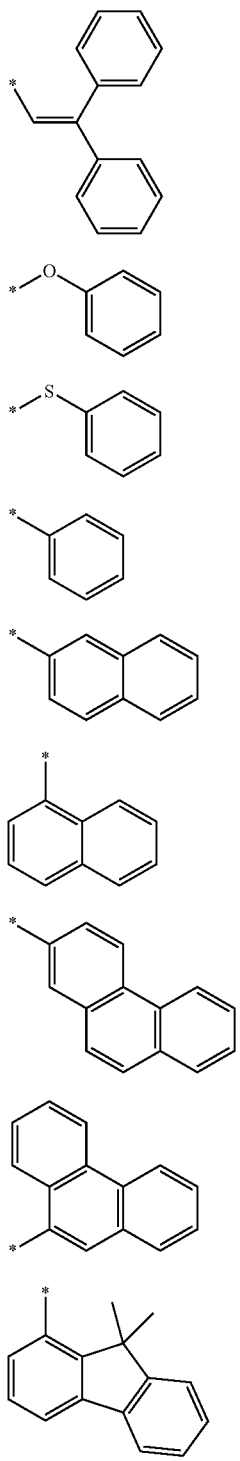

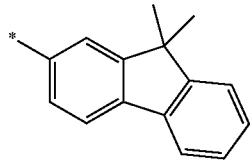

10-10

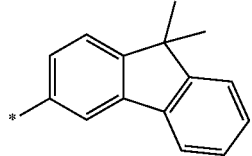

10-11

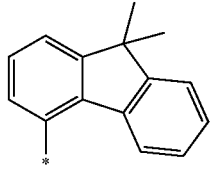

10-12

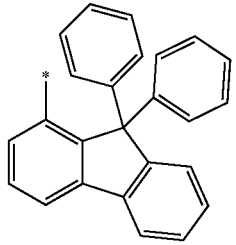

10-13

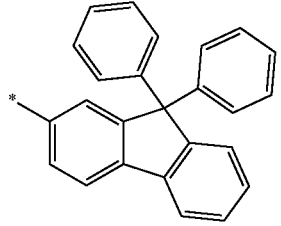

10-14

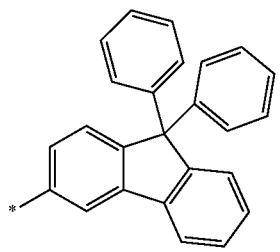

10-15

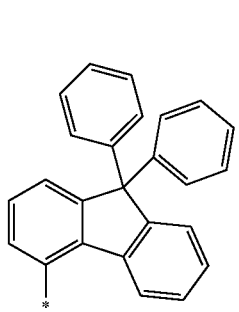

10-16

-continued

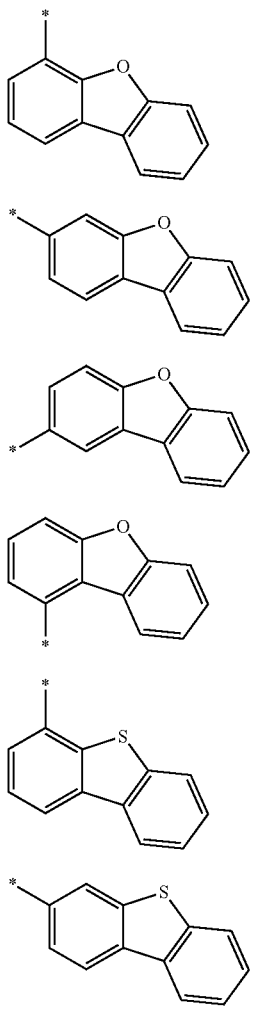

10-17
10-18
10-19
10-20
10-21
10-22

-continued

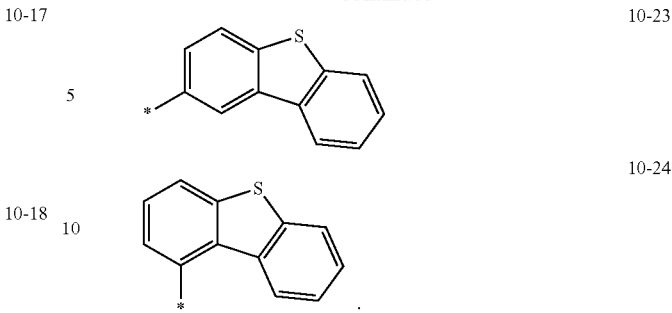

10-23
10-24

In Formulae 10-1 to 10-24,
* indicates a binding site to a neighboring atom.

For example, b211, b212, b221, b222, b235 to b238 and b242 in Formulae 2-1 to 2-4 may be each independently selected from 1 and 2, but embodiments of the present invention are not limited thereto.

For example, n211 and n212 in Formula 2-1 may be selected from 1 and 2, but embodiments of the present invention are not limited thereto.

For example, n221 in Formula 2-2 may be 2, but this is not limited thereto.

For example, n231 to n234 in Formula 2-3 may be 1, but embodiments of the present invention are not limited thereto.

For example, n241 in Formula 2-4 may be selected from 3, 4, and 6, but embodiments of the present invention are not limited thereto.

In some embodiments, $L_{221}$ in Formula 2-2 may not be a substituted or unsubstituted naphthylene group, or at least one selected from $R_{221}$ and $R_{222}$ may not be a substituted or unsubstituted naphthyl group.

For example, the second material represented by one of Formulae 2-1 to 2-4 may be represented by one of Formulae 2-11 to 2-16, but embodiments of the present invention are not limited thereto:

Formula 2-11

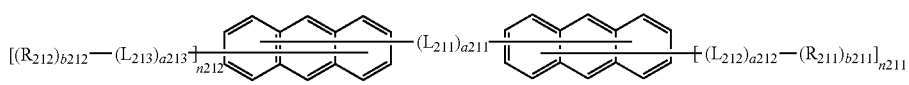

Formula 2-12

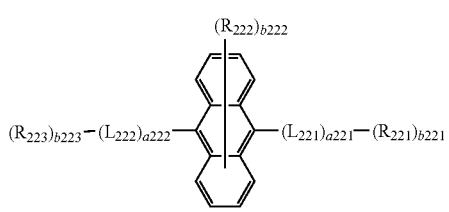

Formula 2-13

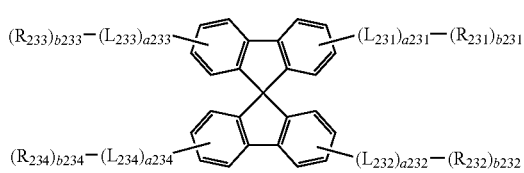

Formula 2-14

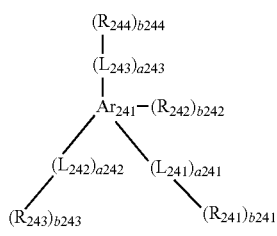

Formula 2-15

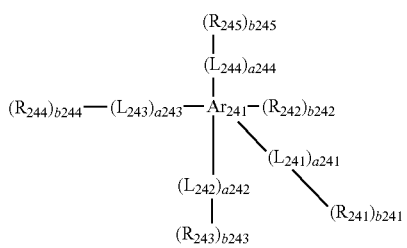

-continued

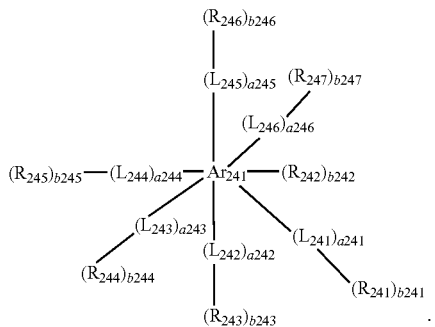

In Formulae 2-11 to 2-16, $Ar_{241}$, $L_{211}$ to $L_{213}$, $L_{221}$, $L_{231}$ to $L_{234}$, $L_{241}$, a211 to a213, a221, a231 to a234, a241, $R_{231}$ to $R_{234}$, $R_{241}$, b231 to b234, b241, $R_{211}$, $R_{212}$, $R_{221}$, $R_{222}$, $R_{235}$ to $R_{238}$, $R_{242}$, b211, b212, b221, b222, b235 to b238, b242, n211 and n212 are the same as defined in connection with Formulae 2-1 to 2-4;

$L_{222}$ is defined in the same manner used to define $L_{221}$ in Formula 2-2; a222 is defined in the same manner used to define a221 in Formula 2-2; $R_{223}$ is defined in the same manner used to define $R_{221}$ in Formula 2-2; and b223 is defined in the same manner used to define b221 in Formula 2-2;

$L_{242}$ to $L_{246}$ are each independently defined in the same manner used to define $L_{241}$ in Formula 2-4; and a242 to a246 are each independently defined in the same manner used to define a241 in Formula 2-4.

In some embodiments, the second material represented by one of Formulae 2-1 to 2-4 may be represented by one of Formulae 2-21 to 2-29, but embodiments of the present invention are not limited thereto:

Formula 2-21

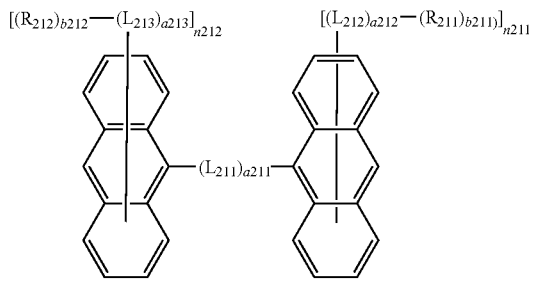

Formula 2-22

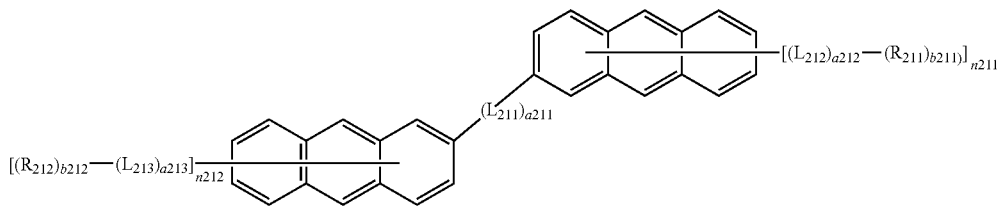

Formula 2-23

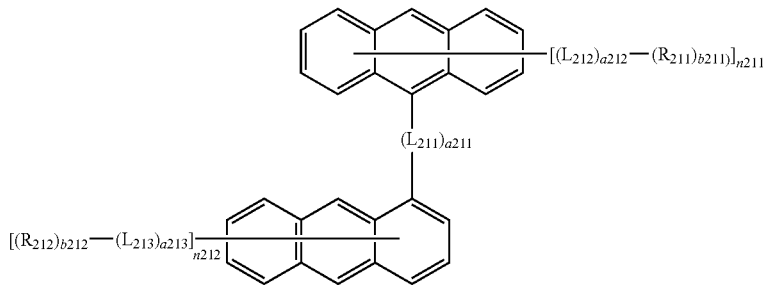

Formula 2-24

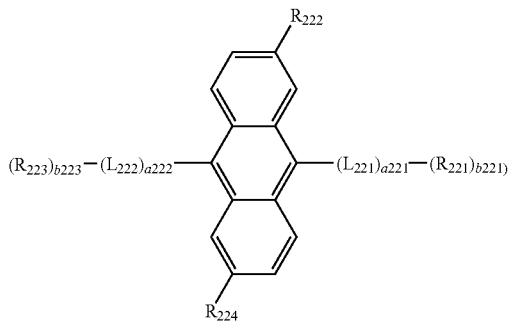

Formula 2-25

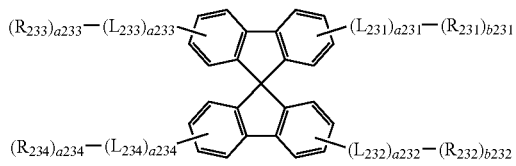

Formula 2-26

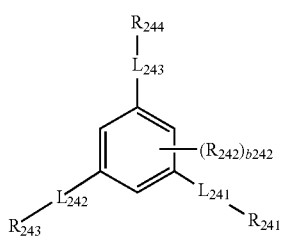

Formula 2-27

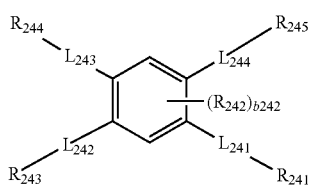

Formula 2-28

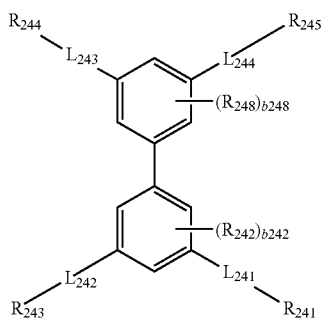

Formula 2-29

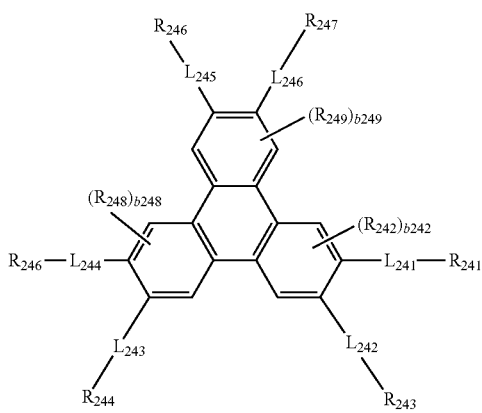

In Formulae 2-21 to 2-29, $Ar_{241}$, $L_{211}$ to $L_{213}$, $L_{221}$, $L_{231}$ to $L_{234}$, $L_{241}$, a211 to a213, a221, a231 to a234, a241, $R_{231}$ to $R_{234}$, $R_{241}$, b231 to b234, b241, $R_{211}$, $R_{212}$, $R_{221}$, $R_{222}$, $R_{235}$ to $R_{238}$, $R_{242}$, b211, b212, b221, b222, b235 to b238, b242, n211 and n212 are defined in the same manner as used in Formulae 2-1 to 2-4;

$L_{222}$ is defined in the same manner as used to define $L_{221}$ in Formula 2-2; a222 is defined in the same manner as used to define a221 in Formula 2-2; $R_{223}$ is defined in the same manner as used to define $R_{221}$ in Formula 2-2; and b223 is defined in the same manner as used to define b221 in Formula 2-2;

$L_{242}$ to $L_{246}$ are each independently defined in the same manner as used to define $L_{241}$ in Formula 2-4; a242 to a246 are each independently defined in the same manner as used to define a241 in Formula 2-4; $R_{248}$ and $R_{249}$ are each independently defined in the same manner as used to define $R_{242}$ in Formula 2-4; and b248 and b249 are each independently defined in the same manner as used to define b242 in Formula 2-4.

In some embodiments, the second material represented by one of Formulae 2-1 to 2-4 may be selected from Compounds H-1 to H-60, but embodiments of the present invention are not limited thereto:

H-1
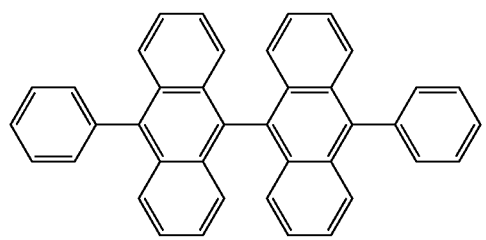
H-2
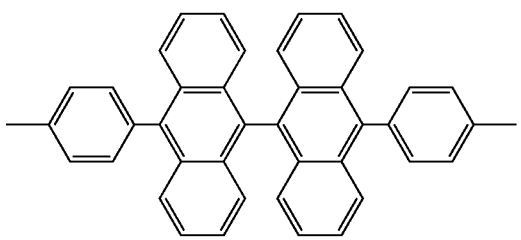
H-3
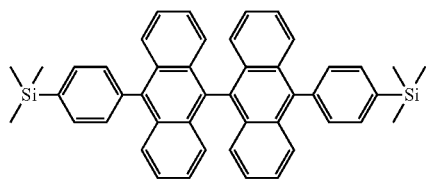
H-4
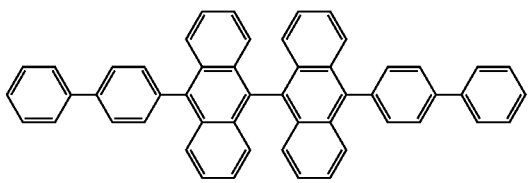
H-5
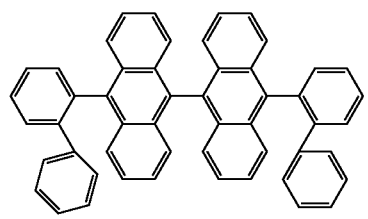
H-6
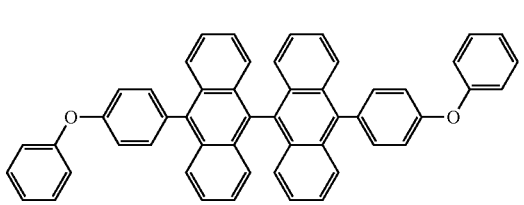
H-7
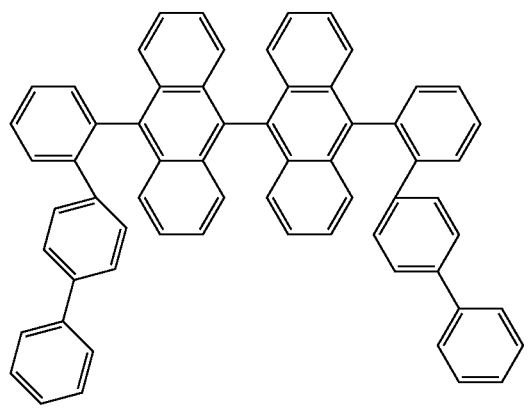
H-8
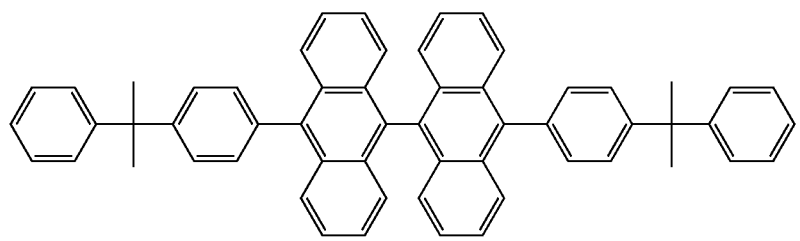
H-9
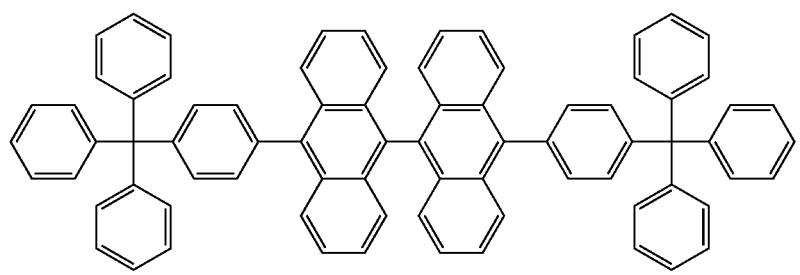

-continued
H-10
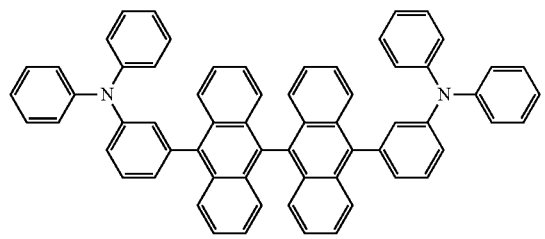
H-11
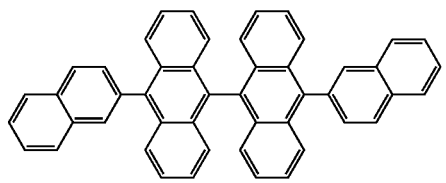
H-12
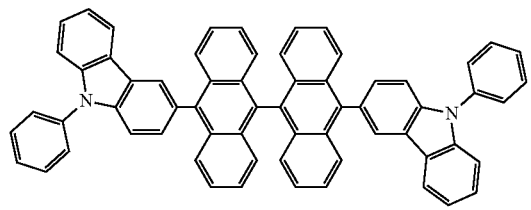
H-13
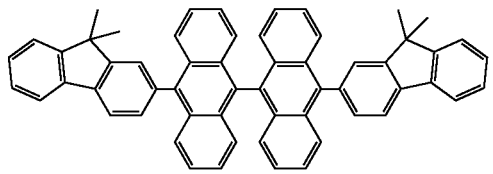
H-14
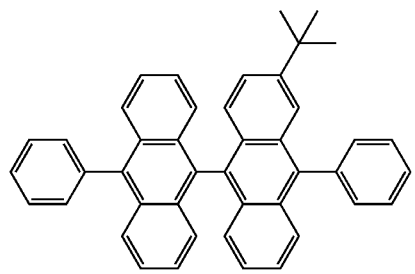
H-15
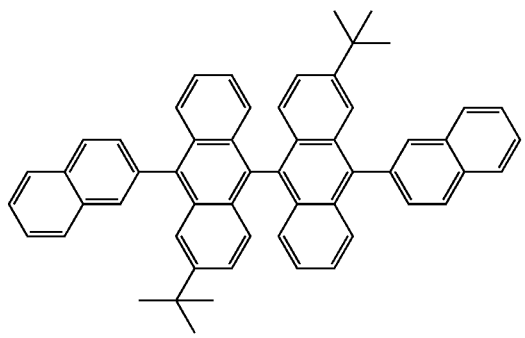
H-16
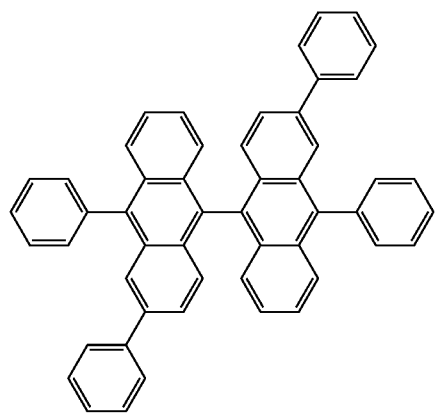
H-17
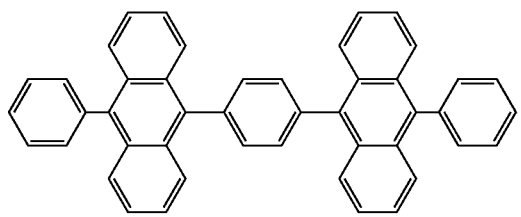
H-18
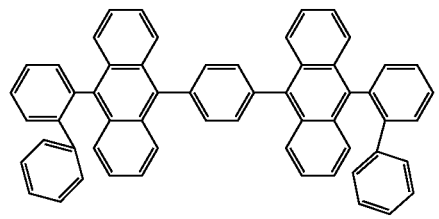
H-19
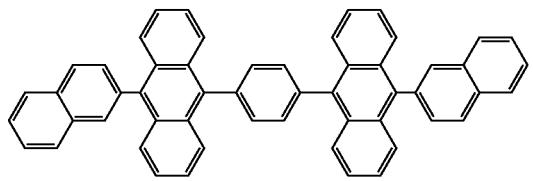

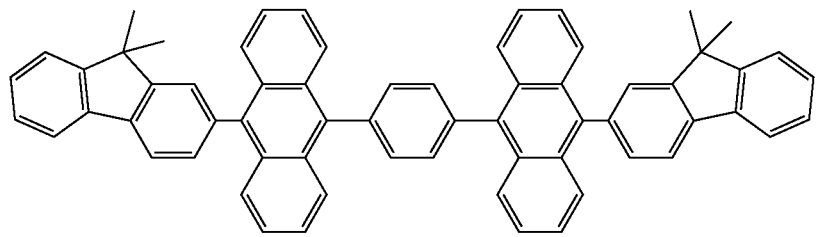
H-20
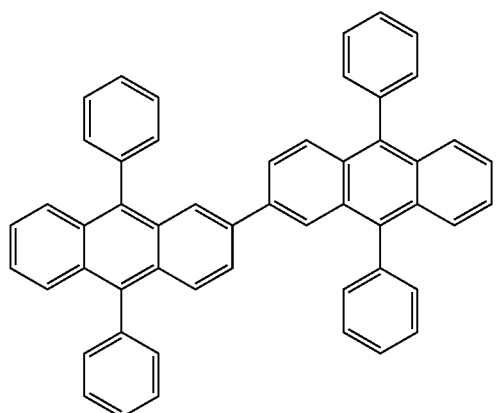
H-21
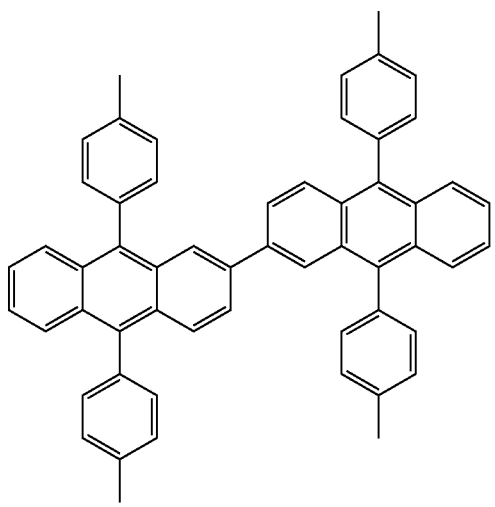
H-22
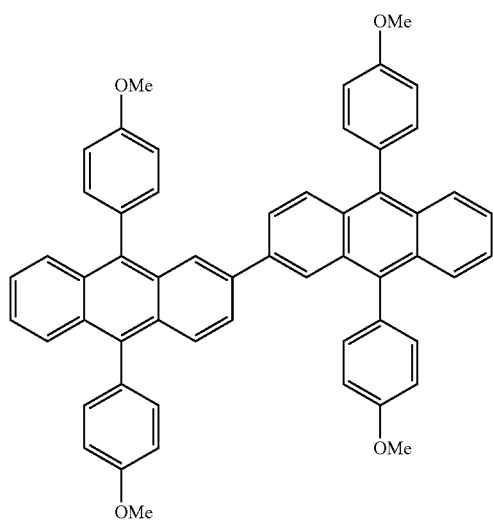
H-23
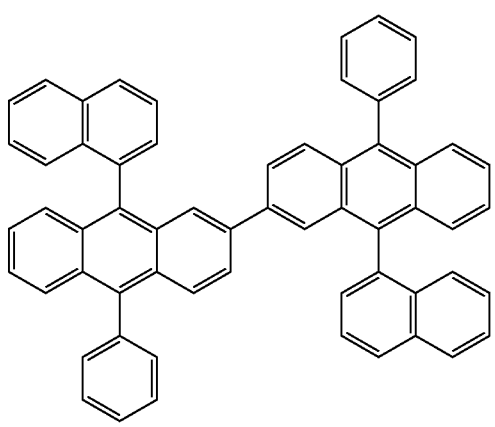
H-24

-continued
H-25
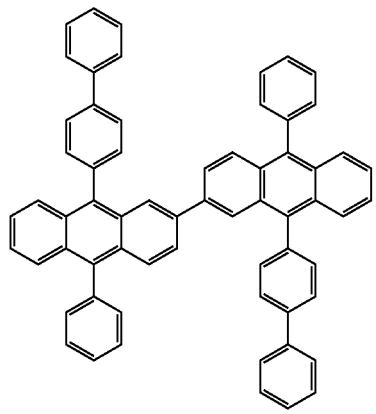
H-26
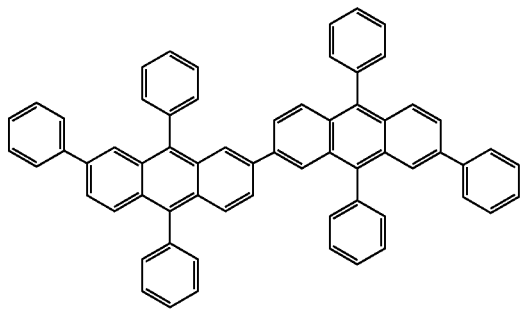
H-27
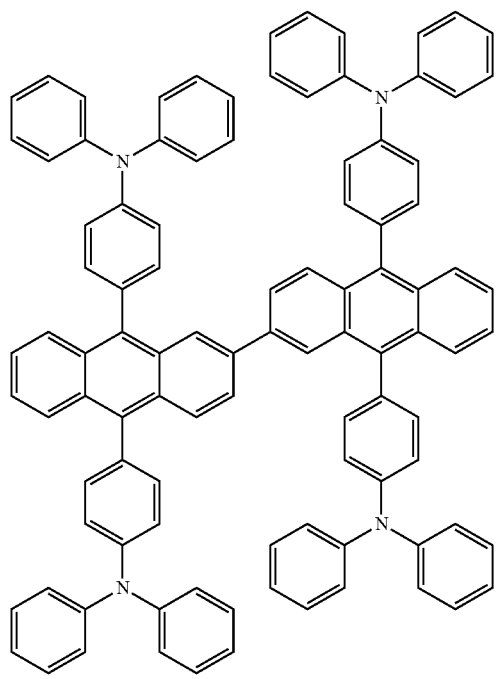
H-28
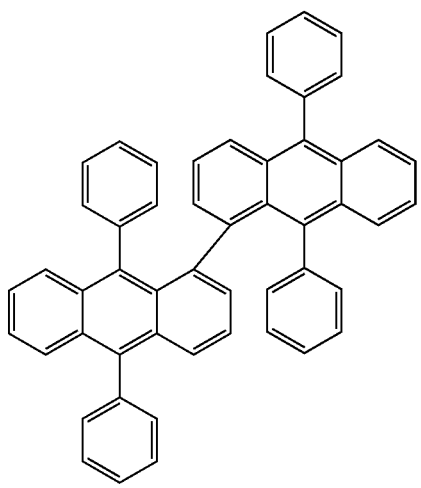

-continued
H-29
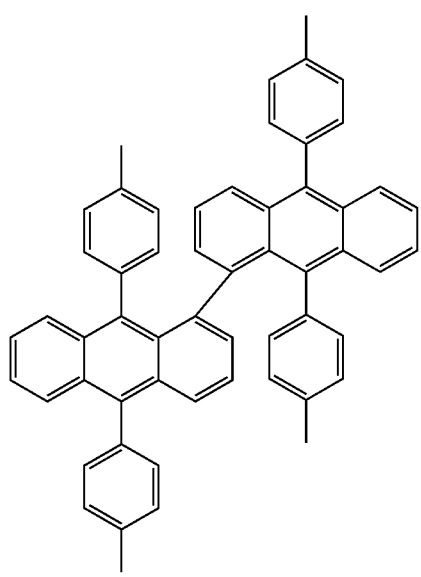
H-30
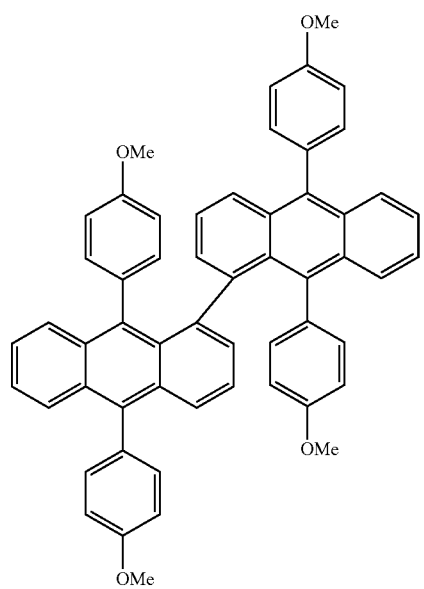
H-31
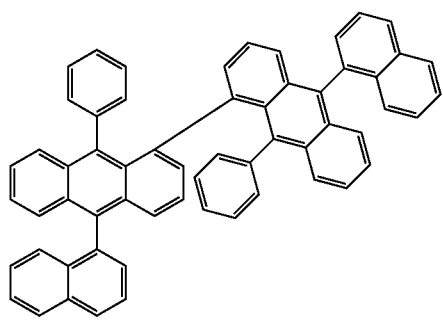
H-32
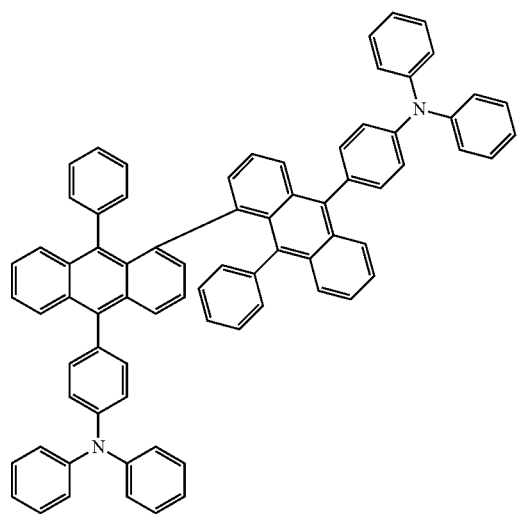
H-33
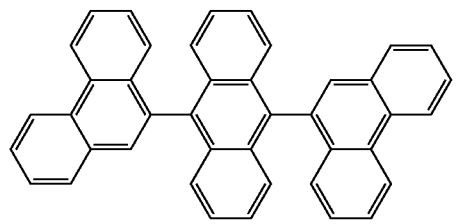
H-34
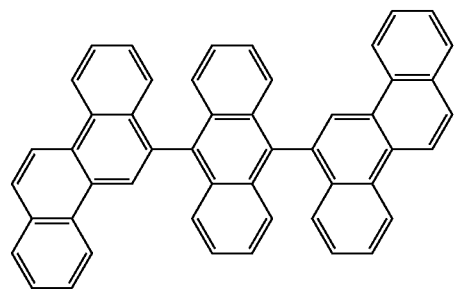
H-35
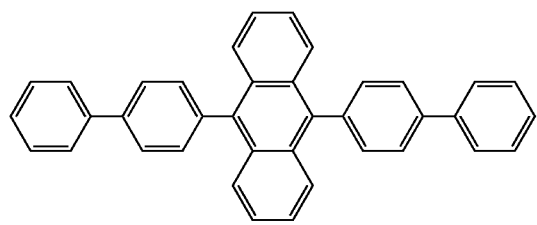

-continued
H-36
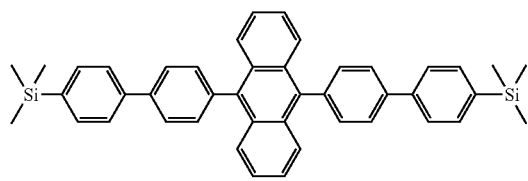
H-37
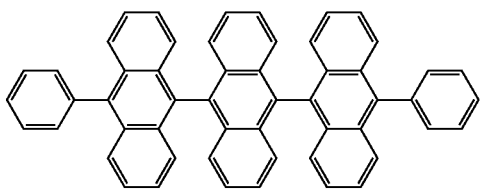
H-38
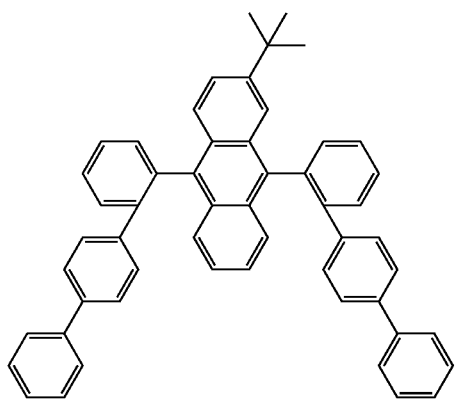
H-39
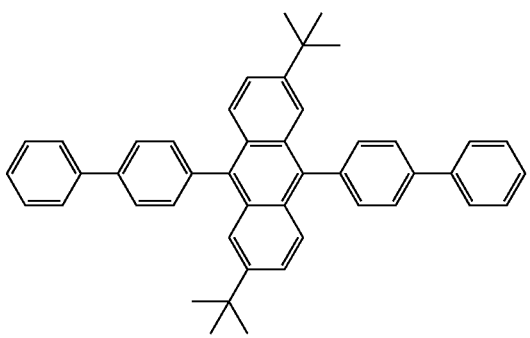
H-40
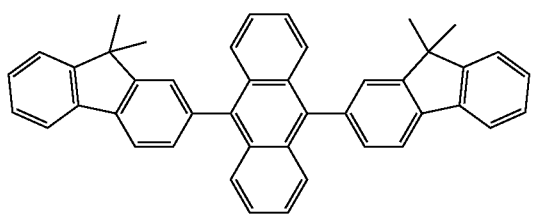
H-41
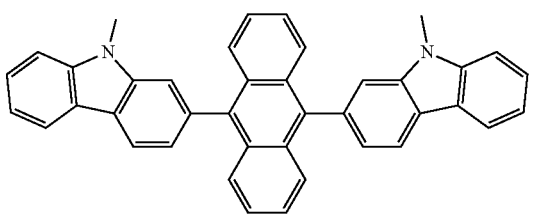
H-42
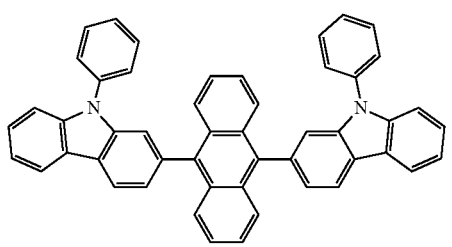
H-43
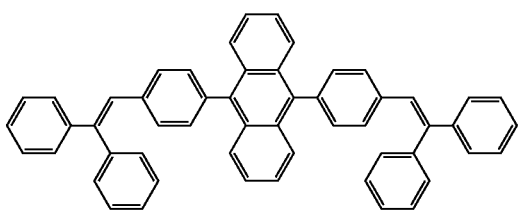
H-44
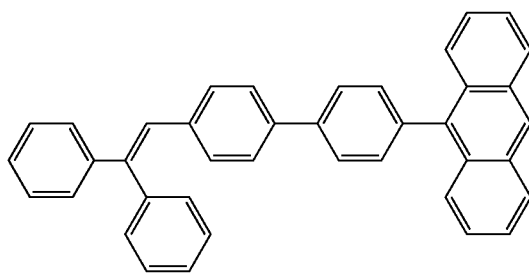
H-45
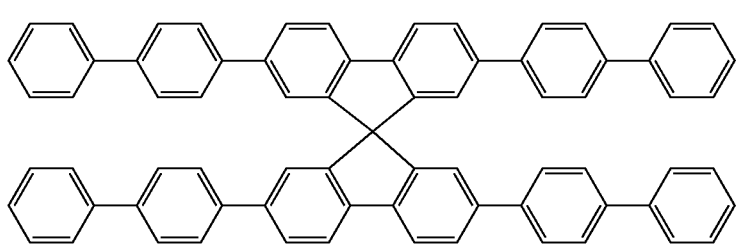

-continued
H-46
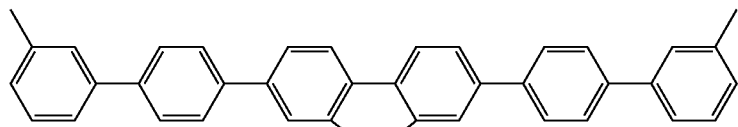
H-47
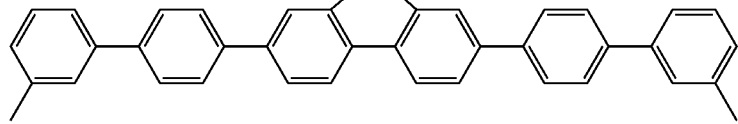
H-48
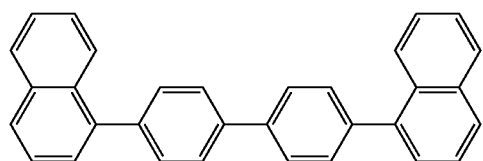
H-49
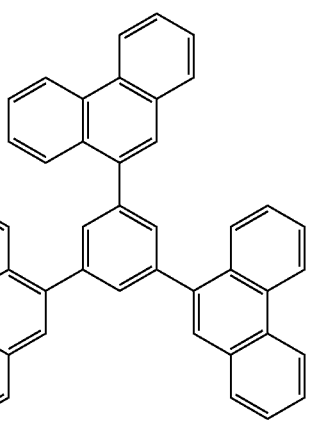
H-50
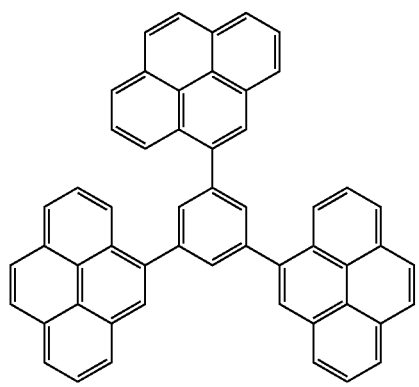
H-51
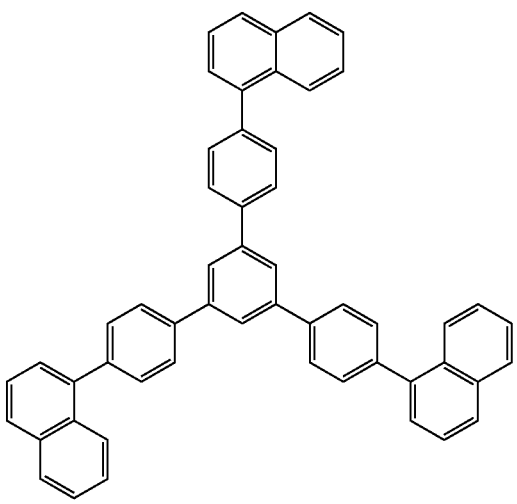

-continued
H-52
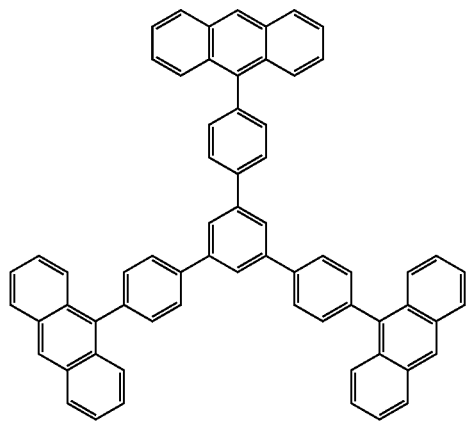
H-53
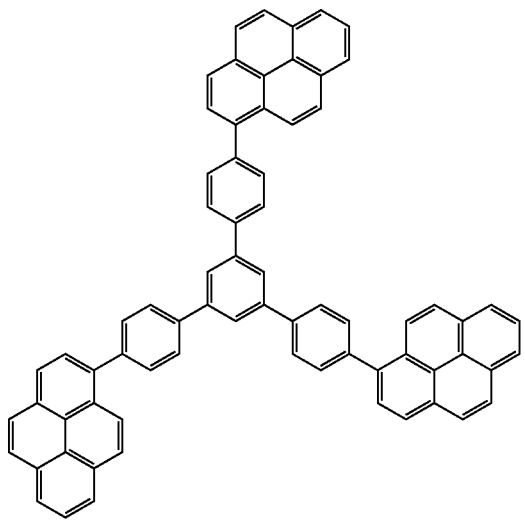
H-54
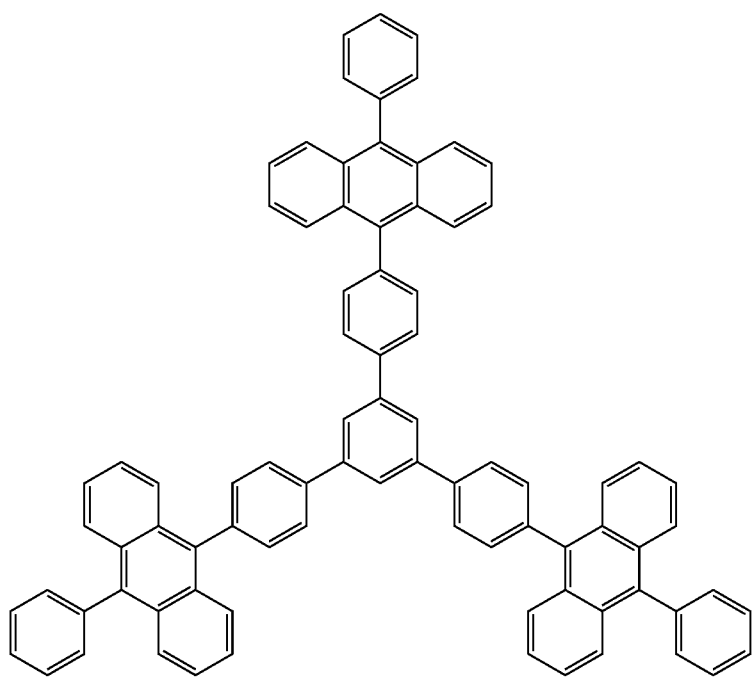
H-55
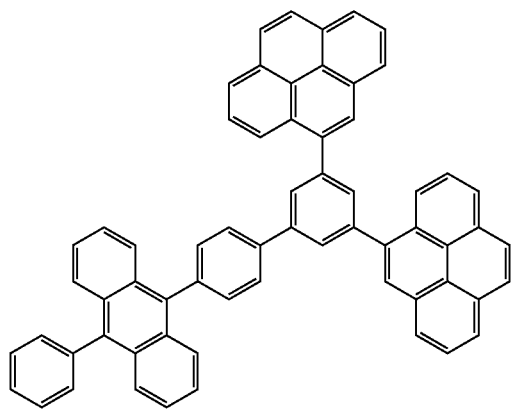
H-56
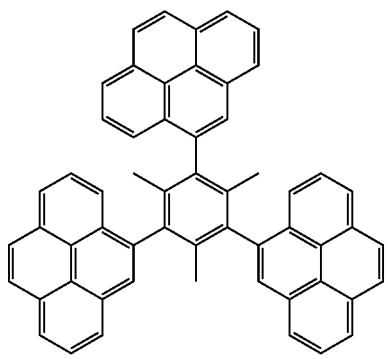

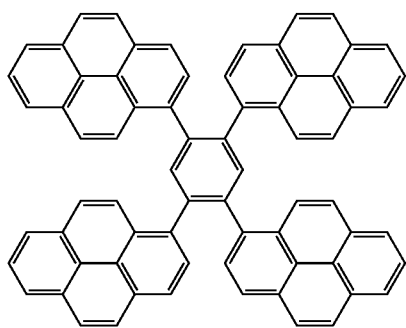

H-57

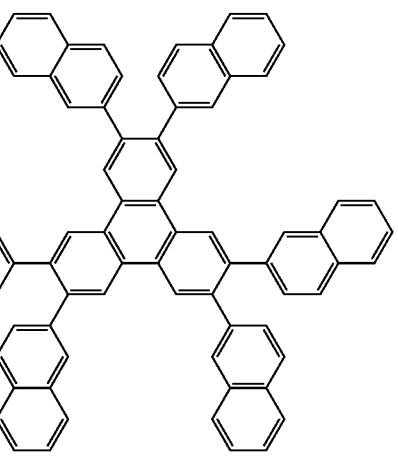

H-58

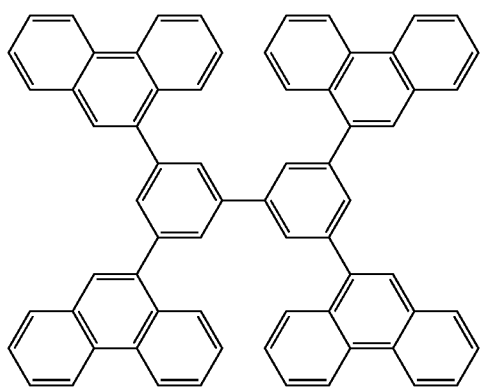

H-59

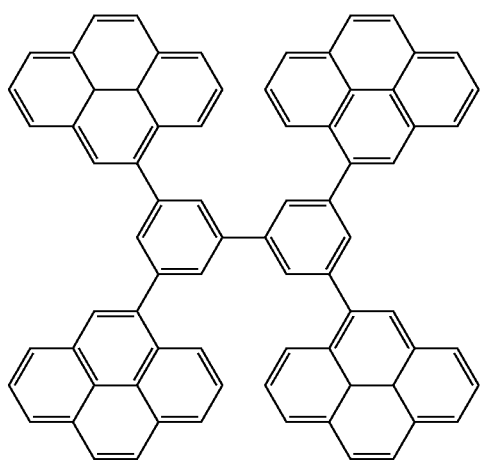

H-60

In some embodiments, the emission layer of the organic light-emitting device may include the condensed cyclic compound represented by Formula 1 as a condensed cyclic compound.

The emission layer of the organic light-emitting device may further include, in addition to the condensed cyclic compound represented by Formula 1, at least one selected from a fluorescent dopant and a phosphorescent dopant.

The phosphorescent dopant may include an organometallic complex represented by Formula 401:

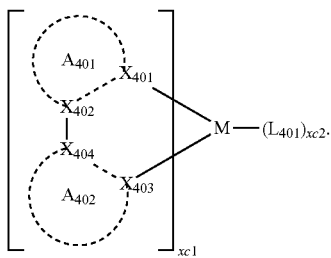

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently a nitrogen atom or a carbon atom;

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrol, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorene, substituted spirofluorene, substituted indene, substituted pyrrol, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ is an organic ligand;

xc1 is 1, 2, or 3; and xc2 is 0, 1, 2, or 3;

$Q_{401}$ to $Q_{407}$, $Q_{411}$ to $Q_{417}$, and $Q_{421}$ to $Q_{427}$ may be each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{401}$ may be a monovalent, divalent, or trivalent organic ligand. For example, $L_{401}$ may be selected from a halogen ligand (for example, Cl and/or F), a diketone ligand (for example, acetylacetonate, 1,3-diphenyl-1,3-propanedionate, 2,2,6,6-tetramethyl-3,5-heptanedionate, and/or hexafluoroacetonate), a carboxylic acid ligand (for example, picolinate, dimethyl-3-pyrazolecarboxylate, and/or benzoate), a carbon monooxide ligand, an isonitrile ligand, a cyano ligand, and a phosphorous ligand (for example, phosphine and/or phosphite), but is not limited thereto.

When $A_{401}$ in Formula 401 has two or more substituents, the substituents of $A_{401}$ may bind to each other to form a saturated or unsaturated ring.

When $A_{402}$ in Formula 401 has two or more substituents, the substituents of $A_{402}$ may bind to each other to form a saturated or unsaturated ring.

When xc1 in Formula 401 is two or more, a plurality of ligands

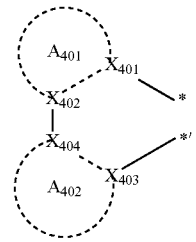

in Formula 401 may be identical to or different from each other. When xc1 in Formula 401 is two or more, $A_{401}$ and/or $A_{402}$ of one ligand may be respectively connected to $A_{401}$ and/or $A_{402}$ of other neighboring ligands either directly (for example, via a single bond) or with a linker (or a linking group) (for example, a $C_1$-$C_5$ alkylene, a $C_2$-$C_5$ alkenylene group, —N(R')— (where R' may be a $C_1$-$C_{10}$ alkyl group or a $C_6$-$C_{20}$ aryl group) and/or C(=O)—) therebetween.

The phosphorescent dopant may include at least one of Compounds PD1 to PD74 below, but is not limited thereto:

PD1

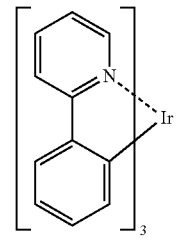

PD2 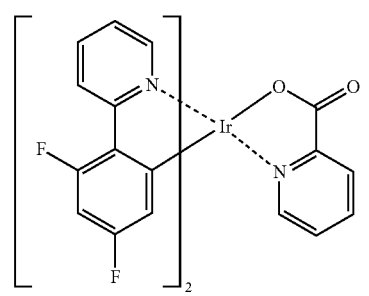
PD3 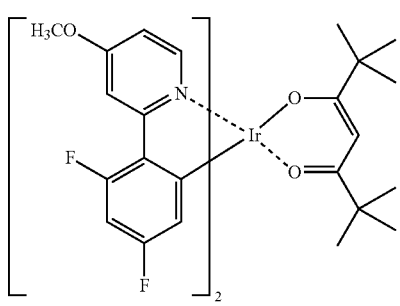
PD4 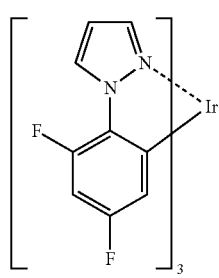
PD5 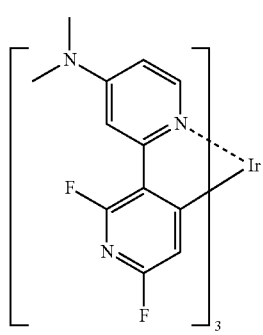
PD6 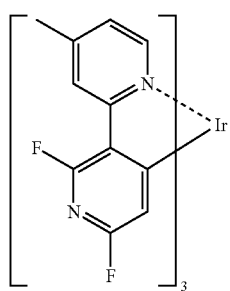
PD7 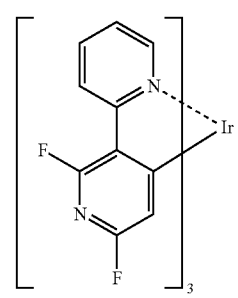
PD8 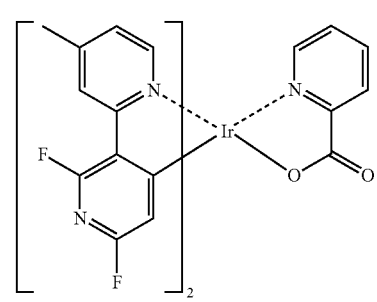
PD9 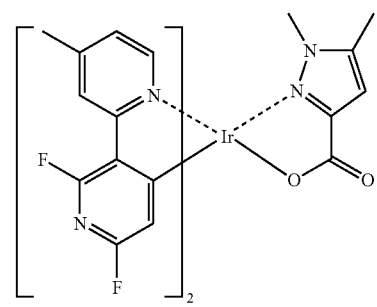
PD10 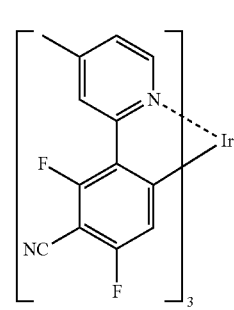
PD11 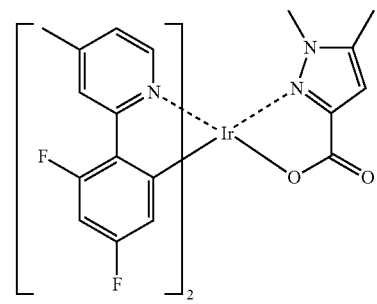

PD12 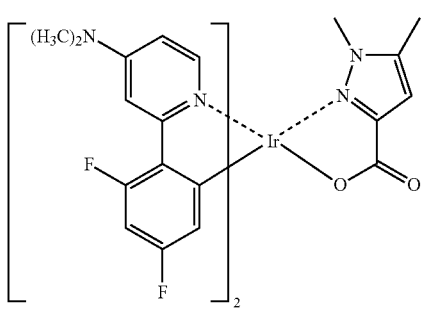
PD13 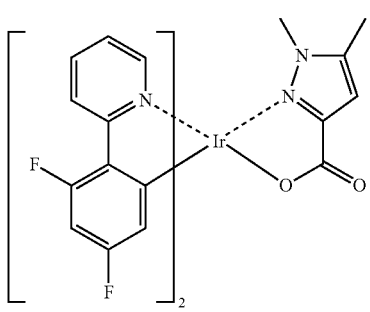
PD14 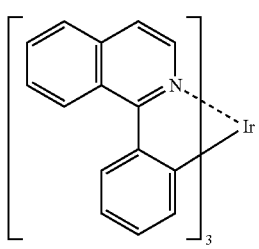
PD15 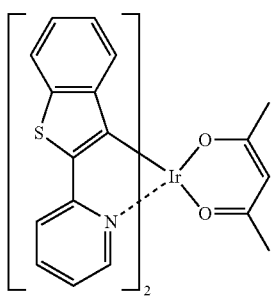
PD16 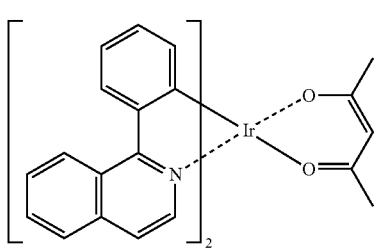
PD17 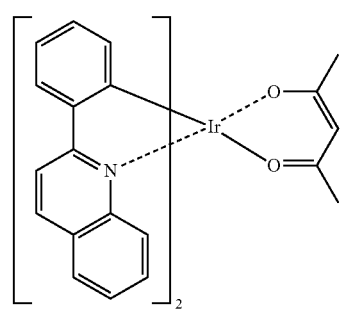
PD18 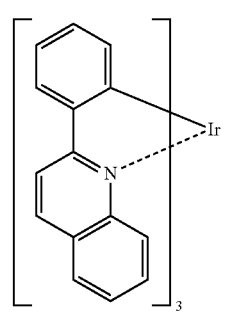
PD19 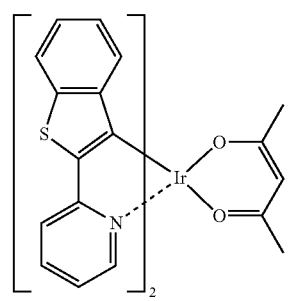
PD20 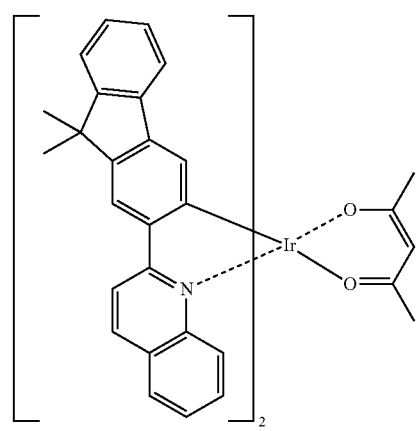

PD21
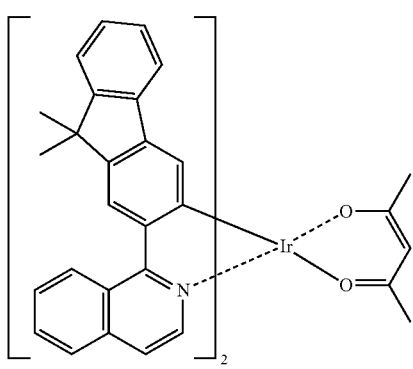
PD22
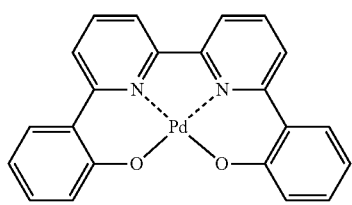
PD23
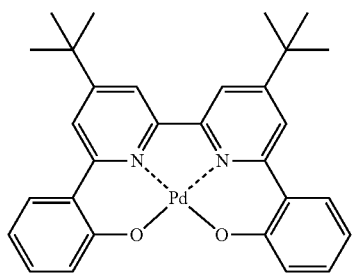
PD24
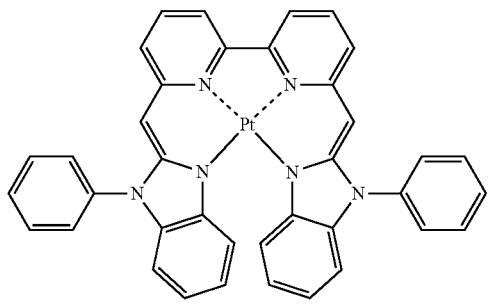
PD25
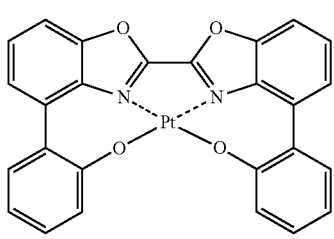
PD26
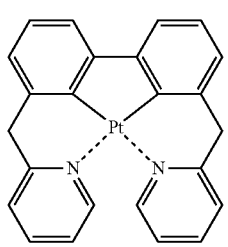
PD27
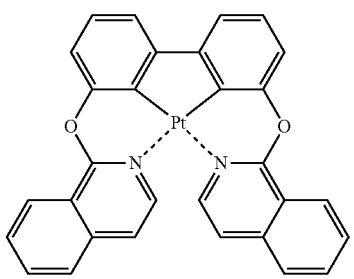
PD28
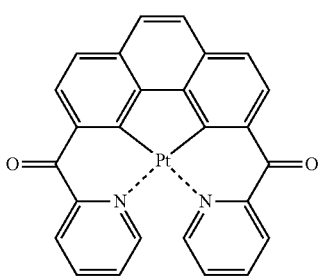
PD29
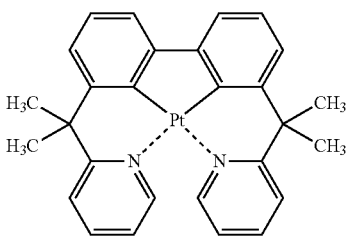
PD30
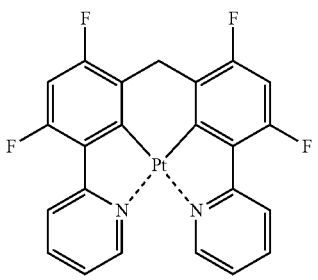
PD31
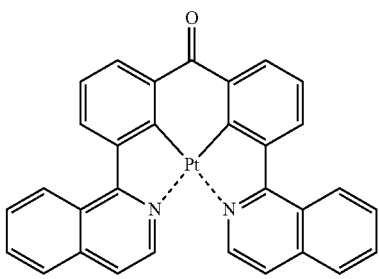
PD32
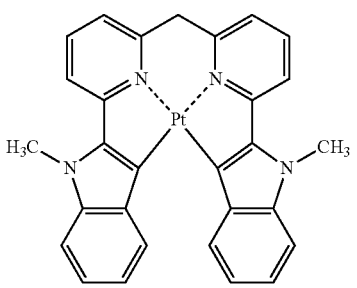

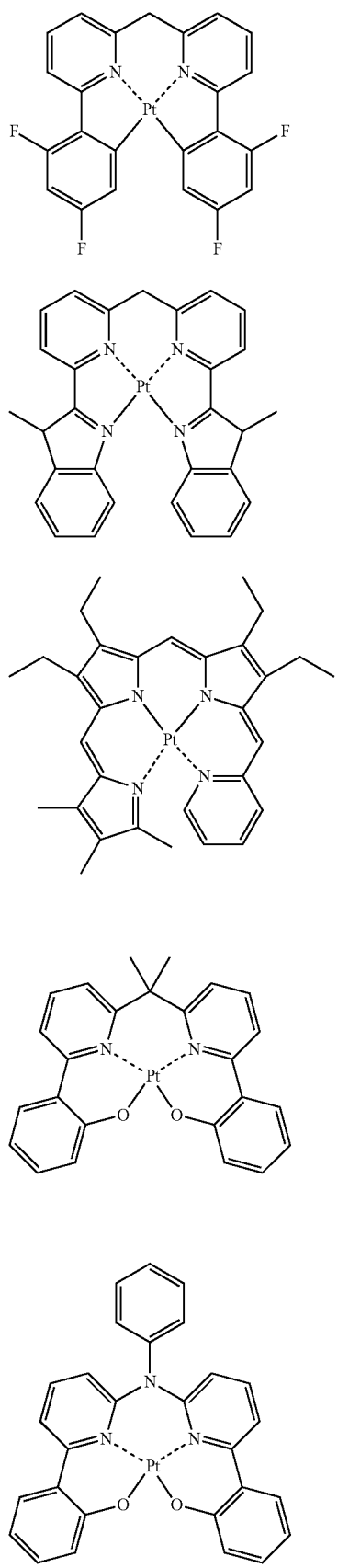
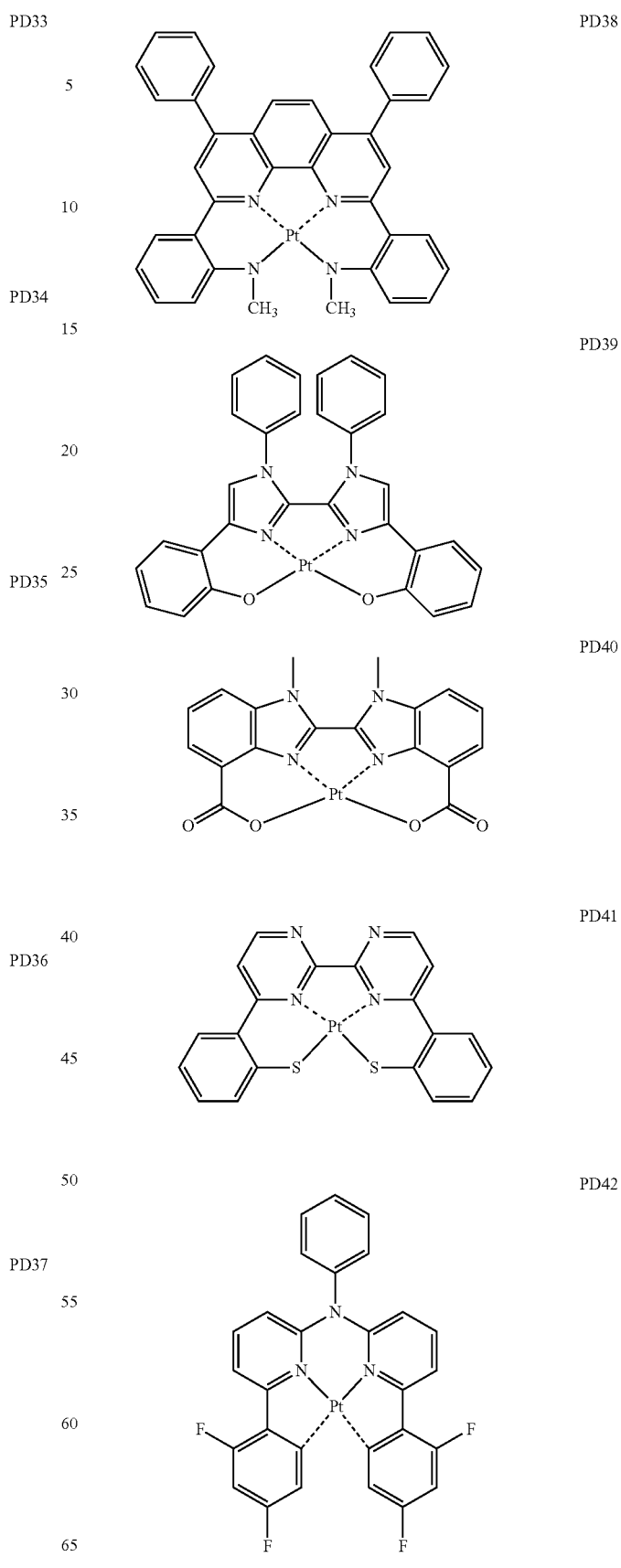

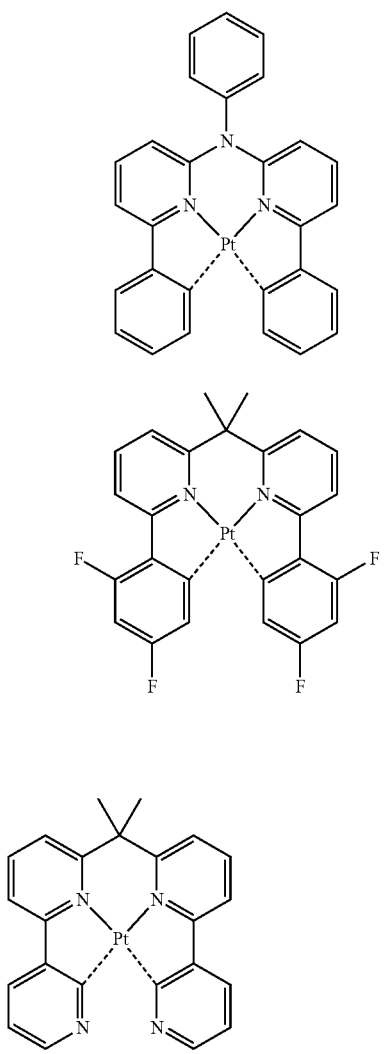
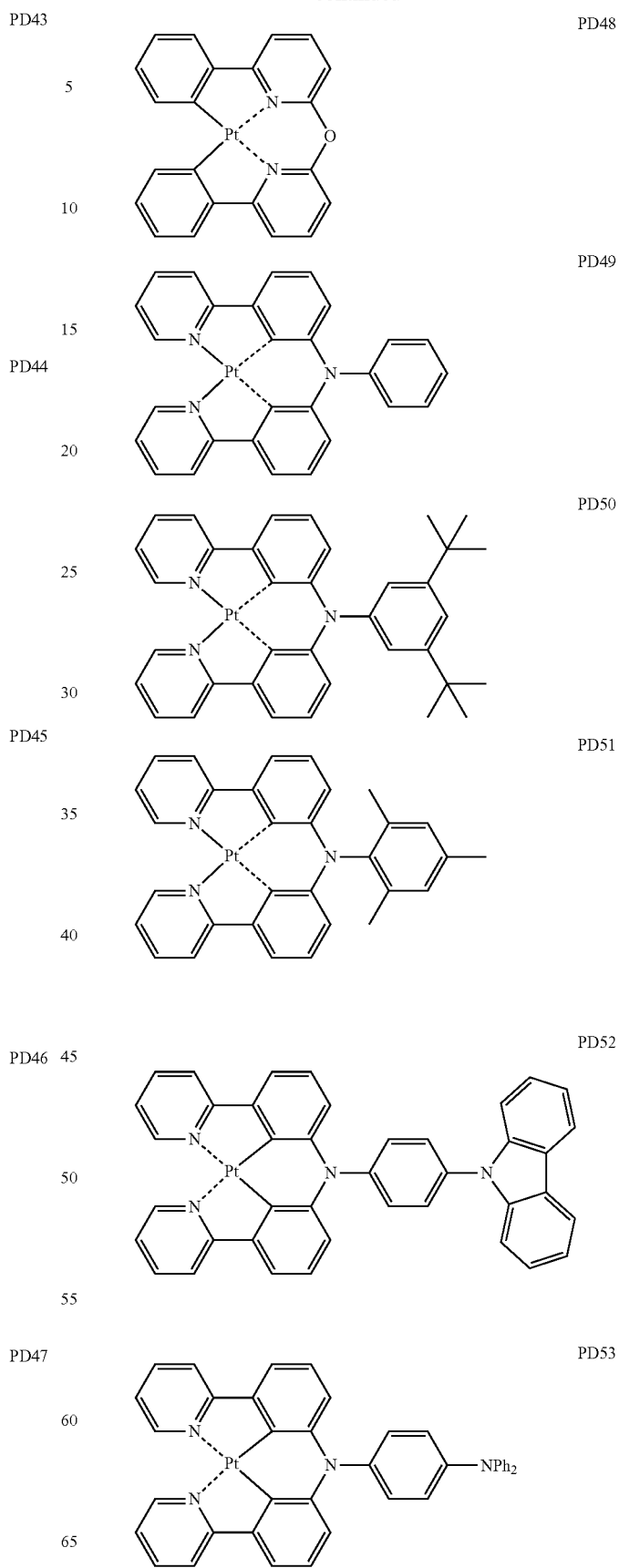

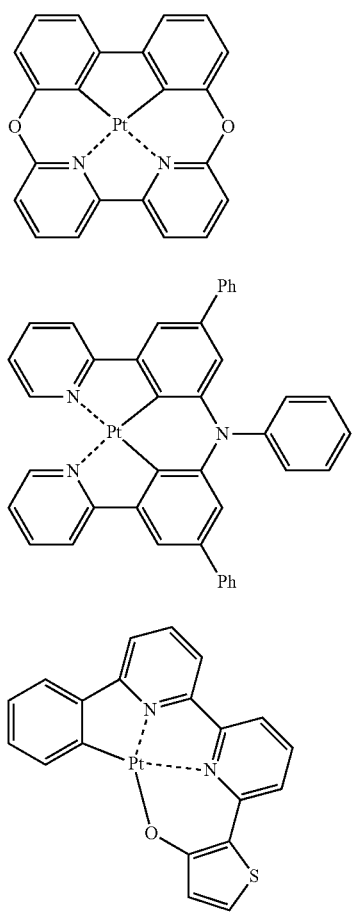
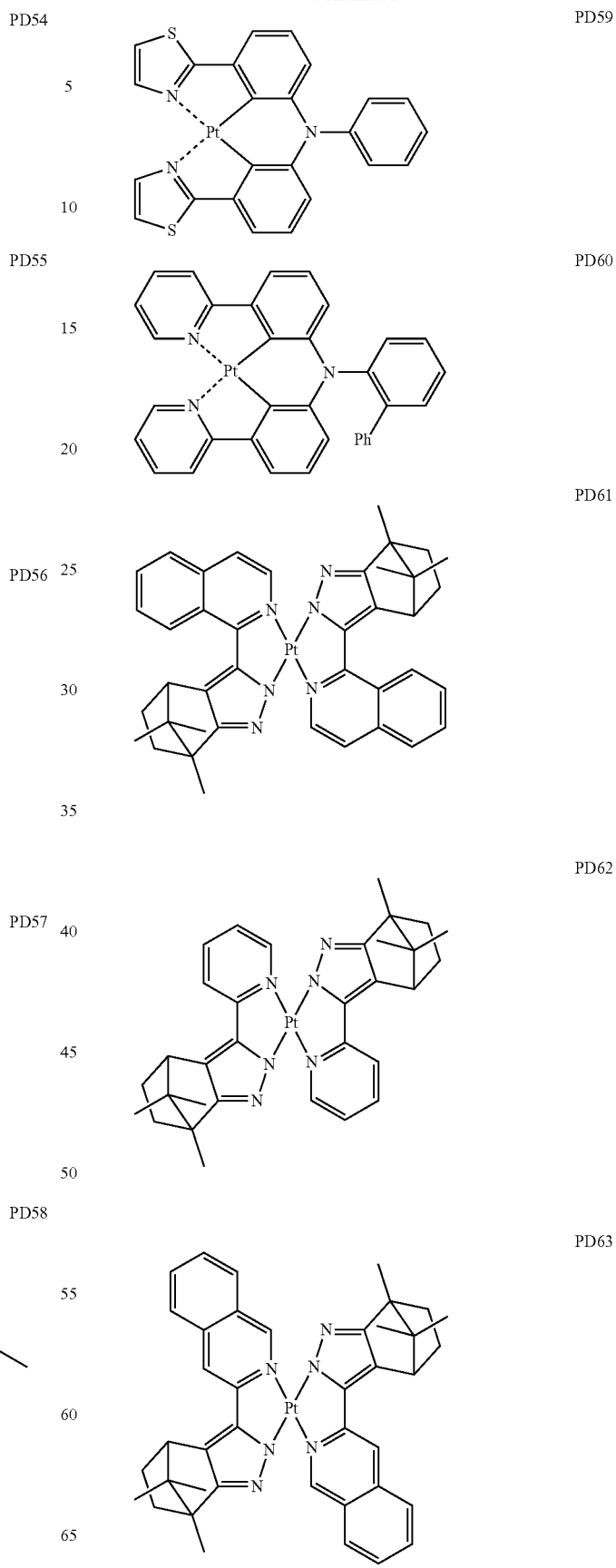

PD64 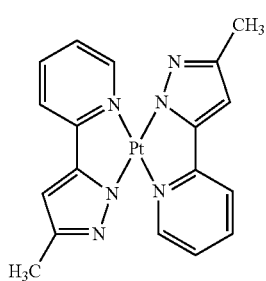
PD65 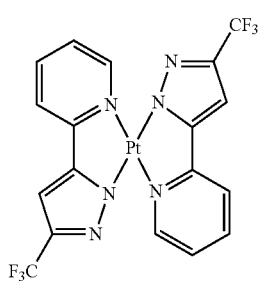
PD66 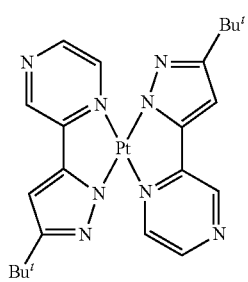
PD67 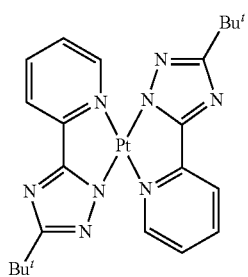
PD68 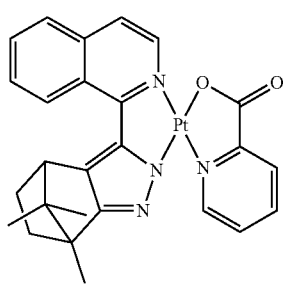
PD69 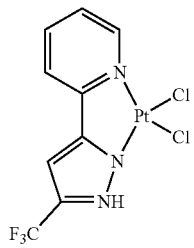
PD70 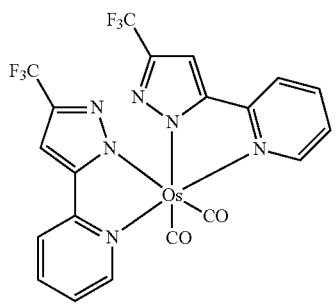
PD71 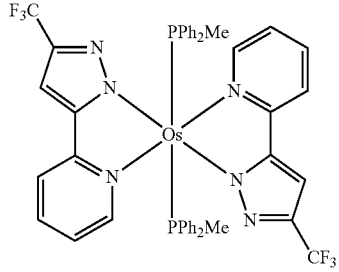
PD72 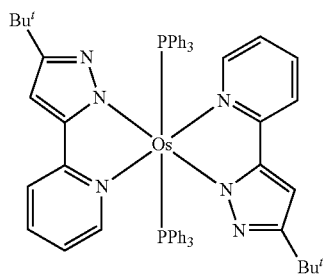
PD73 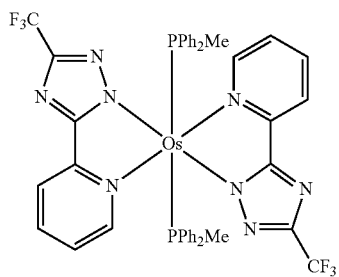

-continued

PD74

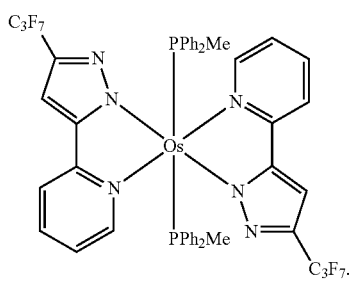

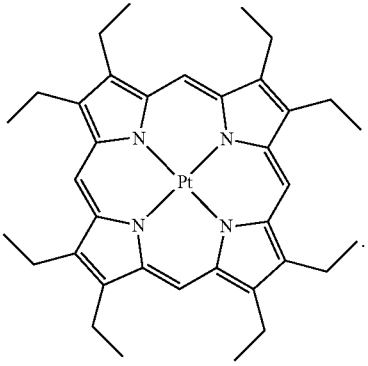

PtOEP

In some embodiments, the phosphorescent dopant may include PtOEP:

The fluorescent dopant may include the condensed cyclic compound represented by Formula 1.

In some embodiments, the fluorescent dopant may include, in addition to the condensed cyclic compound represented by Formula 1, DPVBi, DPAVBi, TBPe, dichloromethane, DCJTB, Coumarin 6, or C545T.

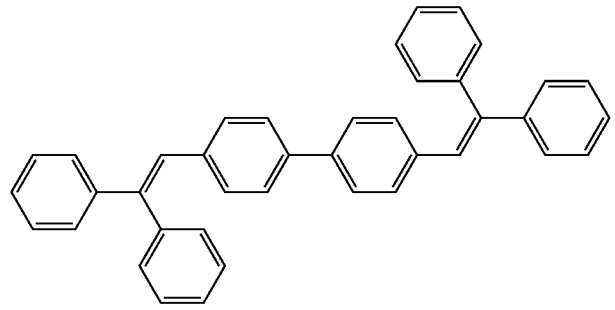

DPVBi

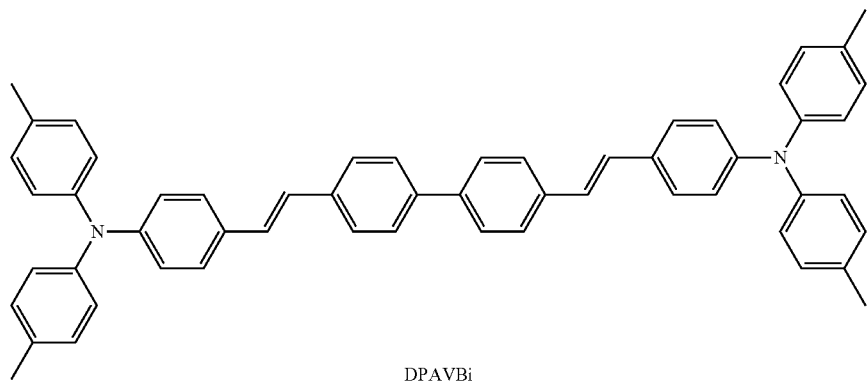

DPAVBi

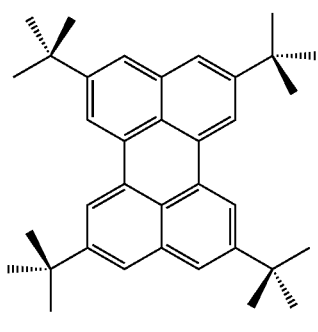
TBPe

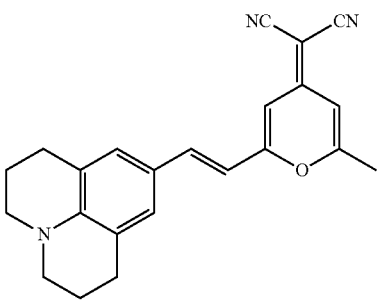
DCM

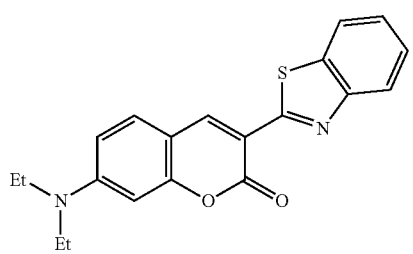
Coumarin 6

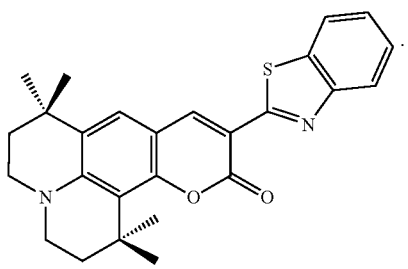
DCJTB

C545T

An amount of the dopant in the emission layer may be, for example, in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within any of these ranges, excellent light-emission characteristics may be obtained without a substantial increase in driving voltage.

An electron transport region may be positioned on the emission layer.

The electron transport region may include at least one selected from a hole blocking layer, an electron transport layer (ETL), and an electron injection layer, but is not limited thereto.

For example, the electron transport region may have a structure of electron transport layer/electron injection layer or a structure of hole blocking layer/electron transport layer/electron injection layer, where the layers of each structure are sequentially stacked from the emission layer in the stated order, but is not limited thereto.

The electron transport region may include a hole blocking layer. When the emission layer includes a phosphorescent dopant, the hole blocking layer may be formed to prevent or substantially reduce the diffusion of excitons or holes into an electron transport layer.

When the electron transport region includes a hole blocking layer, the hole blocking layer may be formed on the emission layer by using one or more suitable methods, such as vacuum deposition, spin coating casting, a Langmuir-Blodgett (LB) method, ink-jet printing, laser-printing, and/or laser-induced thermal imaging. When the hole blocking layer is formed by vacuum deposition and/or spin coating, deposition and coating conditions for the hole blocking layer may be similar to the deposition and coating conditions for the hole injection layer.

The hole blocking layer may include, for example, at least one of BCP and Bphen, but is not limited thereto.

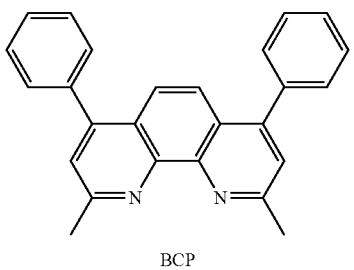

BCP

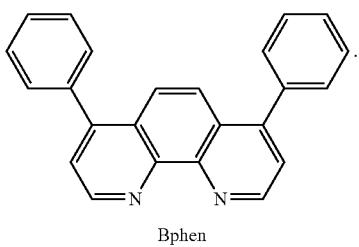

Bphen

A thickness of the hole blocking layer may be in a range of about 20 Å to about 1,000 Å, for example, about 30 Å to about 300 Å. When the thickness of the hole blocking layer is within any of these ranges, the hole blocking layer may have excellent hole blocking characteristics without a substantial increase in driving voltage.

The electron transport region may include an electron transport layer. The electron transport layer may be formed on the emission layer or the hole blocking layer by using one or more suitable methods, such as vacuum deposition, spin coating casting, a LB method, ink-jet printing, laser-printing, and/or laser-induced thermal imaging. When the electron transport layer is formed by vacuum deposition and/or spin coating, deposition and coating conditions for the electron transport layer may be the same as (or similar to) the deposition and coating conditions for the hole injection layer.

The electron transport layer may include at least one selected from BCP, Bphen, Alq$_3$, Balq, TAZ, and NTAZ.

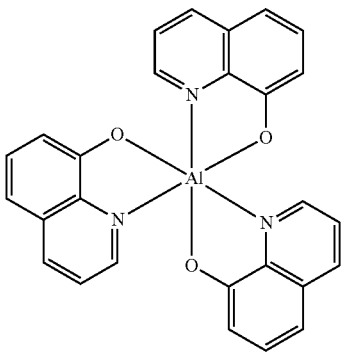

Alq$_3$

-continued

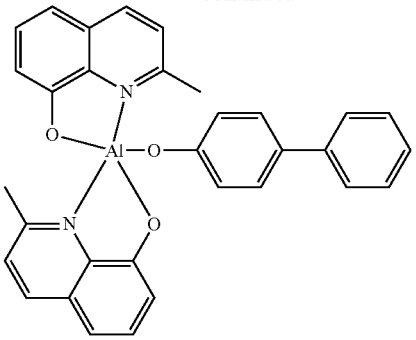

BAlq

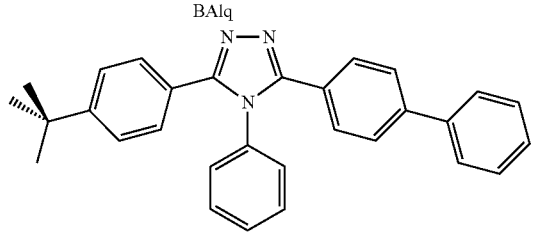

TAZ

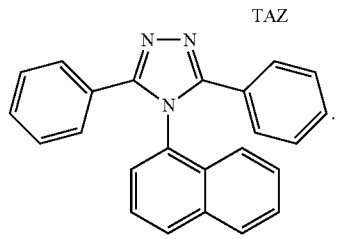

NTAZ

In some embodiments, the electron transport layer may further include at least one of compounds represented by Formula 601 below:

$$Ar_{601}\text{-}[(L_{601})_{xe1}\text{-}E_{601}]_{xe2}.$$ Formula 601

$Ar_{601}$ in Formula 601 may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{301}$)($Q_{302}$)($Q_{303}$) (where $Q_{301}$ to $Q_{303}$ may be each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

a description of $L_{601}$ may be understood by referring to the description provided in connection with $L_{201}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, a pyrrolyl group, a thiophenyl group, a furanyl group, an imidazoleyl group, a pyrazolyl group, a thiazolyl group, an isothiazoleyl group, an oxazoleyl group, an isoxazoleyl group, a pyridinyl group, a pyrazinyl group, a pyrimidinyl group, a pyridazinyl group, a isoindolyl group, an indolyl group, a indazolyl group, a purinyl group, a quinolinyl group, a isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazoleyl group, a triazinyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group;

xe1 may be selected from 0, 1, 2, and 3; and xe2 may be selected from 1, 2, 3, and 4.

In some embodiments, the electron transport layer may include at least one of compounds represented by Formula 602:

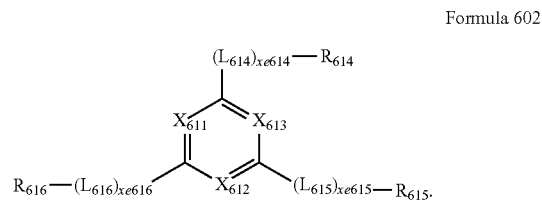

Formula 602

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, and at least one selected from $X_{611}$ to $X_{613}$ may be N;

descriptions of $L_{611}$ to $L_{616}$ are the same as provided in connection with $L_{201}$;

$R_{611}$ to $R_{616}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

A compound represented by Formula 601 and a compound represented by Formula 602 may each independently include at least one selected from Compounds ET1 to ET15:

ET1
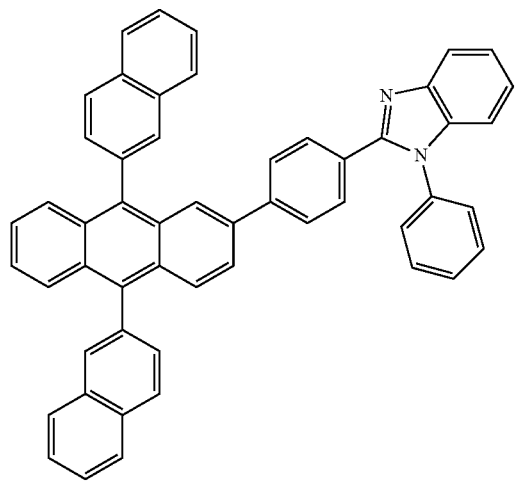
ET2
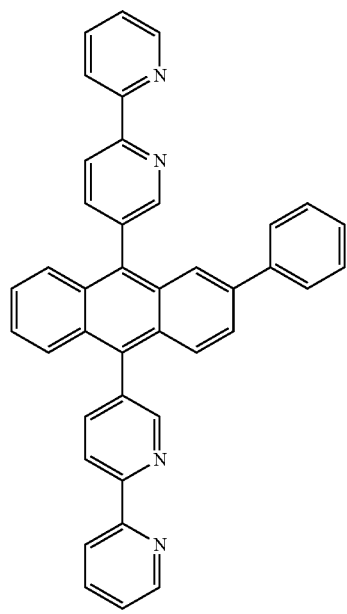
ET3
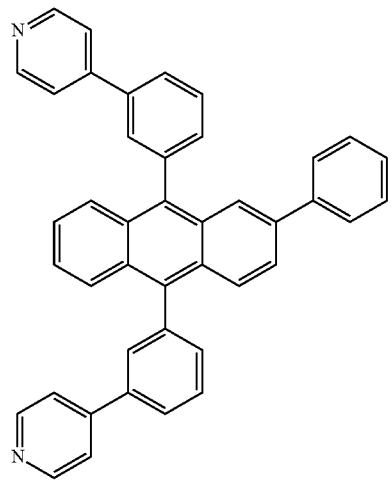
ET4
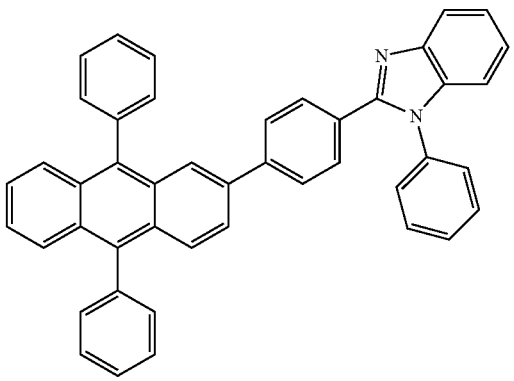
ET5
ET6
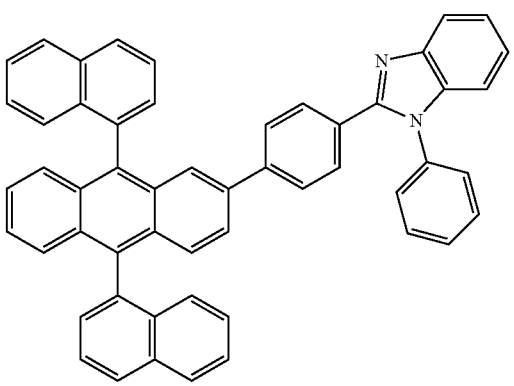

ET7
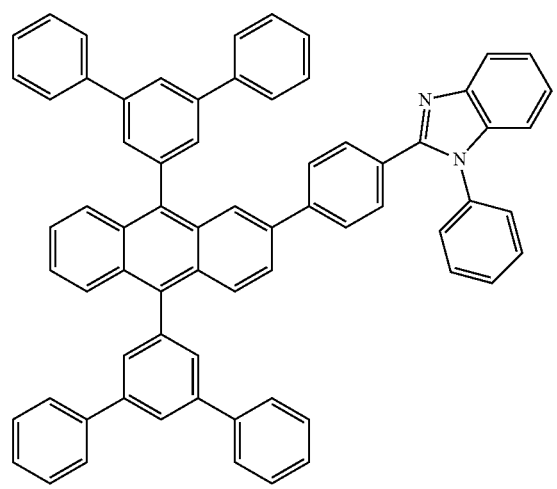
ET8
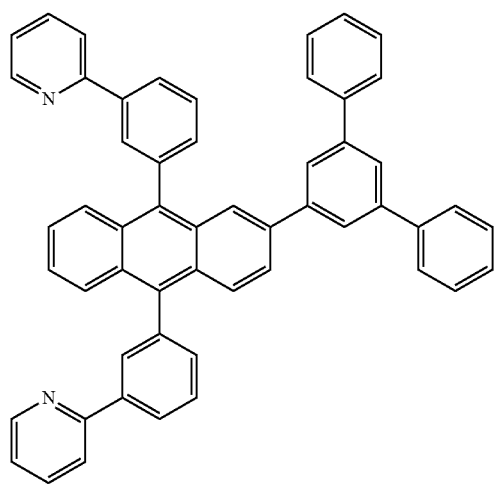
ET9
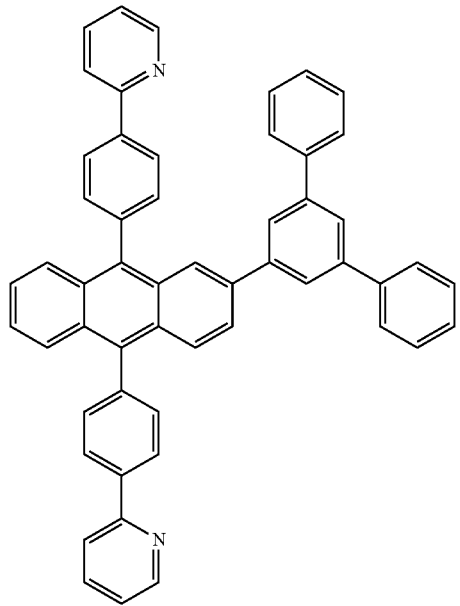
ET10
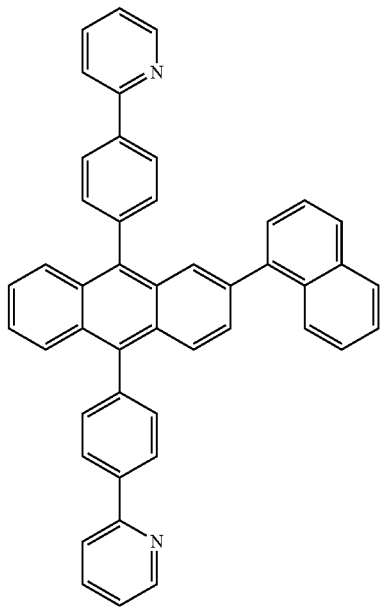
ET11
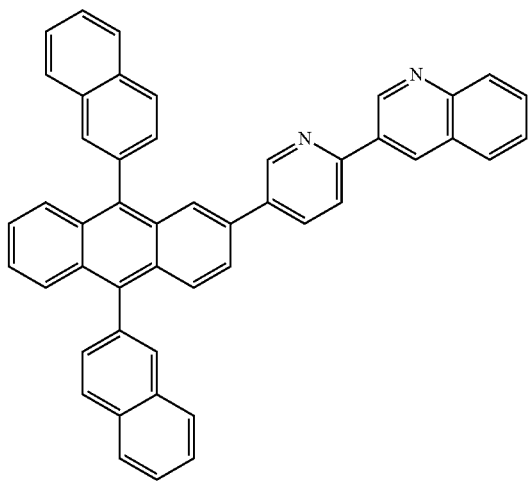
ET12
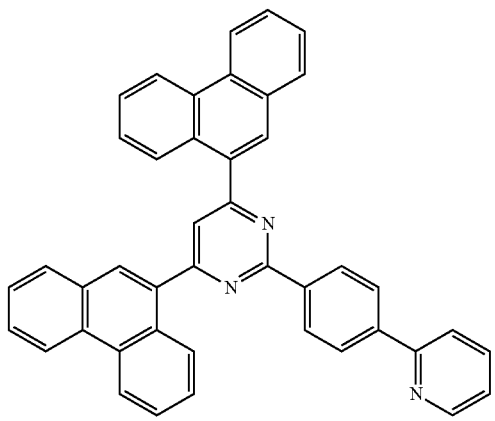

ET13

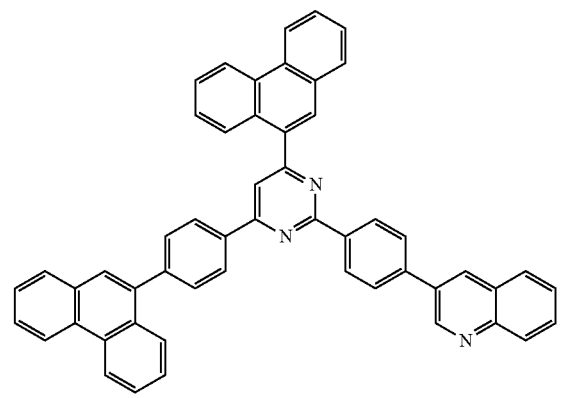

ET14

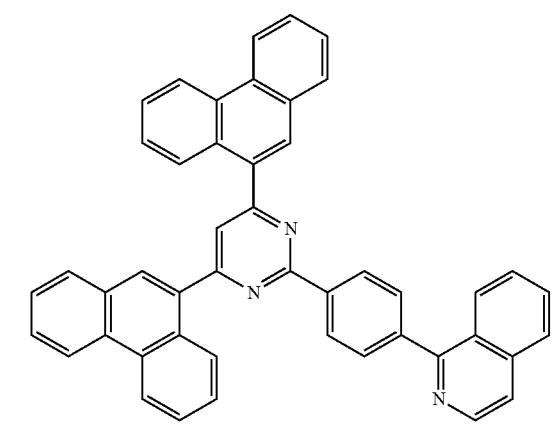

ET15

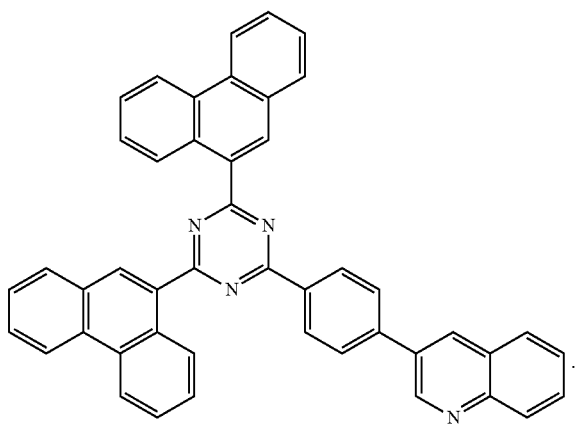

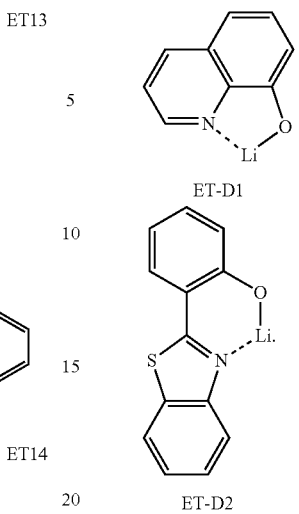

ET-D1

ET-D2

A thickness of the electron transport layer may be in a range of about 100 Å to about 1,000 Å, for example, about 150 Å to about 500 Å. When the thickness of the electron transport layer is within any of the ranges described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) and/or ET-D2.

The electron transport region may include an electron injection layer that allows electrons to be easily provided from the second electrode 190.

The electron injection layer may be formed on the electron transport layer by using one or more suitable methods, such as vacuum deposition, spin coating casting, a LB method, ink-jet printing, laser-printing, and/or laser-induced thermal imaging. When the electron injection layer is formed by vacuum deposition and/or spin coating, deposition and coating conditions for the electron injection layer may be the same as (or similar to) those for the hole injection layer.

The electron injection layer may include at least one selected from LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within any of the ranges described above, the electron injection layer may have satisfactory electron injection characteristics without a substantial increase in driving voltage.

The second electrode 190 may be positioned on the organic layer 150 having the structure as described herein. The second electrode 190 may be a cathode which is an electron injection electrode, and in this regard, a material for forming the second electrode 190 may be selected from a metal, an alloy, an electrically conductive compound, and a mixture thereof, which all have a relatively low work function. Non-limiting examples of the material for forming the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO or IZO. The second electrode 190 may be a reflective electrode, a semi-transmissive electrode, or a transmissive electrode.

Hereinbefore, the organic light-emitting device has been described with reference to the drawing, but embodiments of the present invention are not limited thereto.

A $C_1$-$C_{60}$ alkyl group used herein refers to a linear or branched aliphatic hydrocarbon monovalent group having 1 to 60 carbon atoms in the main chain, and non-limiting examples thereof include a methyl group, an ethyl group, an n-propyl group, an iso-propyl group, an n-butyl group, an iso-butyl group, a sec-butyl group, a tert-butyl group, a pentyl group, an iso-amyl group, and a hexyl group. A $C_1$-$C_{60}$ alkylene group used herein refers to a divalent group having the same structure as that of the $C_1$-$C_{60}$ alkyl group.

A $C_1$-$C_{60}$ alkoxy group used herein refers to a monovalent group represented by –$OA_{101}$ (where $A_{101}$ is the $C_1$-$C_{60}$ alkyl group), and non-limiting examples thereof include a methoxy group, an ethoxy group, and an isopropyloxy group.

A $C_2$-$C_{60}$ alkenyl group used herein refers to a monovalent hydrocarbon group having at least one carbon-carbon double bond at one or more positions along a carbon chain of the $C_2$-$C_{60}$ alkyl group (for example, in the middle or at either terminal end of the $C_2$-$C_{60}$ alkyl group), and non-limiting examples thereof include an ethenyl group, a propenyl group, and a butenyl group. A $C_2$-$C_{60}$ alkenylene group used herein refers to a divalent group having the same structure as that of the $C_2$-$C_{60}$ alkenyl group.

A $C_2$-$C_{60}$ alkynyl group used herein refers to a monovalent hydrocarbon group having at least one carbon-carbon triple bond at one or more positions along a carbon chain of the $C_2$-$C_{60}$ alkyl group (for example, in the middle or at either terminal end of the $C_2$-$C_{60}$ alkyl group), and non-limiting examples thereof include an ethynyl group and a propynyl group. A $C_2$-$C_{60}$ alkynylene group used herein refers to a divalent group having the same structure as that of the $C_2$-$C_{60}$ alkynyl group.

A $C_3$-$C_{10}$ cycloalkyl group used herein refers to a monovalent saturated hydrocarbon monocyclic group having 3 to 10 carbon atoms as ring-forming atoms, and non-limiting examples thereof include a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as that of the $C_3$-$C_{10}$ cycloalkyl group.

A $C_1$-$C_{10}$ heterocycloalkyl group used herein refers to a monovalent monocyclic group having at least one heteroatom selected from N, O, P, and S as a ring-forming atom and 1 to 10 carbon atoms as the remaining ring-forming atoms, and non-limiting examples thereof include a tetrahydrofuranyl group and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms as ring-forming atoms and at least one double bond in the ring thereof and does not have aromaticity, and non-limiting examples thereof include a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, P, and S as a ring-forming atom, 1 to 10 carbon atoms as the remaining ring-forming atoms, at least one double bond in its ring, and does not have aromaticity. Non-limiting examples of the $C_1$-$C_{10}$ heterocycloalkenyl group include a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms as ring-forming atoms, and a $C_6$-$C_{60}$ arylene group used herein refers to a divalent group having a carbocyclic aromatic system having 6 to 60 carbon atoms as ring-forming atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and/or the $C_6$-$C_{60}$ arylene group include two or more rings, the rings may be respectively fused to each other.

A $C_1$-$C_{60}$ heteroaryl group used herein refers to a monovalent group having a carbocyclic aromatic system that has at least one hetero atom selected from N, O, P, and S as a ring-forming atom, and 1 to 60 carbon atoms as the remaining ring-forming atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms as the remaining ring-forming atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and/or the $C_1$-$C_{60}$ heteroarylene group include two or more rings, the rings may be respectively fused to each other.

The $C_6$-$C_{60}$ aryloxy group used herein refers to a group represented by $OA_{102}$ (where $A_{102}$ is the $C_6$-$C_{60}$ aryl group), and the $C_6$-$C_{60}$ arylthio group refers to a group represented by —$SA_{103}$ (where $A_{103}$ is the $C_6$-$C_{60}$ aryl group).

A monovalent non-aromatic condensed polycyclic group used herein refers to a monovalent group that has two or more rings condensed to each other, only carbon atoms as ring-forming atoms, and does not have overall aromaticity. Non-limiting example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group that has two or more rings condensed to each other, has at least one heteroatom selected from N, O P, and S as a ring-forming atom, and carbon atoms as the remaining ring-forming atoms, and does not have overall aromaticity. Non-limiting example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

The term "Ph" used herein refers to phenyl group, the term "Me" used herein refers to methyl group, the term "Et" used herein refers to ethyl group, and the term "ter-Bu" or "But" used herein refers to tert-butyl.

Hereinafter, an organic light-emitting device according to one or more embodiments of the present invention will be described in more detail with reference to Synthesis Examples and Examples. The wording "B was used instead of A" used in describing Synthesis Examples means that a molar equivalent of A was identical to a molar equivalent of B.

EXAMPLES

Synthesis Example 1

Synthesis of Compound 5

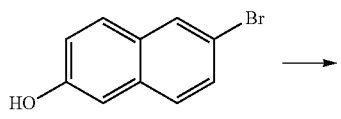

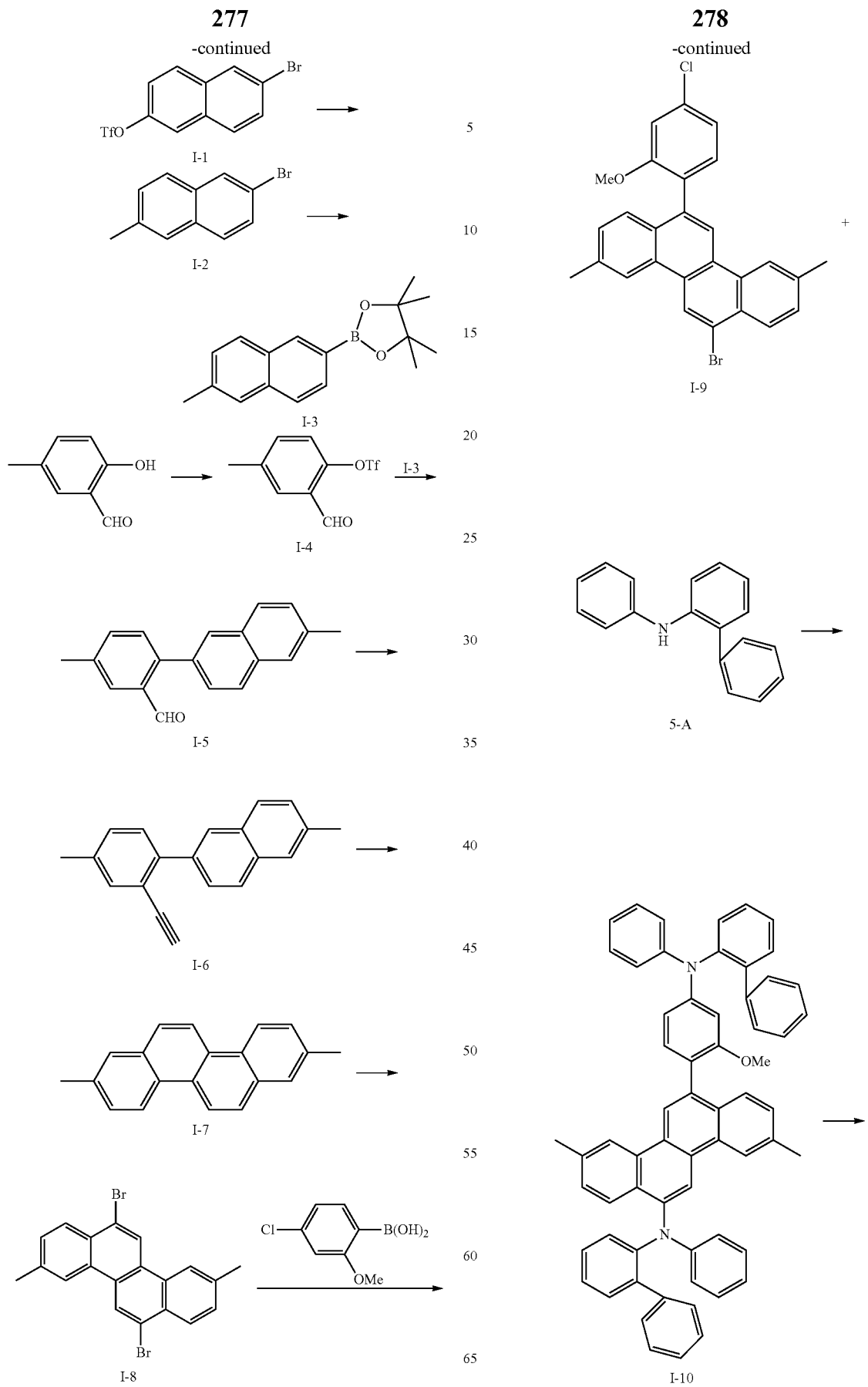

-continued

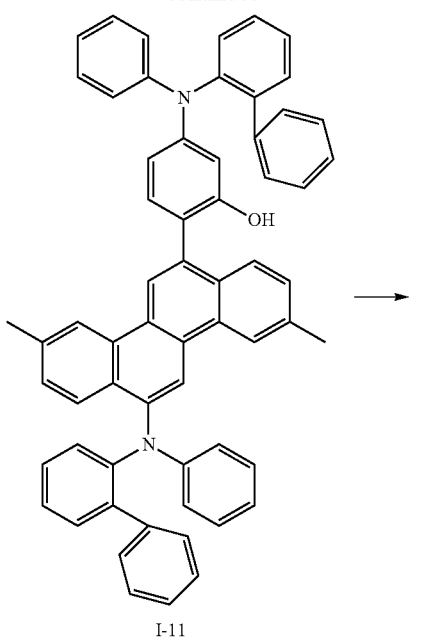

I-11

Synthesis of Intermediate I-1

1.34 g (6.0 mmol) of 6-bromo-2-naphthol was dissolved in 20 mL of toluene and 20 mL of 30% potassium phosphate, and then, at a temperature of 0° C., 2.03 g (7.2 mmol) of anhydrous trifluoromethanesulfonic acid was slowly added dropwise thereto. The reaction solution was cooled to room temperature, and then, stirred for 3 hours. Then, 30 mL of water was added thereto, and then, an extraction process was performed thereon three times by using 30 mL of diethylether, and an organic layer obtained therefrom was dried by using magnesium sulfate and the residual obtained by evaporating a solvent therefrom was separation-purified by silica gel column chromatography to obtain 1.73 g (yield of 81%) of Intermediate I-1. The obtained compound was identified by MS/FAB.

$C_{11}H_6BrF_3O_3S$: calc.: 355.12. Found: 355.11.

Synthesis of Intermediate I-2

1.77 g (5.0 mmol) of Intermediate I-1, 0.30 g (5.0 mmol) of methyl boronic acid, 0.29 g (0.25 mmol) of $Pd(PPh_3)_3$, and 2.07 g (15.0 mmol) of $K_2CO_3$ were dissolved by using 60 mL of a $THF/H_2O$ (a volumetric ratio of 2/1) mixed solution, and then, the resultant solution was stirred at a temperature of 70° C. for 5 hours. The reaction solution was cooled to room temperature, and then, the resulting product was subjected to an extraction process three times by using 50 mL of water and 50 mL of diethylether, and an organic layer obtained therefrom was dried by using magnesium sulfate and the residual obtained by evaporating a solvent therefrom was separation-purified by silica gel column chromatography to obtain 0.95 g (yield of 86%) of Intermediate I-2. The obtained compound was identified by MS/FAB.

$C_{11}H_9Br$: calc.: 221.09. Found: 221.11.

Synthesis of Intermediate I-3

2.21 g (10.0 mmol) of Intermediate I-2, 2.54 g (10.0 mmol) of bis(pinacolato)diborone), 0.36 g (0.5 mmol) of $PdCl_2(dppf)_2$, and 2.94 g (30.0 mmol) of KOAc were dissolved in 40 ml of DMSO, and then, the resulting mixture was stirred at the temperature of 80° C. for 6 hours. The reaction solution was cooled to room temperature, and then, the resulting product was subjected to an extraction process three times by using 50 mL of water and 50 mL of diethylether, and an organic layer obtained therefrom was dried by using magnesium sulfate and the residual obtained by evaporating a solvent therefrom was separation-purified by silica gel column chromatography to obtain 2.14 g (yield of 80%) of Intermediate I-3. The obtained compound was identified by MS/FAB.

$C_{17}H_{21}BO_2$: calc.: 268.16. Found: 268.15.

Synthesis of Intermediate I-4

Intermediate I-4 was synthesized in the same (or substantially the same) manner as used to synthesize Intermediate I-1, except that 2-hydroxy-5-methylbenzaldehyde was used instead of 6-bromo-2-naphthol. The obtained compound was identified by MS/FAB.

$C_9H_7F_3O_4S$: calc.: 268.20. Found: 268.22.

Synthesis of Intermediate I-5

Intermediate I-5 was synthesized in the same (or substantially the same) manner as used to synthesize Intermediate I-2, except that Intermediate I-4 was used instead of Intermediate I-1 and Intermediate I-3 was used instead of the methyl boronic acid. The obtained compound was identified by MS/FAB.

$C_{19}H_{16}O$: calc.: 260.33 found: 260.31.

Synthesis of Intermediate I-6

2.62 g (10.0 mmol) of triphenylphosphine and 1.65 g (5.0 mmol) of carbon tetrabromide were dissolved in dichloromethane in a nitrogen atmosphere, and at a temperature of 0° C., 0.65 g (2.5 mmol) of Intermediate I-5 was slowly added thereto. After one hour of stirring, a 5M $CuSO_4$ solution was added thereto, and an extraction process was performed thereon three times by using 50 mL of water and 50 mL of dichloromethane. An organic layer obtained therefrom was dried by using magnesium sulfate, and the residual obtained by evaporating a solvent therefrom was separation-purified by silica gel column chromatography. The resultant compound was dissolved in 30 mL of diethylether, and then, at a temperature of −78° C., 4.6 mL (2.17M in hexane) of n-BuLi was slowly added dropwise thereto. After 30 minutes of stirring, the reaction solution was heated to room temperature and stirred for one hour, and then, an organic layer obtained by an extraction process using 50 mL of water and 50 mL of diethylether was dried by using magnesium sulfate. The residual obtained by evaporating a solvent therefrom was separation-purified by silica gel column chromatography to obtain 0.49 g (yield of 77%) of Intermediate I-6. The obtained compound was identified by MS/FAB.

$C_{20}H_{16}$: calc.: 256.34. Found: 256.36.

Synthesis of Intermediate I-7

2.56 g (10.0 mmol) of Intermediate I-6 and 0.26 g (1.0 mmol) of $PtCl_2$ were dissolved in 100 mL of toluene, and then, at a temperature of 80° C., the resulting mixture was stirred for 6 hours. The reaction solution was cooled to room temperature, and then, subjected to an extraction process three times by using 50 mL of water and 50 mL of dichloromethane, and an organic layer obtained therefrom was dried by using magnesium sulfate and the residual obtained by evaporating a solvent therefrom was separation-purified by silica gel column chromatography to obtain 2.20 g (yield of 86%) of Intermediate I-7. The obtained compound was identified by MS/FAB.

$C_{20}H_{16}$: calc.: 256.34. Found: 256.36.

Synthesis of Intermediate I-8

0.51 g (2.00 mmol) of Intermediate I-7 was dissolved in 50 ml of dichloromethane, and then, at room temperature, 0.72 g (4.0 mmol) of N-Bromosuccinimide (NBS) was slowly added dropwise thereto, and then, the resulting product was stirred for 24 hours at room temperature. Once the reaction was complete, 50 mL of $H_2O$ was added thereto, and an extraction process was performed three times by using 50 mL of dichloromethane. A collected organic layer was dried by using magnesium sulfate, and then, the residual obtained by evaporating a solvent therefrom was separation-purified by silica gel column chromatography to obtain 0.65 g (yield 79%) of Intermediate I-8. The obtained compound was identified by MS/FAB.

$C_{20}H_{14}Br_2$: calc.: 414.14. Found: 414.16.

Synthesis of Intermediate I-9

5.90 g (22.0 mmol) of (4-chloro-2-methoxyphenyl)-boronic acid, 18.2 g (44.0 mmol) of Intermediate I-8, 1.27 g (1.1 mmol) of tetrakis(triphenylphosphine)palladium [Pd (PPh$_3$)$_4$], and 4.50 g (33 mmol) of $K_2CO_3$ were dissolved by using 200 mL of a THF/$H_2O$ (a volumetric ratio of 2/1) mixed solution, and then, at a temperature of 70° C., the resultant solution was stirred for 5 hours. The reaction solution was cooled to room temperature, and then, 60 mL of water was added thereto, and an extraction process was performed thereon three times with 60 mL of ethylether. A collected organic layer was dried by using magnesium sulfate, and then, the residual obtained by evaporating a solvent therefrom was separation-purified by silica gel column chromatography to obtain 6.70 g (yield of 64%) of Intermediate I-9. The obtained compound was identified by MS/FAB.

$C_{27}H_{20}BrClO$: calc.: 475.81. Found: 475.83.

Synthesis of Intermediate I-10

9.51 g (20.0 mmol) of Intermediate I-9, 9.81 g (40.0 mmol) of Intermediate 5-A, 0.37 g (0.4 mmol) of Pd$_2$(dba)$_3$, 0.08 g (0.4 mmol) of P(t-Bu)$_3$, and 5.76 g (60.0 mmol) of t-BuOK were dissolved in 90 mL of toluene, and then, the resulting mixture was stirred at a temperature of 85° C. for 12 hours. The reaction solution was cooled to room temperature, and then extracted three times with 50 mL of water and 50 mL of diethylether. A collected organic layer was dried by using magnesium sulfate, and then, the residual obtained by evaporating a solvent therefrom was separation-purified by silica gel column chromatography to obtain 14.1 g (yield of 83%) of Intermediate I-10. The obtained compound was identified by MS/FAB.

$C_{63}H_{48}N_2O$: calc.: 849.09. Found: 849.11.

Synthesis of Intermediate I-11

1.70 g (2.00 mmol) of Intermediate I-10 was dissolved in 20 mL of dichloromethane, and then, at a temperature of −78° C., 0.33 mL (3.5 mmol) of BBr$_3$ was slowly added dropwise thereto. The reaction solution was heated to room temperature and then stirred for 24 hours at room temperature. Once the reaction was complete, 5 mL of MeOH and 10 mL of H$_2$O were added thereto, and an extraction process was performed thereon three times by using 10 mL of dichloromethane. A collected organic layer was dried by using magnesium sulfate, and then, the residual obtained by evaporating a solvent therefrom was separation-purified by silica gel column chromatography to obtain 1.25 g (yield of 75%) of Intermediate I-11. The obtained compound was identified by MS/FAB.

$C_{62}H_{46}N_2O$: calc.: 835.06. Found: 835.07.

Synthesis of Compound 5

1.67 g (2.00 mmol) of Intermediate I-11 was dissolved in 10 mL of dimethylformamide, and then, at room temperature, 0.48 mL (6.0 mmol) of CuO was slowly added dropwise thereto. The reaction solution was stirred at a temperature of 140° C. for 48 hours. Once the reaction was complete, the reaction solution was filtered by using celite, and 10 mL of H$_2$O was added to a collected organic layer, which was then subjected to an extraction process three times by using 10 mL of ethylacetate. A collected organic layer was dried by using magnesium sulfate, and then, the residual obtained by evaporating a solvent therefrom was separation-purified by silica gel column chromatography to obtain 1.45 g (yield of 87%) of Compound 5. The obtained compound was identified by $^1$H NMR (CDCl$_3$, 400 MHz) and MS/FAB.

9.26 (s, 1H), 8.46 (s, 1H), 8.23 (s, 1H), 7.78 (s, 1H), 7.60-7.46 (m, 12H), 7.29-6.78 (m, 14H), 6.65-6.60 (m, 3H), 6.48-6.40 (m, 1H), 6.25-6.20 (m, 2H), 6.00-5.98 (m, 2H), 2.55 (s, 3H), 2.50 (s, 3H)

$C_{62}H_{44}N_2O$: calc.: 833.04. Found: 833.06.

Synthesis Example 2

Synthesis of Compound 15

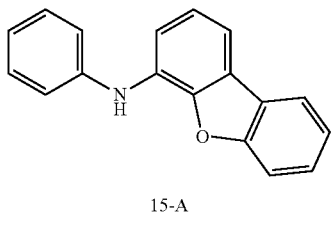 [SMILES: c1ccc(Nc2cccc3c2oc2ccccc23)cc1]

15-A

Compound 15 was synthesized in the same (or substantially the same) manner as used to synthesize Compound 5, except that Intermediate 15-A was used instead of Intermediate 5-A. The obtained compound was identified by $^1$H NMR (CDCl$_3$, 400 MHz) and MS/FAB.

9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

C$_{62}$H$_{40}$N$_2$O$_3$: calc.: 861.01. Found: 861.03.

Synthesis Example 3

Synthesis of Compound 23

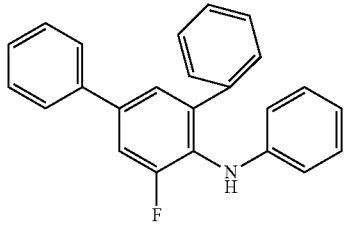

23-A

Compound 23 was synthesized in the same (or substantially the same) manner as used to synthesize Compound 5, except that both Intermediate 5-A and Intermediate 23-A were used instead of using Intermediate 5-A alone. The obtained compound was identified by $^1$H NMR (CDCl$_3$, 400 MHz) and MS/FAB.

9.26 (s, 1H), 8.48 (s, 1H), 8.23 (s, 1H), 7.88 (s, 1H), 7.72-6.84 (m, 29H), 6.60-6.28 (m, 6H), 6.00-5.98 (m, 2H), 2.55 (s, 3H), 2.50 (s, 3H)

C$_{68}$H$_{47}$FN$_2$O: calc.: 927.13. Found: 927.15.

Synthesis Example 4

Synthesis of Compound 39

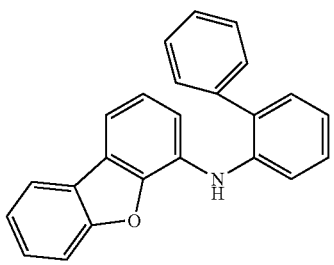

39-A

Compound 39 was synthesized in the same (or substantially the same) manner as used to synthesize Compound 5, except that Intermediate 15-A and Intermediate 39-A were used instead of Intermediate 5-A. The obtained compound was identified by $^1$H NMR (CDCl$_3$, 400 MHz) and MS/FAB.

9.26 (s, 1H), 8.48 (s, 1H), 8.23 (s, 1H), 8.05 (s, 1H), 7.72-7.26 (m, 18H), 7.16-6.80 (m, 11H), 6.75-6.50 (m, 3H), 6.38-6.34 (m, 2H), 2.55 (s, 3H), 2.50 (s, 3H)

C$_{68}$H$_{44}$N$_2$O$_3$: calc.: 937.11. Found: 937.13.

Synthesis Example 5

Synthesis of Compound 54

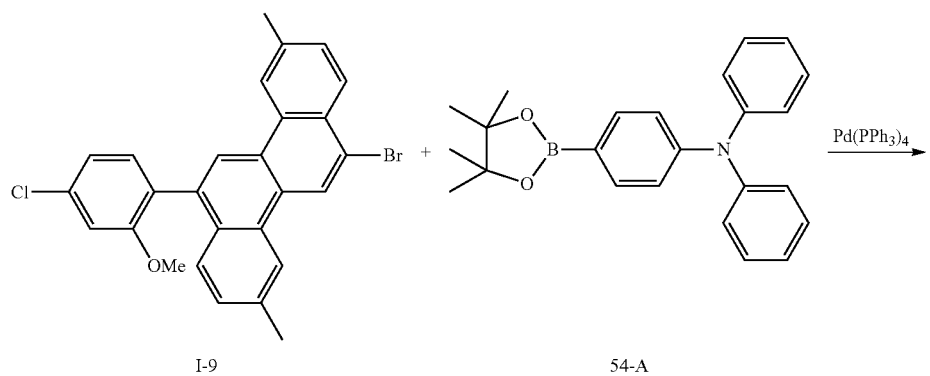

I-9                                    54-A

-continued
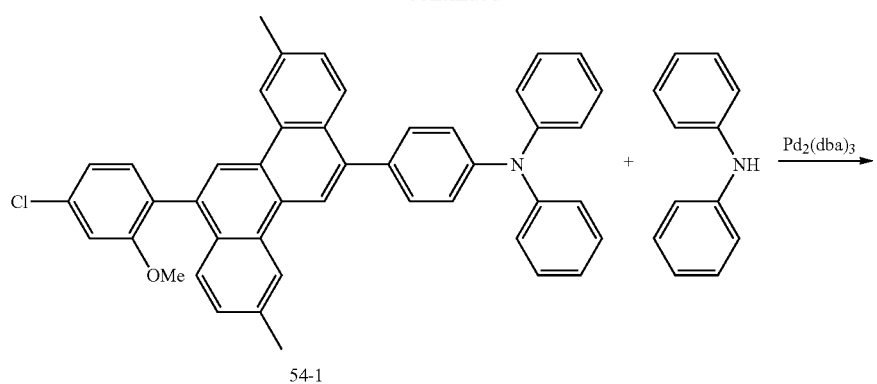
54-1
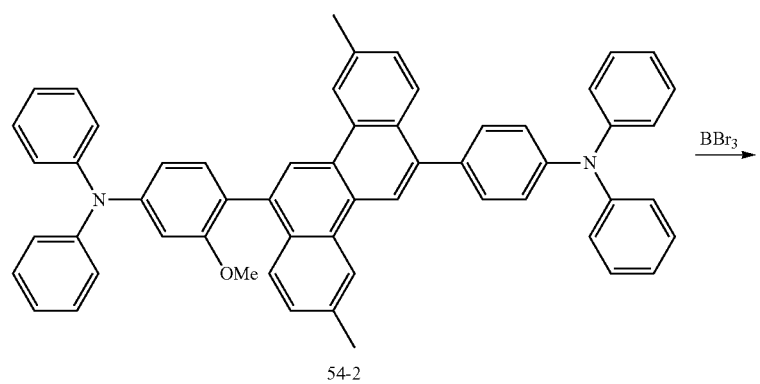
54-2
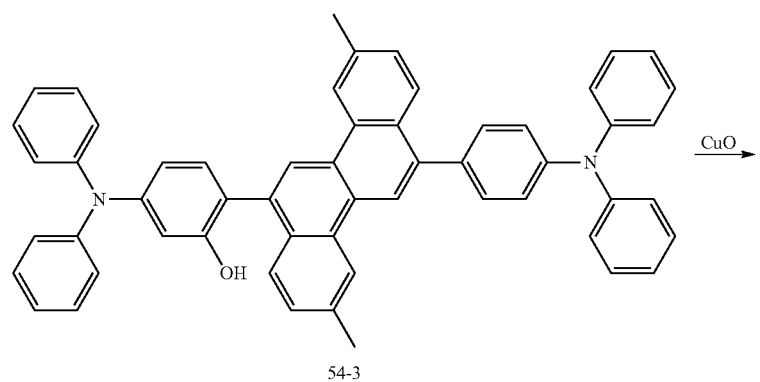
54-3
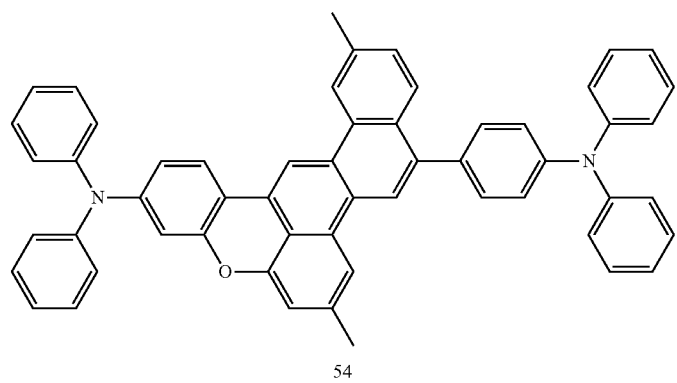
54

Synthesis of Intermediate 54-1

Intermediate 54-1 was synthesized in the same (or substantially the same) manner as used to synthesize Intermediate I-9 in Synthesis Example 1, except that Intermediate I-9 was used instead of Intermediate I-8, and Intermediate 54-A was used instead of (4-chloro-2-methoxyphenyl)-boronic acid. The obtained compound was identified by MS/FAB.

$C_{45}H_{34}ClNO$: calc.: 640.22. Found: 640.24.

Synthesis of Intermediate 54-2

Intermediate 54-2 was synthesized in the same (or substantially the same) manner as used to synthesize Intermediate I-10 in Synthesis Example 1, except that Intermediate 54-1 was used instead of Intermediate I-9, and N,N-diphenylamine was used instead of Intermediate 5-A. The obtained compound was identified by MS/FAB.

$C_{57}H_{44}N_2O$: calc.: 772.99. Found: 773.00.

Synthesis of Intermediate 54-3

Intermediate 54-3 was synthesized in the same (or substantially the same) manner as used to synthesize Intermediate I-11 in Synthesis Example 1, except that Intermediate 54-2 was used instead of Intermediate I-10. The obtained compound was identified by MS/FAB.

$C_{56}H_{42}N_2O$: calc.: 758.96. Found: 758.97.

Synthesis of Compound 54

Compound 54 was synthesized in the same (or substantially the same) manner as used to synthesize Compound 5 in Synthesis Example 1, except that Intermediate 54-3 was used instead of Intermediate I-11. The obtained compound was identified by $^1$H NMR (CDCl$_3$, 400 MHz) and MS/FAB.

9.26 (s, 1H), 8.75 (s, 1H), 8.23 (s, 1H), 7.80-7.46 (m, 6H), 7.08-6.88 (m, 11H), 6.75-6.50 (m, 6H), 6.38-6.30 (m, 4H), 6.25-6.18 (m, 4H), 2.55 (s, 3H), 2.50 (s, 3H)

$C_{56}H_{40}N_2O$: calc.: 756.94. Found: 756.96.

Synthesis Example 6

Synthesis of Compound 63

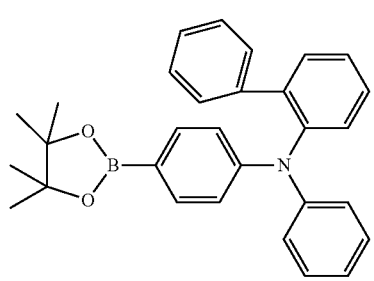
63-A

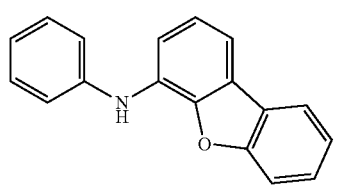
15-A

Compound 63 was synthesized in the same (or substantially the same) manner as used to synthesize Compound 54 in Synthesis Example 5, except that Intermediate 63-A was used instead of Intermediate 54-A, and Intermediate 15-A was used instead of N,N-diphenylamine. The obtained compound was identified by $^1$H NMR (CDCl$_3$, 400 MHz) and MS/FAB.

9.26 (s, 1H), 8.75 (s, 1H), 8.23 (s, 1H), 7.80-7.46 (m, 16H), 7.28-6.88 (m, 13H), 6.75-6.50 (m, 4H), 6.28-6.25 (m, 2H), 6.05-6.00 (m, 2H), 2.55 (s, 3H), 2.50 (s, 3H)

$C_{68}H_{46}N_2O_2$: calc.: 923.12. Found: 923.14.

Synthesis Example 7

Synthesis of Compound 68

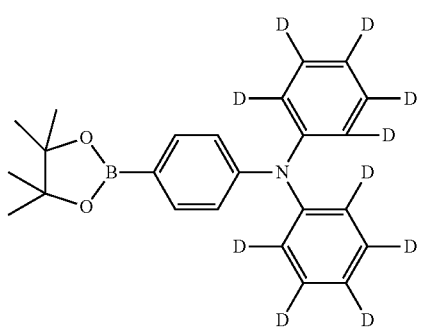
68-A

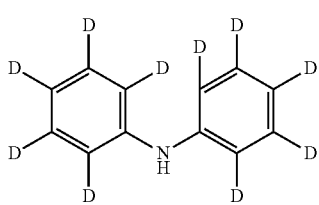
68-B

Compound 68 was synthesized in the same (or substantially the same) manner as used to synthesize Compound 54 in Synthesis Example 5, except that Intermediate 68-A was used instead of Intermediate 54-A, and Intermediate 68-B was used instead of N,N-diphenylamine. The obtained compound was identified by $^1$H NMR (CDCl$_3$, 400 MHz) and MS/FAB.

9.26 (s, 1H), 8.75 (s, 1H), 8.23 (s, 1H), 7.80-7.46 (m, 6H), 7.00-6.88 (m, 3H), 6.75 (s, 1H), 6.52-6.50 (m, 1H), 2.55 (s, 3H), 2.50 (s, 3H)

$C_{56}H_{20}D_{20}N_2O$: calc.: 777.07. Found: 777.09.

Synthesis Example 8

Synthesis of Compound 87

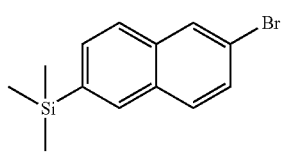
I-11

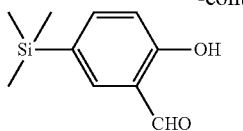

Compound 87 was synthesized in the same (or substantially the same) manner as used to synthesize Compound 5 in Synthesis Example 1, except that Intermediate I-11 was used instead of Intermediate I-2, 2-hydroxy-(5-trimethylsilyl)-benzaldehyde was used instead of 2-hydroxy-5-methylbenzaldehyde, and Intermediate 15-A was used instead of Intermediate 5-A. The obtained compound was identified by $^1$H NMR (CDCl$_3$, 400 MHz) and MS/FAB.

9.18 (s, 1H), 8.66 (s, 1H), 8.32 (s, 1H), 8.15 (s, 1H), 7.90-7.80 (m, 3H), 7.76-7.65 (m, 5H), 7.52-7.38 (m, 6H), 7.08-6.92 (m, 8H), 6.65-6.58 (m, 3H), 6.52-6.48 (m, 1H), 6.36-6.32 (m, 2H), 6.24-6.20 (m, 2H), 0.38 (s, 18H)

$C_{66}H_{52}N_2O_3Si_2$: calc.: 977.32. Found: 977.34.

Synthesis Example 9

Synthesis of Compound 90

Compound 90 was synthesized in the same (or substantially the same) manner as used to synthesize Compound 5 in Synthesis Example 1, except that Intermediate I-11 was used instead of Intermediate I-2, 2-hydroxy-(5-trimethylsilyl)-benzaldehyde was used instead of 2-hydroxy-5-methylbenzaldehyde, and Intermediate 23-A was used instead of Intermediate 5-A. The obtained compound was identified by $^1$H NMR (CDCl$_3$, 400 MHz) and MS/FAB.

9.14 (s, 1H), 8.66 (s, 1H), 8.32 (s, 1H), 7.66-7.44 (m, 15H), 7.20-7.15 (m, 2H), 7.06-6.90 (m, 8H), 6.65-6.60 (m, 2H), 6.50-6.42 (m, 2H), 6.25-6.20 (m, 2H), 6.06-6.02 (m, 2H), 0.38 (s, 18H)

$C_{66}H_{54}F_2N_2OSi_2$: calc.: 985.33. Found: 985.35.

Synthesis Example 10

Synthesis of Compound 94

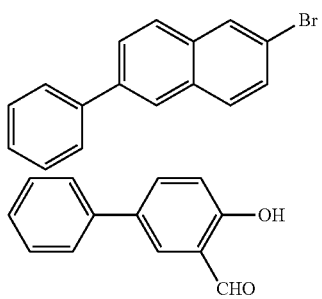

I-12

Compound 94 was synthesized in the same (or substantially the same) manner as used to synthesize Compound 5 in Synthesis Example 1, except that Intermediate I-12 was used instead of Intermediate I-2, and 4-hydroxy-(1,1'-biphenyl)-3-carboaldehyde was used instead of 2-hydroxy-5-methylbenzaldehyde. The obtained compound was identified by $^1$H NMR (CDCl$_3$, 400 MHz) and MS/FAB.

9.50 (s, 1H), 8.75 (s, 1H), 8.46 (s, 1H), 7.48-7.26 (m, 24H), 7.19-6.88 (m, 11H), 6.75-6.50 (m, 2H), 6.38-6.30 (m, 4H), 6.25-6.20 (m, 4H)

$C_{72}H_{48}N_2O$: calc.: 957.18. Found: 957.20.

Synthesis Example 11

Synthesis of Compound 104

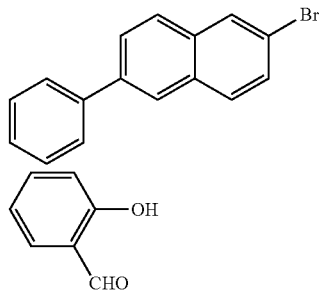

I-12

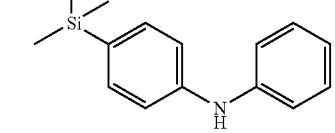

104-A

Compound 104 was synthesized in the same (or substantially the same) manner as used to synthesize Compound 5 in Synthesis Example 1, except that Intermediate I-12 was used instead of Intermediate I-2, 2-hydroxybenzaldehyde was used instead of 2-hydroxy-5-methylbenzaldehyde, and Intermediate 104-A was used instead of Intermediate 5-A. The obtained compound was identified by $^1$H NMR (CDCl$_3$, 400 MHz) and MS/FAB.

9.38 (s, 1H), 8.42-8.38 (m, 2H), 7.72-7.59 (m, 7H), 7.51-7.48 (m, 1H), 7.40-7.34 (m, 5H), 7.28-7.21 (m, 2H), 7.09-7.02 (m, 4H), 6.80-6.60 (m, 5H), 6.55-6.50 (m, 3H), 6.36-6.32 (m, 2H), 6.20-6.154 (m, 2H), 0.38 (s, 18H)

$C_{60}H_{52}N_2OSi_2$: calc.: 873.25. Found: 873.27.

Synthesis Example 12

Synthesis of Compound 107

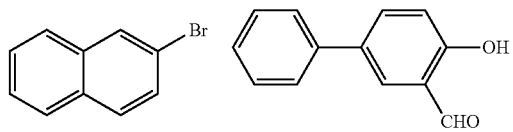

Compound 107 was synthesized in the same (or substantially the same) manner as used to synthesize Compound 5 in Synthesis Example 1, except that 2-bromonaphthalene was used instead of Intermediate I-2, 4-hydroxy-(1,1'-biphenyl)-3-carboaldehyde was used instead of 2-hydroxy-5-methylbenzaldehyde, and Intermediate 15-A was used instead of Intermediate 5-A. The obtained compound was identified by $^1$H NMR (CDCl$_3$, 400 MHz) and MS/FAB.

9.38 (s, 1H), 8.62-8.60 (m, 2H), 7.92-7.39 (m, 20H), 7.10-6.88 (m, 9H), 6.75-6.50 (m, 4H), 6.38-6.30 (m, 4H)

$C_{66}H_{40}N_2O_3$: calc.: 909.05. Found: 909.07.

Additional compounds were synthesized by using the same (or substantially the same) synthesis method as described above and appropriate intermediate materials, and $^1$H NMR and MS/FAB results of the obtained synthetic compounds are shown in Table 1 below.

Methods of synthesizing compounds other than the compounds shown in Table 1 should be apparent to those of ordinary skill in the art by referring to the synthesis path and source materials described above.

TABLE 1

| Compound | $^1$H NMR (CDCl$_3$, 400 MHz) | MS/FAB Calc. | MS/FAB Found |
|---|---|---|---|
| 1 | 9.24 (s, 1H), 8.45 (s, 1H), 8.23 (s, 1H), 7.75-7.72 (m, 1H), 7.60-7.55 (m, 2H), 7.25-7.22 (m, 1H), 7.18-7.00 (m, 8H), 6.80 (s, 1H), 6.75 (s, 1H), 6.65-6.60 (m, 5H), 6.30-6.25 (m, 4H), 6.15-6.10 (m, 4H), 2.55 (s, 3H), 2.50 (s, 3H) | 680.87 | 680.85 |
| 5 | 9.26 (s, 1H), 8.46 (s, 1H), 8.23 (s, 1H), 7.78 (s, 1H), 7.60-7.46 (m, 12H), 7.29-6.78 (m, 14H), 6.65-6.60 (m, 3H), 6.48-6.40 (m, 1H), 6.25-6.20 (m, 2H), 6.00-5.98 (m, 2H), 2.55 (s, 3H), 2.50 (s, 3H) | 833.07 | 833.05 |
| 7 | 9.18 (s, 1H), 8.45-8.42 (m, 1H), 8.20 (s, 1H), 7.75-7.72 (m, 1H), 7.66-7.60 (m, 2H), 7.41-7.36 (m, 4H), 7.30-7.28 (m, 1H), 7.09-7.02 (m, 4H), 6.90 (s, 1H), 6.75-6.72 (m, 1H), 6.70-6.60 (m, 4H), 6.55-6.50 (m, 3H), 6.36-6.33 (m, 2H), 6.18-6.15 (m, 2H), 2.55 (s, 3H), 2.50 (s, 3H), 0.24 (s, 18H) | 825.23 | 825.21 |
| 9 | 9.26 (s, 1H), 8.48 (s, 1H), 8.23 (s, 1H), 7.78 (s, 1H), 7.60-7.48 (m, 12H), 7.29-7.26 (m, 1H), 7.10-6.90 (m, 9H), 6.75-6.50 (m, 5H), 6.28-6.25 (m, 1H), 6.18-6.15 (m, 2H), 6.00-5.98 (m, 2H), 2.55 (s, 3H), 2.50 (s, 3H) | 869.05 | 869.03 |
| 11 | 9.26 (s, 1H), 8.48 (s, 1H), 8.23 (s, 1H), 7.78-4.60 (m, 3H), 7.30-7.25 (m, 5H), 7.10-6.89 (m, 5H), 6.68-6.00 (m, 8H), 2.65 (s, 3H), 2.50 (s, 3H), 2.25 (s, 6H), 2.20 (s, 6H) | 787.00 | 786.98 |
| 15 | 9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H) | 861.03 | 861.01 |
| 17 | 9.26 (s, 1H), 8.48 (s, 1H), 8.23 (s, 1H), 7.82-7.26 (m, 16H), 7.10-7.00 (m, 5H), 6.80-7.52 (m, 6H), 6.45-6.40 (m, 2H), 6.25-6.20 (m, 2H), 2.55 (s, 3H), 2.50 (s, 3H) | 861.03 | 861.01 |
| 23 | 9.26 (s, 1H), 8.48 (s, 1H), 8.23 (s, 1H), 7.88 (s, 1H), 7.72-6.84 (m, 29H), 6.60-6.28 (m, 6H), 6.00-5.98 (m, 2H), 2.55 (s, 3H), 2.50 (s, 3H) | 927.16 | 927.14 |
| 25 | 9.26 (s, 1H), 8.48 (s, 1H), 8.23 (s, 1H), 7.88-7.60 (m, 6H), 7.50-7.25 (m, 3H), 7.12-6.88 (m, 9H), 6.75-6.50 (m, 5H), 6.29-6.20 (m, 6H), 2.55 (s, 3H), 2.50 (s, 3H) | 770.95 | 770.93 |
| 28 | 9.26 (s, 1H), 8.48 (s, 1H), 8.23 (s, 1H), 8.05 (s, 1H), 7.88-7.29 (m, 13H), 7.20-6.80 (m, 11H), 6.75-6.50 (m, 4H), 6.30-6.25 (m, 4H), 2.55 (s, 3H), 2.50 (s, 3H) | 847.05 | 847.03 |
| 32 | 9.18 (s, 1H), 8.48-8.45 (m, 1H), 8.38-8.34 (m, 1H), 8.20-8.16 (m, 2H), 7.85-7.82 (m, 1H), 7.73-7.55 (m, 7H), 7.44-7.36 (m, 3H), 7.30-7.26 (m, 1H), 7.09-7.02 (m, 4H), 6.90 (s, 1H), 6.78-6.75 (m, 1H), 6.72-6.60 (m, 5H), 6.54-6.52 (m, 1H), 6.36-6.32 (m, 2H), 6.00-5.96 (m, 2H), 2.55 (s, 3H), 2.50 (s, 3H), 0.56 (s, 9H) | 853.17 | 853.15 |
| 35 | 9.18 (s, 1H), 8.48-8.45 (m, 1H), 8.18-8.15 (m, 1H), 7.85-7.75 (m, 2H), 7.66-7.60 (m, 3H), 7.55-7.50 (m, 2H), 7.42-7.36 (m, 4H), 7.30-7.26 (m, 1H), 7.09-7.02 (m, 4H), 6.90 (s, 1H), 6.78-6.61 (m, 6H), 6.54-6.52 (m, 1H), 6.36-6.33 (m, 2H), 6.21-6.18 (m, 2H), 2.55 (s, 3H), 2.50 (s, 3H), 0.56 (s, 9H) | 843.13 | 843.11 |
| 39 | 9.26 (s, 1H), 8.48 (s, 1H), 8.23 (s, 1H), 8.05 (s, 1H), 7.72-7.26 (m, 18H), 7.16-6.80 (m, 11H), 6.75-6.50 (m, 3H), 6.38-6.34 (m, 2H), 2.55 (s, 3H), 2.50 (s, 3H) | 937.13 | 937.11 |
| 41 | 9.26 (s, 1H), 8.48-8.45 (m, 2H), 8.23-8.15 (m, 2H), 7.85-7.46 (m, 15H), 7.10-6.86 (m, 8H), 6.68-6.50 (m, 4H), 6.28-6.24 (m, 2H), 6.16-6.10 (m, 2H), 2.55 (s, 3H), 2.50 (s, 3H) | 871.07 | 871.05 |
| 43 | 9.26 (s, 1H), 8.48 (s, 1H), 8.23 (s, 1H), 7.80-7.18 (s, 14H), 7.09-6.88 (m, 9H), 6.70-6.50 (m, 4H), 6.38-6.30 (m, 4H), 2.55 (s, 3H), 2.50 (s, 3H) | 861.03 | 861.01 |
| 50 | 9.26 (s, 1H), 8.48 (s, 1H), 8.23-8.18 (m, 2H), 7.88 (s, 1H), 7.54-7.35 (m, 13H), 7.25-6.88 (m, 14H), 6.75-6.50 (m, 3H), 6.00-5.95 (m, 2H), 2.55 (s, 3H), 2.50 (s, 3H) | 834.05 | 834.03 |
| 54 | 9.26 (s, 1H), 8.75 (s, 1H), 8.23 (s, 1H), 7.80-7.46 (m, 6H), 7.08-6.88 (m, 11H), 6.75-6.50 (m, 6H), 6.38-6.30 (m, 4H), 6.25-6.18 (m, 4H), 2.55 (s, 3H), 2.50 (s, 3H) | 756.97 | 756.95 |

TABLE 1-continued

| Compound | ¹H NMR (CDCl₃, 400 MHz) | MS/FAB Calc. | Found |
|---|---|---|---|
| 58 | 9.26 (s, 1H), 8.75 (s, 1H), 8.23 (s, 1H), 7.80-7.46 (m, 16H), 7.28-6.88 (m, 15H), 6.75-6.65 (m, 3H), 6.44-6.40 (m, 1H), 6.25-6.18 (m, 4H), 2.55 (s, 3H), 2.50 (s, 3H) | 909.16 | 909.14 |
| 59 | 9.26 (s, 1H), 8.75 (s, 1H), 8.23 (s, 1H), 7.80-7.46 (m, 16H), 7.28-6.88 (m, 9H), 6.75-6.65 (m, 3H), 6.50-6.25 (m, 7H), 2.55 (s, 3H), 2.50 (s, 3H) | 937.13 | 937.11 |
| 63 | 9.26 (s, 1H), 8.75 (s, 1H), 8.23 (s, 1H), 7.80-7.46 (m, 16H), 7.28-6.88 (m, 13H), 6.75-6.50 (m, 4H), 6.28-6.25 (m, 2H), 6.05-6.00 (m, 2H), 2.55 (s, 3H), 2.50 (s, 3H) | 923.15 | 923.13 |
| 68 | 9.26 (s, 1H), 8.75 (s, 1H), 8.23 (s, 1H), 7.80-7.46 (m, 6H), 7.00-6.88 (m, 3H), 6.75 (s, 1H), 6.52-6.50 (m, 1H), 2.55 (s, 3H), 2.50 (s, 3H) | 777.09 | 777.07 |
| 71 | 9.26 (s, 1H), 8.75 (s, 1H), 8.23 (s, 1H), 7.80-7.46 (m, 17H), 7.45-6.76 (m, 13H), 6.70-6.56 (m, 3H), 6.46-6.42 (m, 2H), 6.05-6.00 (m, 2H), 2.55 (s, 3H), 2.50 (s, 3H) | 923.15 | 923.13 |
| 74 | 9.26 (s, 1H), 8.75 (s, 1H), 8.23 (s, 1H), 7.80-7.46 (m, 16H), 7.20-6.76 (m, 9H), 6.72-6.56 (m, 4H), 6.46-6.25 (m, 5H), 2.55 (s, 3H), 2.50 (s, 3H), 2.25-2.20 (m, 9H), | 965.23 | 965.21 |
| 76 | 9.26 (s, 1H), 8.46 (s, 1H), 8.23 (s, 1H), 8.05 (s, 1H), 7.80-7.25 (m, 19H), 7.14-7.00 (m, 7H), 6.72-6.56 (m, 3H), 6.46-6.42 (m, 2H), 6.23-6.18 (m, 6H), 2.55 (s, 3H), 2.50 (s, 3H) | 927.16 | 927.14 |
| 79 | 9.26 (s, 1H), 8.76 (s, 1H), 8.28 (s, 1H), 8.05 (s, 1H), 8.00-7.76 (m, 5H), 7.50-7.26 (m, 3H), 7.08-7.00 (m, 9H), 6.76-6.50 (m, 7H), 6.23-6.18 (m, 8H), 2.55 (s, 3H), 2.50 (s, 3H) | 807.03 | 807.01 |
| 81 | 9.26 (s, 1H), 8.75 (s, 1H), 8.23-7.77 (m, 8H), 7.48-7.46 (m, 1H), 7.19-6.88 (m, 11H), 6.75-6.50 (m, 6H), 6.38-6.30 (m, 8H), 2.55 (s, 3H), 2.50 (s, 3H) | 863.11 | 863.09 |
| 87 | 9.18 (s, 1H), 8.66 (s, 1H), 8.32 (s, 1H), 8.15 (s, 1H), 7.90-7.80 (m, 3H), 7.76-7.65 (m, 5H), 7.52-7.38 (m, 6H), 7.08-6.92 (m, 8H), 6.65-6.58 (m, 3H), 6.52-6.48 (m, 1H), 6.36-6.32 (m, 2H), 6.24-6.20 (m, 2H), 0.38 (s, 18H) | 977.34 | 977.32 |
| 90 | 9.14 (s, 1H), 8.66 (s, 1H), 8.32 (s, 1H), 7.66-7.44 (m, 15H), 7.20-7.15 (m, 2H), 7.06-6.90 (m, 8H), 6.65-6.60 (m, 2H), 6.50-6.42 (m, 2H), 6.25-6.20 (m, 2H), 6.06-6.02 (m, 2H), 0.38 (s, 18H) | 985.36 | 985.34 |
| 94 | 9.50 (s, 1H), 8.75 (s, 1H), 8.46 (s, 1H), 7.48-7.26 (m, 24H), 7.19-6.88 (m, 11H), 6.75-6.50 (m, 2H), 6.38-6.30 (m, 4H), 6.25-6.20 (m, 4H) | 957.21 | 957.19 |
| 104 | 9.38 (s, 1H), 8.42-8.38 (m, 2H), 7.72-7.59 (m, 7H), 7.51-7.48 (m, 1H), 7.40-7.34 (m, 5H), 7.28-7.21 (m, 2H), 7.09-7.02 (m, 4H), 6.80-6.60 (m, 5H), 6.55-6.50 (m, 3H), 6.36-6.32 (m, 2H), 6.20-6.154 (m, 2H), 0.38 (s, 18H) | 873.28 | 873.26 |
| 107 | 9.38 (s, 1H), 8.62-8.60 (m, 2H), 7.92-7.39 (m, 20H), 7.10-6.88 (m, 9H), 6.75-6.50 (m, 4H), 6.38-6.30 (m, 4H) | 909.08 | 909.06 |

Example 1

An ITO glass substrate (a product of Corning Co., Ltd) having a thickness of 1200 Å was cut to a size of 50 mm×50 mm×0.7 mm, and then, sonicated by using isopropyl alcohol and pure water, each for 5 minutes, and cleaned by the exposure to ultraviolet rays for 30 minutes, and then ozone, and the obtained ITO glass substrate was mounted onto a vacuum deposition apparatus.

2-TNATA was deposited on the obtained ITO glass substrate to form a hole injection layer having a thickness of 600 Å, and then, NPB was deposited on the hole injection layer to form a hole transport layer having a thickness of 300 Å, and then, ADN and Compound 5 were co-deposited at a weight ratio of 98:2 on the hole transport layer to form an emission layer having a thickness of 300 Å.

Alq$_3$ was deposited on the emission layer to form an electron transport layer having a thickness of 300 Å. LiF was vacuum deposited on the electron transport layer to form an electron injection layer having a thickness of 10 Å, and then, Al was vacuum deposited on the electron injection layer to form a cathode having a thickness of 3000 Å, thus completing the manufacture of an organic light-emitting device.

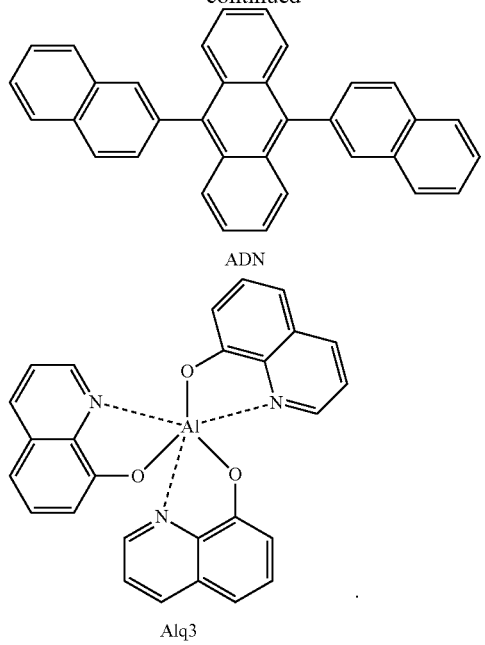

ADN

Alq3

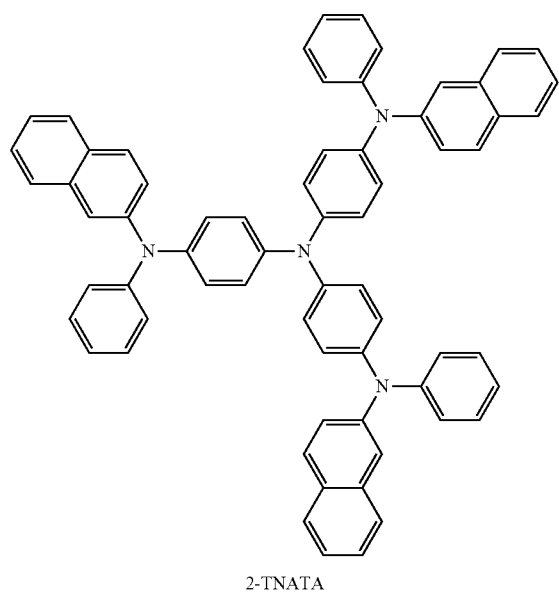

2-TNATA

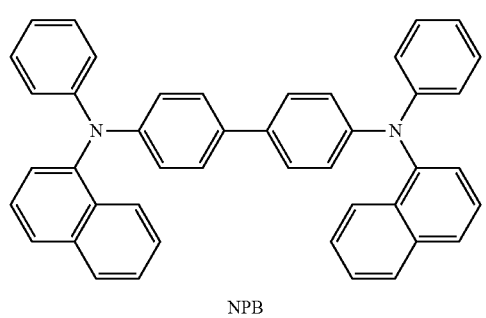

NPB

Example 2

An organic light-emitting device was manufactured in the same (or substantially the same) manner as in Example 1, except that in forming an emission layer, Compound 15 was used instead of Compound 5.

Example 3

An organic light-emitting device was manufactured in the same (or substantially the same) manner as in Example 1, except that in forming an emission layer, Compound 23 was used instead of Compound 5.

Example 4

An organic light-emitting device was manufactured in the same (or substantially the same) manner as in Example 1, except that in forming an emission layer, Compound 39 was used instead of Compound 5.

Example 5

An organic light-emitting device was manufactured in the same (or substantially the same) manner as in Example 1, except that in forming an emission layer, Compound 54 was used instead of Compound 5.

Example 6

An organic light-emitting device was manufactured in the same (or substantially the same) manner as in Example 1, except that in forming an emission layer, Compound 63 was used instead of Compound 5.

Example 7

An organic light-emitting device was manufactured in the same (or substantially the same) manner as in Example 1, except that in forming an emission layer, Compound 68 was used instead of Compound 5.

Example 8

An organic light-emitting device was manufactured in the same (or substantially the same) manner as in Example 1, except that in forming an emission layer, Compound 87 was used instead of Compound 5.

Example 9

An organic light-emitting device was manufactured in the same (or substantially the same) manner as in Example 1, except that in forming an emission layer, Compound 90 was used instead of Compound 5.

Example 10

An organic light-emitting device was manufactured in the same (or substantially the same) manner as in Example 1, except that in forming an emission layer, Compound 94 was used instead of Compound 5.

Example 11

An organic light-emitting device was manufactured in the same (or substantially the same) manner as in Example 1, except that in forming an emission layer, Compound 104 was used instead of Compound 5.

Example 12

An organic light-emitting device was manufactured in the same (or substantially the same) manner as in Example 1, except that in forming an emission layer, Compound 107 was used instead of Compound 5.

Comparative Example 1

An organic light-emitting device was manufactured in the same (or substantially the same) manner as in Example 1, except that in forming an emission layer, Compound A illustrated below was used instead of Compound 5.

Compound A

Comparative Example 2

An organic light-emitting device was manufactured in the same (or substantially the same) manner as in Example 1, except that in forming an emission layer, Compound B illustrated below was used instead of Compound 5.

Compound B

Comparative Example 3

An organic light-emitting device was manufactured in the same (or substantially the same) manner as in Example 1, except that in forming an emission layer, Compound C illustrated below was used instead of Compound 5.

Compound C

Comparative Example 4

An organic light-emitting device was manufactured in the same (or substantially the same) manner as in Example 1, except that in forming an emission layer, Compound D illustrated below was used instead of Compound 5.

Compound D

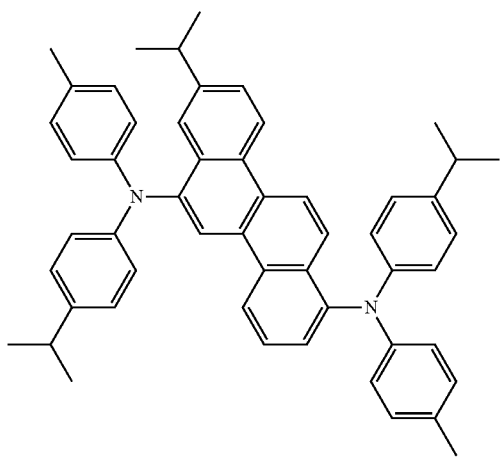

Compound E

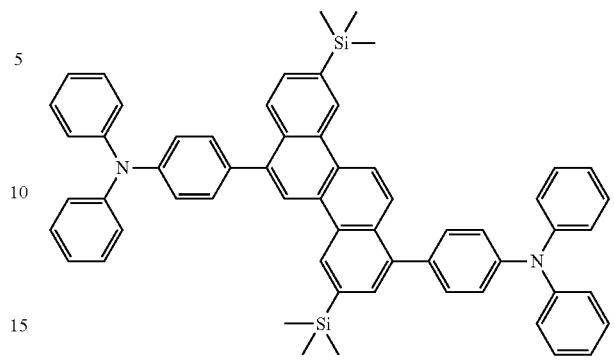

Comparative Example 5

An organic light-emitting device was manufactured in the same (or substantially the same) manner as in Example 1, except that in forming an emission layer, Compound E illustrated below was used instead of Compound 5.

Evaluation Example 1

The driving voltage, current density, brightness, efficiency, and half-lifespan (@100 mA/cm$^2$) of each of the organic light-emitting devices manufactured according to Examples 1 to 12, and Comparative Examples 1 to 5 were measured by using Keithley SMU 236 and a brightness photometer PR650, and results thereof are shown in Table 2. The half-lifespan is a period of time that lapses until the brightness of the organic light-emitting device becomes 50% of the initial brightness.

TABLE 2

| | Dopant | Driving voltage (V) | Current density (mA/cm$^2$) | Brightness (cd/m$^2$) | Efficiency (cd/A) | Emission color | Half lifespan (time) |
|---|---|---|---|---|---|---|---|
| Example 1 | Compound 5 | 6.58 | 50 | 3,110 | 6.22 | Blue | 290 |
| Example 2 | Compound 15 | 6.54 | 50 | 3,320 | 6.64 | Blue | 310 hr |
| Example 3 | Compound 23 | 6.56 | 50 | 3,180 | 6.36 | Blue | 300 hr |
| Example 4 | Compound 39 | 6.56 | 50 | 3,330 | 6.66 | Blue | 345 hr |
| Example 5 | Compound 54 | 6.51 | 50 | 3,140 | 6.28 | Blue | 275 hr |
| Example 6 | Compound 63 | 6.59 | 50 | 3,200 | 6.40 | Blue | 280 hr |
| Example 7 | Compound 68 | 6.60 | 50 | 3,195 | 6.39 | Blue | 305 hr |
| Example 8 | Compound 87 | 6.53 | 50 | 3,325 | 6.65 | Blue | 350 hr |
| Example 9 | Compound 90 | 6.51 | 50 | 3,178 | 6.36 | Blue | 320 hr |
| Example 10 | Compound 94 | 6.60 | 50 | 3,065 | 6.13 | Blue | 295 hr |
| Example 11 | Compound 104 | 6.62 | 50 | 3,080 | 6.16 | Blue | 302 hr |
| Example 12 | Compound 107 | 6.60 | 50 | 3,255 | 6.51 | Blue | 300 hr |
| Comparative Example 1 | Compound A | 6.92 | 50 | 2,560 | 5.12 | Blue | 248 hr |
| Comparative Example 2 | Compound B | 6.96 | 50 | 2,730 | 5.46 | Blue | 248 hr |
| Comparative Example 3 | Compound C | 7.02 | 50 | 2,460 | 4.92 | Blue | 220 hr |
| Comparative Example 4 | Compound D | 6.94 | 50 | 2,680 | 5.36 | Blue | 240 hr |
| Comparative Example 5 | Compound E | 6.94 | 50 | 2,642 | 5.28 | Blue | 275 hr |

From Table 2, it was confirmed that the organic light-emitting devices manufactured according to Examples 1 to 12 have lower driving voltage and higher efficiency than the organic light-emitting devices manufactured according to Comparative Examples 1 to 5, and most of the organic light-emitting devices manufactured according to Examples 1 to 12 had longer half-lifespan than the organic light-emitting devices manufactured according to Comparative Examples 1 to 5.

Accordingly, an organic light-emitting device including the condensed cyclic compound according to embodiments of the present invention may have high efficiency, high durability, and long lifespan.

It should be understood that the embodiments described herein should be considered in a descriptive sense only and not for purposes of limitation. Descriptions of features or aspects within each embodiment should typically be considered as available for other similar features or aspects in other embodiments.

Expressions such as "at least one of" and "one of," when preceding a list of elements, modify the entire list of elements and do not modify the individual elements of the list. Further, the use of "may" when describing embodiments of the present invention refers to "one or more embodiments of the present invention."

In addition, as used herein, the terms "use," "using," and "used" may be considered synonymous with the terms "utilize," "utilizing," and "utilized," respectively. Also, the term "exemplary" is intended to refer to an example or illustration.

As used herein, the term "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112, first paragraph, and 35 U.S.C. § 132(a).

While one or more embodiments have been described with reference to the drawing, it will be understood by those of ordinary skill in the art that various changes in form and details may be made therein without departing from the spirit and scope as defined by the following claims and equivalents thereof.

What is claimed is:

1. A condensed cyclic compound represented by Formula 1:

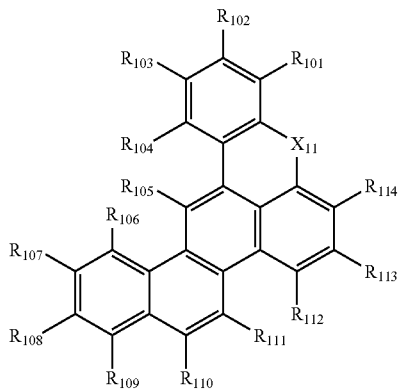

Formula 1

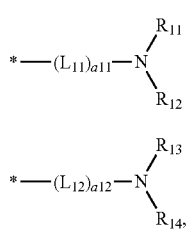

Formula 10-1

Formula 10-2 wherein in Formulae 1, 10-1, and 10-2, $X_{11}$ is selected from an oxygen atom (O) and a sulfur atom (S);

$R_{101}$ to $R_{114}$ are each independently selected from a group represented by Formula 10-1, a group represented by Formula 10-2, hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

at least one selected from the $R_{101}$ to the $R_{114}$ is a group represented by the Formula 10-1;

at least one selected from the $R_{101}$ to the $R_{114}$ is a group represented by the Formula 10-2;

at least one selected from the $R_{101}$ to the $R_{114}$ is selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

$L_{11}$ and $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a11 and a12 are each independently selected from 0, 1, 2, 3, 4, and 5;

$R_{11}$ to $R_{14}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_3$, $Q_{11}$ to $Q_{17}$, $Q_{21}$ to $Q_{27}$, and $Q_{31}$ to $Q_{37}$ are each independently selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound of claim 1, wherein at least one selected from the $R_{101}$ to the $R_{104}$ is a group represented by the Formula 10-1;

at least one selected from the $R_{106}$ to the $R_{111}$ is a group represented by the Formula 10-2.

3. The condensed cyclic compound of claim 1, wherein at least one selected from the $R_{101}$ to the $R_{114}$ is selected from deuterium, a substituted or unsubstituted $C_1$-$C_{60}$ alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), wherein $Q_1$ to $Q_3$ are each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

4. The condensed cyclic compound of claim 1, wherein at least one selected from the $R_{101}$ to the $R_{114}$ is selected from:

a $C_1$-$C_{60}$ alkyl group;

a $C_6$-$C_{60}$ aryl group, a $C_1$-$C_{60}$ heteroaryl group, a monovalent non-aromatic condensed polycyclic group, a monovalent non-aromatic condensed heteropolycyclic group;

a $C_6$-$C_{60}$ aryl group, a $C_1$-$C_{60}$ heteroaryl group, a monovalent non-aromatic condensed polycyclic group, a monovalent non-aromatic condensed heteropolycyclic group, each substituted with at least one selected from a $C_1$-$C_{60}$ alkyl group and a $C_1$-$C_{60}$ alkoxy group; and —Si($Q_1$)($Q_2$)($Q_3$), wherein $Q_1$ to $Q_3$ are each independently selected from a $C_1$-$C_{60}$ alkyl group and a $C_6$-$C_{60}$ aryl group.

5. The condensed cyclic compound of claim 1, wherein at least one selected from the $R_{101}$ to the $R_{114}$ is selected from:

a methyl group, an ethyl group, an n-propyl group, an iso-propyl group, an n-butyl group, a sec-butyl group, an iso-butyl group, and a tert-butyl group;

a phenyl group, a naphthyl group, a fluorenyl group, a phenalenyl group, a phenanthrenyl group, and an anthracenyl group;

a phenyl group, a naphthyl group, a fluorenyl group, a phenalenyl group, a phenanthrenyl group, and an anthracenyl group, each substituted with at least one selected from a methyl group, an ethyl group, an n-propyl group, an iso-propyl group, an n-butyl group, a sec-butyl group, an iso-butyl group, and a tert-butyl group; and —Si($Q_1$)($Q_2$)($Q_3$), wherein $Q_1$ to $Q_3$ are each independently selected from a methyl group, an ethyl group, an n-propyl group, an iso-propyl group, an n-butyl group, a sec-butyl group, an iso-butyl group, and a tert-butyl group.

6. The condensed cyclic compound of claim 1, wherein at least one selected from the $R_{107}$, the $R_{108}$, the $R_{113}$, and the $R_{114}$ is selected from:

a methyl group, an ethyl group, an n-propyl group, an iso-propyl group, an n-butyl group, a sec-butyl group, an iso-butyl group, and a tert-butyl group;

a phenyl group, a naphthyl group, a fluorenyl group, a phenalenyl group, a phenanthrenyl group, and an anthracenyl group;

a phenyl group, a naphthyl group, a fluorenyl group, a phenalenyl group, a phenanthrenyl group, and an anthracenyl group, each substituted with at least one selected from a methyl group, an ethyl group, an n-propyl group, an iso-propyl group, an n-butyl group, a sec-butyl group, an iso-butyl group, and a tert-butyl group; and —Si($Q_1$)($Q_2$)($Q_3$), wherein $Q_1$ to $Q_3$ are each independently selected from a methyl group, an ethyl group, an n-propyl group, an iso-propyl group, an n-butyl group, a sec-butyl group, an iso-butyl group, and a tert-butyl group.

7. The condensed cyclic compound of claim 1, wherein the $R_{107}$, the $R_{108}$, the $R_{113}$, and the $R_{114}$ are each independently selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$.

8. The condensed cyclic compound of claim 1, wherein the $R_{107}$ and the $R_{113}$ are each independently selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$.

9. The condensed cyclic compound of claim 1, wherein the $R_{108}$ and the $R_{114}$ are each independently selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$.

10. The condensed cyclic compound of claim 1, wherein the $R_{107}$, the $R_{108}$, the $R_{113}$, or the $R_{114}$ is selected from:

a methyl group, an iso-propyl group, and an n-butyl group;

a phenyl group and a naphthyl group;

a phenyl group and a naphthyl group, each substituted with at least one selected from a methyl group, an ethyl group, an n-propyl group, an iso-propyl group, an n-butyl group, a sec-butyl group, an iso-butyl group, and a tert-butyl group; and —Si($CH_3$)$_3$.

11. The condensed cyclic compound of claim 1, wherein the $L_{11}$ and the $L_{12}$ are each independently selected from a phenylene group, a pentalenylene group, an indenylene group, a naphthylene group, an azulenylene group, a heptalenylene group, an indacenylene group, an acenaphthylene group, a fluorenylene group, an spiro-fluorenylene group, an benzofluorenylene group, an dibenzofluorenylene group, a phenalenylene group, a phenanthrenylene group, an anthracenylene group, a fluoranthenylene group, an triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, a imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, a oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group.

12. The condensed cyclic compound of claim 1, wherein the $L_{11}$ and the $L_{12}$ are each independently selected from groups represented by Formulae 3-1 to 3-31:

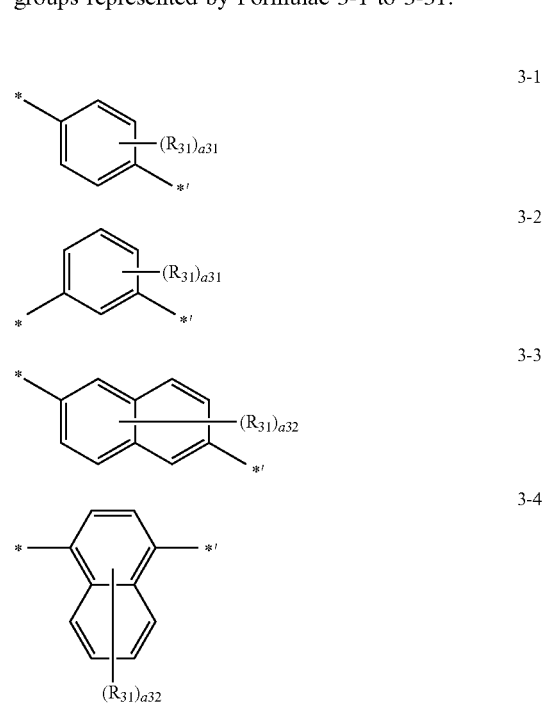

-continued
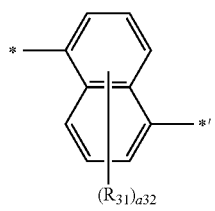
3-5
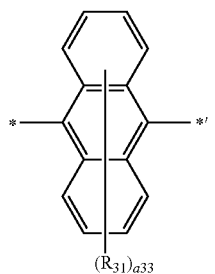
3-6
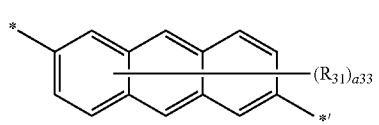
3-7
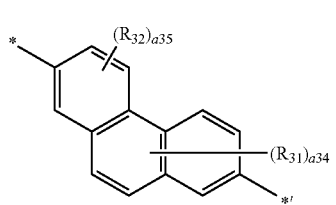
3-8
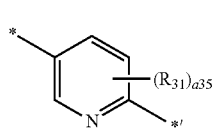
3-9
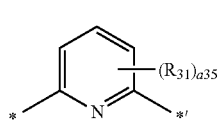
3-10
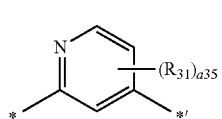
3-11
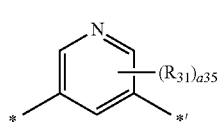
3-12
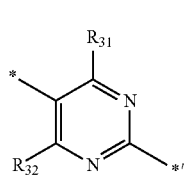
3-13
-continued
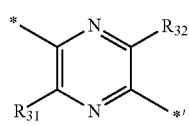
3-14
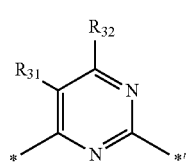
3-15
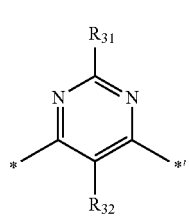
3-16
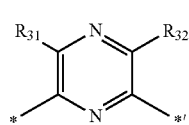
3-17
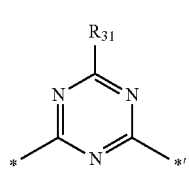
3-18
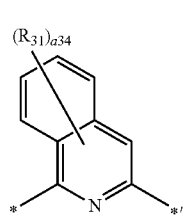
3-19
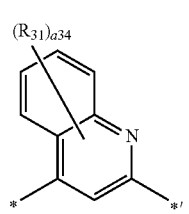
3-20
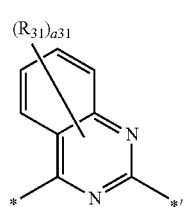
3-21

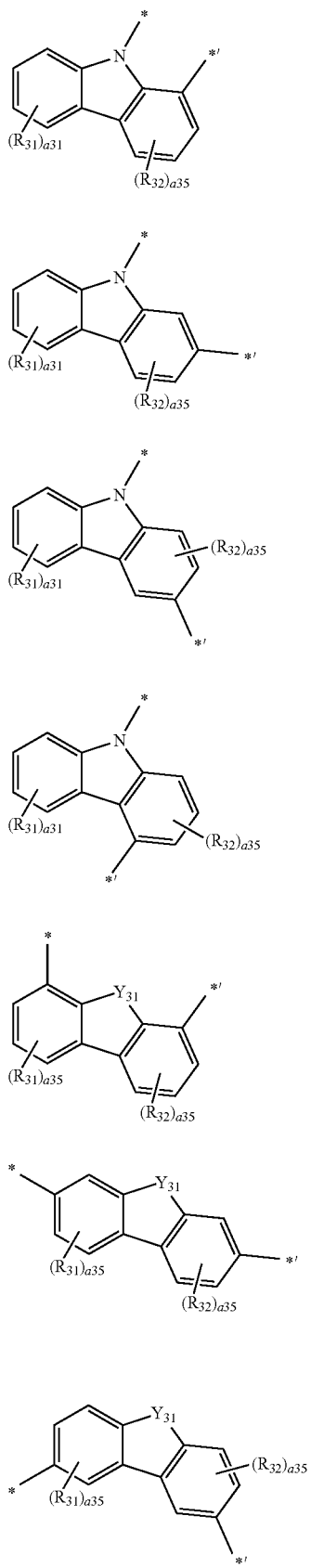
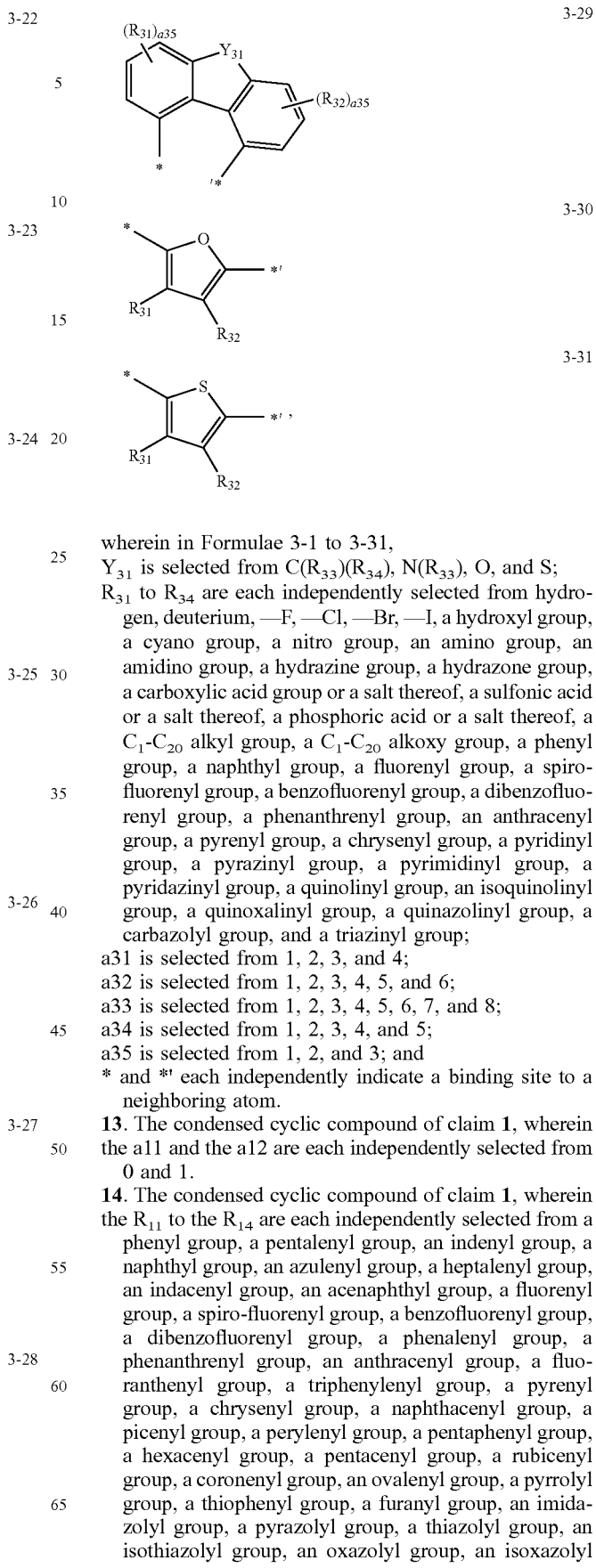

wherein in Formulae 3-1 to 3-31,

Y$_{31}$ is selected from C(R$_{33}$)(R$_{34}$), N(R$_{33}$), O, and S;

R$_{31}$ to R$_{34}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a31 is selected from 1, 2, 3, and 4;

a32 is selected from 1, 2, 3, 4, 5, and 6;

a33 is selected from 1, 2, 3, 4, 5, 6, 7, and 8;

a34 is selected from 1, 2, 3, 4, and 5;

a35 is selected from 1, 2, and 3; and

* and *' each independently indicate a binding site to a neighboring atom.

13. The condensed cyclic compound of claim 1, wherein the a11 and the a12 are each independently selected from 0 and 1.

14. The condensed cyclic compound of claim 1, wherein the R$_{11}$ to the R$_{14}$ are each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a biphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ are each independently selected from a $C_1$-$C_{60}$ alkyl group and a $C_6$-$C_{60}$ aryl group.

15. The condensed cyclic compound of claim 1, wherein the $R_{11}$ to the $R_{14}$ are each independently selected from groups represented by Formulae 5-1 to 5-33:

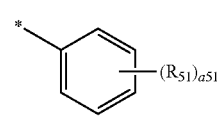

5-1

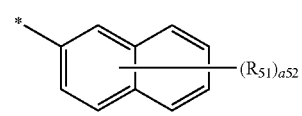

5-2

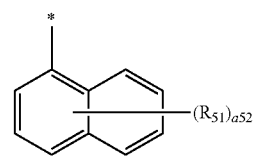

5-3

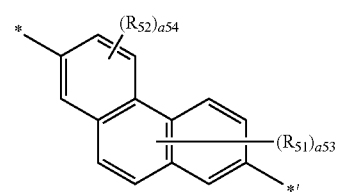

5-4

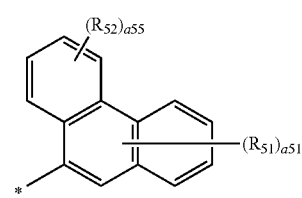

5-5

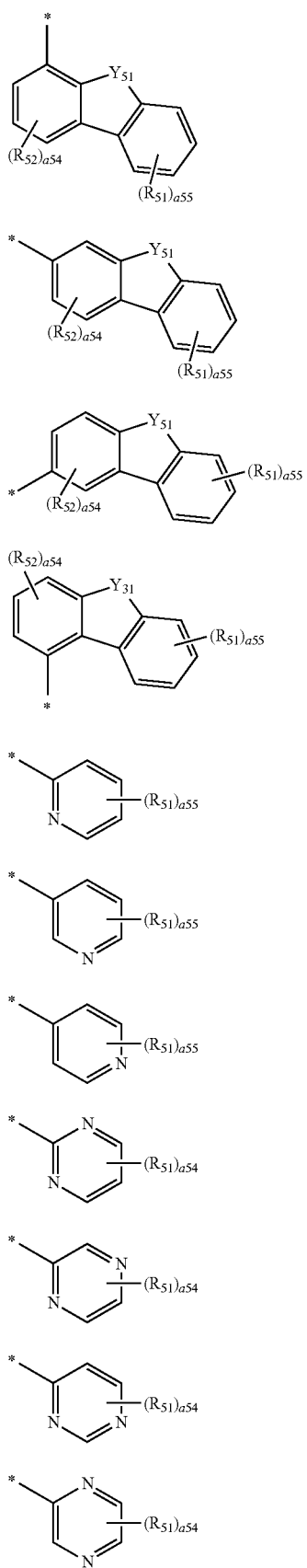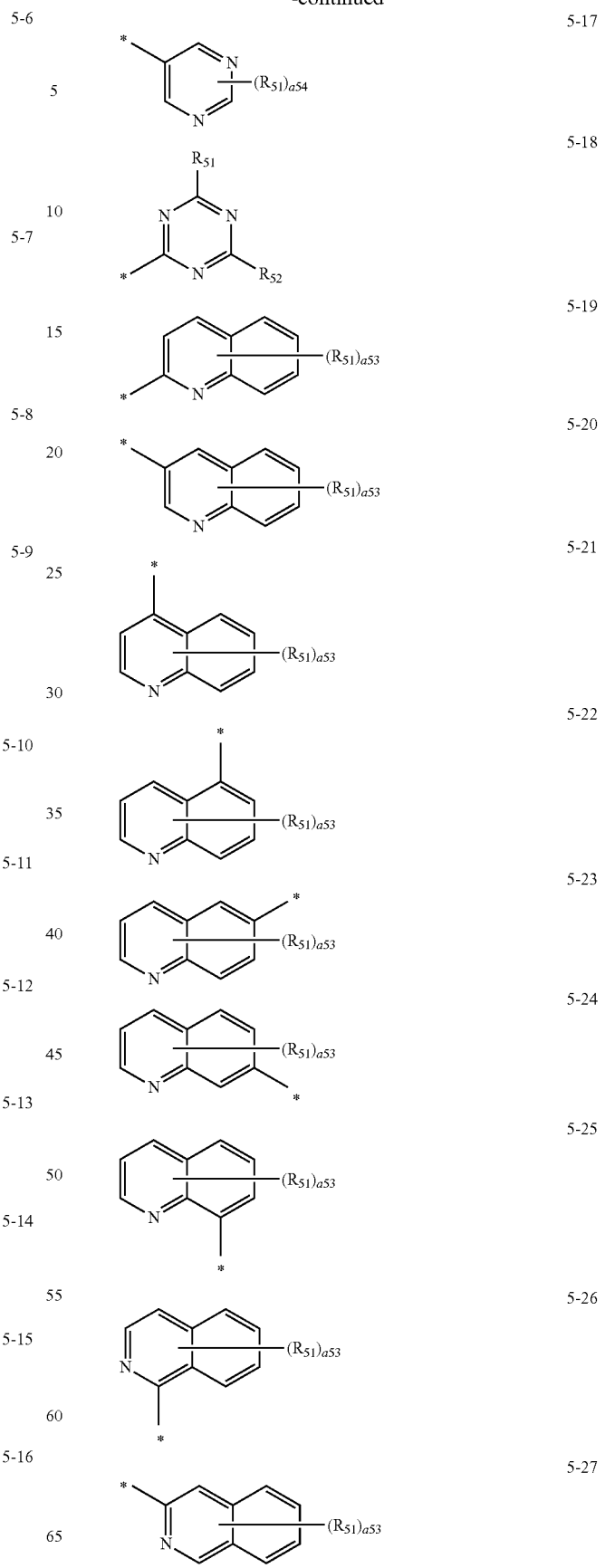

-continued 5-28
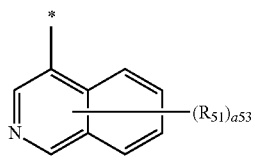

5-29
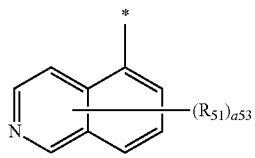

5-30
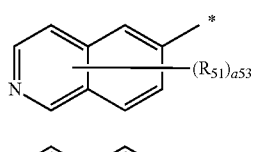

5-31
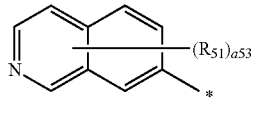

5-32
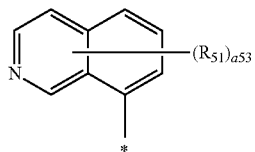

5-33
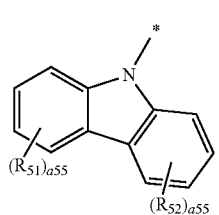

wherein in Formulae 5-1 to 5-33, $Y_{51}$ is selected from $C(R_{53})(R_{54})$, $N(R_{53})$, O, and S;

$R_{51}$ to $R_{54}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl group, —$CD_3$, —$CF_3$, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, —Si$(Q_{33})(Q_{34})(Q_{35})$, wherein $Q_{33}$ to $Q_{35}$ are each independently selected from a methyl group, an ethyl group, ter-butyl group, a phenyl group, and a naphthyl group;

a51 is selected from 1, 2, 3, 4, and 5;

a52 is selected from 1, 2, 3, 4, 5, 6, and 7;

a53 is selected from 1, 2, 3, 4, 5, and 6;

a54 is selected from 1, 2, and 3;

a55 is selected from 1, 2, 3, and 4; and

* indicates a binding site to a neighboring atom.

16. The condensed cyclic compound of claim 1, wherein the condensed cyclic compound is represented by Formula 1-1:

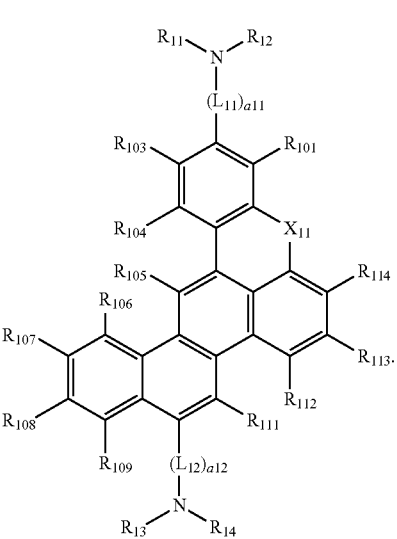

Formula 1-1

17. The condensed cyclic compound of claim 1, wherein the condensed cyclic compound is selected from Compounds 1 to 111:

1

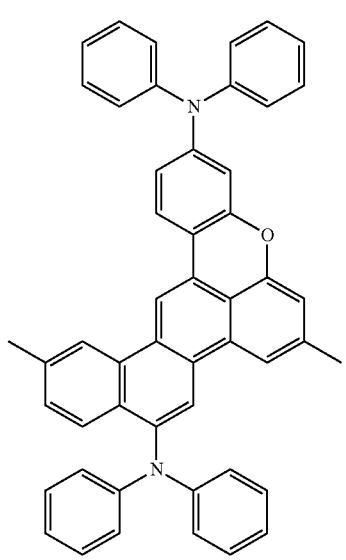

319
-continued
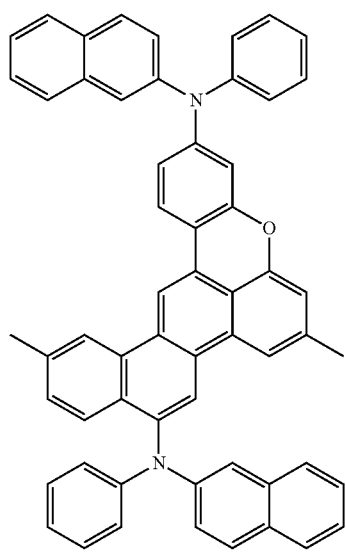
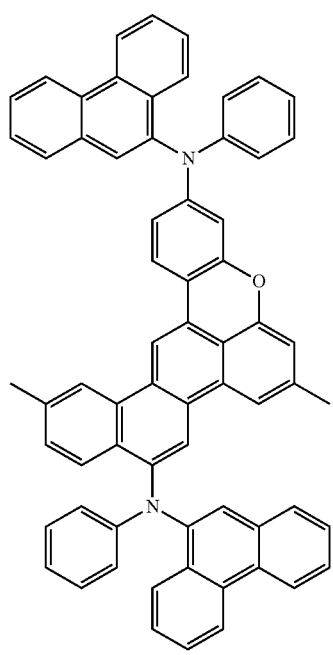
320
-continued
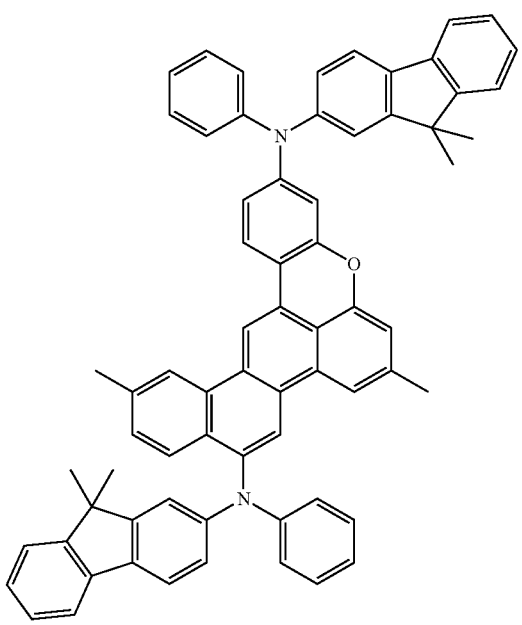
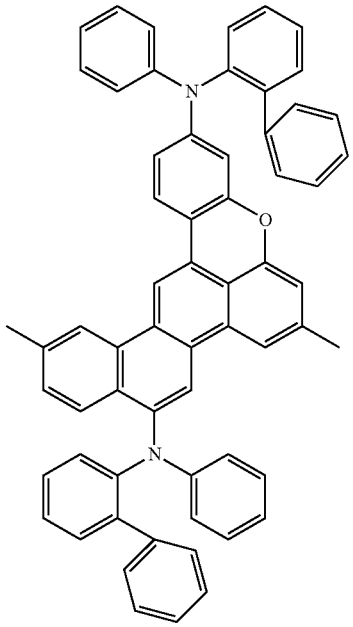

321
-continued
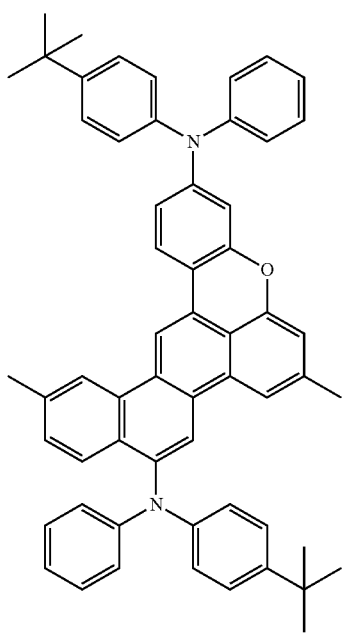
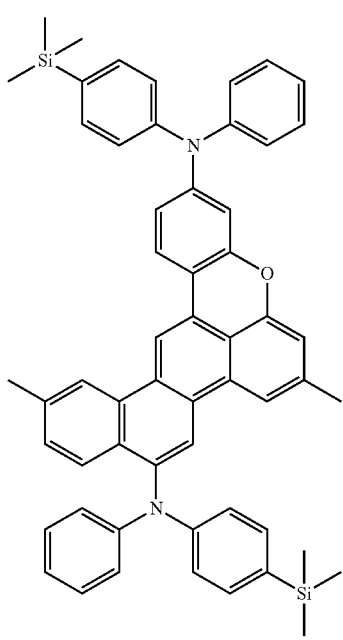
322
-continued
6
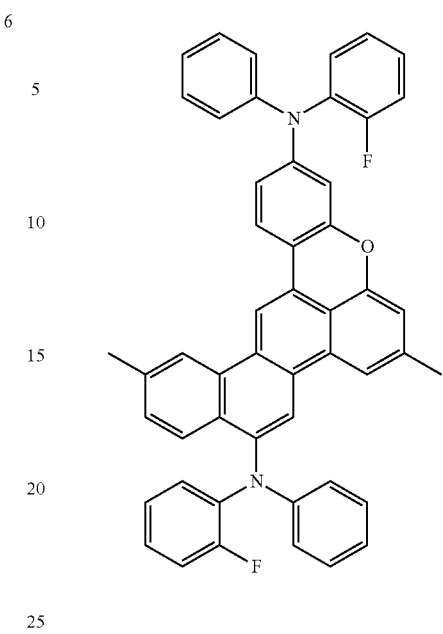
7
8
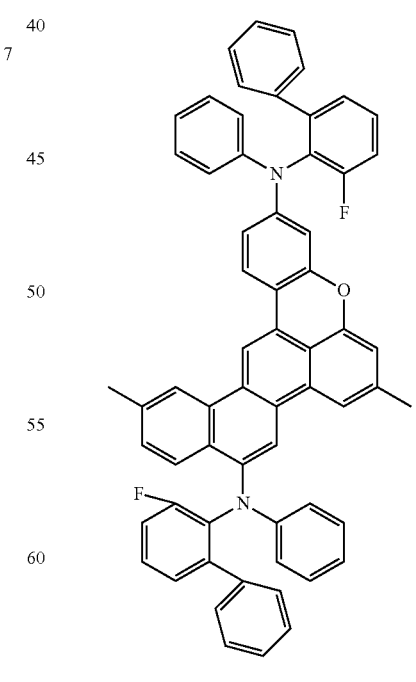
9

323
-continued
324
-continued
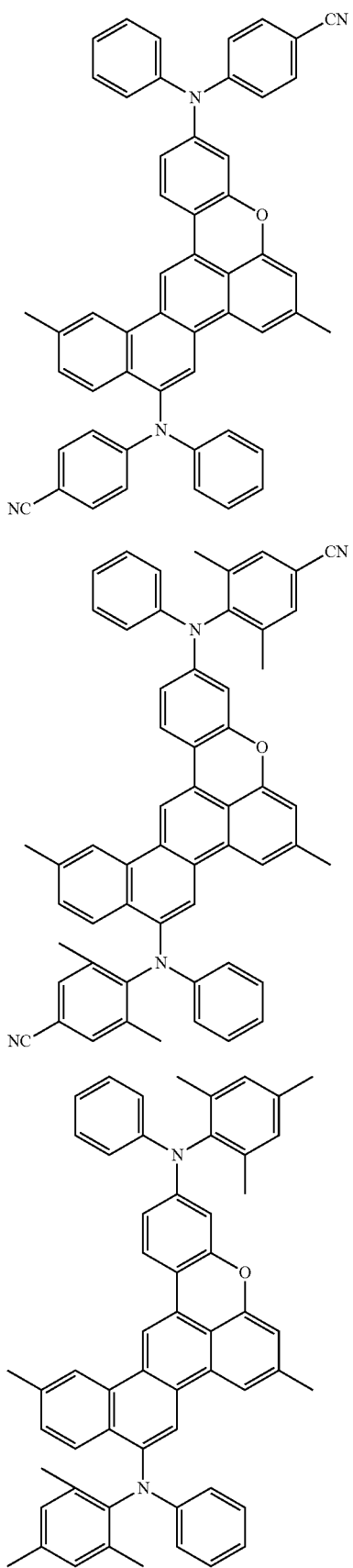
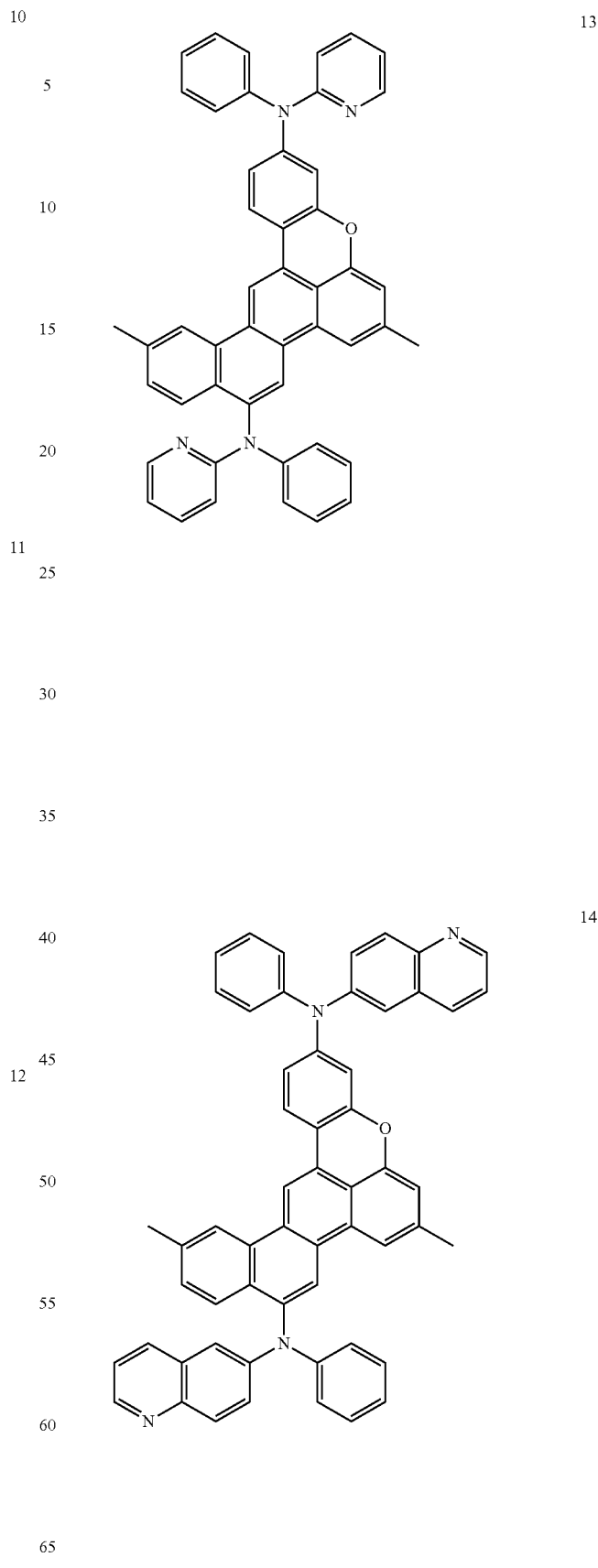

325
-continued
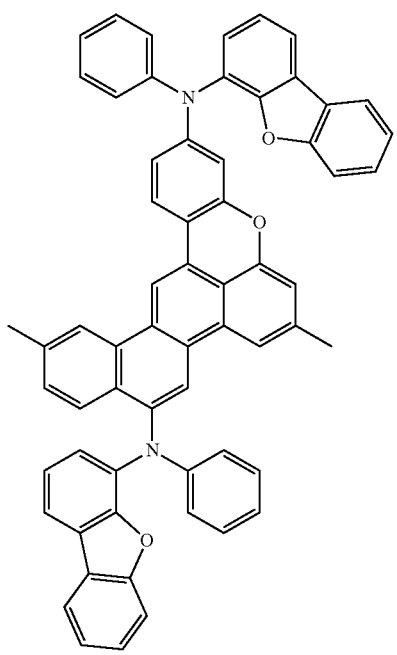
15
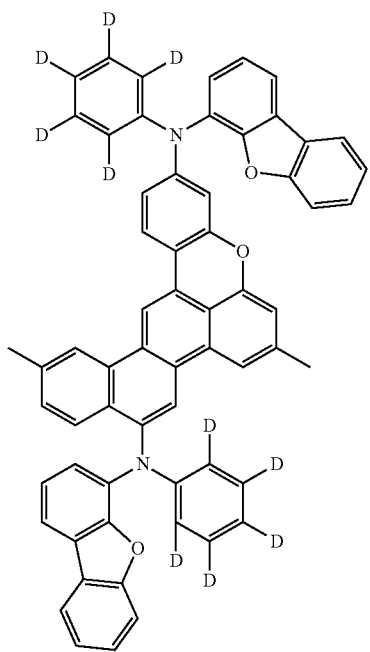
16
326
-continued
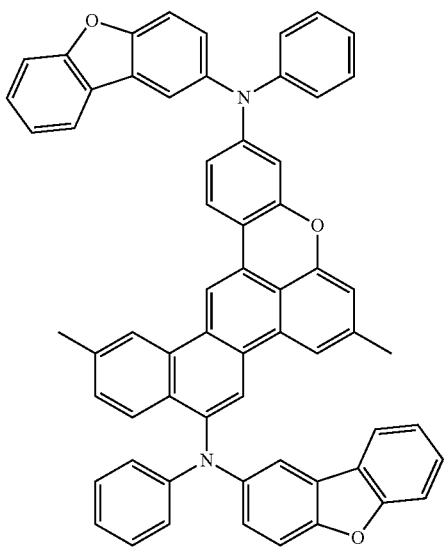
17
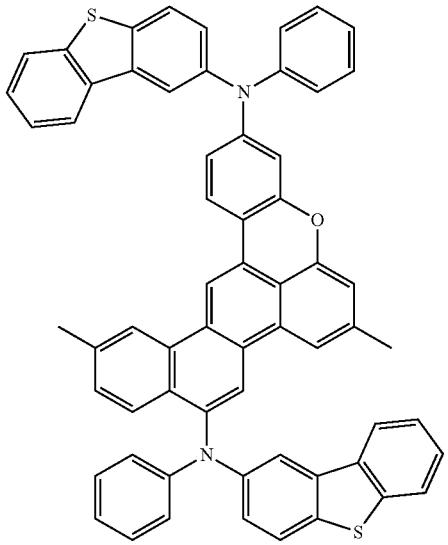
18

327
-continued
19
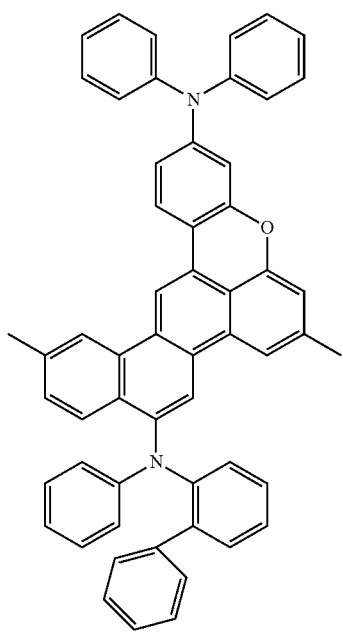
20
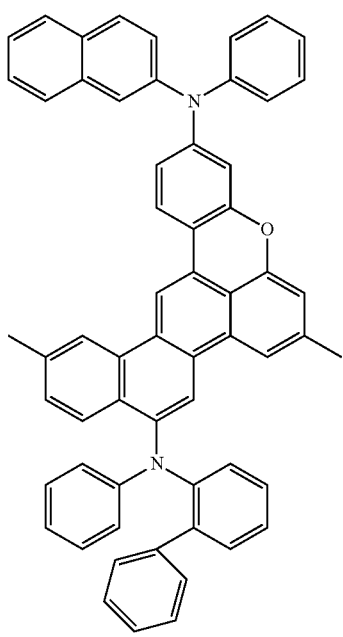
328
-continued
21
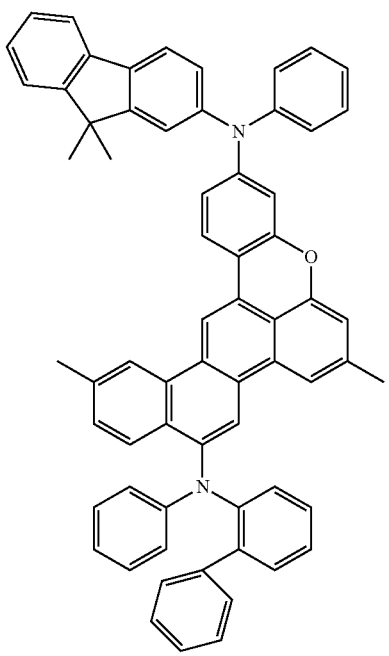
22
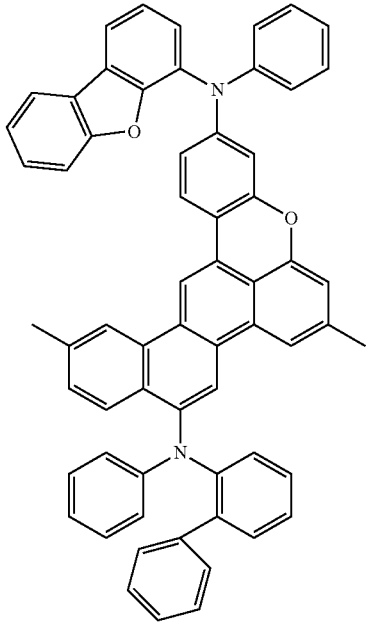

329
-continued
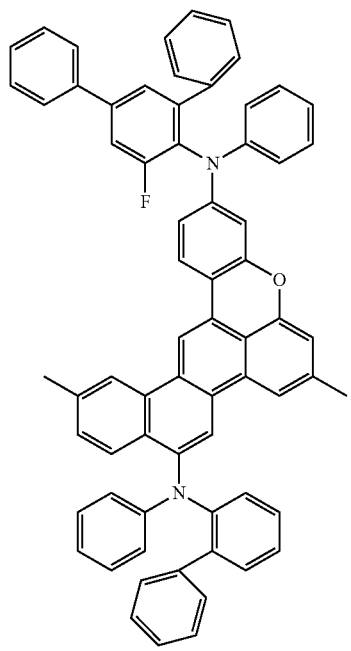
330
-continued
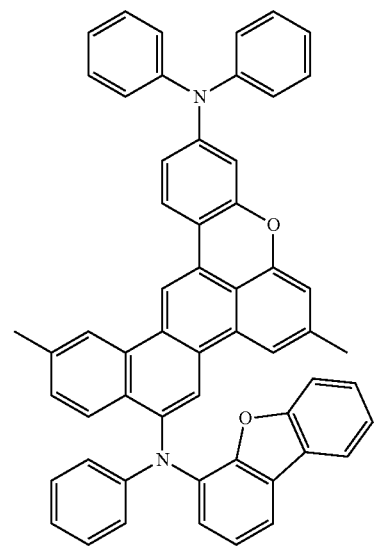
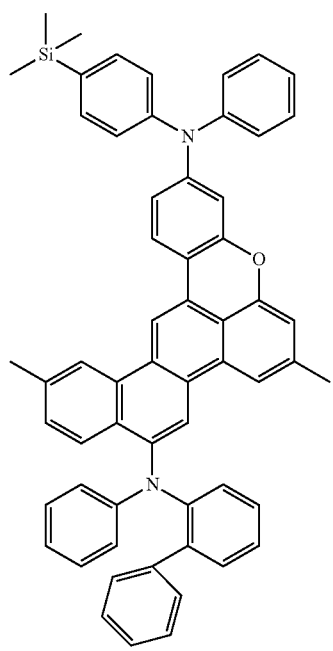
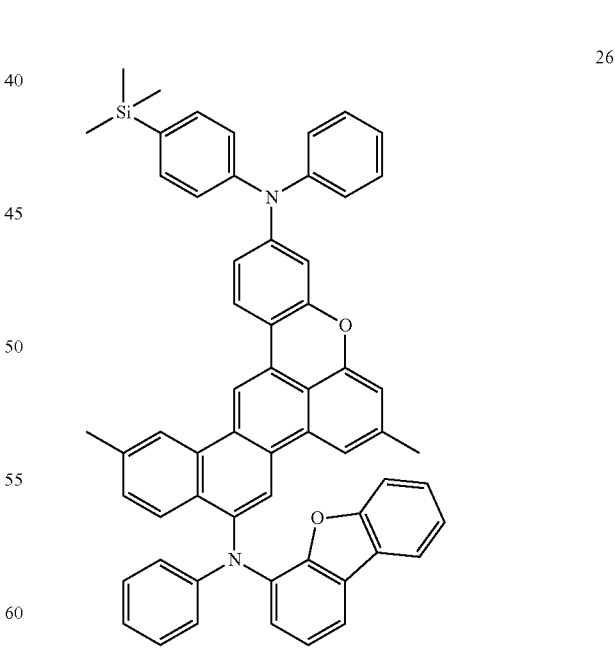

331
-continued
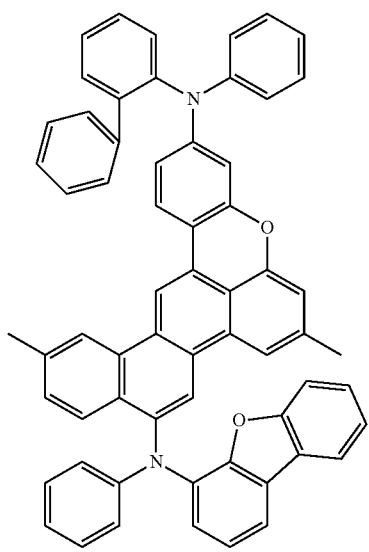
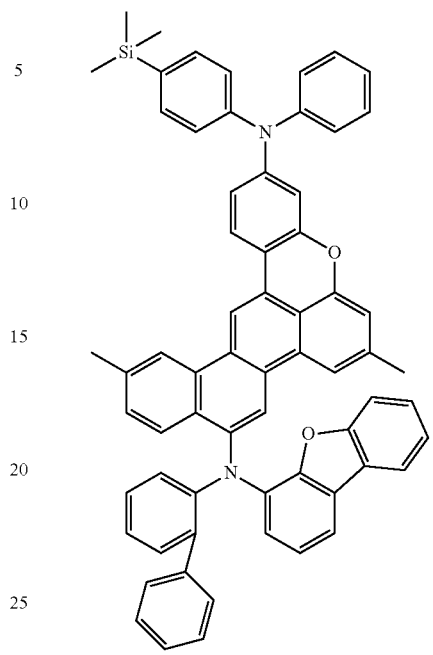
332
-continued
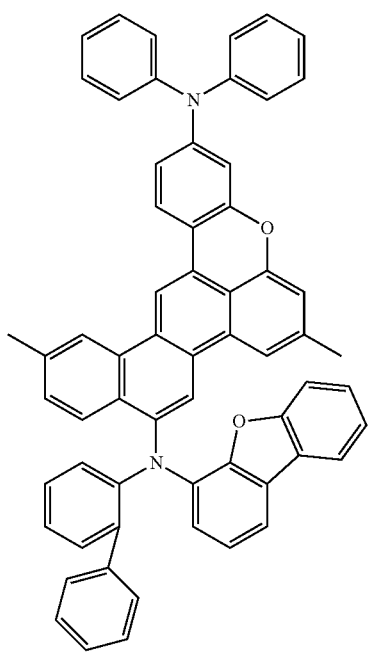
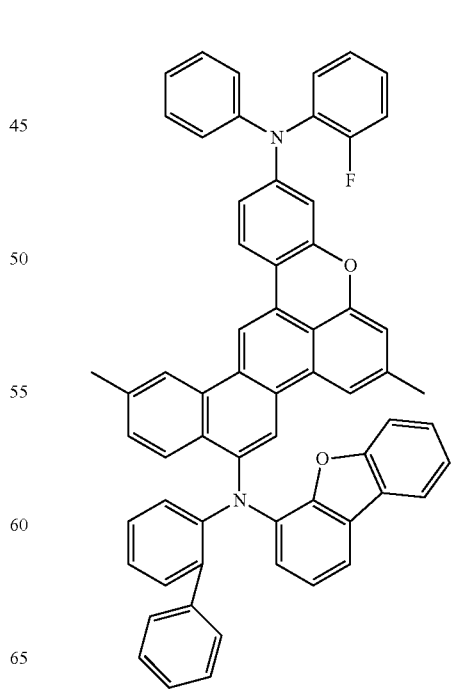

333
-continued
31
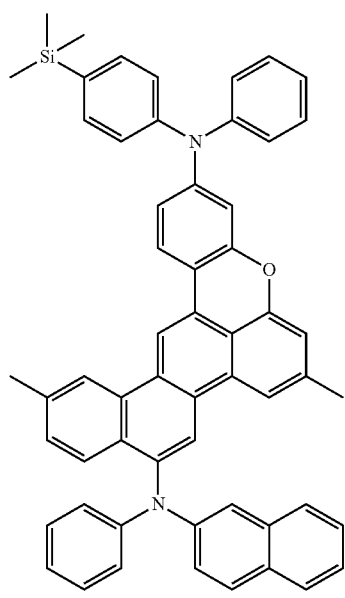
32
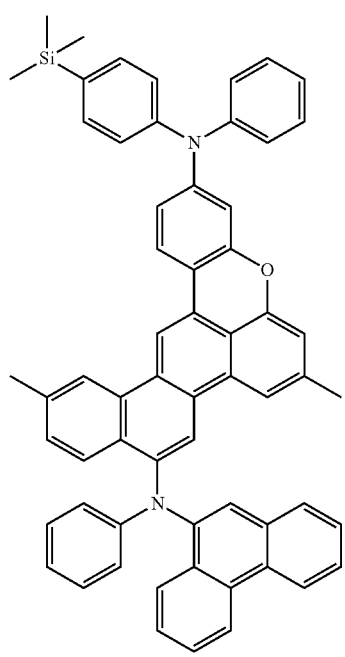
334
-continued
33
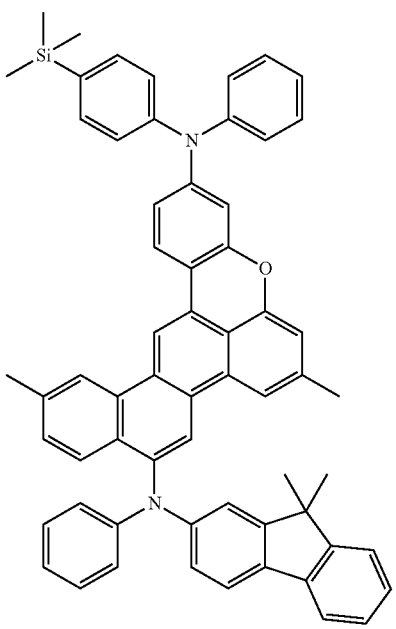
34
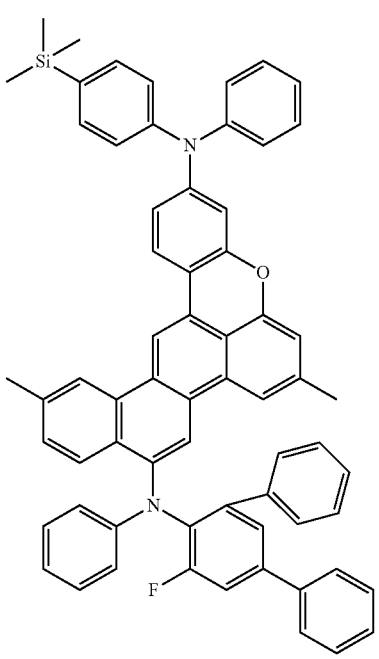

335
-continued
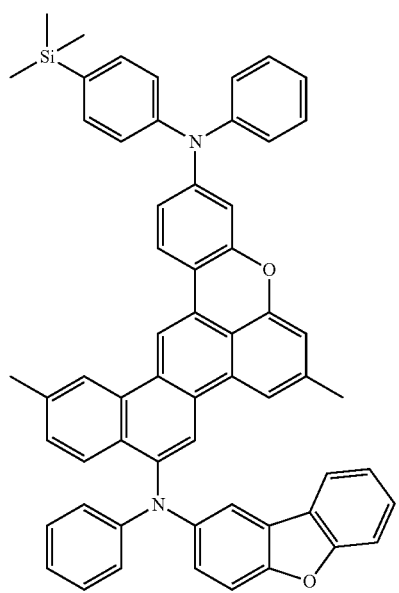
36
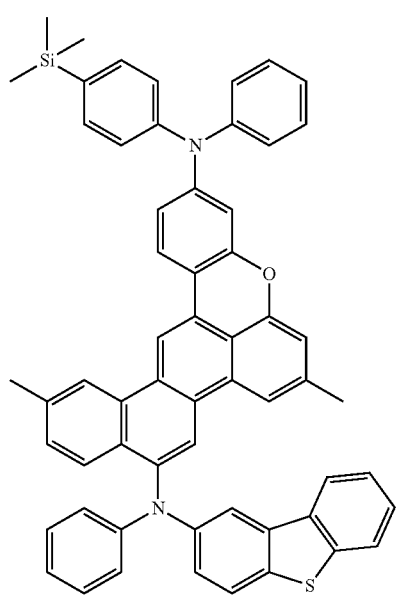
336
-continued
37
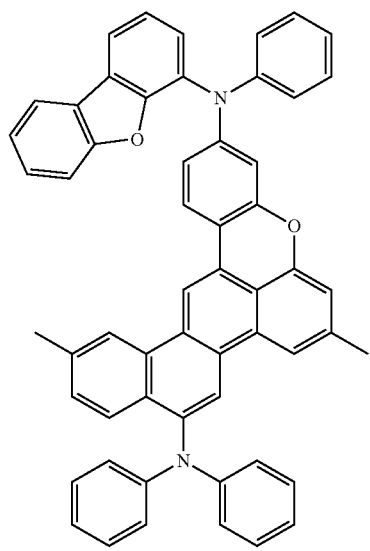
38
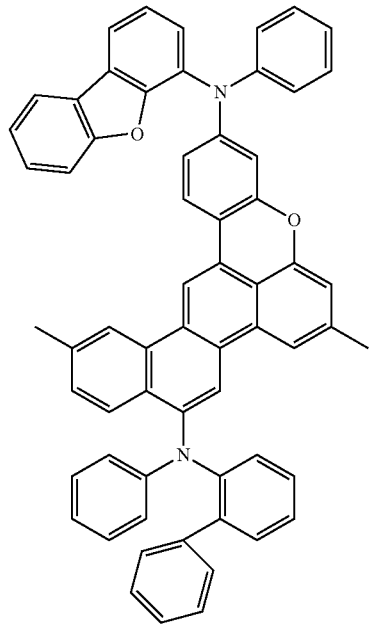

337
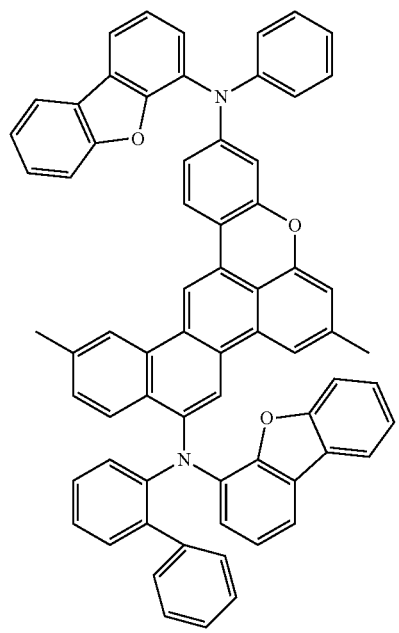
338
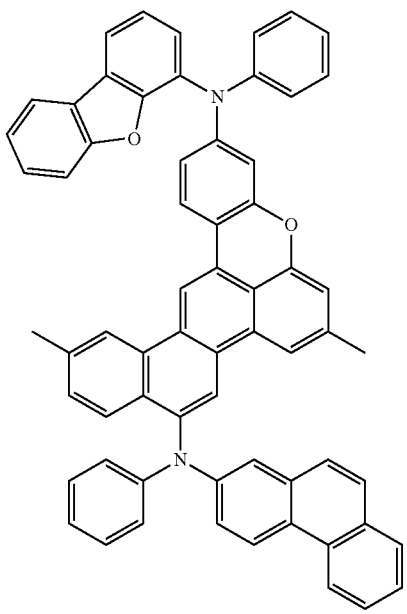
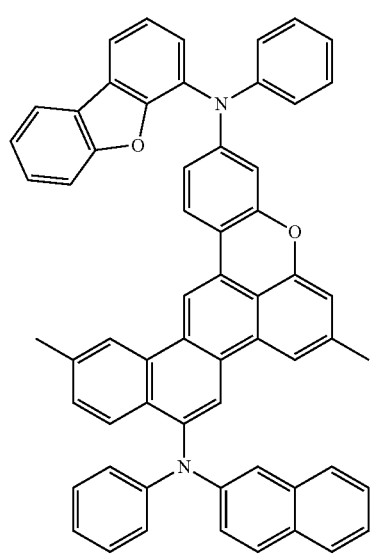
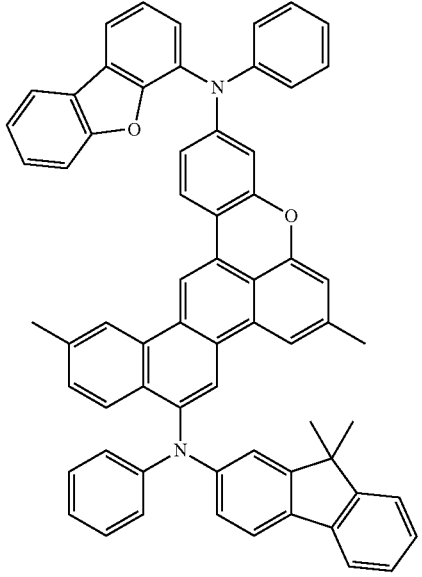

339
-continued
340
-continued
43
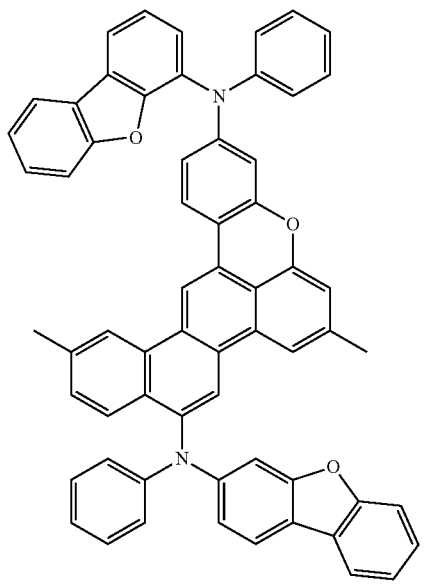
44
45
46
47
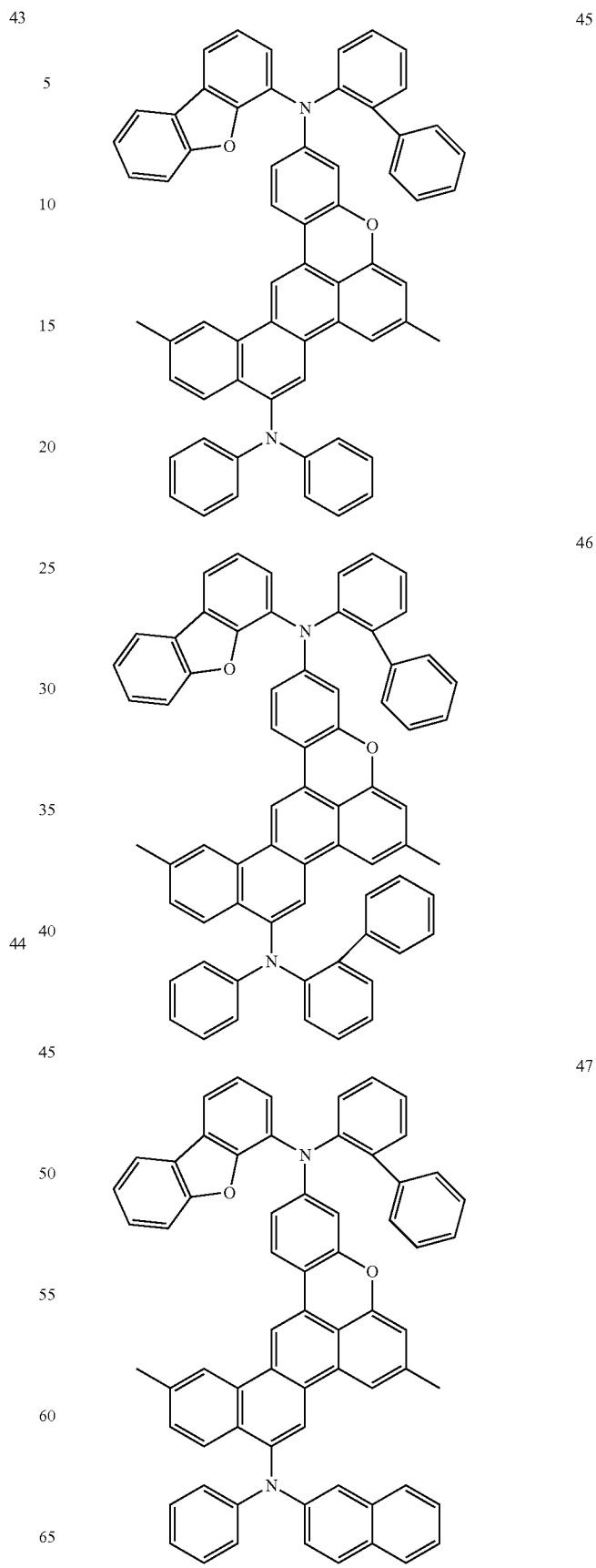

-continued
48
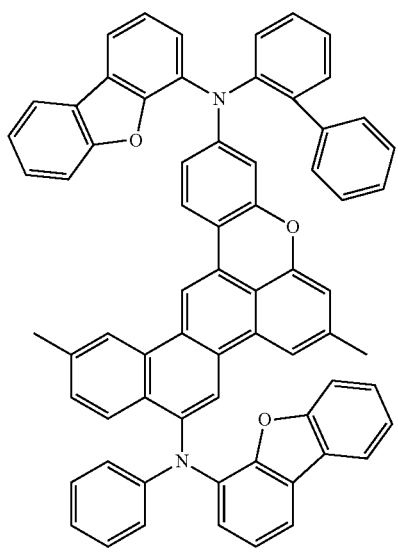
49
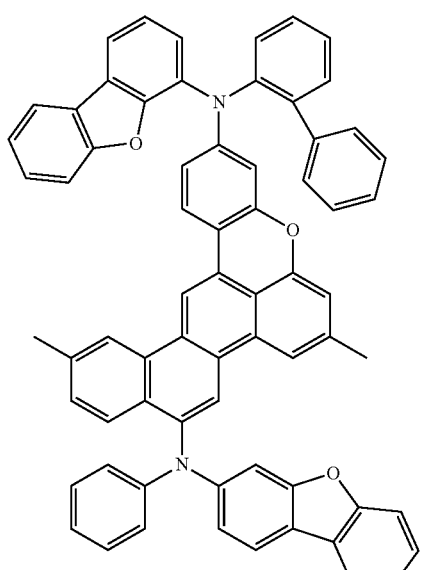
-continued
50
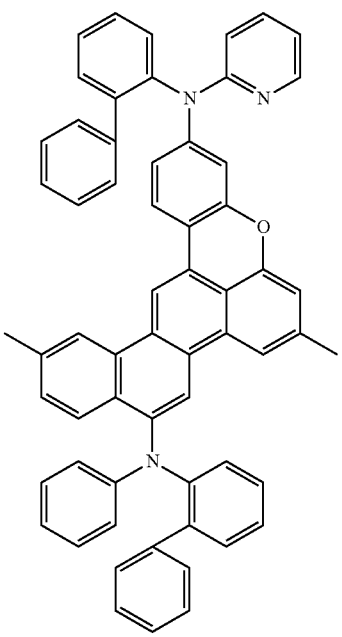
51
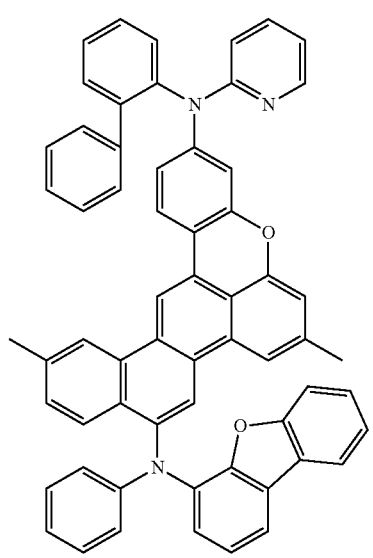

343
-continued
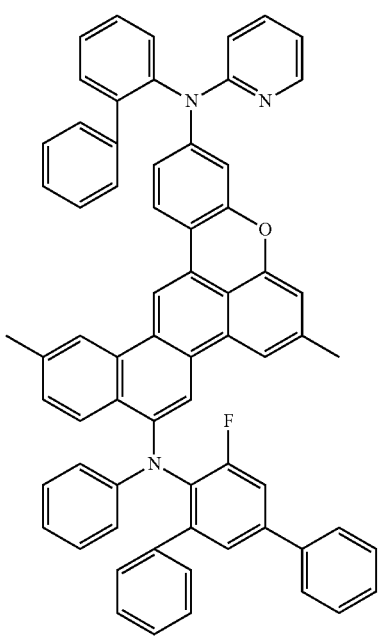
52
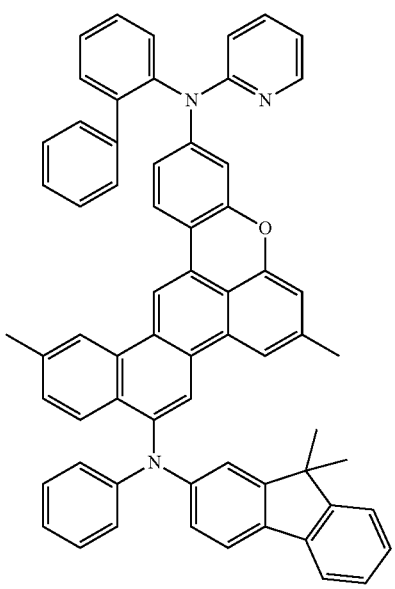
53
344
-continued
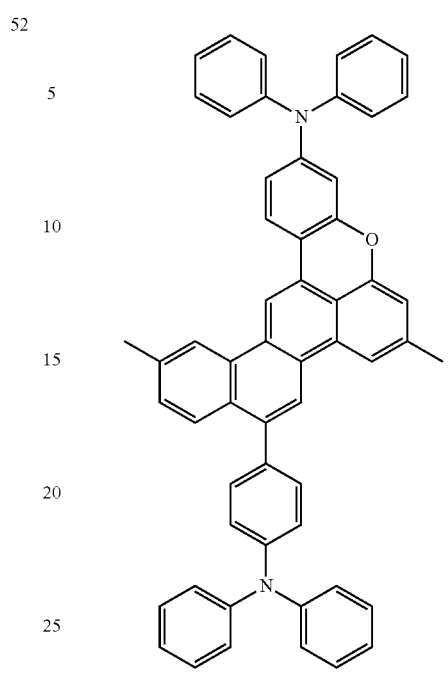
54
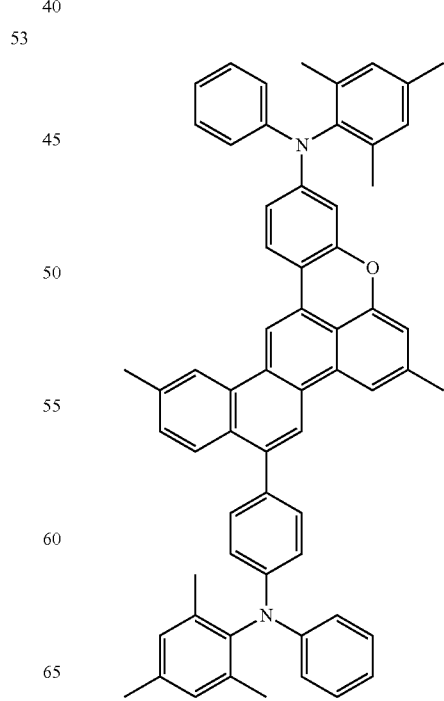
55

345
-continued
| 56 | 58 |
|---|---|
| 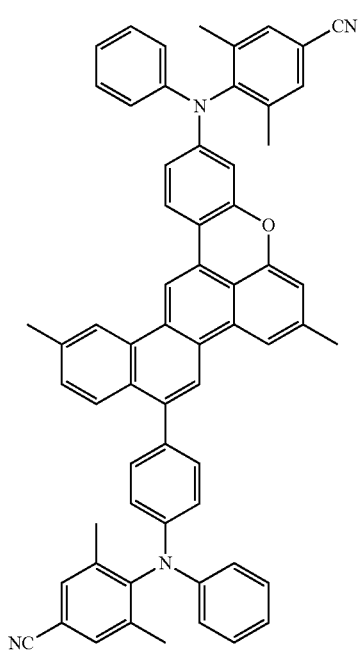 | 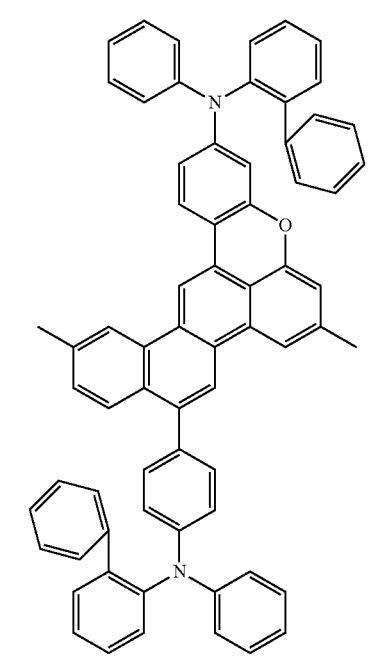 |
| 57 | 59 |
| 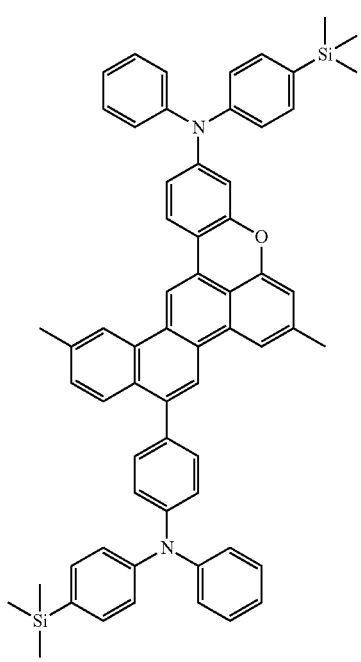 | 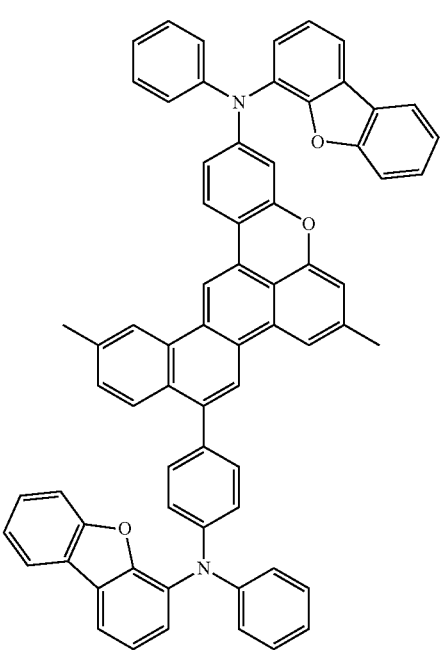 |
346
-continued 347
-continued
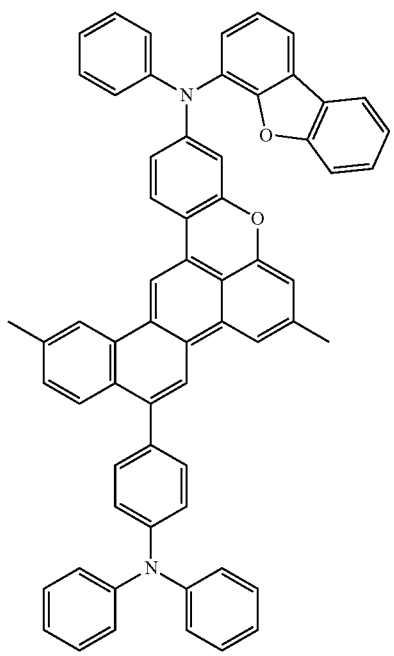
348
-continued
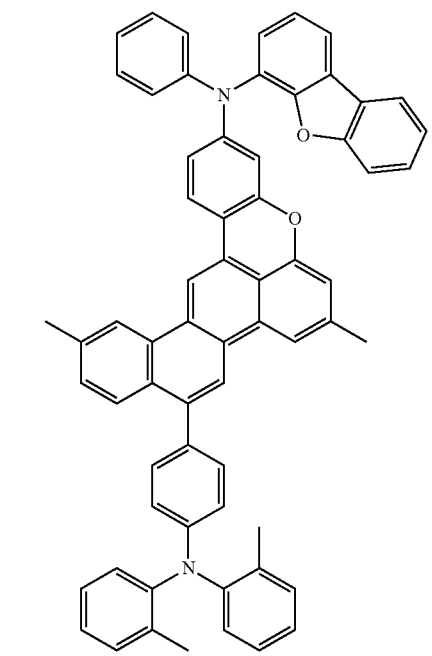
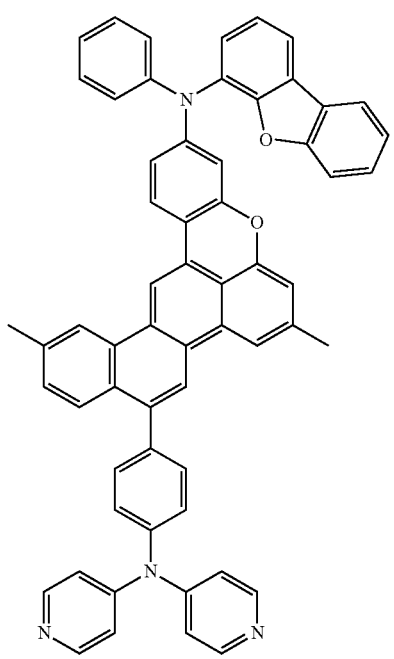
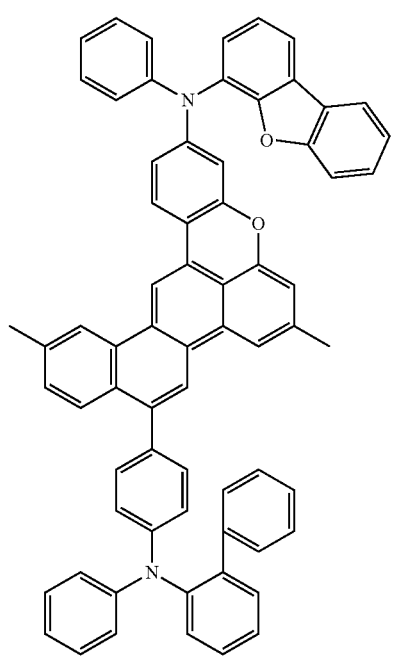

349
-continued
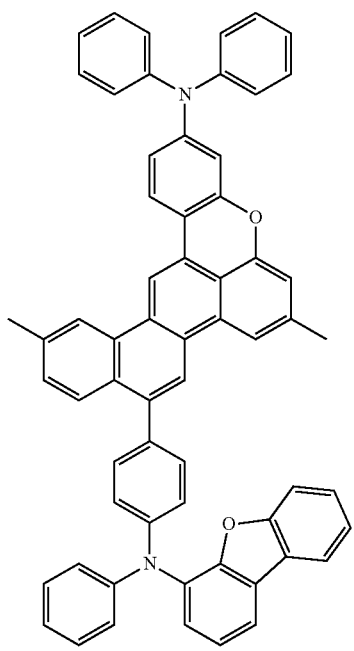
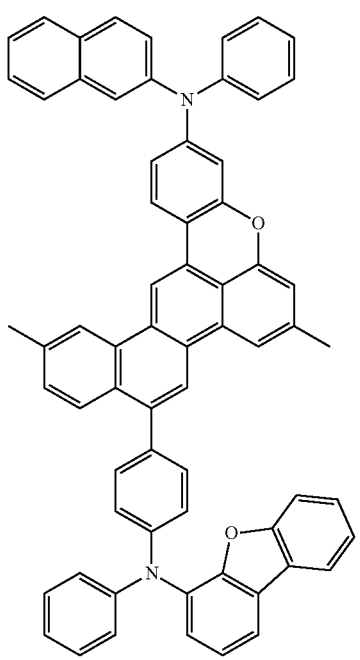
350
-continued
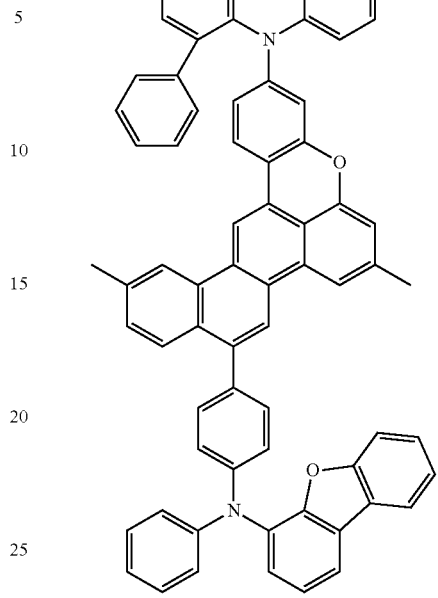
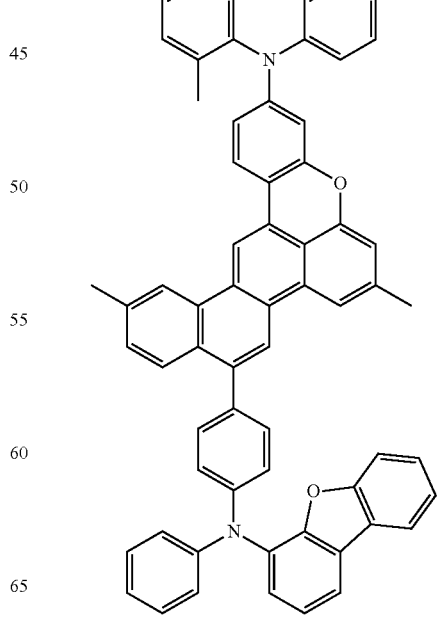

351
-continued
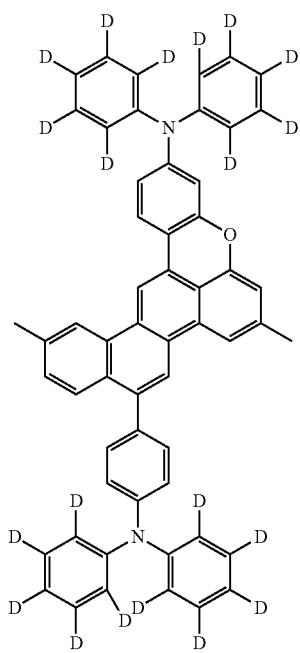
68
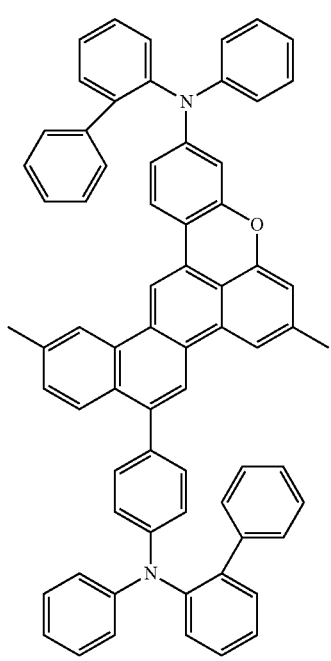
69
352
-continued
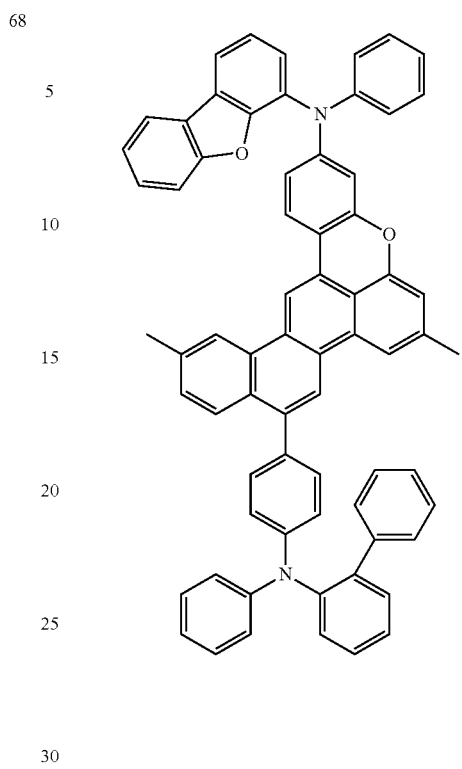
70
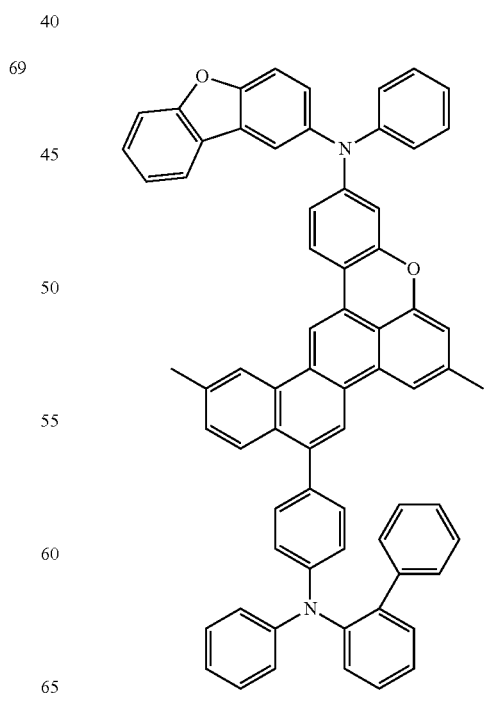
71

353
-continued
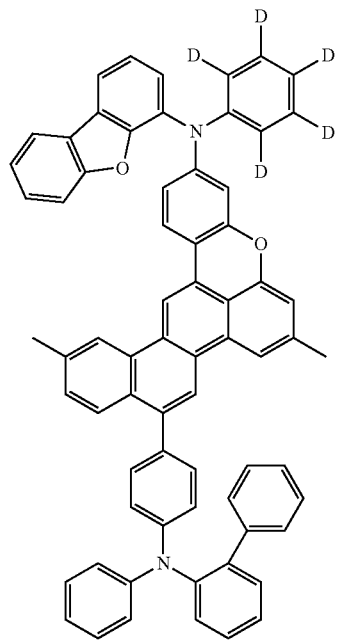
72
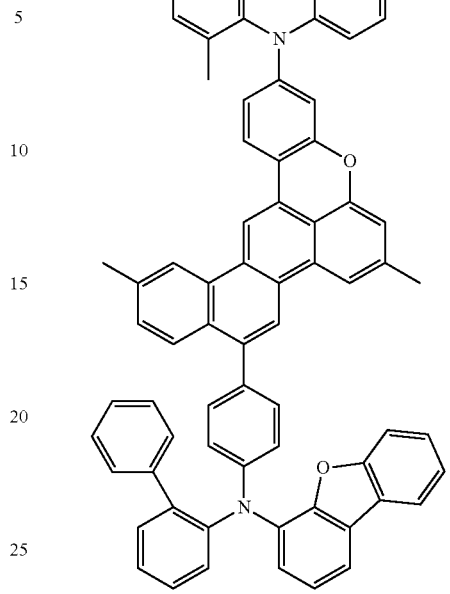
73
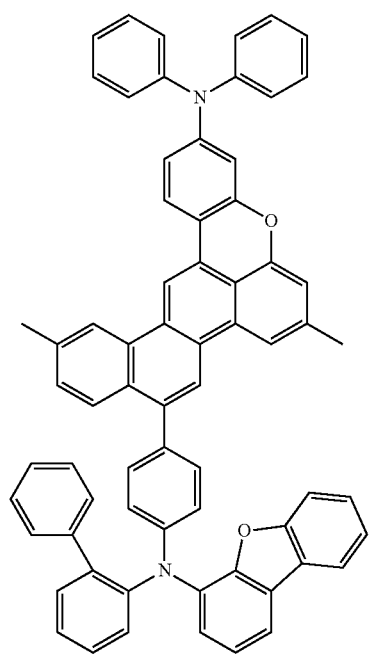
354
-continued
74
75
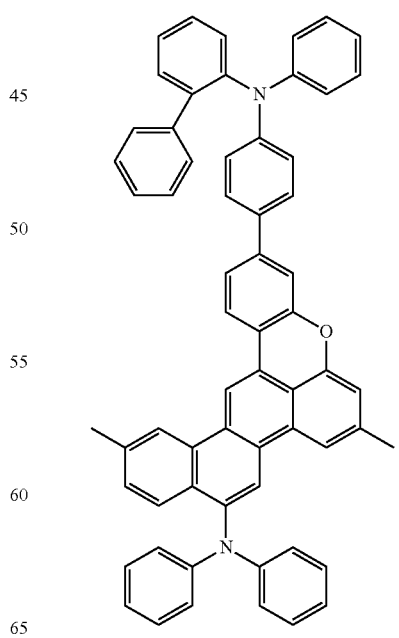

355
-continued
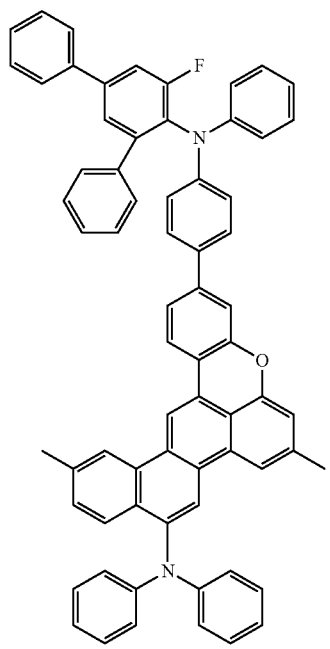
76
356
-continued
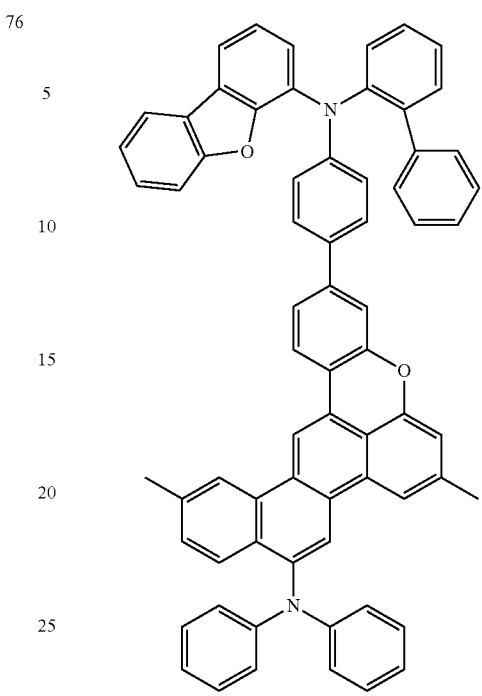
78
77
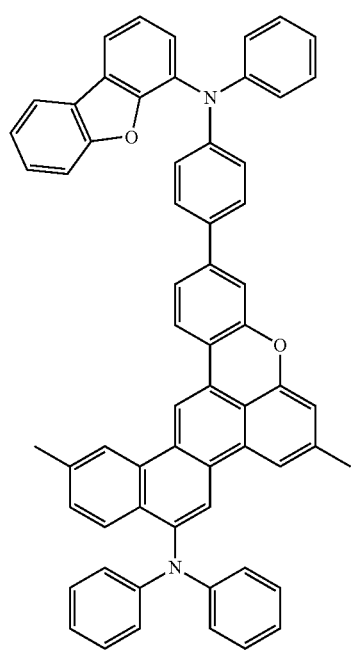
79
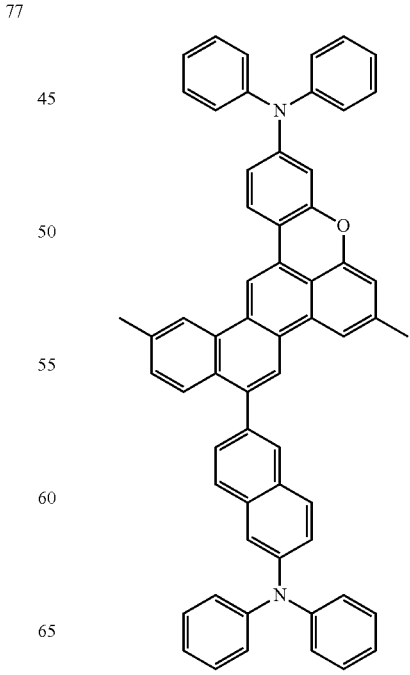

357
-continued
358
-continued
80
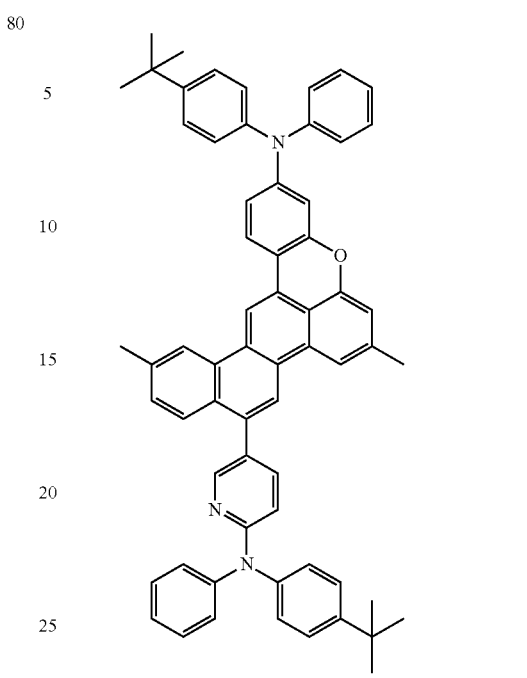
82
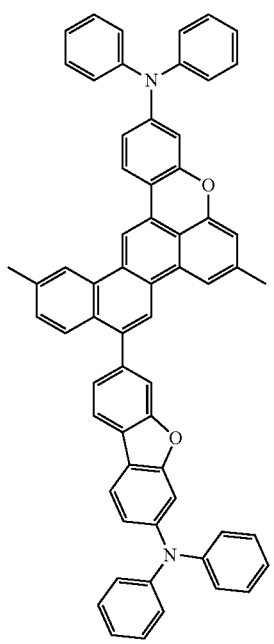
81
83
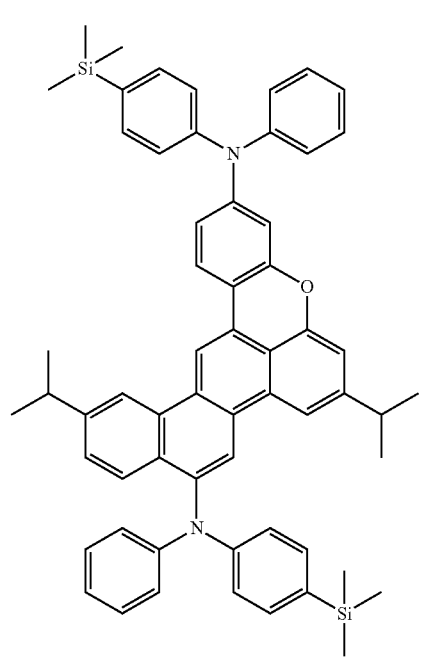

84
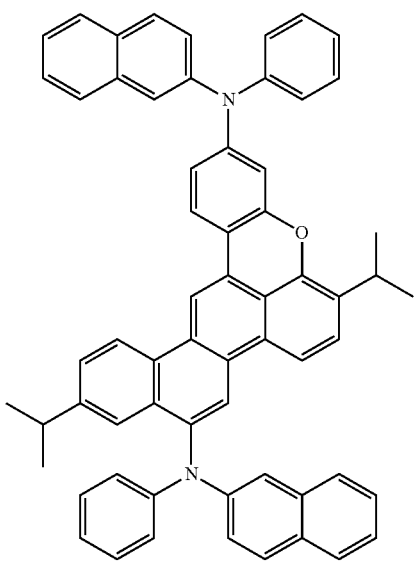
85
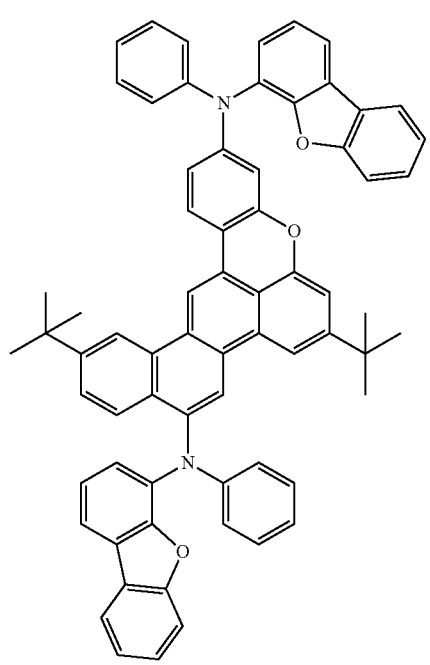
86
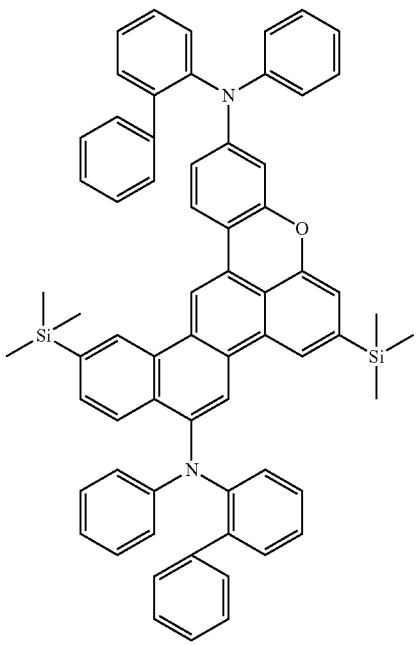
87
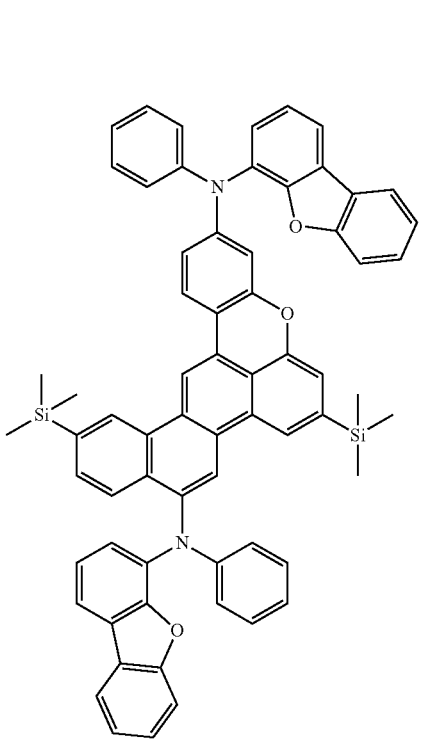

88
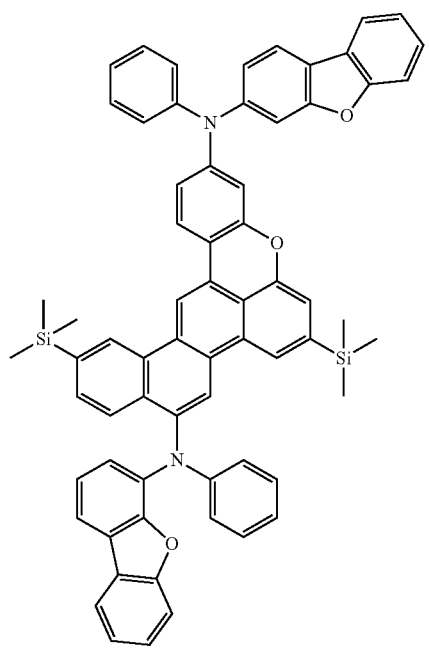
89
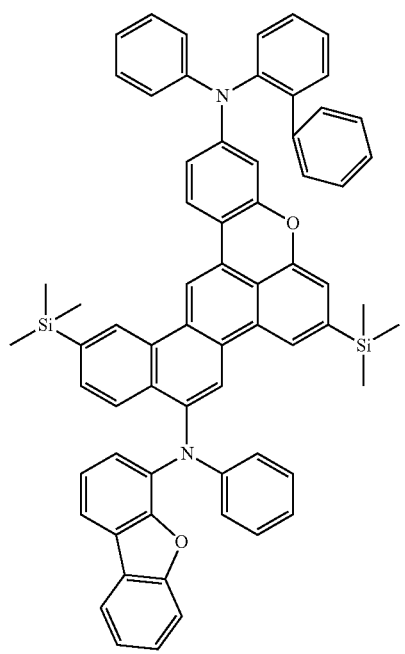
90
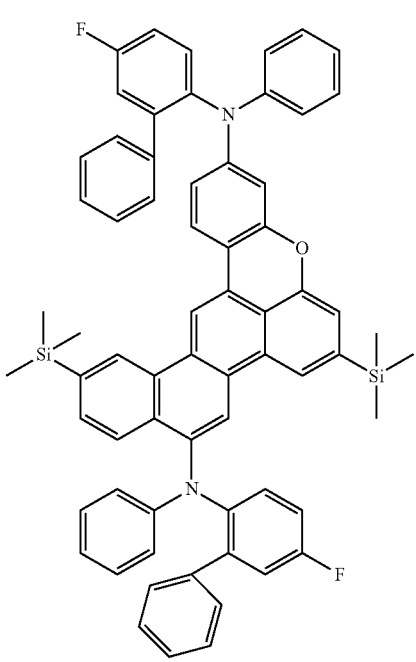
91
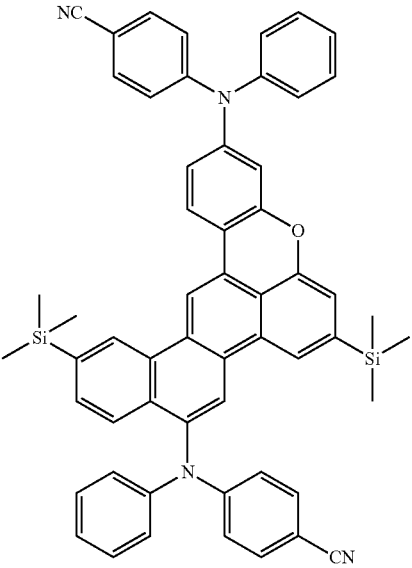

363
-continued
92
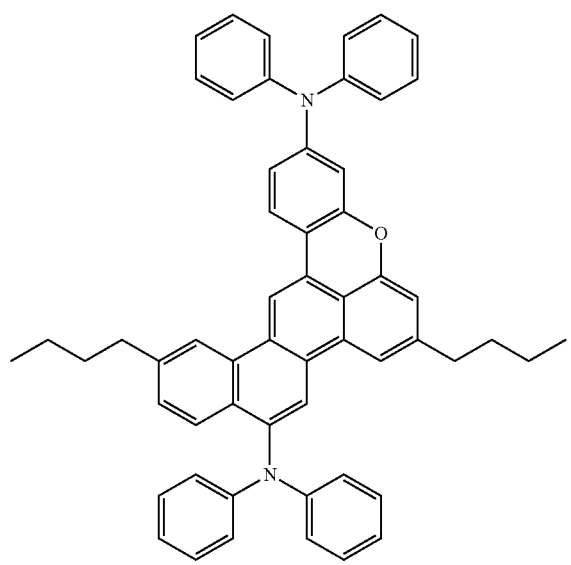
93
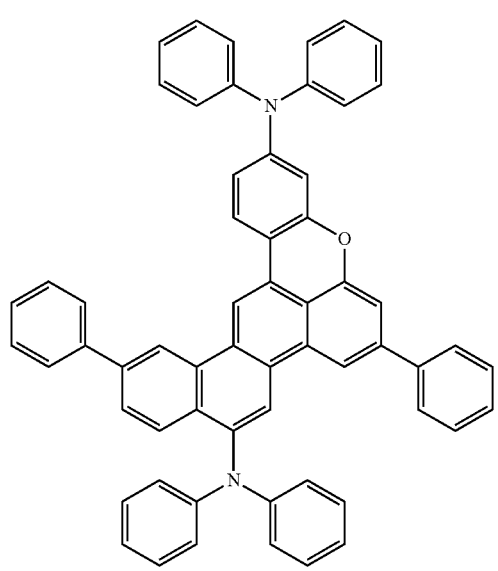
364
-continued
94
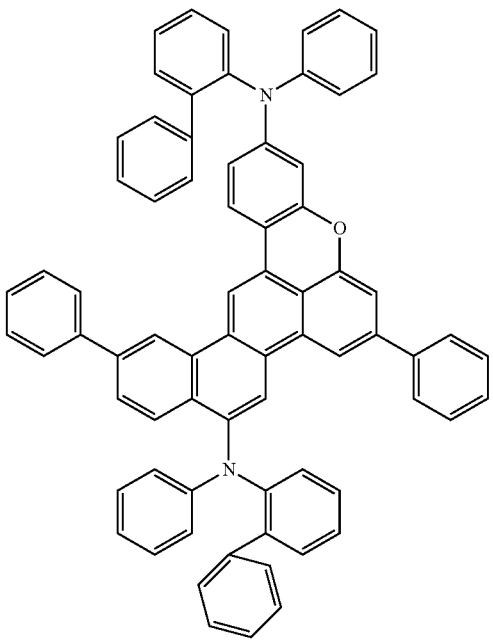
95
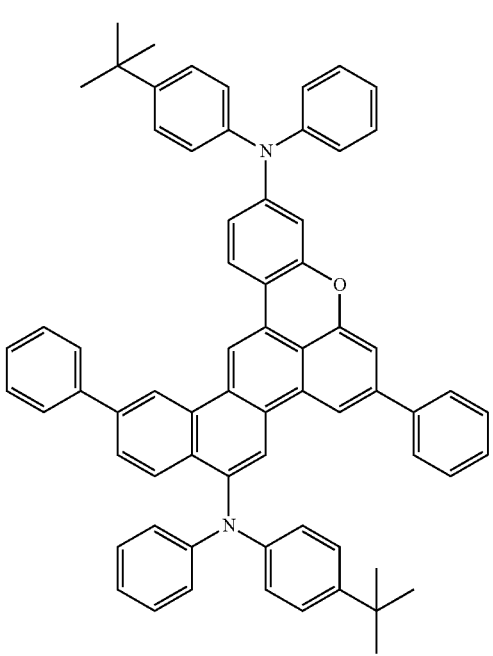

365
-continued
96
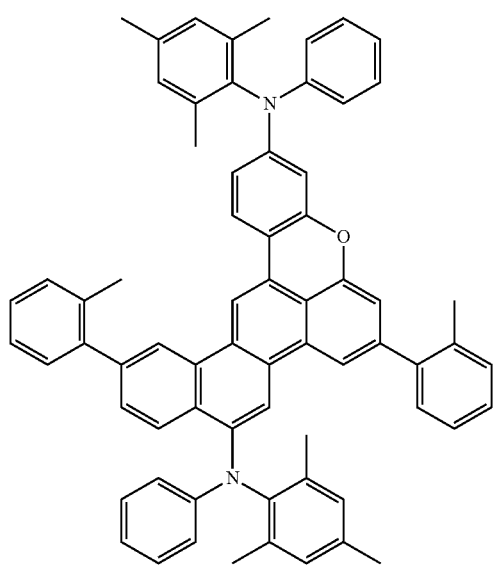
97
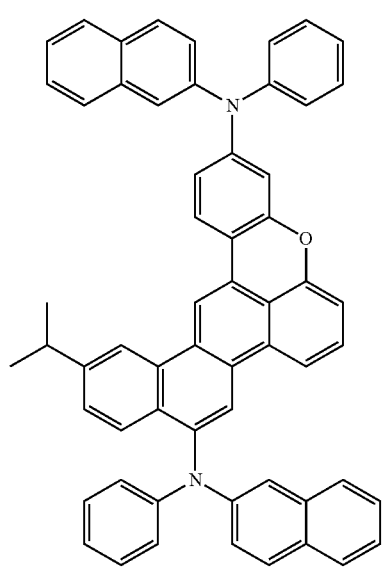
366
-continued
98
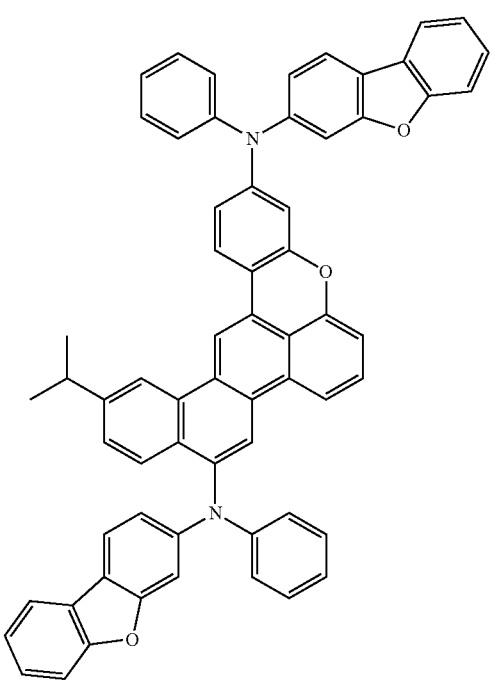
99
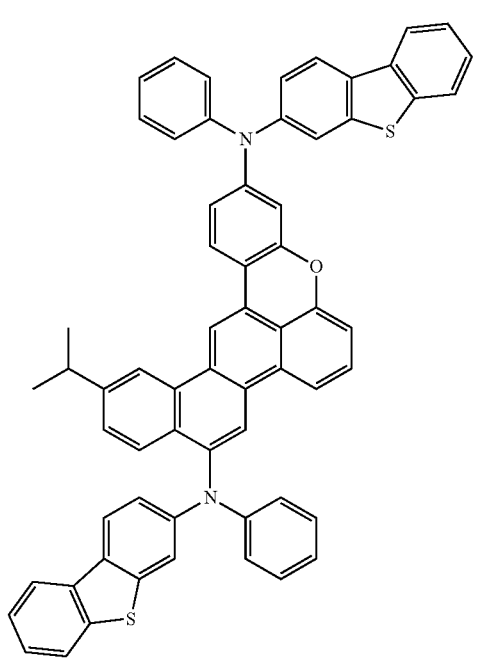

367
-continued
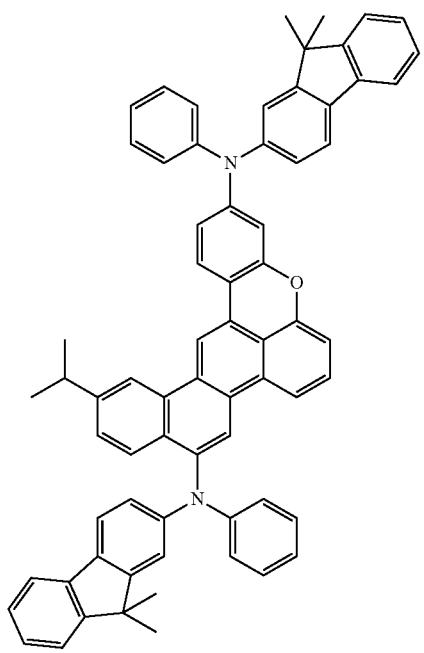
100
368
-continued
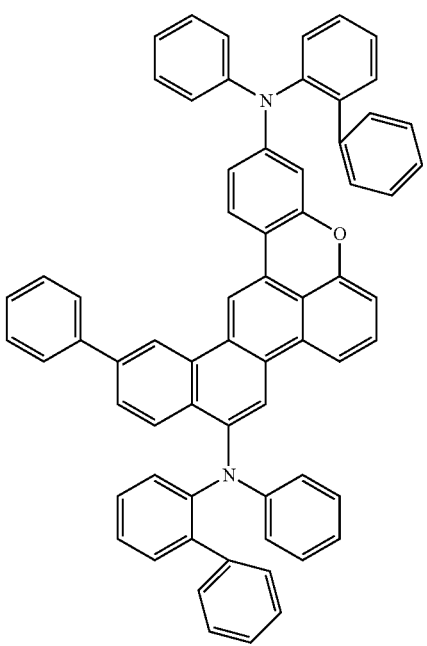
102
101
103

369
-continued
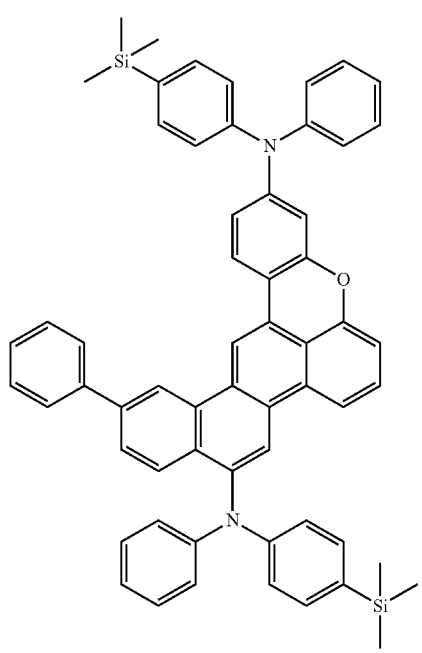
104
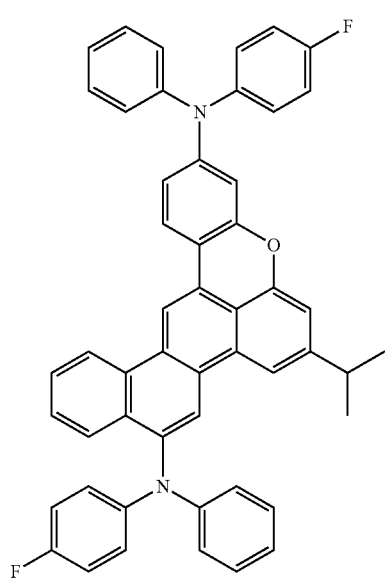
105
370
-continued
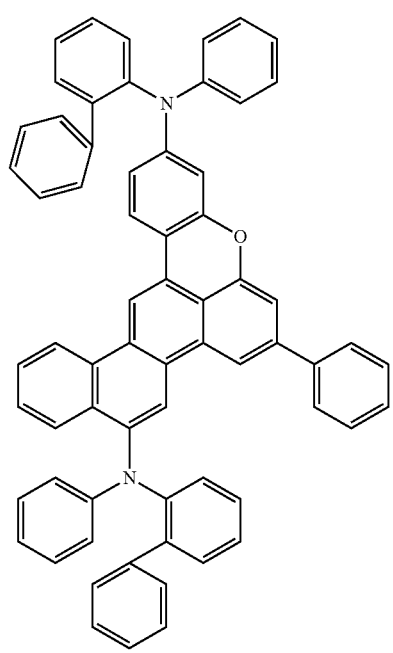
106
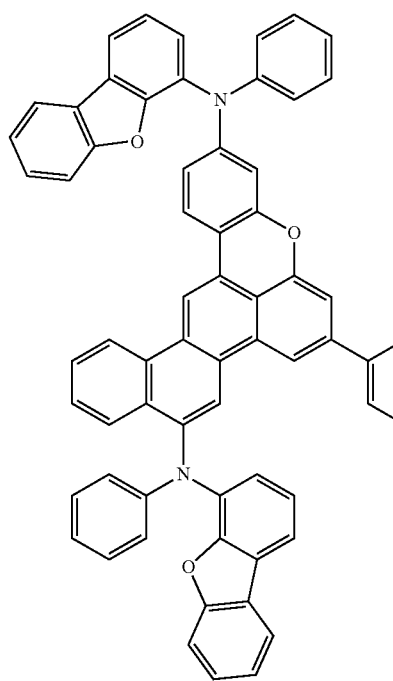
107

371
-continued

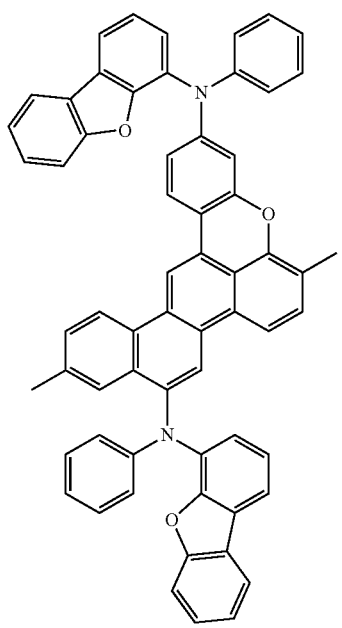

372
-continued

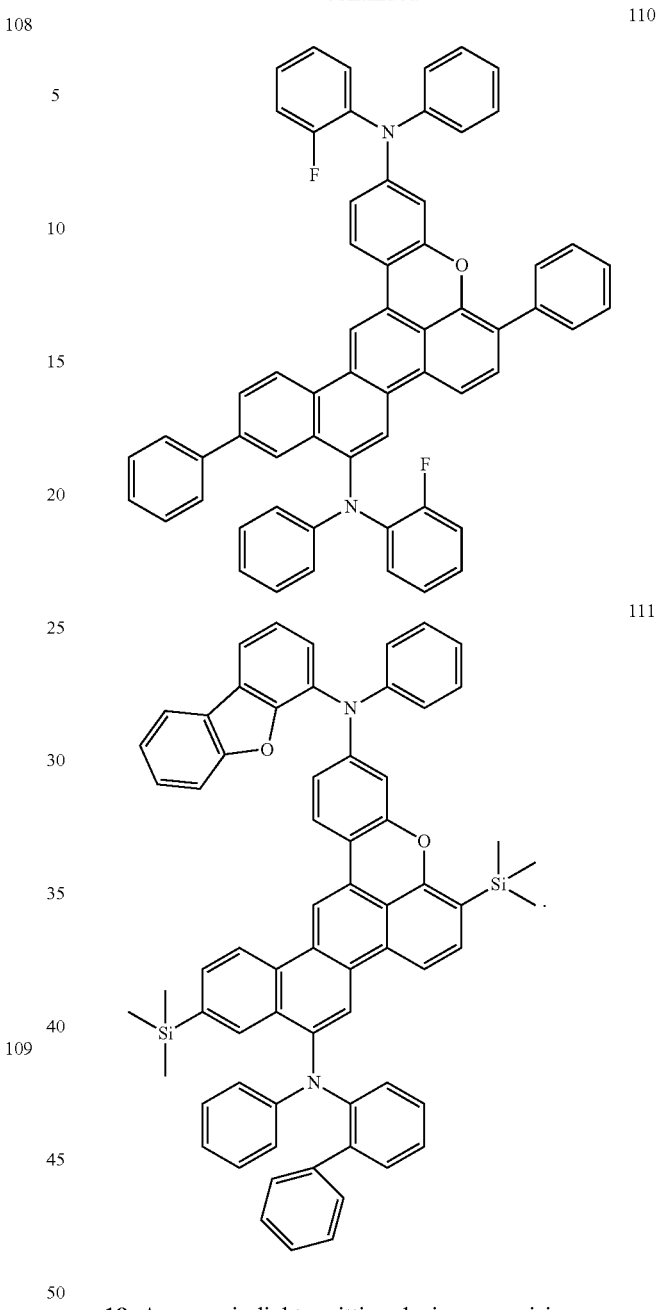

18. An organic light-emitting device comprising:
    a first electrode;
    a second electrode; and
    an organic layer between the first electrode and the second electrode, the organic layer comprising an emission layer,
    wherein the organic layer comprises the condensed cyclic compound of claim 1.

19. The organic light-emitting device of claim 18, wherein the emission layer comprises a host and a dopant, and the condensed cyclic compound acts as the dopant.

20. The organic light-emitting device of claim 19, wherein the host comprises a material represented by any one of Formulae 2 and 2-1 to 2-4:

Formula 2

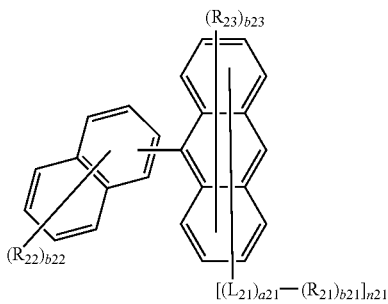

[(L_{21})_{a21}—(R_{21})_{b21}]_{n21}

Formula 2-1

[(R_{212})_{b212}—(L_{213})_{a213}]_{n212}—Ar_{211}—(L_{211})_{a211}—Ar_{212}—[(L_{212})_{a212}—(R_{211})_{b211}]_{n211}

Formula 2-2

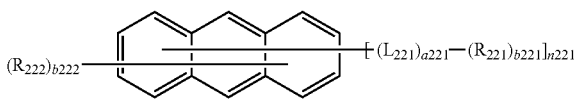

Formula 2-3

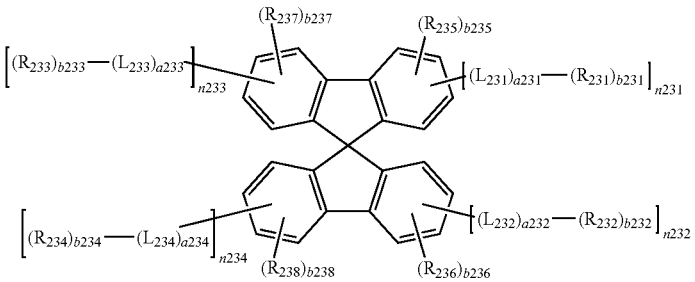

Formula 2-4

$(R_{242})_{b242}$—$Ar_{241}$—$[(L_{241})_{a241}$—$(R_{241})_{b241}]_{n241}$, wherein in the Formulae 2 and 2-1 to 2-4, $Ar_{211}$ is selected from a naphthalene, an anthracene, a triphenylene, a pyrene, a chrysene, and a perylene;

$Ar_{212}$ is selected from an anthracene, a triphenylene, a pyrene, a chrysene, and a perylene;

$Ar_{241}$ is selected from a benzene, a biphenyl, and a triphenylene;

$L_{21}$, $L_{211}$ to $L_{213}$, $L_{221}$, $L_{231}$ to $L_{234}$, and $L_{241}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a21 is selected from 0, 1, 2, and 3;

a211 to a213, a221, a231 to a234 and a241 are each independently selected from 0, 1, and 2;

$R_{21}$ to $R_{23}$ are each independently selected from hydrogen, deuterium, F, —Cl, —Br, —I, a hydroxyl group, a cyano group, a nitro group, a substituted or unsubstituted $C_1$-$C_{60}$ alkyl group, a substituted or unsubstituted $C_2$-$C_{60}$ alkenyl group, a substituted or unsubstituted $C_1$-$C_{60}$ alkoxy group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b21 to b23 are each independently selected from 1, 2, 3, 4, 5, and 6;

n21 is selected from 1, 2 and 3;

$R_{231}$ to $R_{234}$ and $R_{241}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b231 to b234, and b241 are each independently selected from 1, 2, and 3;

$R_{211}$, $R_{212}$, $R_{221}$, $R_{222}$, $R_{235}$ to $R_{238}$, and $R_{242}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{211}$)($C_{212}$)($Q_{213}$), —N($Q_{214}$)($Q_{215}$), and —B($Q_{216}$)($Q_{217}$);

b211, b212, b221, b222, b235 to b238, and b242 are each independently selected from 1, 2, and 3;

n211, n212, and n221 are each independently selected from 1, 2, and 3;

n231 to n234 are each independently selected from 0, 1, and 2, and a sum of n231 to n234 is selected from 1, 2, 3, 4, 5, and 6;

n241 is selected from 3, 4, 5, 6, 7, and 8; and at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{211}$ to $Q_{217}$, $Q_1$ to $Q_7$, $Q_{11}$ to $Q_{17}$, $Q_{21}$ to $Q_{27}$, and $Q_{31}$ to $Q_{37}$ are each independently selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

* * * * *